US012227482B2

(12) United States Patent
Peto et al.

(10) Patent No.: US 12,227,482 B2
(45) Date of Patent: Feb. 18, 2025

(54) COMPOUNDS AND COMPOSITIONS FOR THE TREATMENT OF CANCER

(71) Applicants: The Regents of the University of California, Oakland, CA (US); RasCal Therapeutics, Inc., Southlake, TX (US)

(72) Inventors: Csaba Peto, San Francisco, CA (US); Bhairavi Tolani, San Francisco, CA (US); Gavitt Woodard, San Francisco, CA (US); Tsze Tsang, El Cerrito, CA (US); Michael Mann, San Francisco, CA (US); David M. Jablons, San Francisco, CA (US); Biao He, Foster City, CA (US)

(73) Assignees: The Regents of the University of California, Oakland, CA (US); Rascal Therapeutics, Inc., Los Altos Hills, CA (US)

( * ) Notice: Subject to any disclaimer, the term of this patent is extended or adjusted under 35 U.S.C. 154(b) by 116 days.

(21) Appl. No.: 18/075,198

(22) Filed: Dec. 5, 2022

(65) Prior Publication Data
US 2023/0150942 A1 May 18, 2023

Related U.S. Application Data

(62) Division of application No. 16/305,377, filed as application No. PCT/US2017/039806 on Jun. 28, 2017, now Pat. No. 11,560,356.

(60) Provisional application No. 62/356,261, filed on Jun. 29, 2016.

(51) Int. Cl.
C07D 231/06 (2006.01)
C07D 405/04 (2006.01)
C07D 409/04 (2006.01)

(52) U.S. Cl.
CPC ......... *C07D 231/06* (2013.01); *C07D 405/04* (2013.01); *C07D 409/04* (2013.01)

(58) Field of Classification Search
None
See application file for complete search history.

(56) References Cited

U.S. PATENT DOCUMENTS

| | | | |
|---|---|---|---|
| 5,622,929 A | 4/1997 | Willner | |
| 6,214,345 B1 | 4/2001 | Firestone | |
| 7,714,014 B2* | 5/2010 | He | A61P 35/00 514/403 |
| 9,370,521 B2 | 6/2016 | He | |
| 9,840,470 B2 | 12/2017 | He | |
| 11,560,356 B2* | 1/2023 | Peto | C07D 498/04 |
| 2009/0131365 A1 | 5/2009 | Zhang | |
| 2014/0303160 A1 | 10/2014 | He | |
| 2015/0361048 A1 | 12/2015 | He | |
| 2021/0009523 A1 | 1/2021 | Peto | |

FOREIGN PATENT DOCUMENTS

WO 2006055184 A2 5/2006
WO 2018005697 A1 1/2018

OTHER PUBLICATIONS

Li et al, Bioorganic & Medicinal Chemistry Letters, vol. 22, pp. 3589-3593 (Year: 2012).*
Albright, S.R. et al. (2000). "Tafs Revisited: More Data Reveal New Twists And Confirm Old Ideas," Gene 242(1-2):1-13.
Berge, S. et al. (Jan. 1977). "Pharmaceutical Salts," Journal of Pharmaceutical Sciences 66(1):1-19.
European Search Report mailed on May 21, 2024, for EP Application No. 23199886.5, filed on Jun. 28, 2017, 5 pages.
European Search Report mailed on Oct. 29, 2019, for EP Application No. 17821174.4, filed on Jun. 28, 2017, six pages.
Freshney, R.I. et al. (1994). "Culture of Animal Cells a Manual of Basic Technique," 3rd Edition, Wiley-Liss, Inc.: New York, pp. 231-241.
Goodrich, J.A., et al. (Jun. 1, 1994). "TBP-TAF Complexes: Selectivity Factors For Eukaryotic Transcription," Current Opinion In Cell Biology 6(3): 403-409.
Hui, C.-C. et al. (Apr. 1, 1994). "Expression Of Three Mouse Homologs Of The Drosophila Segment Polarity Gene Cubitus Interruptus, Gli, Gli-2, And Gli-3, In Ectoderm-And Mesoderm-Derived Tissues Suggests Multiple Roles During Postimplantation Development," Developmental Biology 162(2):402-413.
International Preliminary Report on Patentability, issued Jan. 1, 2019, for International Application No. PCT/US2017/039806 filed on Jun. 28, 2017, 6 pages.
International Search Report and Written Opinion mailed on Nov. 2, 2017 for PCT Application No. PCT/US2017/039806 filed on Jun. 28, 2017, 5 pages.
Katoh, Y. et al. (Oct. 1, 2005). "Hedgehog Signaling Pathway And Gastric Cancer," Cancer Biology & Therapy 4 (10):1050-1054, 6 pages.
Klemm, R.D. et al. (Jun. 20, 1995). "Molecular Cloning And Expression Of The 32-Kda Subunit Of Human TFIID Reveals Interactions With VP16 And TFIIB That Mediate Transcriptional Activation," Proceedings of the National Academy of Sciences 92(13):5788-5792.
Lu, H. et al. (May 23, 1995). "Human TAFII31 Protein Is A Transcriptional Coactivator Of The P53 Protein." Proceedings of the National Academy of Sciences 92(11):5154-5158.
Ruiz I Altaba, A. et al. (May 2002). "Gli And Hedgehog In Cancer: Tumours, Embryos And Stem Cells," Nature Reviews Cancer 2(5):361-372.
Shimizu, H. et al. (Dec. 1997). "Transformation By Wnt Family Proteins Correlates With Regulation Of Beta-Catenin," Cell Growth & Differentiation: The Molecular Biology Journal Of The American Association For Cancer Research 8(12):1349-1358.

(Continued)

*Primary Examiner* — Zinna Northington Davis
(74) *Attorney, Agent, or Firm* — Morrison & Foerster LLP

(57) ABSTRACT

The present disclosure provides compounds, pharmaceutical compositions, and methods for the treatment of cancer and fibrosis. The disclosed pharmaceutical compositions may include one or more pyrazolyl-containing compounds, or a derivative thereof.

27 Claims, No Drawings

(56) References Cited

OTHER PUBLICATIONS

Singleton, P. et al. (1994). Dictionary of Microbiology and Molecular Biology, 2nd ed. New York, New York, 8 pages.
Still, W.C. et al. (Jul. 1978). "Rapid Chromatographic Technique For Preparative Separations With Moderate Resolution," The Journal of Organic Chemistry 43(14):2923-2925.
Wang, Y. et al. (2007). "Convenient Synthesis Of Highly Functionalized Pyrazolines Via Mild, Photoactivated 1, 3- Dipolar Cycloaddition," Organic Letters 9(21):4155-4158.

* cited by examiner

COMPOUNDS AND COMPOSITIONS FOR THE TREATMENT OF CANCER

CROSS-REFERENCE TO RELATED APPLICATIONS

This application is a divisional application of U.S. Nonprovisional application Ser. No. 16/305,377, filed Nov. 28, 2018, which is a national stage application under 35 U.S.C. § 371 of International Application No. PCT/US2017/039806, filed Jun. 28, 2017, which claims priority pursuant to 35 U.S.C. § 119(e) to U.S. Provisional Application No. 62/356,261, filed Jun. 29, 2016, the disclosures of which are incorporated herein by reference in their entireties.

INTRODUCTION

Hedgehog (Shh or Hh), WNT, FGF and BMP signaling pathways network together during embryogenesis, tissue regeneration, and carcinogenesis. Aberrant activation of Hh signaling pathways may lead to pathological consequences in a variety of human tumors. In addition, the Hh signaling pathway plays an important role in fibrosis. Hh signaling can activate stromal cells, resulting in increased stromal and epithelial proliferation, and is also involved in myofibroblast transdifferentiation and proliferation. In response to tissue injury, Hedgehogs are secreted glycoproteins that initiate Hh signal transduction by binding to a transmembrane protein complex including PATCHED1 (ptch1) and SMOOTHENED (smo) and eliciting a cascade of cytoplasmic signal transduction events, including the inhibition of a protein kinase A that leads to the transcription of the GLI zinc-finger transcription factors. The GLI family of zinc-finger transcription factors then translate the extra-cellular Hh-stimulus into defined transcriptional programs in a context-dependent and cell-type specific manner (Ruiz I Altaba et al., 2002, *Nat. Rev. Cancer* 2:361-72).

Several proteins, including GLI proteins, are involved in mediating Hh signaling (Katoh and Katoh, 2005, *Cancer Biol. Ther.* 4:1050-4). Vertebrates have at least three distinct GLI proteins, GLI (also referred to as GLI1), GLI2, and GLI3. These proteins are members of the GLI family of zinc finger transcription factors and share a highly conserved $C_2$—$H_2$ zinc finger domain (having five zinc finger DNA-binding motifs) with *Drosophila* Cubitus interruptus (Ci) and the *Caenorhabditis elegans* sex-determining gene tra-1 (Hui et al., 1994, *Dev. Biol.* 162:402-13).

Although research has investigated Hh-signaling in Drosiphila and murine development, understanding of the molecular mechanisms, tumorigenic programs, and fibrogenic pathways that are activated in response to Hh-signaling and GLI activity in human cancer and fibrosis is still limited. However, a common property of Hh-associated cancer and fibrosis is the elevated expression level of one or more GLI proteins.

RAS is a family of related proteins which belong to the small GTPase class of proteins. Small GTPases are a family of hydrolase enzymes found in the cytosol that can bind and hydrolyze guanosine triphosphate (GTP). As such, RAS proteins are involved in transmitting signals within cells. For instance, when RAS is activated by incoming signals, it subsequently switches on other proteins, which then leads to activation of genes involved in cell growth, differentiation and survival. As a result, mutations in Ras genes can lead to the production of mutant RAS proteins, such as for example, RAS proteins that are more active than wild-type RAS. This can cause unintended and overactive signaling inside the cell, even in the absence of incoming cellular signals. Because RAS signals are involved in cell growth, differentiation and survival, overactive RAS signaling may lead to cancer. In addition, RAS signaling can induce Hedgehog signaling during the formation of certain tumors. For instance, Ras activation may regulate Hedgehog signaling during tumor formation.

SUMMARY

The present disclosure relates to compounds, compositions and methods of inhibiting tumorigenesis, tumor growth and tumor survival. The compositions include compounds effective for the treatment of cancer. The present disclosure also relates to compounds, compositions and methods of inhibiting fibrosis. The compositions include compounds effective for the treatment of fibrosis.

In some cases, the compositions include compounds effective for inhibiting Hedgehog and GLI signaling pathways. For example, the compounds, compositions and methods find use in treating cancers where GLI proteins are overexpressed. In some cases, the compounds, compositions and methods find use in treating fibrosis where GLI proteins are overexpressed In some cases, the compounds, compositions and methods find use in treating RAS-mutant cancers (e.g., cancers that overexpress mutant RAS protein(s)).

The embodiments of the present disclosure provide compounds, pharmaceutical compositions, kits and methods useful for treatment of a various types of cancers. Such cancers include, but are not limited to, lung cancer (e.g., NSCLC), colon cancer, pancreatic cancer, breast cancer, mesothelioma, melanoma, sarcoma, prostate cancer, ovarian cancer, renal cancer, esophageal cancer, gastric cancer, hepatocellular cancer, nasopharyngeal cancer, glioma, and others.

The embodiments of the present disclosure provide compounds, pharmaceutical compositions, kits and methods useful for treatment of a various types of fibrosis. Types of fibrosis that can be treated include, but are not limited to, kidney fibrosis, pulmonary fibrosis, cirrhosis, endomyocardial fibrosis, arthofibrosis, Crohn's disease, mediastinal fibrosis, myelofibrosis, retroperitoneal fibrosis, and others.

Aspects of the present disclosure include a compound of formula (I):

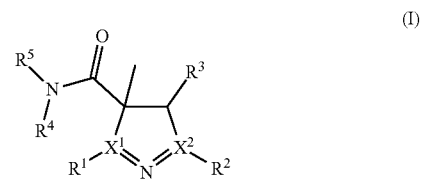

wherein
each of $X^1$ and $X^2$ is independently N or C, wherein one of $X^1$ and $X^2$ is N and one of $X^1$ and $X^2$ is C, such that the ring N forms a double bond with whichever of $X^1$ and $X^2$ is C;
$R^1$ is aryl or substituted aryl;
$R^2$ is aryl or substituted aryl;
$R^3$ is selected from alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl and substituted heteroaryl;

R⁴ is selected from hydrogen, alkyl and substituted alkyl; and

R⁵ is selected from alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl and substituted heteroaryl;

and salts, hydrates, solvates or stereoisomers thereof.

In some embodiments, $X^1$ is N and $X^2$ is C.

In some embodiments, $X^1$ is C and $X^2$ is N.

In some embodiments, $R^1$ is substituted aryl.

In some embodiments, $R^2$ is substituted aryl.

In some embodiments, $R^3$ is selected from $C_1$-$C_6$ alkyl, heteroaryl and substituted heteroaryl.

In some embodiments, $R^4$ is hydrogen.

In some embodiments, $R^4$ is alkyl or substituted alkyl.

In some embodiments, $R^5$ is substituted alkyl.

In some embodiments, $R^5$ is selected from: 5-hydroxy-4,4-dimethylpentyl; 5-hydroxy-5-methylhexyl; 3-methoxypropyl; 3-oxo-3-methoxypropyl; 2-methoxyethyl; 3-(dimethylamino)propyl; 4-methoxybutyl; 2-ethoxyethyl; 5-hydroxypentyl; 6-hydroxyhexyl; 4-hydroxybutyl; and methyl acetate.

In some embodiments, $R^5$ is heterocyclyl or substituted heterocyclyl.

In some embodiments, $R^5$ is selected from: (4-methylmorpholin-2-yl)methyl; 4-(methoxymethyl)-1-methylpiperidin-4-yl; 3-(methoxymethyl)-1-methylazetidin-3-yl; 3-(methoxymethyl)oxetan-3-yl; 3-((dimethylamino)methyl)oxetan-3-yl; oxetan-3-yl; 4-methoxy-1-methylpyrrolidin-3-yl; 6-methoxyhexahydrofuro[3,2-b]furan-3-yl; and 6-(dimethylamino)hexahydrofuro[3,2-b]furan-3-yl; or stereoisomers thereof.

In some embodiments, the compound is of formula (Ia)

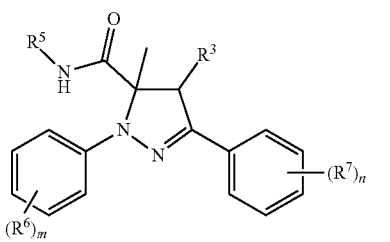

wherein
$R^3$ is selected from alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl and substituted heteroaryl;

$R^5$ is selected from alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl and substituted heteroaryl; and $R^6$ and $R^7$ are each independently selected from hydrogen, halogen, alkyl, substituted alkyl, alkoxy, substituted alkoxy and sulfonyl, wherein m and n are each independently selected from an integer from 1 to 5;

and salts, hydrates, solvates or stereoisomers thereof.

In some embodiments, $R^3$ is selected from $C_1$-$C_6$ alkyl, heteroaryl and substituted heteroaryl.

In some embodiments, at least one $R^6$ is halogen.

In some embodiments, at least one $R^7$ is halogen.

In some embodiments, the compound is of formula (Ib):

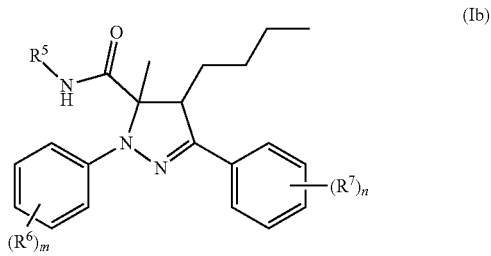

wherein
$R^5$ is selected from alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl and substituted heteroaryl; and $R^6$ and $R^7$ are each independently selected from hydrogen, halogen, alkyl, substituted alkyl, alkoxy, substituted alkoxy and sulfonyl, wherein m and n are each independently selected from an integer from 1 to 5;

and salts, hydrates, solvates or stereoisomers thereof.

In some embodiments, at least one $R^6$ is halogen.

In some embodiments, at least one $R^7$ is halogen.

In some embodiments, the compound is of formula (Ic):

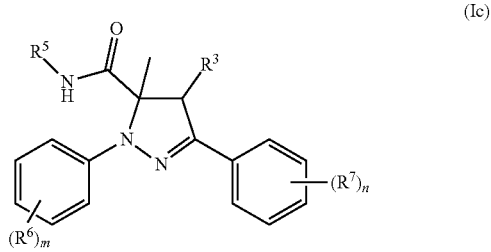

wherein
$R^3$ is furanyl or substituted furanyl;
$R^5$ is selected from alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl and substituted heteroaryl; and $R^6$ and $R^7$ are each independently selected from hydrogen, halogen, alkyl, substituted alkyl, alkoxy, substituted alkoxy and sulfonyl, wherein m and n are each independently selected from an integer from 1 to 5;

and salts, hydrates, solvates or stereoisomers thereof.

In some embodiments, at least one $R^6$ is halogen.

In some embodiments, at least one $R^7$ is halogen.

In some embodiments, the compound is selected from:

4-butyl-3-(4-fluorophenyl)-N-(5-hydroxy-4,4-dimethylpentyl)-5-methyl-1-phenyl-4,5-dihydro-1H-pyrazole-5-carboxamide (Compound 1);

4-butyl-3-(4-fluorophenyl)-N-(5-hydroxy-5-methylhexyl)-5-methyl-1-phenyl-4,5-dihydro-1H-pyrazole-5-carboxamide (Compound 2);

4-butyl-1-(2,4-difluorophenyl)-3-(4-fluorophenyl)-N-(5-hydroxy-4,4-dimethylpentyl)-5-methyl-4,5-dihydro-1H-pyrazole-5-carboxamide (Compound 3);

4-butyl-1-(2,4-difluorophenyl)-3-(4-fluorophenyl)-N-(5-hydroxy-5-methylhexyl)-5-methyl-4,5-dihydro-1H-pyrazole-5-carboxamide (Compound 4);

4-butyl-1-(2,4-difluorophenyl)-3-(4-fluorophenyl)-N-(3-methoxypropyl)-5-methyl-4,5-dihydro-1H-pyrazole-5-carboxamide (Compound 5);

4-butyl-1-(2,4-difluorophenyl)-3-(4-fluorophenyl)-N-(2-methoxyethyl)-5-methyl-4,5-dihydro-1H-pyrazole-5-carboxamide (Compound 6);

4-butyl-1-(3-fluorophenyl)-3-(4-fluorophenyl)-N-(5-hydroxy-5-methylhexyl)-5-methyl-4,5-dihydro-1H-pyrazole-5-carboxamide (Compound 7);

4-butyl-1-(3-fluorophenyl)-3-(4-fluorophenyl)-N-(3-methoxypropyl)-5-methyl-4,5-dihydro-1H-pyrazole-5-carboxamide (Compound 8);

4-butyl-1-(2,5-difluorophenyl)-3-(4-fluorophenyl)-N-(5-hydroxy-5-methylhexyl)-5-methyl-4,5-dihydro-1H-pyrazole-5-carboxamide (Compound 9);

4-butyl-3-(3,4-difluorophenyl)-N-(5-hydroxy-5-methylhexyl)-5-methyl-1-phenyl-4,5-dihydro-1H-pyrazole-5-carboxamide (Compound 10);

4-butyl-1-(3-chloro-4-fluorophenyl)-3-(4-fluorophenyl)-N-(5-hydroxy-5-methylhexyl)-5-methyl-4,5-dihydro-1H-pyrazole-5-carboxamide (Compound 11);

4-butyl-1-(4-chlorophenyl)-3-(4-fluorophenyl)-N-(5-hydroxy-4,4-dimethylpentyl)-5-methyl-4,5-dihydro-1H-pyrazole-5-carboxamide (Compound 12);

4-butyl-1-(4-chlorophenyl)-3-(4-fluorophenyl)-N-(3-methoxypropyl)-5-methyl-4,5-dihydro-1H-pyrazole-5-carboxamide (Compound 13);

4-butyl-1,3-bis(4-fluorophenyl)-N-(3-methoxypropyl)-5-methyl-4,5-dihydro-1H-pyrazole-5-carboxamide (Compound 14);

4-butyl-3-(4-fluorophenyl)-N-(5-hydroxy-4,4-dimethylpentyl)-5-methyl-1-p-tolyl-4,5-dihydro-1H-pyrazole-5-carboxamide (Compound 15);

4-butyl-3-(4-fluorophenyl)-N-(3-methoxypropyl)-5-methyl-1-p-tolyl-4,5-dihydro-1H-pyrazole-5-carboxamide (Compound 16);

4-butyl-1-(3-chlorophenyl)-3-(4-fluorophenyl)-N-(5-hydroxy-4,4-dimethylpentyl)-5-methyl-4,5-dihydro-1H-pyrazole-5-carboxamide (Compound 17);

4-butyl-1-(4-fluoro-3-methoxyphenyl)-3-(4-fluorophenyl)-N-(5-hydroxy-4,4-dimethylpentyl)-5-methyl-4,5-dihydro-1H-pyrazole-5-carboxamide (Compound 18);

4-butyl-1-(4-fluoro-3-methoxyphenyl)-3-(4-fluorophenyl)-N-(3-methoxypropyl)-5-methyl-4,5-dihydro-1H-pyrazole-5-carboxamide (Compound 19);

3-(4-fluorophenyl)-N-(5-hydroxy-4,4-dimethylpentyl)-5-methyl-1-phenyl-4-(thiophen-2-yl)-4,5-dihydro-1H-pyrazole-5-carboxamide (Compound 20);

3-(4-fluorophenyl)-N-(5-hydroxy-4,4-dimethylpentyl)-5-methyl-1-phenyl-4-(pyridin-4-yl)-4,5-dihydro-1H-pyrazole-5-carboxamide (Compound 21);

4-butyl-1-(2-chloro-4-fluorophenyl)-3-(4-fluorophenyl)-N-(5-hydroxy-4,4-dimethylpentyl)-5-methyl-4,5-dihydro-1H-pyrazole-5-carboxamide (Compound 22);

4-butyl-1-(4-chloro-2-fluorophenyl)-3-(4-fluorophenyl)-N-(5-hydroxy-4,4-dimethylpentyl)-5-methyl-4,5-dihydro-1H-pyrazole-5-carboxamide (Compound 23);

4-butyl-1-(2,4-difluorophenyl)-N-(3-(dimethylamino)propyl)-3-(4-fluorophenyl)-5-methyl-4,5-dihydro-1H-pyrazole-5-carboxamide (Compound 24);

4-butyl-1-(2,4-difluorophenyl)-3-(4-fluorophenyl)-N-(4-methoxybutyl)-5-methyl-4,5-dihydro-1H-pyrazole-5-carboxamide (Compound 25);

4-butyl-1-(2,4-difluorophenyl)-3-(4-fluorophenyl)-N-(3-methoxypropyl)-N,5-dimethyl-4,5-dihydro-1H-pyrazole-5-carboxamide (Compound 26);

4-butyl-3-(4-fluorophenyl)-N-(5-hydroxy-4,4-dimethylpentyl)-5-methyl-1-(4-(trifluoromethyl)phenyl)-4,5-dihydro-1H-pyrazole-5-carboxamide (Compound 28);

4-butyl-1-(4-chloro-2-methylphenyl)-3-(4-fluorophenyl)-N-(5-hydroxy-4,4-dimethylpentyl)-5-methyl-4,5-dihydro-1H-pyrazole-5-carboxamide (Compound 29);

4-butyl-1-(4-chloro-2-methylphenyl)-3-(4-fluorophenyl)-N-(3-methoxypropyl)-5-methyl-4,5-dihydro-1H-pyrazole-5-carboxamide (Compound 30);

methyl 3-(4-butyl-1-(2,4-difluorophenyl)-3-(4-fluorophenyl)-5-methyl-4,5-dihydro-1H-pyrazole-5-carboxamido)propanoate (Compound 31);

4-butyl-1-(2,4-difluorophenyl)-N-(2-ethoxyethyl)-3-(4-fluorophenyl)-5-methyl-4,5-dihydro-1H-pyrazole-5-carboxamide (Compound 32);

4-butyl-3-(4-fluorophenyl)-N-(5-hydroxypentyl)-5-methyl-1-phenyl-4,5-dihydro-1H-pyrazole-5-carboxamide (Compound 33);

4-butyl-3-(4-fluorophenyl)-N-(6-hydroxyhexyl)-5-methyl-1-phenyl-4,5-dihydro-1H-pyrazole-5-carboxamide (Compound 34);

4-butyl-3-(4-fluorophenyl)-N-(4-hydroxybutyl)-5-methyl-1-phenyl-4,5-dihydro-1H-pyrazole-5-carboxamide (Compound 35);

4-butyl-3-(4-fluorophenyl)-N-(4-hydroxybenzyl)-5-methyl-1-phenyl-4,5-dihydro-1H-pyrazole-5-carboxamide (Compound 36);

4-butyl-3-(4-fluorophenyl)-N-(1-hydroxy-2-methylpropan-2-yl)-5-methyl-1-phenyl-4,5-dihydro-1H-pyrazole-5-carboxamide (Compound 37);

4-butyl-3-(4-fluorophenyl)-N-(4-hydroxyphenethyl)-5-methyl-1-phenyl-4,5-dihydro-1H-pyrazole-5-carboxamide (Compound 38);

4-butyl-N-(3-chlorobenzyl)-3-(4-fluorophenyl)-5-methyl-1-phenyl-4,5-dihydro-1H-pyrazole-5-carboxamide (Compound 39);

4-butyl-N-(3,4-dichlorobenzyl)-3-(4-fluorophenyl)-5-methyl-1-phenyl-4,5-dihydro-1H-pyrazole-5-carboxamide (Compound 40);

4-butyl-N-(3,5-dichlorobenzyl)-3-(4-fluorophenyl)-5-methyl-1-phenyl-4,5-dihydro-1H-pyrazole-5-carboxamide (Compound 41);

4-butyl-3-(4-fluorophenyl)-5-methyl-1-phenyl-N-((S)-1-phenylethyl)-4,5-dihydro-1H-pyrazole-5-carboxamide (Compound 42);

4-butyl-3-(4-fluorophenyl)-5-methyl-1-phenyl-N-((R)-1-phenylethyl)-4,5-dihydro-1H-pyrazole-5-carboxamide (Compound 43);

4-butyl-3-(4-fluorophenyl)-N-(2-methoxybenzyl)-5-methyl-1-phenyl-4,5-dihydro-1H-pyrazole-5-carboxamide (Compound 44);

4-butyl-N-(2,3-dimethoxybenzyl)-3-(4-fluorophenyl)-5-methyl-1-phenyl-4,5-dihydro-1H-pyrazole-5-carboxamide (Compound 45);

4-butyl-N-(2,4-dimethoxybenzyl)-3-(4-fluorophenyl)-5-methyl-1-phenyl-4,5-dihydro-1H-pyrazole-5-carboxamide (Compound 46);

4-butyl-N-(3,4-dimethoxybenzyl)-3-(4-fluorophenyl)-N,5-dimethyl-1-phenyl-4,5-dihydro-1H-pyrazole-5-carboxamide (Compound 47);

4-butyl-N-(4-(dimethylamino)benzyl)-3-(4-fluorophenyl)-5-methyl-1-phenyl-4,5-dihydro-1H-pyrazole-5-carboxamide (Compound 48);

4-butyl-N-(3-(dimethylamino)propyl)-3-(4-fluorophenyl)-5-methyl-1-phenyl-4,5-dihydro-1H-pyrazole-5-carboxamide (Compound 49);

4-butyl-N-(3-(dimethylamino)-2,2-dimethylpropyl)-3-(4-fluorophenyl)-5-methyl-1-phenyl-4,5-dihydro-1H-pyrazole-5-carboxamide (Compound 50);

4-butyl-N-(cyclohexylmethyl)-3-(4-fluorophenyl)-5-methyl-1-phenyl-4,5-dihydro-1H-pyrazole-5-carboxamide (Compound 51);

4-butyl-N-(3,5-dimethoxybenzyl)-3-(4-fluorophenyl)-N,5-dimethyl-1-phenyl-4,5-dihydro-1H-pyrazole-5-carboxamide (Compound 52);

4-butyl-3-(4-chloro-2-fluorophenyl)-N-(5-hydroxy-4,4-dimethylpentyl)-5-methyl-1-phenyl-4,5-dihydro-1H-pyrazole-5-carboxamide (Compound 53);

4-butyl-3-(4-chloro-2-fluorophenyl)-N-(2-methoxyethyl)-5-methyl-1-phenyl-4,5-dihydro-1H-pyrazole-5-carboxamide (Compound 54);

4-butyl-3-(4-fluorophenyl)-N-(2-methoxyethyl)-5-methyl-1-m-tolyl-4,5-dihydro-1H-pyrazole-5-carboxamide (Compound 55);

4-butyl-3-(2,4-difluorophenyl)-N-(5-hydroxy-4,4-dimethylpentyl)-5-methyl-1-phenyl-4,5-dihydro-1H-pyrazole-5-carboxamide (Compound 56);

4-butyl-3-(2,4-difluorophenyl)-N-(2-methoxyethyl)-5-methyl-1-phenyl-4,5-dihydro-1H-pyrazole-5-carboxamide (Compound 57);

4-butyl-3-(4-chlorophenyl)-N-(2-methoxyethyl)-5-methyl-1-phenyl-4,5-dihydro-1H-pyrazole-5-carboxamide (Compound 58);

4-butyl-3-(4-fluorophenyl)-N-(2-methoxyethyl)-5-methyl-1-p-tolyl-4,5-dihydro-1H-pyrazole-5-carboxamide (Compound 59);

1-(2,4-difluorophenyl)-3-(4-fluorophenyl)-N-(2-methoxyethyl)-5-methyl-4-(thiophen-2-yl)-4,5-dihydro-1H-pyrazole-5-carboxamide (Compound 60);

4-butyl-3-(4-fluorophenyl)-N-(5-hydroxy-4,4-dimethylpentyl)-5-methyl-1-m-tolyl-4,5-dihydro-1H-pyrazole-5-carboxamide (Compound 61);

4-butyl-3-(4-fluorophenyl)-N-(5-hydroxy-4,4-dimethylpentyl)-5-methyl-1-p-tolyl-4,5-dihydro-1H-pyrazole-5-carboxamide (Compound 62);

3-(4-fluorophenyl)-N-(2-methoxyethyl)-5-methyl-4-(thiophen-2-yl)-1-p-tolyl-4,5-dihydro-1H-pyrazole-5-carboxamide (Compound 63);

4-butyl-1-(4-chloro-2-fluorophenyl)-3-(4-fluorophenyl)-N-(2-methoxyethyl)-5-methyl-4,5-dihydro-1H-pyrazole-5-carboxamide (Compound 64);

4-butyl-3-(4-fluorophenyl)-5-methyl-N-(3-morpholinopropyl)-1-phenyl-4,5-dihydro-1H-pyrazole-5-carboxamide (Compound 65);

4-butyl-3-(4-fluorophenyl)-N-(4-hydroxy-3-methoxybenzyl)-5-methyl-1-phenyl-4,5-dihydro-1H-pyrazole-5-carboxamide (Compound 66);

4-butyl-3-(4-fluorophenyl)-5-methyl-1-phenyl-N-(thiophen-2-ylmethyl)-4,5-dihydro-1H-pyrazole-5-carboxamide (Compound 67);

4-butyl-3-(4-fluorophenyl)-5-methyl-1-phenyl-N-((tetrahydro-2H-pyran-2-yl)methyl)-4,5-dihydro-1H-pyrazole-5-carboxamide (Compound 68);

4-butyl-3-(4-fluorophenyl)-5-methyl-N-(1-(4-(methylsulfonyl)phenyl)ethyl)-1-phenyl-4,5-dihydro-1H-pyrazole-5-carboxamide (Compound 69);

4-butyl-N-(2-fluoroethyl)-3-(4-fluorophenyl)-5-methyl-1-phenyl-4,5-dihydro-1H-pyrazole-5-carboxamide (Compound 70);

4-butyl-3-(4-fluorophenyl)-5-methyl-1-phenyl-N-(3-(piperidin-1-yl)propyl)-4,5-dihydro-1H-pyrazole-5-carboxamide (Compound 71);

4-butyl-3-(4-fluorophenyl)-5-methyl-N-neopentyl-1-phenyl-4,5-dihydro-1H-pyrazole-5-carboxamide (Compound 72);

4-butyl-N-(cyclopropylmethyl)-3-(4-fluorophenyl)-5-methyl-1-phenyl-4,5-dihydro-1H-pyrazole-5-carboxamide (Compound 73);

4-butyl-N-(2-(dimethylamino)-2-methylpropyl)-3-(4-fluorophenyl)-5-methyl-1-phenyl-4,5-dihydro-1H-pyrazole-5-carboxamide (Compound 74);

4-butyl-N-(3-(dimethylamino)butyl)-3-(4-fluorophenyl)-5-methyl-1-phenyl-4,5-dihydro-1H-pyrazole-5-carboxamide (Compound 75);

4-butyl-N-(2-(dimethylamino)propyl)-3-(4-fluorophenyl)-5-methyl-1-phenyl-4,5-dihydro-1H-pyrazole-5-carboxamide (Compound 76);

4-butyl-N-(3-(dimethylamino)-2-methylpropyl)-3-(4-fluorophenyl)-5-methyl-1-phenyl-4,5-dihydro-1H-pyrazole-5-carboxamide (Compound 77);

N-benzyl-4-butyl-3-(4-fluorophenyl)-N-(2-hydroxyethyl)-5-methyl-1-phenyl-4,5-dihydro-1H-pyrazole-5-carboxamide (Compound 78);

4-butyl-3-(4-fluorophenyl)-5-methyl-N-(2-(methylsulfonyl)ethyl)-1-phenyl-4,5-dihydro-1H-pyrazole-5-carboxamide (Compound 79);

4-butyl-3-(4-fluorophenyl)-5-methyl-N-(4-(morpholinomethyl)benzyl)-1-phenyl-4,5-dihydro-1H-pyrazole-5-carboxamide (Compound 80);

methyl 2-(4-butyl-1-(2,4-difluorophenyl)-3-(4-fluorophenyl)-5-methyl-4,5-dihydro-1H-pyrazole-5-carboxamido)acetate (Compound 81);

2-(4-butyl-1-(2,4-difluorophenyl)-3-(4-fluorophenyl)-5-methyl-4,5-dihydro-1H-pyrazole-5-carboxamido)acetic acid (Compound 82);

4-butyl-N-(2-cyanoethyl)-1-(2,4-difluorophenyl)-3-(4-fluorophenyl)-5-methyl-4,5-dihydro-1H-pyrazole-5-carboxamide (Compound 83);

4-butyl-1-(2,4-difluorophenyl)-3-(4-fluorophenyl)-N-(2-hydroxyethyl)-5-methyl-4,5-dihydro-1H-pyrazole-5-carboxamide (Compound 84);

1-(2,4-difluorophenyl)-3-(4-fluorophenyl)-N-(5-hydroxy-4,4-dimethylpentyl)-5-methyl-4-(thiophen-3-yl)-4,5-dihydro-1H-pyrazole-5-carboxamide (Compound 85);

1-(2,4-difluorophenyl)-3-(4-fluorophenyl)-N-(2-methoxyethyl)-5-methyl-4-(thiophen-3-yl)-4,5-dihydro-1H-pyrazole-5-carboxamide (Compound 86);

4-butyl-1-(2,4-difluorophenyl)-3-(4-fluorophenyl)-N-(5-hydroxy-4,4-dimethylpentyl)-4,5-dimethyl-4,5-dihydro-1H-pyrazole-5-carboxamide (Compound 87);

4-butyl-1-(2,4-difluorophenyl)-3-(4-fluorophenyl)-N-(2-methoxyethyl)-4,5-dimethyl-4,5-dihydro-1H-pyrazole-5-carboxamide (Compound 88);

4-butyl-1,3-bis(2,4-difluorophenyl)-N-(5-hydroxy-4,4-dimethylpentyl)-5-methyl-4,5-dihydro-1H-pyrazole-5-carboxamide (Compound 89);

4-butyl-1,3-bis(2,4-difluorophenyl)-N-(2-methoxyethyl)-5-methyl-4,5-dihydro-1H-pyrazole-5-carboxamide (Compound 90);

1-(2,4-difluorophenyl)-3-(4-fluorophenyl)-4-(furan-2-yl)-N-(5-hydroxy-4,4-dimethylpentyl)-5-methyl-4,5-dihydro-1H-pyrazole-5-carboxamide (Compound 91);

1-(2,4-difluorophenyl)-3-(4-fluorophenyl)-4-(furan-2-yl)-N-(2-methoxyethyl)-5-methyl-4,5-dihydro-1H-pyrazole-5-carboxamide (Compound 92);

1-(2,4-difluorophenyl)-3-(4-fluorophenyl)-N-(5-hydroxy-4,4-dimethylpentyl)-5-methyl-4-(1-methyl-1H-pyrrol-2-yl)-4,5-dihydro-1H-pyrazole-5-carboxamide (Compound 93);

1-(2,4-difluorophenyl)-3-(4-fluorophenyl)-N-(2-methoxyethyl)-5-methyl-4-(1-methyl-1H-pyrrol-2-yl)-4,5-dihydro-1H-pyrazole-5-carboxamide (Compound 94);

1-(2,4-difluorophenyl)-3-(4-fluorophenyl)-N-(5-hydroxy-4,4-dimethylpentyl)-5-methyl-4-(1-methyl-1H-pyrazol-4-yl)-4,5-dihydro-1H-pyrazole-5-carboxamide (Compound 95);

1-(2,4-difluorophenyl)-3-(4-fluorophenyl)-N-(2-methoxyethyl)-5-methyl-4-(1-methyl-1H-pyrazol-4-yl)-4,5-dihydro-1H-pyrazole-5-carboxamide (Compound 96);

4-butyl-1-(2,4-difluorophenyl)-N-(5-hydroxy-4,4-dimethylpentyl)-5-methyl-3-(2,4,6-trifluorophenyl)-4,5-dihydro-1H-pyrazole-5-carboxamide (Compound 97);

methyl 2-(4-butyl-1-(2,4-difluorophenyl)-5-methyl-3-(2,4,6-trifluorophenyl)-4,5-dihydro-1H-pyrazole-5-carboxamido)acetate (Compound 98);

1-(2,4-difluorophenyl)-3-(4-fluorophenyl)-N-(5-hydroxy-4,4-dimethylpentyl)-5-methyl-4-(5-methylthiophen-2-yl)-4,5-dihydro-1H-pyrazole-5-carboxamide (Compound 99);

1-(2,4-difluorophenyl)-3-(4-fluorophenyl)-N-(2-methoxyethyl)-5-methyl-4-(5-methylthiophen-2-yl)-4,5-dihydro-1H-pyrazole-5-carboxamide (Compound 100);

4-(5-chlorothiophen-2-yl)-1-(2,4-difluorophenyl)-3-(4-fluorophenyl)-N-(5-hydroxy-4,4-dimethylpentyl)-5-methyl-4,5-dihydro-1H-pyrazole-5-carboxamide (Compound 101);

4-(5-chlorothiophen-2-yl)-1-(2,4-difluorophenyl)-3-(4-fluorophenyl)-N-(2-methoxyethyl)-5-methyl-4,5-dihydro-1H-pyrazole-5-carboxamide (Compound 102);

methyl 2-(1-(2,4-difluorophenyl)-3-(4-fluorophenyl)-5-methyl-4-(thiophen-2-yl)-4,5-dihydro-1H-pyrazole-5-carboxamido)acetate (Compound 103);

1-(2,4-difluorophenyl)-3-(4-fluorophenyl)-N-(2-(2-hydroxy-2-methylpropylamino)-2-oxoethyl)-5-methyl-4-(thiophen-2-yl)-4,5-dihydro-1H-pyrazole-5-carboxamide (Compound 104);

1-(2,4-difluorophenyl)-3-(4-fluorophenyl)-5-methyl-N-(1,1-dioxo-1-thiomorpholine-2-oxoethyl)-4-(thiophen-2-yl)-4,5-dihydro-1H-pyrazole-5-carboxamide (Compound 105);

1-(2,4-difluorophenyl)-3-(4-fluorophenyl)-5-methyl-N-(2-morpholino-2-oxoethyl)-4-(thiophen-2-yl)-4,5-dihydro-1H-pyrazole-5-carboxamide (Compound 106);

1-(2,4-difluorophenyl)-N-(2-(2-(dimethylamino)ethylamino)-2-oxoethyl)-3-(4-fluorophenyl)-5-methyl-4-(thiophen-2-yl)-4,5-dihydro-1H-pyrazole-5-carboxamide (Compound 107);

1-(2,4-difluorophenyl)-3-(4-fluorophenyl)-5-methyl-N-(2-(oxetan-3-ylamino)-2-oxoethyl)-4-(thiophen-2-yl)-4,5-dihydro-1H-pyrazole-5-carboxamide (Compound 108);

1-(2,4-difluorophenyl)-3-(4-fluorophenyl)-5-methyl-N-(2-(2-(methylsulfonyl)ethylamino)-2-oxoethyl)-4-(thiophen-2-yl)-4,5-dihydro-1H-pyrazole-5-carboxamide (Compound 109);

1-(2,4-difluorophenyl)-3-(4-fluorophenyl)-N-(2-(3-hydroxy-3-methylcyclobutylamino)-2-oxoethyl)-5-methyl-4-(thiophen-2-yl)-4,5-dihydro-1H-pyrazole-5-carboxamide (Compound 110);

1-(2,4-difluorophenyl)-3-(4-fluorophenyl)-N-(2-(methoxy(methyl)amino)-2-oxoethyl)-5-methyl-4-(thiophen-2-yl)-4,5-dihydro-1H-pyrazole-5-carboxamide (Compound 111);

1-(2,4-difluorophenyl)-3-(4-fluorophenyl)-N-(2-(2-hydroxyethylamino)-2-oxoethyl)-5-methyl-4-(thiophen-2-yl)-4,5-dihydro-1H-pyrazole-5-carboxamide (Compound 112);

4-butyl-1-(2,4-difluorophenyl)-N-(5-hydroxy-4,4-dimethylpentyl)-5-methyl-3-(4-(methylsulfonyl)phenyl)-4,5-dihydro-1H-pyrazole-5-carboxamide (Compound 113);

4-butyl-1-(2,4-difluorophenyl)-N-(2-methoxyethyl)-5-methyl-3-(4-(methylsulfonyl)phenyl)-4,5-dihydro-1H-pyrazole-5-carboxamide (Compound 114);

1,3-bis(2,4-difluorophenyl)-4-(furan-2-yl)-N-(5-hydroxy-4,4-dimethylpentyl)-5-methyl-4,5-dihydro-1H-pyrazole-5-carboxamide (Compound 115);

1,3-bis(2,4-difluorophenyl)-4-(furan-2-yl)-N-(2-methoxyethyl)-5-methyl-4,5-dihydro-1H-pyrazole-5-carboxamide (Compound 116);

1,3-bis(2,4-difluorophenyl)-N-(5-hydroxy-4,4-dimethylpentyl)-5-methyl-4-(thiophen-3-yl)-4,5-dihydro-1H-pyrazole-5-carboxamide (Compound 117);

1,3-bis(2,4-difluorophenyl)-N-(2-methoxyethyl)-5-methyl-4-(thiophen-3-yl)-4,5-dihydro-1H-pyrazole-5-carboxamide (Compound 118);

methyl 2-(1,3-bis(2,4-difluorophenyl)-5-methyl-4-(thiophen-3-yl)-4,5-dihydro-1H-pyrazole-5-carboxamido)acetate (Compound 119);

4-(5-chlorofuran-2-yl)-1,3-bis(2,4-difluorophenyl)-N-(2-methoxyethyl)-5-methyl-4,5-dihydro-1H-pyrazole-5-carboxamide (Compound 120);

methyl 2-(4-(5-chlorofuran-2-yl)-1,3-bis(2,4-difluorophenyl)-5-methyl-4,5-dihydro-1H-pyrazole-5-carboxamido)acetate (Compound 121);

1-(2,4-difluorophenyl)-3-(4-fluorophenyl)-5-methyl-N-(3-morpholinopropyl)-4-(thiophen-2-yl)-4,5-dihydro-1H-pyrazole-5-carboxamide (Compound 122);

1-(2,4-difluorophenyl)-3-(4-fluorophenyl)-5-methyl-N-(2-(methylamino)-2-oxoethyl)-4-(thiophen-2-yl)-4,5-dihydro-1H-pyrazole-5-carboxamide (Compound 123);

1-(2,4-difluorophenyl)-N-(2,4-dihydroxybutyl)-3-(4-fluorophenyl)-5-methyl-4-(thiophen-2-yl)-4,5-dihydro-1H-pyrazole-5-carboxamide (Compound 124);

1-(2,4-difluorophenyl)-3-(4-fluorophenyl)-5-methyl-N-(2-(5-((3aS,6aR)-2-oxohexahydro-1H-thieno[3,4-d]imidazol-4-yl)pentanamido)ethyl)-4-(thiophen-2-yl)-4,5-dihydro-1H-pyrazole-5-carboxamide (Compound 125);

1-(2,4-difluorophenyl)-3-(4-fluorophenyl)-5-methyl-N-(2-morpholinoethyl)-4-(thiophen-2-yl)-4,5-dihydro-1H-pyrazole-5-carboxamide (Compound 126);

1-(2,4-difluorophenyl)-3-(4-fluorophenyl)-5-methyl-N-((4-methylmorpholin-2-yl)methyl)-4-(thiophen-2-yl)-4,5-dihydro-1H-pyrazole-5-carboxamide (Compound 127);

2-hydroxyethyl 2-(1-(2,4-difluorophenyl)-3-(4-fluorophenyl)-5-methyl-4-(thiophen-2-yl)-4,5-dihydro-1H-pyrazole-5-carboxamido)acetate (Compound 128);

1,3-bis(2,4-difluorophenyl)-4-(furan-3-yl)-N-(5-hydroxy-4,4-dimethylpentyl)-5-methyl-4,5-dihydro-1H-pyrazole-5-carboxamide (Compound 129);

1,3-bis(2,4-difluorophenyl)-4-(furan-3-yl)-N-(2-methoxyethyl)-5-methyl-4,5-dihydro-1H-pyrazole-5-carboxamide (Compound 130);

methyl 2-(1,3-bis(2,4-difluorophenyl)-4-(furan-3-yl)-5-methyl-4,5-dihydro-1H-pyrazole-5-carboxamido)acetate (Compound 131);

(2S)-methyl 2-(1,3-bis(2,4-difluorophenyl)-4-(furan-3-yl)-5-methyl-4,5-dihydro-1H-pyrazole-5-carboxamido)propanoate (Compound 132);

4-(5-chlorofuran-2-yl)-1,3-bis(2,4-difluorophenyl)-N-(5-hydroxy-4,4-dimethylpentyl)-5-methyl-4,5-dihydro-1H-pyrazole-5-carboxamide (Compound 133);

methyl 2-(4-(5-chlorofuran-2-yl)-1,3-bis(2,4-difluorophenyl)-5-methyl-4,5-dihydro-1H-pyrazole-5-carboxamido)acetate (Compound 134);

4-(5-chlorofuran-2-yl)-1,3-bis(2,4-difluorophenyl)-5-methyl-N-((4-methylmorpholin-2-yl)methyl)-4,5-dihydro-1H-pyrazole-5-carboxamide (Compound 135);

5-(5-chlorofuran-2-yl)-1,3-bis(2,4-difluorophenyl)-N-(5-hydroxy-4,4-dimethylpentyl)-4-methyl-4,5-dihydro-1H-pyrazole-4-carboxamide (Compound 136);

methyl 2-(5-(5-chlorofuran-2-yl)-1,3-bis(2,4-difluorophenyl)-4-methyl-4,5-dihydro-1H-pyrazole-4-carboxamido)acetate (Compound 137);

tert-butyl 2-((4-(5-chlorofuran-2-yl)-1,3-bis(2,4-difluorophenyl)-5-methyl-4,5-dihydro-1H-pyrazole-5-carboxamido)methyl)morpholine-4-carboxylate (Compound 138);

4-(5-chlorofuran-2-yl)-1,3-bis(2,4-difluorophenyl)-5-methyl-N-(((R)-4-methylmorpholin-2-yl)methyl)-4,5-dihydro-1H-pyrazole-5-carboxamide (Compound 139);

(4S,5R)-4-(5-chlorofuran-2-yl)-1,3-bis(2,4-difluorophenyl)-5-methyl-N-(((R)-4-methylmorpholin-2-yl)methyl)-4,5-dihydro-1H-pyrazole-5-carboxamide (Compound 140);

(4R,5S)-4-(5-chlorofuran-2-yl)-1,3-bis(2,4-difluorophenyl)-5-methyl-N-(((R)-4-methylmorpholin-2-yl)methyl)-4,5-dihydro-1H-pyrazole-5-carboxamide (Compound 141);

4-(5-chlorofuran-2-yl)-1,3-bis(2,4-difluorophenyl)-5-methyl-N-(((S)-4-methylmorpholin-2-yl)methyl)-4,5-dihydro-1H-pyrazole-5-carboxamide (Compound 142);

(4S,5R)-4-(5-chlorofuran-2-yl)-1,3-bis(2,4-difluorophenyl)-5-methyl-N-(((S)-4-methylmorpholin-2-yl)methyl)-4,5-dihydro-1H-pyrazole-5-carboxamide (Compound 143);

(4R,5S)-4-(5-chlorofuran-2-yl)-1,3-bis(2,4-difluorophenyl)-5-methyl-N-(((S)-4-methylmorpholin-2-yl)methyl)-4,5-dihydro-1H-pyrazole-5-carboxamide (Compound 144);

4-(5-chlorofuran-2-yl)-1,3-bis(2,4-difluorophenyl)-N-((4-ethylmorpholin-2-yl)methyl)-5-methyl-4,5-dihydro-1H-pyrazole-5-carboxamide (Compound 145);

4-(5-chlorofuran-2-yl)-N-((4-cyclopropylmorpholin-2-yl)methyl)-1,3-bis(2,4-difluorophenyl)-5-methyl-4,5-dihydro-1H-pyrazole-5-carboxamide (Compound 146);

4-(5-chlorofuran-2-yl)-1,3-bis(2,4-difluorophenyl)-N-((4-isopropylmorpholin-2-yl)methyl)-5-methyl-4,5-dihydro-1H-pyrazole-5-carboxamide (Compound 147);

1,3-bis(2,4-difluorophenyl)-5-methyl-4-(5-methylfuran-2-yl)-N-((4-methylmorpholin-2-yl)methyl)-4,5-dihydro-1H-pyrazole-5-carboxamide (Compound 148);

1,3-bis(2,4-difluorophenyl)-5-methyl-N-((4-methylmorpholin-2-yl)methyl)-4-(5-(trifluoromethyl)furan-2-yl)-4,5-dihydro-1H-pyrazole-5-carboxamide (Compound 149);

1,3-bis(2,4-difluorophenyl)-5-methyl-4-(5-(methylcarbamoyl)furan-2-yl)-N-((4-methylmorpholin-2-yl)methyl)-4,5-dihydro-1H-pyrazole-5-carboxamide (Compound 150);

4-(5-chlorofuran-2-yl)-1,3-bis(2,4-difluorophenyl)-N-((4-methoxy-1-methylpiperidin-3-yl)methyl)-5-methyl-4,5-dihydro-1H-pyrazole-5-carboxamide (Compound 151);

4-(5-chlorofuran-2-yl)-1,3-bis(2,4-difluorophenyl)-N-(4-(methoxymethyl)-1-methylpiperidin-4-yl)-5-methyl-4,5-dihydro-1H-pyrazole-5-carboxamide (Compound 152);

4-(5-chlorofuran-2-yl)-1,3-bis(2,4-difluorophenyl)-N-((3-methoxy-1-methylazetidin-3-yl)methyl)-5-methyl-4,5-dihydro-1H-pyrazole-5-carboxamide (Compound 153);

4-(5-chlorofuran-2-yl)-1,3-bis(2,4-difluorophenyl)-N-(3-(methoxymethyl)-1-methylazetidin-3-yl)-5-methyl-4,5-dihydro-1H-pyrazole-5-carboxamide (Compound 154);

4-(5-chlorofuran-2-yl)-1,3-bis(2,4-difluorophenyl)-N-((3-methoxyoxetan-3-yl)methyl)-5-methyl-4,5-dihydro-1H-pyrazole-5-carboxamide (Compound 155);

4-(5-chlorofuran-2-yl)-1,3-bis(2,4-difluorophenyl)-N-(3-(methoxymethyl)oxetan-3-yl)-5-methyl-4,5-dihydro-1H-pyrazole-5-carboxamide (Compound 156);

4-(5-chlorofuran-2-yl)-1,3-bis(2,4-difluorophenyl)-N-(3-(dimethylamino)oxetan-3-yl)methyl)-5-methyl-4,5-dihydro-1H-pyrazole-5-carboxamide (Compound 157);

4-(5-chlorofuran-2-yl)-1,3-bis(2,4-difluorophenyl)-N-(3-((dimethylamino)methyl)oxetan-3-yl)-5-methyl-4,5-dihydro-1H-pyrazole-5-carboxamide (Compound 158);

4-(5-chlorofuran-2-yl)-1,3-bis(2,4-difluorophenyl)-N-((4,6-dimethylmorpholin-2-yl)methyl)-5-methyl-4,5-dihydro-1H-pyrazole-5-carboxamide (Compound 159);

4-(5-chlorofuran-2-yl)-1,3-bis(2,4-difluorophenyl)-5-methyl-N-((4,6,6-trimethylmorpholin-2-yl)methyl)-4,5-dihydro-1H-pyrazole-5-carboxamide (Compound 160);

4-(5-chlorofuran-2-yl)-1,3-bis(2,4-difluorophenyl)-5-methyl-N-((7-methyl-4-oxa-7-azaspiro[2.5]octan-5-yl)methyl)-4,5-dihydro-1H-pyrazole-5-carboxamide (Compound 161);

4-(5-chlorofuran-2-yl)-1,3-bis(2,4-difluorophenyl)-5-methyl-N-((8-methyl-2,5-dioxa-8-azaspiro[3.5]nonan-6-yl)methyl)-4,5-dihydro-1H-pyrazole-5-carboxamide (Compound 162);

4-(5-chlorofuran-2-yl)-1,3-bis(2,4-difluorophenyl)-N-((2,8-dimethyl-5-oxa-2,8-diazaspiro[3.5]nonan-6-yl)methyl)-5-methyl-4,5-dihydro-1H-pyrazole-5-carboxamide (Compound 163);

4-(5-chlorofuran-2-yl)-1,3-bis(2,4-difluorophenyl)-N-((4,5-dimethylmorpholin-2-yl)methyl)-5-methyl-4,5-dihydro-1H-pyrazole-5-carboxamide (Compound 164);

4-(5-chlorofuran-2-yl)-1,3-bis(2,4-difluorophenyl)-5-methyl-N-((4,5,5-trimethylmorpholin-2-yl)methyl)-4,5-dihydro-1H-pyrazole-5-carboxamide (Compound 165);

4-(5-chlorofuran-2-yl)-1,3-bis(2,4-difluorophenyl)-5-methyl-N-((4-methyl-7-oxa-4-azaspiro[2.5]octan-6-yl)methyl)-4,5-dihydro-1H-pyrazole-5-carboxamide (Compound 166);

4-(5-chlorofuran-2-yl)-1,3-bis(2,4-difluorophenyl)-5-methyl-N-((5-methyl-2,8-dioxa-5-azaspiro[3.5]nonan-7-yl)methyl)-4,5-dihydro-1H-pyrazole-5-carboxamide (Compound 167);

4-(5-chlorofuran-2-yl)-1,3-bis(2,4-difluorophenyl)-N-((2,5-dimethyl-8-oxa-2,5-diazaspiro[3.5]nonan-7-yl)methyl)-5-methyl-4,5-dihydro-1H-pyrazole-5-carboxamide (Compound 168);

4-(5-chlorofuran-2-yl)-1,3-bis(2,4-difluorophenyl)-5-methyl-N-((4,5,6-trimethylmorpholin-2-yl)methyl)-4,5-dihydro-1H-pyrazole-5-carboxamide (Compound 169);

4-(5-chlorofuran-2-yl)-1,3-bis(2,4-difluorophenyl)-5-methyl-N-(oxetan-3-yl)-4,5-dihydro-1H-pyrazole-5-carboxamide (Compound 170);

4-(5-chlorofuran-2-yl)-1,3-bis(2,4-difluorophenyl)-N-(2-(2-(dimethylamino)ethoxy)ethyl)-5-methyl-4,5-dihydro-1H-pyrazole-5-carboxamide (Compound 171);

4-(5-chlorofuran-2-yl)-1,3-bis(2,4-difluorophenyl)-N-(3-(dimethylamino)-2-methoxypropyl)-5-methyl-4,5-dihydro-1H-pyrazole-5-carboxamide (Compound 172);

4-(5-chlorofuran-2-yl)-1,3-bis(2,4-difluorophenyl)-N-(4-methoxy-1-methylpyrrolidin-3-yl)-5-methyl-4,5-dihydro-1H-pyrazole-5-carboxamide (Compound 173);

4-(5-chlorofuran-2-yl)-1,3-bis(2,4-difluorophenyl)-N-((3S,6R)-6-methoxyhexahydrofuro[3,2-b]furan-3-yl)-5-methyl-4,5-dihydro-1H-pyrazole-5-carboxamide (Compound 174);

4-(5-chlorofuran-2-yl)-1,3-bis(2,4-difluorophenyl)-N-((3S,6S)-6-(dimethylamino)hexahydrofuro[3,2-b]furan-3-yl)-5-methyl-4,5-dihydro-1H-pyrazole-5-carboxamide (Compound 175);

4-(5-chlorofuran-2-yl)-1,3-bis(2,4-difluorophenyl)-N-(((8aS)-hexahydro-1H-pyrrolo[2,1-c][1,4]oxazin-3-yl)methyl)-5-methyl-4,5-dihydro-1H-pyrazole-5-carboxamide (Compound 176);

4-(5-chlorofuran-2-yl)-1,3-bis(2,4-difluorophenyl)-N-(((8aR)-hexahydro-1H-pyrrolo[2,1-c][1,4]oxazin-3-yl)methyl)-5-methyl-4,5-dihydro-1H-pyrazole-5-carboxamide (Compound 177);

4-(5-chlorofuran-2-yl)-1,3-bis(2,4-difluorophenyl)-N-(((9aS)-hexahydro-1H-[1,4]oxazino[3,4-c][1,4]oxazin-3-yl)methyl)-5-methyl-4,5-dihydro-1H-pyrazole-5-carboxamide (Compound 178);

4-(5-chlorofuran-2-yl)-1,3-bis(2,4-difluorophenyl)-N-(((9aR)-hexahydro-1H-[1,4]oxazino[3,4-c][1,4]oxazin-3-yl)methyl)-5-methyl-4,5-dihydro-1H-pyrazole-5-carboxamide (Compound 179);

4-(5-chlorofuran-2-yl)-1-(2,4-difluorophenyl)-3-(4-fluorophenyl)-5-methyl-N-((4-methylmorpholin-2-yl)methyl)-4,5-dihydro-1H-pyrazole-5-carboxamide (Compound 180);

4-butyl-1-(4-chloro-2-fluorophenyl)-3-(4-fluorophenyl)-5-methyl-N-((4-methylmorpholin-2-yl)methyl)-4,5-dihydro-1H-pyrazole-5-carboxamide (Compound 181);

4-butyl-1-(4-chloro-2-fluorophenyl)-3-(4-fluorophenyl)-N-((3-methoxy-1-methylazetidin-3-yl)methyl)-5-methyl-4,5-dihydro-1H-pyrazole-5-carboxamide (Compound 182);

1-(4-chloro-2-fluorophenyl)-4-(5-chlorofuran-2-yl)-3-(4-fluorophenyl)-5-methyl-N-((4-methylmorpholin-2-yl)methyl)-4,5-dihydro-1H-pyrazole-5-carboxamide (Compound 183);

4-(5-chlorofuran-2-yl)-3-(4-chlorophenyl)-1-(2,4-difluorophenyl)-5-methyl-N-((4-methylmorpholin-2-yl)methyl)-4,5-dihydro-1H-pyrazole-5-carboxamide (Compound 184);

4-butyl-1-(2,4-difluorophenyl)-3-(4-fluorophenyl)-5-methyl-N-((4-methylmorpholin-2-yl)methyl)-4,5-dihydro-1H-pyrazole-5-carboxamide (Compound 185);

4-butyl-1-(2,4-difluorophenyl)-3-(4-fluorophenyl)-N-((3-methoxy-1-methylazetidin-3-yl)methyl)-5-methyl-4,5-dihydro-1H-pyrazole-5-carboxamide (Compound 186);

4-butyl-1-(2,4-difluorophenyl)-3-(4-fluorophenyl)-N-((3-methoxyoxetan-3-yl)methyl)-5-methyl-4,5-dihydro-1H-pyrazole-5-carboxamide (Compound 187);

4-(5-chlorofuran-2-yl)-3-(4-fluorophenyl)-5-methyl-N-((4-methylmorpholin-2-yl)methyl)-1-(p-tolyl)-4,5-dihydro-1H-pyrazole-5-carboxamide (Compound 188);

4-butyl-3-(4-fluorophenyl)-5-methyl-N-((4-methylmorpholin-2-yl)methyl)-1-(p-tolyl)-4,5-dihydro-1H-pyrazole-5-carboxamide (Compound 189);

4-butyl-3-(4-fluorophenyl)-N-((3-methoxy-1-methylazetidin-3-yl)methyl)-5-methyl-1-(p-tolyl)-4,5-dihydro-1H-pyrazole-5-carboxamide (Compound 190); and 4-butyl-3-(4-fluorophenyl)-N-((3-methoxyoxetan-3-yl)methyl)-5-methyl-1-(p-tolyl)-4,5-dihydro-1H-pyrazole-5-carboxamide (Compound 191).

Aspects of the present disclosure include a pharmaceutical composition that includes a compound as disclosed herein, and a pharmaceutically acceptable carrier.

Aspects of the present disclosure include a method for treating a subject with a cancerous condition. The method includes administering to the subject a therapeutically effective amount of a compound or pharmaceutical composition of the present disclosure, where the cancerous condition is characterized by expressing a GLI protein, and where the administering results in treatment of the subject.

Aspects of the present disclosure include a method for treating a subject with a cancerous condition. The method includes administering to the subject a therapeutically effective amount of a compound or pharmaceutical composition of the present disclosure, where the cancerous condition is a RAS-mutant cancer, and where the administering results in treatment of the subject.

Aspects of the present disclosure include a method for treating a fibrosis in a subject. The method includes administering to the subject a therapeutically effective amount of a compound or pharmaceutical composition of the present disclosure, where the administering results in treatment of a fibrosis in the subject.

DETAILED DESCRIPTION

Aspects of the present disclosure include compounds, pharmaceutical compositions, methods and kits useful for the treatment of a cancer in a subject. In some cases, the cancerous condition is characterized by expressing a GLI polypeptide. In some cases, the cancerous condition is a RAS-mutant cancer (e.g., a cancer where mutant RAS protein(s) is overexpressed). The subject compounds, pharmaceutical compositions, methods and kits are also useful for the treatment of a fibrosis in a subject.

Before the embodiments of the present disclosure are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the embodiments. The upper and lower limits of these smaller ranges may independently be included in the smaller ranges is also encompassed within the embodiments, subject to any specifically excluded limit in the stated range. Where the stated range includes one or both of the limits, ranges excluding either both of those included limits are also included in the embodiments.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, exemplary methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It must be noted that as used herein and in the appended claims, the singular forms "a", "and", and "the" include plural referents unless the context clearly dictates otherwise. Thus, for example, reference to a "compound" includes a plurality of such compounds and equivalents thereof known to those skilled in the art, and so forth.

Terms

Unless defined otherwise, all technical and scientific terms used herein have the meaning commonly understood by a person skilled in the art to which this invention belongs. The following references provide one of skill with a general definition of many of the terms used in this invention: Singleton et al., *Dictionary of Microbiology and Molecular Biology* (2nd ed. 1994); *The Cambridge Dictionary of Science and Technology* (Walker ed., 1988); *The Glossary of Genetics*, 5th Ed., R. Rieger et al. (eds.), Springer Verlag (1991); and Hale & Marham, *The Harper Collins Dictionary of Biology* (1991). As used herein, the following terms have the meanings ascribed to them unless specified otherwise.

As used herein, the term "alkyl" refers to a straight or branched chain hydrocarbon radical, and can include di- and multivalent radicals, having the number of carbon atoms designated (e.g., $C_1$-$C_{10}$ means one to ten carbons). Examples of saturated hydrocarbon radicals include groups such as methyl, ethyl, n-propyl, isopropyl, n-butyl, t-butyl, isobutyl, sec-butyl, homologs and isomers of, for example, n-pentyl, n-hexyl, n-heptyl, n-octyl, and the like.

As used herein, the term "alkenyl" refers to an unsaturated alkyl group one having one or more double bonds. Examples of alkenyl groups include vinyl, 2-propenyl, crotyl, 2-isopentenyl, 2-(butadienyl), 2,4-pentadienyl and 3-(1,4-pentadienyl), and the higher homologs and isomers.

As used herein, the term "alkynyl" refers to an unsaturated alkyl group one having one or more triple bonds. Examples of alkynyl groups include ethynyl (acetylenyl), 1-propynyl, 1- and 2-butynyl, and the higher homologs and isomers.

As used herein, the term "aryl" refers to a polyunsaturated, aromatic, hydrocarbon substituent having 5-12 ring members, which can be a single ring or multiple rings (e.g., up to three rings) which are fused together or linked covalently. Non-limiting examples of aryl groups include phenyl, 1-naphthyl, 2-naphthyl, 4-biphenyl, and benzyl. Other aryl groups are also useful in the embodiments.

As used herein, the term "cycloalkyl" refers to a saturated cyclic hydrocarbon having 3 to 15 carbons, and 1 to 3 rings that can be fused or linked covalently. Cycloalkyl groups useful in the embodiments include, but are not limited to, cyclopropyl, cyclobutyl, cyclopentyl, cyclohexyl, cycloheptyl and cyclooctyl. Bicycloalkyl groups useful in the embodiments include, but are not limited to, [3.3.0]bicyclooctanyl, [2.2.2]bicyclooctanyl, [4.3.0]bicyclononane, [4.4.0]bicyclodecane (decalin), spiro[3.4]octanyl, spiro[2.5]octanyl, and so forth.

As used herein, the term "cycloalkenyl" refers to an unsaturated cyclic hydrocarbon having 3 to 15 carbons, and 1 to 3 rings that can be fused or linked covalently. Cycloalkenyl groups useful in the embodiments include, but are not limited to, cyclopentenyl, cyclohexenyl, cycloheptenyl and cyclooctenyl. Bicycloalkenyl groups are also useful in the embodiments.

As used herein, the term "halogen" refers to the elements including fluorine (F), chlorine (Cl), bromine (Br) and iodine (I).

As used herein, the term "heteroaryl" refers to a polyunsaturated, aromatic, hydrocarbon substituent having 5-12 ring members, which can be a single ring or multiple rings (e.g., up to three rings) which are fused together or linked covalently, and which has at least one heteroatom in the ring, such as N, O, or S. A heteroaryl group can be attached to the remainder of the molecule through a heteroatom, or a heteroaryl group can be attached to the remainder of the molecule through a carbon atom of the heteroaryl group. Non-limiting examples of heteroaryl groups include 1-pyrrolyl, 2-pyrrolyl, 3-pyrrolyl, 1-pyrazolyl, 2-pyrazolyl, 3-pyrazolyl, 4-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, furan-2-yl, furan-3-yl, thiophen-2-yl, thiophen-3-yl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Additional heteroaryl groups useful in the embodiments include pyridyl N-oxide, tetrazolyl, benzofuranyl, benzothienyl, indazolyl, or any of the radicals substituted, especially mono- or di-substituted.

As used herein, the term "heterocyclyl" refers to a saturated cyclic hydrocarbon having 3 to 15 ring members, and 1 to 3 rings that can be fused or linked covalently, and which has at least one heteroatom in the ring, such as N, O, or S. Additionally, a heteroatom can occupy the position at which the heterocycle is attached to the remainder of the molecule. Examples of heterocyclyl groups include 1-(1,2,5,6-tetrahydropyridyl), 1-piperidinyl, 2-piperidinyl, 3-piperidinyl, 1-pyrrolidinyl, 2-pyrrolidinyl, 3-pyrrolidinyl, 4-morpholinyl, 3-morpholinyl, tetrahydro-2H-pyran-2-yl, tetrahydro-2H-pyran-3-yl, tetrahydro-2H-pyran-4-yl, tetrahydrofuran-2-yl, tetrahydrofuran-3-yl, tetrahydrothien-2-yl, tetrahydrothien-3-yl, 1-piperazinyl, 2-piperazinyl, oxiranyl, oxetanyl, hexahydro-1H-thieno[3,4-d]imidazole-4-yl, hexahydro-1H-thieno[3,4-d]imidazole-6-yl, and the like.

"Alkoxy" refers to the group —O-alkyl, wherein alkyl is as defined herein. Alkoxy includes, by way of example, methoxy, ethoxy, n-propoxy, isopropoxy, n-butoxy, t-butoxy, sec-butoxy, n-pentoxy, and the like. The term "alkoxy" also refers to the groups alkenyl-O—, cycloalkyl-O—, cycloalkenyl-O—, and alkynyl-O—, where alkenyl, cycloalkyl, cycloalkenyl, and alkynyl are as defined herein.

The term "substituted alkoxy" refers to the groups substituted alkyl-O—, substituted alkenyl-O—, substituted cycloalkyl-O—, substituted cycloalkenyl-O—, and substituted alkynyl-O-where substituted alkyl, substituted alkenyl, substituted cycloalkyl, substituted cycloalkenyl and substituted alkynyl are as defined herein.

"Amino" refers to the group —$NH_2$.

The term "substituted amino" refers to the group —NRR where each R is independently selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl, and heterocyclyl provided that at least one R is not hydrogen.

"Acylamino" refers to the groups —$NR^{20}C(O)$alkyl, —$NR^{20}C(O)$substituted alkyl, N $R^{20}C(O)$cycloalkyl, —NR²⁰C(O)substituted cycloalkyl, —NR²⁰C(O)cycloalkenyl, —NR²⁰C(O)substituted cycloalkenyl, —NR²⁰C(O)alkenyl, —NR²⁰C(O)substituted alkenyl, —NR²⁰C(O)alkynyl, —NR²⁰C(O)substituted alkynyl, —NR²⁰C(O)aryl, —NR²⁰C(O)substituted aryl, —NR²⁰C(O)heteroaryl, —NR²⁰C(O)substituted heteroaryl, —NR²⁰C(O)heterocyclic, and —NR²⁰C(O)substituted heterocyclic, wherein R²⁰ is hydrogen or alkyl and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminocarbonyl" or the term "aminoacyl" refers to the group —C(O)NR²¹R²², wherein R²¹ and R²² independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R²¹ and R²² are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Sulfonyl" refers to the group SO₂-alkyl, SO₂-substituted alkyl, SO₂-alkenyl, SO₂-substituted alkenyl, SO₂-cycloalkyl, SO₂-substituted cycloalkyl, SO₂-cycloalkenyl, SO₂-substituted cylcoalkenyl, SO₂-aryl, SO₂-substituted aryl, SO₂-heteroaryl, SO₂-substituted heteroaryl, SO₂-heterocyclic, and SO₂-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. Sulfonyl includes, by way of example, methyl-SO₂—, phenyl-SO₂—, and 4-methylphenyl-SO₂—.

"Oxo" refers to the atom (=O).

The term "acyloxy" refers to the groups alkyl-C(O)O—, substituted alkyl-C(O)O—, cycloalkyl-C(O)O—, substituted cycloalkyl-C(O)O—, aryl-C(O)O—, heteroaryl-C(O)O—, and heterocyclyl-C(O)O— wherein alkyl, substituted alkyl, cycloalkyl, substituted cycloalkyl, aryl, heteroaryl, and heterocyclyl are as defined herein.

"Carboxyl ester" or "carboxy ester" or the terms "carboxyalkyl" or "carboxylalkyl" refers to the groups —C(O)O-alkyl, —C(O)O-substituted alkyl, —C(O)O-alkenyl, —C(O)O-substituted alkenyl, —C(O)O-alkynyl, —C(O)O-substituted alkynyl, —C(O)O-aryl, —C(O)O-substituted aryl, —C(O)O-cycloalkyl, —C(O)O-substituted cycloalkyl, —C(O)O-cycloalkenyl, —C(O)O-substituted cycloalkenyl, —C(O)O-heteroaryl, —C(O)O-substituted heteroaryl, —C(O)O-heterocyclic, and —C(O)O-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Cyano" or "nitrile" refers to the group —CN.

As used herein, the term "stereoisomers" refers to compounds of the embodiments that possess asymmetric carbon atoms (optical centers) or double bonds. The racemates, diastereomers, enantiomers, geometric isomers (i.e., cis/trans isomers) and individual stereoisomers are all intended to be encompassed within the scope of the embodiments.

A "label" or a "detectable moiety" is a composition detectable by spectroscopic, photochemical, biochemical, immunochemical, chemical, or other physical means. For example, useful labels include ³H, ¹⁵²I, ³²P, fluorescent dyes, electron-dense reagents, enzymes (e.g., as commonly used in an ELISA), biotin, digoxigenin, or haptens and proteins or other entities which can be made detectable, e.g., by incorporating a radiolabel into a small molecule compound. The labels may be incorporated into a compound at any position.

The term "pharmaceutically acceptable" refers to compositions that are physiologically tolerable and do not typically produce an allergic or similar untoward reaction when administered to a subject, such as a human subject. For example, the term "pharmaceutically acceptable" also can mean approved by a regulatory agency of a Federal or state government or listed in the U.S. Pharmacopeia or other generally recognized pharmacopeia for use in animals, such as in humans.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers, those containing modified residues, and non-naturally occurring amino acid polymer.

As used herein, the term "prodrug" refers to compounds that readily undergo chemical changes under physiological conditions to provide the compounds of the embodiments. Additionally, prodrugs can be converted to the compounds of the embodiments by chemical or biochemical methods in an ex vivo environment. For example, prodrugs can be slowly converted to the compounds of the embodiments when placed in a transdermal patch reservoir with a suitable enzyme or chemical reagent.

As used herein, the term "salts" refers to salts of compounds which are prepared with relatively nontoxic acids or bases, depending on the substituents found on the compounds described herein. When compounds of the embodiments contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the embodiments contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al, "Pharmaceutical Salts", *Journal of Pharmaceutical Science*, 1977, 66, 1-19).

Certain specific compounds of the embodiments contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the embodiments.

As used herein, the term "solvates" refers to compounds of the embodiments that are complexed to a solvent. Solvents that can form solvates with the compounds of the embodiments include common organic solvents such as alcohols (methanol, ethanol, etc.), ethers, acetone, ethyl acetate, halogenated solvents (methylene chloride, chloroform, etc.), hexane and pentane. Additional solvents include water. When water is the complexing solvent, the complex is termed a "hydrate."

"Substituted" refers to a group in which one or more hydrogen atoms are each independently replaced with the same or different substituent(s). Typical substituents include, but are not limited to, —X, —$R^{14}$, —O—, =O, —$OR^{14}$, —$SR^{14}$, —S$^-$, =S, —$NR^{14}R^{15}$, =$NR^{14}$, —$CX_3$, —$CF_3$, —CN, —OCN, —SCN, —NO, —$NO_2$, =$N_2$, —$N_3$, —$S(O)_2O$—, —$S(O)_2OH$, —$S(O)_2R^{14}$, —$OS(O_2)O^-$, —OS$(O)_2R^{14}$, —$P(O)(O-)_2$, —$P(O)(OR^{14})(O^-)$, —OP(O)$(OR^{14})(OR^{15})$, —$C(O)R^{14}$, —$C(S)R^{14}$, —$C(O)OR^{14}$, —$C(O)NR^{14}R^{15}$, —C(O)O—, —$C(S)OR^{14}$, —$NR^{16}C(O)NR^{14}R^{15}$, —$NR^{16}C(S)NR^{14}R^{15}$, —$NR^{17}C(NR^{16})NR^{14}R^{15}$ and —$C(NR^{16})NR^{14}R^{15}$, where each X is independently a halogen, and where "$R^{14}$", "$R^{15}$", "$R^{16}$", and "$R^{17}$" are independently hydrogen, alkyl, substituted alkyl, aryl, arylalkyl, cycloalkyl, cycloheteroalkyl, substituted cycloheteroalkyl, heteroalkyl, substituted heteroalkyl, heteroaryl, substituted heteroaryl, heteroarylalkyl, substituted heteroarylalkyl, —$NR^{18}R^{19}$, —$C(O)R^{18}$ or —$S(O)_2R^{18}$ or optionally $R^{18}$ and $R^{19}$ together with the atom to which they are both attached form a cycloheteroalkyl or substituted cycloheteroalkyl ring, and where "$R^{18}$", "$R^{19}$", and "$R^{22}$" are each independently selected from the group consisting of hydrogen, substituted or unsubstituted alkyl, substituted or unsubstituted aryl, substituted or unsubstituted arylalkyl, substituted or unsubstituted cycloalkyl, substituted or unsubstituted cycloheteroalkyl, substituted or unsubstituted heteroalkyl, substituted or unsubstituted heteroaryl, and substituted or unsubstituted heteroarylalkyl.

It is understood that in all substituted groups defined above, polymers arrived at by defining substituents with further substituents to themselves (e.g., substituted aryl having a substituted aryl group as a substituent which is itself substituted with a substituted aryl group, which is further substituted by a substituted aryl group, etc.) are not intended for inclusion herein. In such cases, the maximum number of such substitutions is three. For example, serial substitutions of substituted aryl groups are limited to substituted aryl-(substituted aryl)-substituted aryl.

"Biological sample" as used herein is a sample of biological tissue or fluid that contains nucleic acids or polypeptides. Such samples are typically from humans, but include tissues isolated from non-human primates, or rodents, e.g., mice, and rats. Biological samples may also include sections of tissues such as biopsy and autopsy samples, frozen sections taken for histological purposes, blood, plasma, serum, sputum, stool, tears, mucus, hair, skin, etc. Biological samples also include explants and primary and/or transformed cell cultures derived from patient tissues.

A "biological sample" also refers to a cell or population of cells or a quantity of tissue or fluid from an animal. Most often, the biological sample has been removed from an animal, but the term "biological sample" can also refer to cells or tissue analyzed in vivo, i.e., without removal from the animal. Typically, a "biological sample" will contain cells from the animal, but the term can also refer to noncellular biological material, such as noncellular fractions of blood, saliva, or urine, that can be used to measure the cancer-associated polynucleotide or polypeptide levels. Numerous types of biological samples can be used in the embodiments, including, but not limited to, a tissue biopsy, a blood sample, a buccal scrape, a saliva sample, or a nipple discharge. As used herein, a "tissue biopsy" refers to an amount of tissue removed from an animal, such as a human, for diagnostic analysis. In a patient with cancer, tissue may be removed from a tumor, allowing the analysis of cells within the tumor. "Tissue biopsy" can refer to any type of biopsy, such as needle biopsy, fine needle biopsy, surgical biopsy, etc.

"Providing a biological sample" means to obtain a biological sample for use in methods described in the embodiments. Most often, this will be done by removing a sample of cells from a patient, but can also be accomplished by using previously isolated cells (e.g., isolated by another person, at another time, and/or for another purpose), or by performing the methods of the embodiments in vivo. Archival tissues, having treatment or outcome history, will be particularly useful.

"Cancer cells," "transformed" cells or "transformation" in tissue culture, refers to spontaneous or induced phenotypic changes that do not necessarily involve the uptake of new genetic material. Although transformation can arise from infection with a transforming virus and incorporation of new genomic DNA, or uptake of exogenous DNA, it can also arise spontaneously or following exposure to a carcinogen, thereby mutating an endogenous gene. Transformation is associated with phenotypic changes, such as immortalization of cells, aberrant growth control, nonmorphological changes, and/or malignancy (see, Freshney, *Culture of Animal Cells a Manual of Basic Technique* (3rd ed. 1994)).

The phrase "changes in cell growth" refers to any change in cell growth and proliferation characteristics in vitro or in vivo, such as formation of foci, anchorage independence, semi-solid or soft agar growth, changes in contact inhibition and density limitation of growth, loss of growth factor or serum requirements, changes in cell morphology, gaining or losing immortalization, gaining or losing tumor specific markers, ability to form or suppress tumors when injected into suitable animal hosts, and/or immortalization of the cell. See, e.g., Freshney, *Culture of Animal Cells a Manual of Basic Technique* pp. 231-241 ($3^{rd}$ ed. 1994).

"Correlating the amount" means comparing an amount of a substance, molecule or marker (such as Gli or GLI) that has been determined in one sample to an amount of the same substance, molecule or marker determined in another sample. The amount of the same substance, molecule or marker determined in another sample may be specific for a given cancer.

Synonyms of the term "determining the amount" are contemplated within the scope of the embodiments and include, but are not limited to, detecting, measuring, testing or determining, the presence, absence, amount or concentration of a molecule, such as Gli or GLI.

Synonyms of the term, "determining" are contemplated within the scope of the embodiments and include, but are not limited to, detecting, measuring, assaying, testing or determining, the presence, absence, amount or concentration of a molecule, such as a GLI polypeptide, a label, a compound of the embodiments. The term refers to both qualitative and quantitative determinations.

The terms "down-regulate" or "inhibiting" in the context of Shh signaling, GLI signaling, or Wnt2 signaling refer to partially or totally blocking Shh signaling, GLI signaling, or Wnt2 signaling as measured by known assays for Shh signaling, GLI signaling, or Wnt2 signaling. In the context of G protein signaling or RAS signaling, the terms "down-regulate" or "inhibiting" refer to partially or totally blocking G protein signaling or RAS signaling as measured by known assays for G protein signaling or RAS signaling. Inhibitors, for example, are compounds of the embodiments of the present disclosure.

An "effective amount", "effective dose", "sufficient amount" or grammatical equivalents thereof of a compound of the embodiments for treatment is an amount that is sufficient to ameliorate, or in some manner, reduce a symptom or stop or reverse progression of a condition. Amelioration of a symptom of a particular condition, e.g., cancer, by administration of a particular pharmaceutical composition refers to any lessening, whether permanent or temporary, lasting or transit that can be associated with the administration of the pharmaceutical composition. An "effective amount" can be administered in vivo and in vitro.

The term "GLI" refers to a family of GLI proteins. GLI proteins include GLI (also referred to as GLI1), GLI2, and GLI3. Examples of GLI proteins include GLI1, GLI2, and GLI3.

A "GLI" polypeptide includes both naturally occurring or recombinant forms. Therefore, in some embodiments, a GLI polypeptide and a GLI subdomain polypeptide as described herein can comprise a sequence that corresponds to a human GLI sequence. Thus, exemplary GLI are provided herein and are known in the art. For example, several vertebrate GLI1, GLI2, and GLI3 proteins have been characterized, for example, human GLI1 (GenBank Accession Nos. NM_005269, P08151), mouse GLI1 (GenBank Accession Nos. NM_010296, AB025922, AAC09169, P47806), zebrafish GLI1 (GenBank Accession No. NM_178296), human GLI2 (GenBank Accession Nos. NM_030381; NM_030380; NM-030379, DQ086814), mouse GLI2 (GenBank Accession No.XM_922107), human GLI3 (GenBank Accession Nos. NM_000168, AJ250408, M57609, P10071, AAY87165), chimpanzee GLI3 (GenBank Accession Nos. NM_001034190, AY665272, Q5IS56), mouse GLI3 (GenBank Accession Nos. X95255, NM_008130, NP_032156, Q61602), rat GLI3 (GenBank Accession No. XM_225411), zebrafish GLI3 (GenBank Accession Nos. NM_205728, AY377429).

A GLI protein may be a full-length GLI protein or it may be a partial GLI protein, such as a subdomain of a GLI protein. For example, a "GLI3" polypeptide refers to a polypeptide and polymorphic variants, alleles, mutants of human GLI3 that: (i) has an amino acid sequence that has greater than about 60% amino acid sequence identity, 65%, 70%, 75%, 80%, 85%, 90%, or 91%, 92%, 93%, 94%, 95%, 96%, 97%, 98% or 99% or greater amino acid sequence identity, over a region of at least about 100, 150, 200, 250, 300, 500 or more amino acids, to a human GLI3 selected from GenBank Accession Nos. NM_000168, AJ250408, M57609, P10071, and AAY87165), (ii) comprises the amino acid motif FXXΦΦ(F=phenylalanine; X=any residue; Φ=any hydrophobic residue), such as the amino acid sequence FDAII, (iii) comprises a transcription activation domain, (iv) binds to a GLI DNA binding site and/or (v) binds to a TAF.

The term "GLI protein activity" refers to GLI signaling and includes, for example, transcriptional activation of a down-stream gene by GLI, binding of GLI protein to a GLI DNA binding site, and binding of GLI protein to other proteins, e.g., a TAF or to co-activators, such as CBP (Creb Protein Binding Protein).

The term "Gli" refers to a gene encoding a GLI protein. Thus, Gli1, Gli2, and Gli3 are genes encoding a GLI1, GLI2 and GLI3 protein, respectively.

A "Gli nucleic acid" or "gli polynucleotide" refers to a vertebrate gene encoding a GLI, GLI2, or GLI3 protein. A "Gli nucleic acid" includes both naturally occurring or recombinant forms. A Gli polynucleotide or GLI polypeptide encoding sequence is typically from a human, but may be from other mammals, but not limited to, a non-human primate, a rodent, e.g., a rat, mouse, or hamster; a cow, a pig, a horse, a sheep, or other mammal. Gli nucleic acids useful for practicing the embodiments, have been cloned and characterized, for example, human Gli1 (GenBank Accession Nos. NM_005269), mouse Gli1 (GenBank Accession Nos. NM_010296, AB025922), zebrafish Gli1 (GenBank Accession No. NM_178296), human Gli2 (GenBank Accession Nos. NM_030381; NM_030380; NM-030379, DQ086814), mouse Gli2 (GenBank Accession No.XM_922107), human Gli3 (GenBank Accession Nos. NM_000168, AJ250408, M57609), chimpanzee Gli3 (GenBank Accession Nos. NM_001034190, AY665272), mouse Gli3 (GenBank Accession Nos. X95255, NM_008130), rat Gli3 (GenBank Accession No. XM_225411), zebrafish Gli3 (GenBank Accession Nos. NM_205728, AY377429). A Gli polynucleotide may be a full-length Gli polynucleotide, i.e., encoding a complete GLI protein or it may be a partial Gli polynucleotide encoding a subdomain of a GLI protein.

The terms "GLI pathway", "GLI signaling" or "GLI signaling pathway" are used interchangeably and refer to the signaling pathway initiated by a hedgehog protein binding to its receptor(s) leading to the expression and/or activity of a GLI protein.

The term "hedgehog" is used interchangeably with the term "Hh" and is a cytokine that binds to a Hh receptor thereby initiating the Hh signaling pathway leading to the expression or activation of GLI proteins. There are three Hh family genes in mammals, Sonic hedgehog (Shh), Indian hedgehog (Ihh), and Desert hedgehog (Dhh). Several vertebrate hedgehog proteins are known in the art, for example, human SHH, murine SHH, rat SHH, human IHH, and murine DHH.

The terms "level of Gli mRNA" or "level of Wnt2 mRNA" in a biological sample refer to the amount of mRNA transcribed from a Gli or Wnt gene, respectively, that is present in a cell or a biological sample. The mRNA generally encodes a functional GLI or WNT protein, although mutations may be present that alter or eliminate the function of the encoded protein. A "level of Gli mRNA" or "level of Wnt2 mRNA" need not be quantified, but can simply be detected, e.g., a subjective, visual detection by a human, with or without comparison to a level from a control sample or a level expected of a control sample.

The "level of GLI polypeptide" or "level of Wnt2 polypeptide" in a biological sample refers to the amount of polypeptide translated from a Gli or Wnt2 mRNA, respectively, which is present in a cell or biological sample. The polypeptide may or may not have GLI or WNT2 protein activity. A "level of GLI polypeptide" or "WNT2 polypeptide" need not be quantified, but can simply be detected, e.g., a subjective, visual detection by a human, with or without comparison to a level from a control sample or a level expected of a control sample.

The term "RAS" refers to a family of G proteins referred to a small GTPases, which can bind and hydrolyze guanosine triphosphate (GTP). RAS proteins include, for example, KRAS, NRAS, and HRAS. A "RAS" polypeptide includes both naturally occurring or recombinant forms. Therefore, in some embodiments, a RAS polypeptide as described herein can include a sequence that corresponds to a human RAS sequence.

A RAS protein may be a full-length RAS protein or it may be a partial RAS protein, such as a subdomain of a RAS protein. For example, a RAS polypeptide may refer to a polypeptide and polymorphic variants, alleles, mutants of human RAS that have an amino acid sequence with greater than about 60% amino acid sequence identity, 65%, 70%, 75%, 80%, 85%, 90%, or 91%, 92%, 93%, 94%, 95%, 96%, 97%, 98% or 99% or greater amino acid sequence identity, over a region of at least about 100, 150, 200, 250, 300, 500 or more amino acids, to a human RAS. RAS polypeptides can bind and hydrolyze guanosine triphosphate (GTP).

The term "RAS protein activity" refers to the activity of a RAS protein in controlling intracellular signaling networks. For example, RAS-regulated signal pathways control processes, such as actin cytoskeletal integrity, proliferation, differentiation, cell adhesion, apoptosis, and cell migration. In some instances, RAS and RAS-related proteins may be deregulated in cancers, thus leading to increased invasion and metastasis, and decreased apoptosis.

The term "Ras" refers to a gene encoding a RAS protein. Thus, KRas, NRas, and HRas are genes encoding a KRAS, NRAS and HRAS protein, respectively.

A "Ras nucleic acid" or "Ras polynucleotide" refers to a vertebrate gene encoding a RAS protein. A "Ras nucleic acid" includes both naturally occurring and recombinant forms. A Ras polynucleotide or RAS polypeptide encoding sequence is typically from a human, but may be from other mammals, but not limited to, a non-human primate, a rodent, e.g., a rat, mouse, or hamster; a cow, a pig, a horse, a sheep, or other mammal. Ras nucleic acids useful for practicing the embodiments include, for example, KRas, NRas, and HRas.

The terms "RAS pathway", "RAS signaling" or "RAS signaling pathway" are used interchangeably and refer to the signaling pathway initiated by a RAS protein.

The "level of RAS polypeptide" in a biological sample refers to the amount of RAS polypeptide, which is present in a cell or biological sample. The RAS polypeptide may or may not have RAS protein activity. A "level of RAS polypeptide" need not be quantified, but can simply be detected, e.g., a subjective, visual detection by a human, with or without comparison to a level from a control sample or a level expected of a control sample.

As used herein a "modulator" of the level or activity of a polypeptide, such as a GLI or RAS protein, includes an activator and/or inhibitor of that polypeptide and is used to refer to compounds that activate or inhibit the level of expression of the polypeptide or the activity of the polypeptide. In certain embodiments, polypeptides are GLI1, GLI2, or GLI3. In certain embodiments, polypeptides are KRAS, NRAS, or HRAS. Activators are compounds that, e.g., induce or activate the expression of a polypeptide of the embodiments or bind to, stimulate, increase, open, activate, facilitate, or enhance activation, sensitize or up regulate the activity of a polypeptide of the embodiments. Activators include naturally occurring and synthetic compounds, small chemical molecules, and the like. Assays for activators include, e.g., applying candidate compounds to cells expressing a polypeptide and then determining the functional effects. Samples or assays comprising a polypeptide that are treated with a potential activator are compared to control samples without the activator to examine the extent of effect. Control samples (untreated with candidate compounds) are assigned a relative activity value of 100%. Activation of the polypeptide is achieved when the polypeptide activity value relative to the control is 110%, optionally 130%, 150%, optionally 200%, 300%, 400%, 500%, or 1000-3000% or more higher. Inhibitors are compounds that, e.g., repress or inactivate the expression of a polypeptide of the embodiments or bind to, decrease, close, inactivate, impede, or reduce activation, desensitize or down regulate the activity of a polypeptide of the embodiments. Inhibitors include, for example, nucleic acids such as siRNA and antisense RNA that interfere with the expression of a GLI protein, as well as naturally occurring and synthetic compounds, small chemical molecules and the like. Assays for inhibitors are described herein. Samples or assays comprising a polypeptide that are treated with a potential inhibitor are compared to control samples without the inhibitor to examine the extent of effect. Control samples (untreated with candidate compounds) are assigned a relative activity value of 100%. Inhibition of the polypeptide is achieved when the polypeptide activity value relative to the control is reduced by 10%, optionally 20%, optionally 30%, optionally 40%, optionally 50%, 60%, 70%, 80%, or 90-100%.

A "promoter" is defined as an array of nucleic acid control sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription.

A "constitutive" promoter is a promoter that is active under most environmental and developmental conditions. An "inducible" promoter is a promoter that is active under environmental or developmental regulation. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, e.g., recombinant cells express genes that are not found within the native (non-recombinant) form of the cell or express native genes that are otherwise abnormally expressed, under expressed or not expressed at all. By the term "recombinant nucleic acid" herein is meant nucleic acid, originally formed in vitro, in general, by the manipulation of nucleic acid, e.g., using polymerases and endonucleases, in a form not normally found in nature. In this manner, operably linkage of different sequences is achieved. Thus an isolated nucleic acid, in a linear form, or an expression vector formed in vitro by ligating DNA molecules that are not normally joined, are both considered recombinant. It is understood that once a recombinant nucleic acid is made and reintroduced into a host cell or organism, it will replicate non-recombinantly, i.e., using the in vivo cellular machinery of the host cell rather than in vitro manipulations; however, such nucleic acids, once produced recombinantly, although subsequently replicated non-recombinantly, are still considered recombinant. Similarly, a "recombinant protein" is a protein made using recombinant techniques, i.e., through the expression of a recombinant nucleic acid as depicted above.

By "resistant to chemotherapeutic agents" herein is meant a tumor that does not respond to treatment with a chemotherapeutic agent, i.e., is not killed by, or growth-inhibited by, such treatment.

The terms "subject" or "patient" refer to a mammal, such as a human, in need of treatment for a condition, such as cancer, disorder, or disease.

The term "TAF" refers to a TBP-associated factor. In certain embodiments, the TAF is a $TAFr_{II}$, i.e., a TAF protein involved in mediating transcriptional activation of a eukaryotic gene transcribed by RNA polymerase II. A TAF protein interacts with other transcriptional activators or repressors (Goodrich and Tjian, *Curr Opin Cell Biol* 6(3):403-9 (1994); Albright and Tjian, *Gene* 242(1-2):1-13 (2000)). A TAF can be from human, mouse, *Drosophila* or yeast. An example of a TAF protein interacting with a GLI is a $TAF_{II}31$ protein. Klemm et al. cloned a human TFIID subunit, which they termed $hTAF_{II}32$ (Klemm et al. 1995, *Proc Natl Acad Sci USA*, 92(13):5788-92). The 32-kD protein was isolated from HeLa cell nuclear extracts and partially sequenced. The identified cDNA has a deduced amino acid sequence of 264 residues and is related to the *Drosophila* $TAF_{II}40$. Klemm et al. showed that $TAF_{II}32$ interacts with GTF2B and with the viral transcriptional transactivator VP16 (Klemm et al. 1995, *Proc Natl Acad Sci USA*, 92(13):5788-92). The authors showed that recombinantly expressed $TAF_{II}32$ was functional in a partial recombinant $TFr_{II}D$ complex and that the recombinant complex mediated activation by a GAL4-VP16 fusion protein. $TAF_{II}32$ and $TAF_{II}31$ are two names for the same protein, which is nowadays also referred to as TAF9. Lu et al. cloned TAF9, which they called TAF31. TAF9 encodes a 264-amino acid protein. Immunoprecipitation and binding analyses showed interaction of TAF9 with the N-terminal domain of p53 at sites identical to those bound by MDM2, the major cellular negative regulator of p53 activity. (Lu et al., 1995, *Proc Natl Acad Sci USA*, 92(11): 5154-8). Human $TAF_{II}31$ nucleotide and protein sequences can be found, e.g., at GenBank accession numbers U25112, U21858, and NM_016283.

As used herein, the terms "treat", "treating", and "treatment" include: (1) preventing a disease, such as cancer, i.e. causing the clinical symptoms of the disease not to develop in a subject that may be predisposed to the disease but does not yet experience any symptoms of the disease; (2) inhibiting the disease, i.e. arresting or reducing the development of the disease or its clinical symptoms; or (3) relieving the disease, i.e. causing regression of the disease or its clinical symptoms. Treatment means any manner in which the symptoms or pathology of a condition, disorder, or disease are ameliorated or otherwise beneficially altered. In certain embodiments, the subject in need of such treatment is a mammal, such as a human.

"Tumor cell" refers to precancerous, cancerous, and normal cells in a tumor.

The terms "Wnt" refer to a family of mammalian genes and encoded proteins related to the *Drosophila* segment polarity gene, *wingless*. In humans, the Wnt family of genes typically encodes 38 to 43 kDa cysteine rich glycoproteins having hydrophobic signal sequence, and a conserved asparagine-linked oligosaccharide consensus sequence (Shimizu et al., *Cell Growth Differ* 8(12):1349-58 (1997)). The Wnt family contains at least 19 mammalian members. Exemplary Wnt proteins include Wnt1, Wnt2, Wnt3, Wnt3A, Wnt4, Wnt5A, Wnt5B, Wnt6, Wnt7A, Wnt7B, Wnt8A, Wnt8B, WNT10A, Wnt10B, Wnt11, Wnt12, Wnt13, Wnt14, Wnt15, and Wnt16. In certain embodiments, a Wnt protein is Wnt2, such as a human Wnt2 protein.

In describing the embodiments, the structure of the compounds will be discussed. Then, pharmaceutical compositions containing the compounds will be discussed, followed by a description of their methods of use, and kits.

Compounds

The compositions of the present disclosure include compounds as described below. Pharmaceutical compositions and methods of the present disclosure also include compounds of as described herein.

Formula I

The present disclosure provides a compound of formula (I):

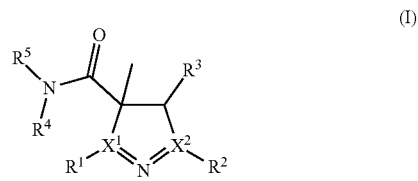

wherein
each of $X^1$ and $X^2$ is independently N or C, wherein one of $X^1$ and $X^2$ is N and one of $X^1$ and $X^2$ is C, such that the ring N forms a double bond with whichever of $X^1$ and $X^2$ is C;
$R^1$ is aryl or substituted aryl;
$R^2$ is aryl or substituted aryl;
$R^3$ is selected from alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl and substituted heteroaryl;
$R^4$ is selected from hydrogen, alkyl and substituted alkyl; and
$R^5$ is selected from alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl and substituted heteroaryl;
and salts, hydrates, solvates or stereoisomers thereof.

In certain embodiments, the compound is a compound of formula (Ia):

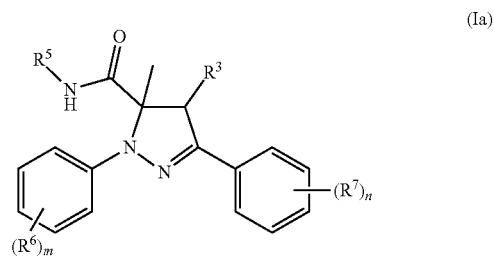

wherein
R³ is selected from alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl and substituted heteroaryl;
R⁵ is selected from alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl and substituted heteroaryl; and
R⁶ and R⁷ are each independently selected from hydrogen, halogen, alkyl, substituted alkyl, alkoxy, substituted alkoxy and sulfonyl, wherein m and n are each independently selected from an integer from 1 to 5;
and salts, hydrates, solvates or stereoisomers thereof.

In certain embodiments, the compound is a compound of formula (Ib):

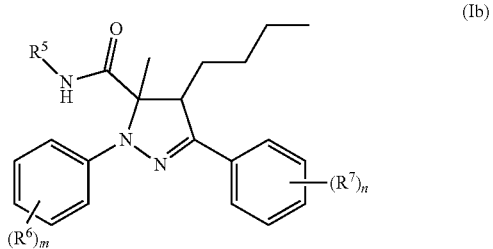

(Ib)

wherein
R⁵ is selected from alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl and substituted heteroaryl; and
R⁶ and R⁷ are each independently selected from hydrogen, halogen, alkyl, substituted alkyl, alkoxy, substituted alkoxy and sulfonyl, wherein m and n are each independently selected from an integer from 1 to 5;
and salts, hydrates, solvates or stereoisomers thereof.

In certain embodiments, the compound is a compound of formula (Ic):

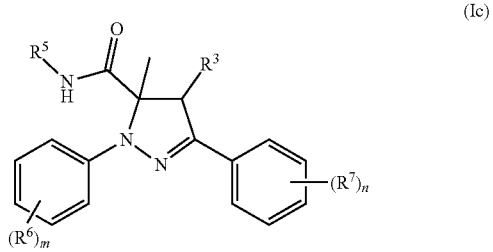

(Ic)

wherein
R³ is furanyl or substituted furanyl;
R⁵ is selected from alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl and substituted heteroaryl; and
R⁶ and R⁷ are each independently selected from hydrogen, halogen, alkyl, substituted alkyl, alkoxy, substituted alkoxy and sulfonyl, wherein m and n are each independently selected from an integer from 1 to 5;
and salts, hydrates, solvates or stereoisomers thereof.

References to formula (I) as used herein are also meant to refer to formula (Ia), (Ib) and (Ic), respectively.

In certain embodiments of formula (I), each of $X^1$ and $X^2$ is independently N or C, where one of $X^1$ and $X^2$ is N and one of $X^1$ and $X^2$ is C, such that the ring N forms a double bond with whichever of $X^1$ and $X^2$ is C. In certain embodiments, $X^1$ is N and $X^2$ is C. In certain embodiments, $X^1$ is C and $X^2$ is N.

In certain embodiments of formula (I), $R^1$ is aryl or substituted aryl. In certain embodiments, $R^1$ is aryl, for example phenyl. In certain embodiments, $R^1$ is substituted aryl, for example substituted phenyl. In certain embodiments, $R^1$ is substituted aryl (e.g., substituted phenyl), where the aryl is substituted by one or more halogen, alkyl, substituted alkyl, alkoxy, substituted alkoxy or sulfonyl. In certain embodiments, $R^1$ is substituted aryl (e.g., substituted phenyl), where the aryl is substituted by one or more halogen, such as F, Cl, Br or I. In certain embodiments, $R^1$ is substituted aryl (e.g., substituted phenyl), where the aryl is substituted by one or more F, such as one or two F. In certain embodiments, $R^1$ is substituted aryl (e.g., substituted phenyl), where the aryl is substituted by one or more Cl, such as one or two Cl. In certain embodiments, $R^1$ is substituted aryl (e.g., substituted phenyl), where the aryl is substituted by one or more alkyl, such as $C_{1-10}$ alkyl, or $C_{1-8}$ alkyl, or $C_{1-6}$ alkyl, or $C_{1-3}$ alkyl. In certain embodiments, $R^1$ is substituted aryl (e.g., substituted phenyl), where the aryl is substituted by one or more methyl. In certain embodiments, $R^1$ is substituted aryl (e.g., substituted phenyl), where the aryl is substituted by one or more substituted alkyl. In certain embodiments, $R^1$ is substituted aryl (e.g., substituted phenyl), where the aryl is substituted by one or more substituted alkyl, such as an alkyl substituted with one or more halogen (e.g., F, Cl, Br or I). In certain embodiments, $R^1$ is substituted aryl (e.g., substituted phenyl), where the aryl is substituted by one or more fluoromethyl, difluoromethyl or trifluoromethyl. In certain embodiments, $R^1$ is substituted aryl (e.g., substituted phenyl), where the aryl is substituted by one or more trifluoromethyl. In certain embodiments, $R^1$ is substituted aryl (e.g., substituted phenyl), where the aryl is substituted by one or more alkoxy, such as $C_{1-10}$ alkoxy, or $C_{1-8}$ alkoxy, or $C_{1-6}$ alkoxy, or $C_{1-3}$ alkoxy. In certain embodiments, $R^1$ is substituted aryl (e.g., substituted phenyl), where the aryl is substituted by one or more methoxy. In certain embodiments, $R^1$ is substituted aryl (e.g., substituted phenyl), where the aryl is substituted by one or more substituted alkoxy, such as substituted $C_{1-10}$ alkoxy, or substituted $C_{1-8}$ alkoxy, or substituted $C_{1-6}$ alkoxy, or substituted $C_{1-3}$ alkoxy. In certain embodiments, $R^1$ is substituted aryl (e.g., substituted phenyl), where the aryl is substituted by one or more sulfonyl, such as methylsulfonyl.

In certain embodiments of formula (I), $R^2$ is aryl or substituted aryl. In certain embodiments, $R^2$ is aryl, for example phenyl. In certain embodiments, $R^2$ is substituted aryl, for example substituted phenyl. In certain embodiments, $R^2$ is substituted aryl (e.g., substituted phenyl), where the aryl is substituted by one or more halogen, alkyl, substituted alkyl, alkoxy, substituted alkoxy or sulfonyl. In certain embodiments, $R^2$ is substituted aryl (e.g., substituted phenyl), where the aryl is substituted by one or more halogen, such as F, Cl, Br or I. In certain embodiments, $R^2$ is substituted aryl (e.g., substituted phenyl), where the aryl is substituted by one or more F, such as one or two F. In certain embodiments, $R^2$ is substituted aryl (e.g., substituted phenyl), where the aryl is substituted by one or more Cl, such as one or two Cl. In certain embodiments, $R^2$ is substituted aryl (e.g., substituted phenyl), where the aryl is substituted by one or more alkyl, such as $C_{1-10}$ alkyl, or $C_{1-8}$ alkyl, or $C_{1-6}$ alkyl, or $C_{1-3}$ alkyl. In certain embodiments, $R^2$ is substituted aryl (e.g., substituted phenyl), where the aryl is substituted by one or more methyl. In certain embodiments, $R^2$ is substituted aryl (e.g., substituted phenyl), where the aryl is substituted by one or more substituted alkyl. In certain embodiments, $R^2$ is substituted aryl (e.g., substituted phenyl), where the aryl is substituted by one or more substituted alkyl, such as an alkyl substituted with one or more halogen (e.g., F, Cl, Br or I). In certain embodiments, $R^2$ is substituted aryl (e.g., substituted phenyl), where the aryl is substituted by one or more fluoromethyl, difluoromethyl or trifluoromethyl. In certain embodiments, $R^2$ is substituted aryl (e.g., substituted phenyl), where the aryl is substituted by one or more trifluoromethyl. In certain embodiments, $R^2$ is substituted aryl (e.g., substituted phenyl), where the aryl is substituted by one or more alkoxy, such as $C_{1-10}$ alkoxy, or $C_{1-8}$ alkoxy, or $C_{1-6}$ alkoxy, or $C_{1-3}$ alkoxy. In certain embodiments, $R^2$ is substituted aryl (e.g., substituted phenyl), where the aryl is substituted by one or more methoxy. In certain embodiments, $R^2$ is substituted aryl (e.g., substituted phenyl), where the aryl is substituted by one or more substituted alkoxy, such as substituted $C_{1-10}$ alkoxy, or substituted $C_{1-8}$ alkoxy, or substituted $C_{1-6}$ alkoxy, or substituted $C_{1-3}$ alkoxy. In certain embodiments, $R^2$ is substituted aryl (e.g., substituted phenyl), where the aryl is substituted by one or more sulfonyl, such as methylsulfonyl.

In certain embodiments of formula (I), $R^3$ is selected from alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl and substituted heteroaryl. In certain embodiments, $R^3$ is alkyl or substituted alkyl. In certain embodiments, $R^3$ is alkyl, such as $C_{1-10}$ alkyl, or $C_{1-8}$ alkyl, or $C_{1-6}$ alkyl, or $C_{1-3}$ alkyl. In certain embodiments, $R^3$ is n-butyl. In certain embodiments, $R^3$ is alkenyl or substituted alkenyl. In certain embodiments, $R^3$ is alkynyl or substituted alkynyl. In certain embodiments, $R^3$ is cycloalkyl or substituted cycloalkyl. In certain embodiments, $R^3$ is heterocyclyl or substituted heterocyclyl. In certain embodiments, $R^3$ is aryl or substituted aryl. In certain embodiments, $R^3$ is heteroaryl or substituted heteroaryl. In certain embodiments, $R^3$ is heteroaryl, such as thiophenyl (e.g., thiophen-2-yl or thiophen-3-yl), pyridinyl (e.g., 2-pyridyl, 3-pyridyl, or 4-pyridyl), furanyl (e.g., furan-2-yl or furan-3-yl), pyrrolyl (e.g., 1-pyrrolyl, 2-pyrrolyl, or 3-pyrrolyl), or pyrazolyl (e.g., 1-pyrazolyl, 2-pyrazolyl, 3-pyrazolyl, 4-pyrazolyl). In certain embodiments, $R^3$ is substituted heteroaryl, such as substituted thiophenyl (e.g., substituted thiophen-2-yl or substituted thiophen-3-yl), substituted pyridinyl (e.g., substituted 2-pyridyl, substituted 3-pyridyl, or substituted 4-pyridyl), substituted furanyl (e.g., substituted furan-2-yl or substituted furan-3-yl), substituted pyrrolyl (e.g., substituted 1-pyrrolyl, substituted 2-pyrrolyl, or substituted 3-pyrrolyl), or substituted pyrazolyl (e.g., substituted 1-pyrazolyl, substituted 2-pyrazolyl, substituted 3-pyrazolyl, substituted 4-pyrazolyl).

For example, $R^3$ may be substituted heteroaryl, where the heteroaryl is substituted by one or more halogen, alkyl or substituted alkyl. In some cases, $R^3$ is substituted heteroaryl, where the heteroaryl is substituted by one or more halogen, such as F, Cl, Br or I. In some cases, $R^3$ is substituted heteroaryl, where the heteroaryl is substituted by one or more F. In some cases, $R^3$ is substituted heteroaryl, where the heteroaryl is substituted by one or more Cl. In some cases, $R^3$ is substituted heteroaryl, where the heteroaryl is substituted by one or more alkyl, such as $C_{1-10}$ alkyl, or $C_{1-8}$ alkyl, or $C_{1-6}$ alkyl, or $C_{1-3}$ alkyl. In some cases, $R^3$ is substituted heteroaryl, where the heteroaryl is substituted by one or more methyl. In some cases, $R^3$ is substituted heteroaryl, where the heteroaryl is substituted by one or more substituted alkyl, such as substituted $C_{1-10}$ alkyl, or substituted $C_{1-8}$ alkyl, or substituted $C_{1-6}$ alkyl, or substituted $C_{1-3}$ alkyl. In some cases, $R^3$ is substituted heteroaryl, where the heteroaryl is substituted by one or more substituted methyl, such as fluoromethyl, difluoromethyl or trifluoromethyl. In some cases, $R^3$ is substituted heteroaryl, where the heteroaryl is substituted by one or more substituted methyl, such as methylcarbamoyl.

In certain embodiments, $R^4$ is selected from hydrogen, alkyl and substituted alkyl. In certain embodiments, $R^4$ is hydrogen. In certain embodiments, $R^4$ is alkyl, such as $C_{1-10}$ alkyl, or $C_{1-8}$ alkyl, or $C_{1-6}$ alkyl, or $C_{1-3}$ alkyl. In certain embodiments, $R^4$ is methyl. In certain embodiments, $R^4$ is substituted alkyl, such as substituted $C_{1-10}$ alkyl, or substituted $C_{1-8}$ alkyl, or substituted $C_{1-6}$ alkyl, or substituted $C_{1-3}$ alkyl. For example, in some instances, $R^4$ is substituted alkyl, such as 2-hydroxyethyl.

In certain embodiments, $R^5$ is selected from alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl and substituted heteroaryl. In certain embodiments, $R^5$ is alkyl or substituted alkyl, such as $C_{1-10}$ alkyl, or $C_{1-8}$ alkyl, or $C_{1-6}$ alkyl, or $C_{1-3}$ alkyl, or substituted $C_{1-10}$ alkyl, or substituted $C_{1-8}$ alkyl, or substituted $C_{1-6}$ alkyl, or substituted $C_{1-3}$ alkyl. In certain embodiments, $R^5$ is alkenyl or substituted alkenyl. In certain embodiments, $R^5$ is alkynyl or substituted alkynyl. In certain embodiments, $R^5$ is cycloalkyl or substituted cycloalkyl. In certain embodiments, $R^5$ is heterocyclyl or substituted heterocyclyl. For example, $R^5$ may be heterocyclyl, such as piperidin-2-yl, piperidin-3-yl, piperidin-4-yl, azetidin-2-yl, azetindin-3-yl, oxetan-2-yl, oxetan-3-yl, pyrrolidin-2-yl, pyrrolidin-3-yl, or hexahydrofuro[3,2-b]furan-3-yl, and the like. For example, $R^5$ may be substituted heterocyclyl, such as substituted piperidin-2-yl, substituted piperidin-3-yl, substituted piperidin-4-yl, substituted azetidin-2-yl, substituted azetindin-3-yl, substituted oxetan-2-yl, substituted oxetan-3-yl, substituted pyrrolidin-2-yl, substituted pyrrolidin-3-yl, or substituted hexahydrofuro[3,2-b]furan-3-yl, and the like. In certain embodiments, $R^5$ is aryl or substituted aryl. In certain embodiments, $R^5$ is heteroaryl or substituted heteroaryl.

In certain embodiments, $R^5$ is alkyl, such as $C_{1-10}$ alkyl, or $C_{1-8}$ alkyl, or $C_{1-6}$ alkyl, or $C_{1-3}$ alkyl. In certain embodiments, $R^5$ is substituted alkyl, such as substituted $C_{1-10}$ alkyl, or substituted $C_{1-8}$ alkyl, or substituted $C_{1-6}$ alkyl, or substituted $C_{1-3}$ alkyl. In certain embodiments, $R^5$ is substituted alkyl, where the alkyl is substituted with one or more halogen, hydroxy, alkyl, substituted alkyl, alkoxy, substituted alkoxy, amino, substituted amino, oxo, acyloxy, carboxyl ester, sulfonyl, cyano, acylamino, aminocarbonyl, cycloalkyl, substituted cycloalkyl, heterocyclyl, substituted heterocyclyl, aryl, substituted aryl, heteroaryl, or substituted heteroaryl.

In certain embodiments, $R^5$ is substituted alkyl, where the alkyl is substituted with one or more halogen, such as F, Cl, Br or I. In certain embodiments, $R^5$ is substituted alkyl, where the alkyl is substituted with one or more hydroxyl.

In certain embodiments, $R^5$ is substituted alkyl, where the alkyl is substituted with one or more alkyl or substituted alkyl. For example, $R^5$ may be substituted alkyl, where the alkyl is substituted with one or more $C_{1-10}$ alkyl, or $C_{1-8}$ alkyl, or $C_{1-6}$ alkyl, or $C_{1-3}$ alkyl. For example, $R^5$ may be substituted alkyl, where the alkyl is substituted with one or more methyl.

In certain embodiments, $R^5$ is substituted alkyl, where the alkyl is substituted with one or more alkoxy or substituted alkoxy. For example, $R^5$ may be substituted alkyl, where the alkyl is substituted with methoxy or ethoxy.

In certain embodiments, $R^5$ is substituted alkyl, where the alkyl is substituted with one or more amino or substituted amino. For example, $R^5$ may be substituted alkyl, where the alkyl is substituted with dimethylamino.

In certain embodiments, $R^5$ is substituted alkyl, where the alkyl is substituted with one or more oxo. In certain embodiments, $R^5$ is substituted alkyl, where the alkyl is substituted with one or more acyloxy. In certain embodiments, $R^5$ is substituted alkyl, where the alkyl is substituted with one or more carboxyl ester. For example, $R^5$ may be substituted alkyl, where the alkyl is substituted with —C(O)OCH$_3$. For example, $R^5$ may be methyl acetate. In certain embodiments, $R^5$ is substituted alkyl, where the alkyl is substituted with one or more sulfonyl. For example, $R^5$ may be substituted alkyl, where the alkyl is substituted with methylsulfonyl.

In certain embodiments, $R^5$ is substituted alkyl, where the alkyl is substituted with one or more cyano. In certain embodiments, $R^5$ is substituted alkyl, where the alkyl is substituted with one or more acylamino. In certain embodiments, $R^5$ is substituted alkyl, where the alkyl is substituted with one or more aminocarbonyl.

In certain embodiments, $R^5$ is substituted alkyl, where the alkyl is substituted with one or more cycloalkyl or substituted cycloalkyl. For example, $R^5$ may be substituted alkyl, where the alkyl is substituted with cycloalkyl, such as cyclopropyl, cyclobutyl, cyclopentyl, or cyclohexyl.

In certain embodiments, $R^5$ is substituted alkyl, where the alkyl is substituted with one or more heterocyclyl or substituted heterocyclyl. For example, $R^5$ may be substituted alkyl, where the alkyl is substituted with heterocyclyl, such as morpholin-2-yl, morpholin-3-yl, tetrahydro-2H-pyranyl, piperidin-2-yl, piperidin-3-yl, piperidin-4-yl, azetidin-2-yl, azetidin-3-yl, oxetan-2-yl, oxetan-3-yl, hexahydro-1H-pyrrolo[2,1-c][1,4]oxazin-3-yl, or hexahydro-1H-[1,4]oxazino[3,4-c][1,4]oxazin-3-yl, and the like. For example, $R^5$ may be substituted alkyl, where the alkyl is substituted with substituted heterocyclyl, such as substituted morpholin-2-yl, substituted morpholin-3-yl, substituted tetrahydro-2H-pyranyl, substituted piperidin-2-yl, substituted piperidin-3-yl, substituted piperidin-4-yl, substituted azetidin-2-yl, substituted azetidin-3-yl, substituted oxetan-2-yl, substituted oxetan-3-yl, substituted hexahydro-1H-pyrrolo[2,1-c][1,4]oxazin-3-yl, or substituted hexahydro-1H-[1,4]oxazino[3,4-c][1,4]oxazin-3-yl, and the like. For example, $R^5$ may be substituted alkyl, where the alkyl is substituted with a substituted heterocyclyl, such as 4-methylmorpholinyl, 4-ethylmorpholinyl, N-tert-butyl-carboxyl-morpholinyl, 4-cyclopropylmorpholinyl, 4-isopropylmorpholinyl, 1-methylpiperidin-4-yl, 1-methylpiperidin-3-yl, 4,6-dimethylmorpholin-2-yl, 4,6,6-trimethylmorpholin-2-yl, 7-methyl-4-oxa-7-azaspiro[2.5]octan-5-yl, 8-methyl-2,5-dioxa-8-azaspiro[3.5]nonan-6-yl)methyl, 2,8-dimethyl-5-oxa-2,8-diazaspiro[3.5]nonan-6-yl)methyl, 4,5-dimethylmorpholin-2-yl, 4,5,5-trimethylmorpholin-2-yl, 4-methyl-7-oxa-4-azaspiro[2.5]octan-6-yl, 5-methyl-2,8-dioxa-5-azaspiro[3.5]nonan-7-yl, 2,5-dimethyl-8-oxa-2,5-diazaspiro[3.5]nonan-7-yl, 4,5,6-trimethylmorpholin-2-yl, or 1-methylazetidin-3-yl, and the like.

In certain embodiments, $R^5$ is substituted alkyl, where the alkyl is substituted with one or more aryl or substituted aryl. For example, $R^5$ may be substituted alkyl, where the alkyl is substituted with aryl, such as phenyl. For example, $R^5$ may be substituted alkyl, where the alkyl is substituted with substituted phenyl. For example, $R^5$ may be substituted alkyl, where the alkyl is substituted with substituted phenyl, where the phenyl is substituted with one or more halogen (e.g., F, Cl, Br or I), hydroxy, alkoxy (e.g., methoxy), amino, substituted amino (e.g., dimethylamino), sulfonyl (e.g., methylsulfonyl), alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, or substituted heteroaryl. In certain embodiments, $R^5$ is substituted alkyl, where the alkyl is substituted with one or more heteroaryl or substituted heteroaryl. For example, $R^5$ may be substituted alkyl, where the alkyl is substituted with heteroaryl, such as thiophenyl (e.g., thiophen-2-yl or thiophen-3-yl).

Examples of $R^5$ include, but are not limited to: 5-hydroxy-4,4-dimethylpentyl; 5-hydroxy-5-methylhexyl; 3-methoxypropyl; 2-methoxyethyl; 3-(dimethylamino)propyl; 4-methoxybutyl; 3-oxo-3-methoxypropyl; 2-ethoxyethyl; 5-hydroxypentyl; 6-hydroxyhexyl; 4-hydroxybutyl; 4-hydroxybenzyl; 1-hydroxy-2-methylpropan-2-yl; 4-hydroxyphenethyl; 3-chlorobenzyl; 3,4-dichlorobenzyl; 3,5-dichlorobenzyl; 1-phenylethyl; 2-methoxybenzyl; 2,3-dimethoxybenzyl; 2,4-dimethoxybenzyl; 3,4-dimethoxybenzyl; 3,5-dimethoxybenzyl; 4-(dimethylamino)benzyl; 3-(dimethylamino)propyl; 3-(dimethylamino)-2,2-dimethylpropyl; cyclohexylmethyl; 3-morpholinopropyl; 4-hydroxy-3-methoxybenzyl; thiophen-2-ylmethyl; tetrahydro-2H-pyran-2-yl)methyl; 1-(4-(methylsulfonyl)phenyl)ethyl; 2-fluoroethyl; 3-(piperidin-1-yl)propyl; neopentyl; cyclopropylmethyl; 2-(dimethylamino)-2-methylpropyl; 3-(dimethylamino)butyl; 2-(dimethylamino)propyl; 3-(dimethylamino)-2-methylpropyl; 2-(methylsulfonyl)ethyl; 4-(morpholinomethyl)benzyl; methyl acetate (e.g., 2-oxo-2-methoxyethyl); acetic acid (e.g., 2-oxo-2-hydroxyethyl); 2-cyanoethyl; 2-hydroxyethyl; 2-(2-hydroxy-2-methylpropylamino)-2-oxoethyl; 1,1-dioxo-1-thiomorpholine-2-oxoethyl; 2-morpholino-2-oxoethyl; 2-(dimethylamino)ethylamino)-2-oxoethyl; 2-(oxetan-3-ylamino)-2-oxoethyl; 2-(2-(methylsulfonyl)ethylamino)-2-oxoethyl; 2-(3-hydroxy-3-methylcyclobutylamino)-2-oxoethyl; 2-(methoxy(methyl)amino)-2-oxoethyl; 2-(2-hydroxyethylamino)-2-oxoethyl; 2-(methylamino)-2-oxoethyl; 2,4-dihydroxybutyl; 2-(5-((3aS,6aR)-2-oxohexahydro-1H-thieno[3,4-d]imidazol-4-yl)pentanamido)ethyl; 2-morpholinoethyl; 4-methylmorpholin-2-yl-methyl; 2-hydroxyethyl acetate (e.g., 2-hydroxyethoxy-2-oxoethyl); 3-oxo-3-methoxy-prop-2-yl; 4-(tert-butoxy-oxomethyl)-morpholin-2-yl-methyl; 4-ethylmorpholin-2-yl-methyl; 4-cyclopropylmorpholin-2-yl-methyl; 4-isopropylmorpholin-2-yl-methyl; 4-methoxy-1-methylpiperidin-3-yl-methyl; 4-(methoxymethyl)-1-methylpiperidin-4-yl; 3-methoxy-1-methylazetidin-3-yl-methyl; 3-(methoxymethyl)-1-methylazetidin-3-yl; 3-methoxyoxetan-3-yl-methyl; 3-(methoxymethyl)oxetan-3-yl; 3-(dimethylamino)oxetan-3-yl-methyl; 3-((dimethylamino)methyl)oxetan-3-yl; 4,6-dimethylmorpholin-2-yl-methyl; 4,6,6-trimethylmorpholin-2-yl-methyl; 7-methyl-4-oxa-7-azaspiro[2.5]octan-5-yl-methyl; 8-methyl-2,5-dioxa-8-azaspiro[3.5]nonan-6-yl-methyl; 2,8-dimethyl-5-oxa-2,8-diazaspiro[3.5]nonan-6-yl-methyl; 4,5-dimethylmorpholin- 2-yl-methyl; 4,5,5-trimethylmorpholin-2-yl-methyl; 4-methyl-7-oxa-4-azaspiro[2.5]octan-6-yl-methyl; 5-methyl-2,8-dioxa-5-azaspiro[3.5]nonan-7-yl-methyl; 2,5-dimethyl-8-oxa-2,5-diazaspiro[3.5]nonan-7-yl-methyl; 4,5,6-trimethylmorpholin-2-yl-methyl; oxetan-3-yl; 2-(2-(dimethylamino)ethoxy)ethyl; 3-(dimethylamino)-2-methoxypropyl; 4-methoxy-1-methylpyrrolidin-3-yl; (3S,6R)-6-methoxyhexahydrofuro[3,2-b]furan-3-yl; (3S,6S)-6-(dimethylamino)hexahydrofuro[3,2-b]furan-3-yl; (8aS)-hexahydro-1H-pyrrolo[2,1-c][1,4]oxazin-3-yl-methyl; and (9aS)-hexahydro-1H-[1,4]oxazino[3,4-c][1,4]oxazin-3-yl-methyl; or stereoisomers thereof.

For example, $R^5$ may be selected from: 5-hydroxy-4,4-dimethylpentyl; 5-hydroxy-5-methylhexyl; 3-methoxypropyl; 3-oxo-3-methoxypropyl; 2-methoxyethyl; 3-(dimethylamino)propyl; 4-methoxybutyl; 2-ethoxyethyl; 5-hydroxypentyl; 6-hydroxyhexyl; 4-hydroxybutyl; and methyl acetate; or stereoisomers thereof.

For example, $R^5$ may be selected from: (4-methylmorpholin-2-yl)methyl; 4-(methoxymethyl)-1-methylpiperidin-4-yl; 3-(methoxymethyl)-1-methylazetidin-3-yl; 3-(methoxymethyl)oxetan-3-yl; 3-((dimethylamino)methyl)oxetan-3-yl; oxetan-3-yl; 4-methoxy-1-methylpyrrolidin-3-yl; 6-methoxyhexahydrofuro[3,2-b]furan-3-yl; and 6-(dimethylamino)hexahydrofuro[3,2-b]furan-3-yl; or stereoisomers thereof.

In certain embodiments, $R^6$ and $R^7$ are each independently selected from hydrogen, halogen, alkyl, substituted alkyl, alkoxy, substituted alkoxy and sulfonyl, where m and n are each independently selected from an integer from 1 to 5.

In certain embodiments, $R^6$ is selected from hydrogen, halogen, alkyl, substituted alkyl, alkoxy, substituted alkoxy and sulfonyl, where m is an integer from 1 to 5. In certain embodiments, $R^6$ is hydrogen. In certain embodiments, $R^6$ is halogen, such as F, Cl, Br or I. In certain embodiments, $R^6$ is F. In certain embodiments, $R^6$ is Cl. In certain embodiments, $R^6$ is alkyl, such as $C_{1-10}$ alkyl, or $C_{1-8}$ alkyl, or $C_{1-6}$ alkyl, or $C_{1-3}$ alkyl. In certain embodiments, $R^6$ is methyl. In certain embodiments, $R^6$ is substituted alkyl, such as an alkyl substituted with one or more halogen (e.g., F, Cl, Br or I). For example, $R^6$ may be substituted alkyl, such as fluoromethyl, difluoromethyl or trifluoromethyl. For example, $R^6$ may be trifluoromethyl. In certain embodiments, $R^6$ is alkoxy, such as $C_{1-10}$ alkoxy, or $C_{1-8}$ alkoxy, or $C_{1-6}$ alkoxy, or $C_{1-3}$ alkoxy. For example, $R^6$ may be methoxy. In certain embodiments, $R^6$ is substituted alkoxy, such as substituted $C_{1-10}$ alkoxy, or substituted $C_{1-8}$ alkoxy, or substituted $C_{1-6}$ alkoxy, or substituted $C_{1-3}$ alkoxy. In certain embodiments, $R^6$ is sulfonyl, such as methylsulfonyl.

In certain embodiments, $R^7$ is selected from hydrogen, halogen, alkyl, substituted alkyl, alkoxy, substituted alkoxy and sulfonyl, where n is an integer from 1 to 5. In certain embodiments, $R^7$ is hydrogen. In certain embodiments, $R^7$ is halogen, such as F, Cl, Br or I. In certain embodiments, $R^7$ is F. In certain embodiments, $R^7$ is Cl. In certain embodiments, $R^7$ is alkyl, such as $C_{1-10}$ alkyl, or $C_{1-8}$ alkyl, or $C_{1-6}$ alkyl, or $C_{1-3}$ alkyl. In certain embodiments, $R^7$ is methyl. In certain embodiments, $R^7$ is substituted alkyl, such as an alkyl substituted with one or more halogen (e.g., F, Cl, Br or I). For example, $R^7$ may be substituted alkyl, such as fluoromethyl, difluoromethyl or trifluoromethyl. For example, $R^7$ may be trifluoromethyl. In certain embodiments, $R^7$ is alkoxy, such as $C_{1-10}$ alkoxy, or $C_{1-8}$ alkoxy, or $C_{1-6}$ alkoxy, or $C_{1-3}$ alkoxy. For example, $R^7$ may be methoxy. In certain embodiments, $R^7$ is substituted alkoxy, such as substituted $C_{1-10}$ alkoxy, or substituted $C_{1-8}$ alkoxy, or substituted $C_{1-6}$ alkoxy, or substituted $C_{1-3}$ alkoxy. In certain embodiments, $R^7$ is sulfonyl, such as methylsulfonyl.

In certain embodiments, m is an integer from 1 to 5. For example, m may be 1, 2, 3, 4 or 5. In certain embodiments, m is 1. In certain embodiments, m is 2. In certain embodiments, m is 3. In certain embodiments, m is 4. In certain embodiments, m is 5.

In certain embodiments, n is an integer from 1 to 5. For example, n may be 1, 2, 3, 4 or 5. In certain embodiments, n is 1. In certain embodiments, n is 2. In certain embodiments, n is 3. In certain embodiments, n is 4. In certain embodiments, n is 5.

In certain embodiments, a compound of the present disclosure is one of the following compounds:

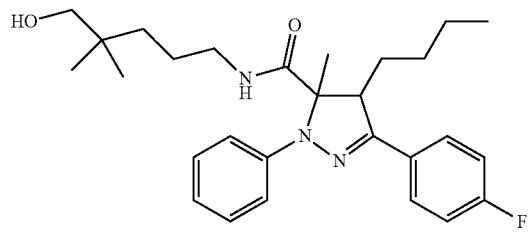 [SMILES: CCCCC1C(c2ccc(F)cc2)=NN(c2ccccc2)C1(C)C(=O)NCCCC(C)(C)CO]

4-butyl-3-(4-fluorophenyl)-N-(5-hydroxy-4,4-dimethylpentyl)-5-methyl-1-phenyl-4,5-dihydro-1H-pyrazole-5-carboxamide (Compound 1);

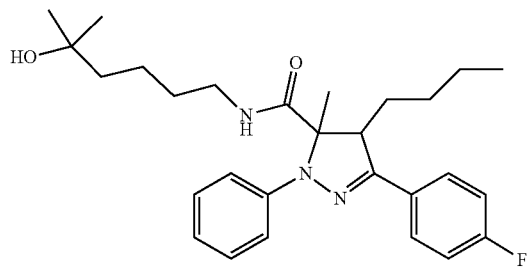 [SMILES: CCCCC1C(c2ccc(F)cc2)=NN(c2ccccc2)C1(C)C(=O)NCCCCC(C)(C)O]

4-butyl-3-(4-fluorophenyl)-N-(5-hydroxy-5-methylhexyl)-5-methyl-1-phenyl-4,5-dihydro-1H-pyrazole-5-carboxamide (Compound 2);

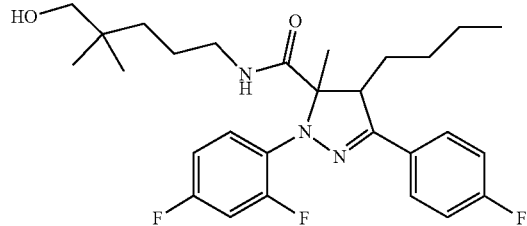 [SMILES: CCCCC1C(c2ccc(F)cc2)=NN(c2ccc(F)cc2F)C1(C)C(=O)NCCCC(C)(C)CO]

4-butyl-1-(2,4-difluorophenyl)-3-(4-fluorophenyl)-N-(5-hydroxy-4,4-dimethylpentyl)-5-methyl-4,5-dihydro-1H-pyrazole-5-carboxamide (Compound 3);

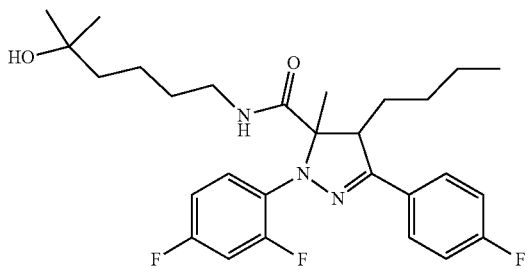 [SMILES: CCCCC1C(c2ccc(F)cc2)=NN(c2ccc(F)cc2F)C1(C)C(=O)NCCCCC(C)(C)O]

4-butyl-1-(2,4-difluorophenyl)-3-(4-fluorophenyl)-N-(5-hydroxy-5-methylhexyl)-5-methyl-4,5-dihydro-1H-pyrazole-5-carboxamide (Compound 4);

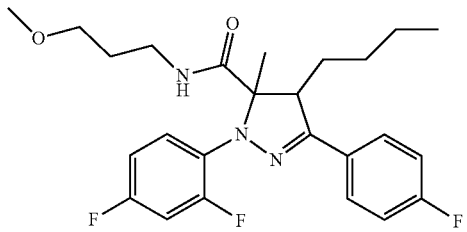

4-butyl-1-(2,4-difluorophenyl)-3-(4-fluorophenyl)-N-(3-methoxypropyl)-5-methyl-4,5-dihydro-1H-pyrazole-5-carboxamide (Compound 5);

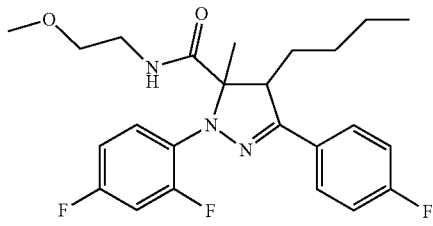 [SMILES: CCCCC1C(c2ccc(F)cc2)=NN(c2ccc(F)cc2F)C1(C)C(=O)NCCOC]

4-butyl-1-(2,4-difluorophenyl)-3-(4-fluorophenyl)-N-(2-methoxyethyl)-5-methyl-4,5-dihydro-1H-pyrazole-5-carboxamide (Compound 6);

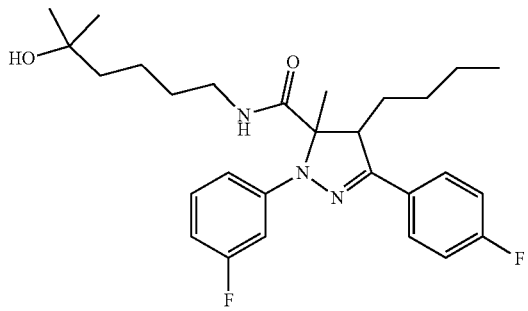 [SMILES: CCCCC1C(c2ccc(F)cc2)=NN(c2cccc(F)c2)C1(C)C(=O)NCCCCC(C)(C)O]

4-butyl-1-(3-fluorophenyl)-3-(4-fluorophenyl)-N-(5-hydroxy-5-methylhexyl)-5-methyl-4,5-dihydro-1H-pyrazole-5-carboxamide (Compound 7);

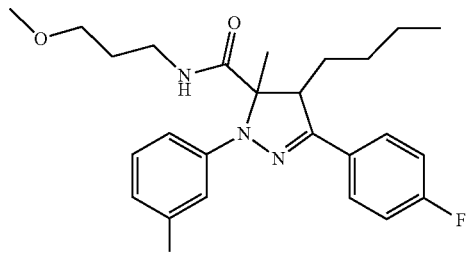

4-butyl-1-(3-fluorophenyl)-3-(4-fluorophenyl)-N-(3-methoxypropyl)-5-methyl-4,5-dihydro-1H-pyrazole-5-carboxamide (Compound 8);

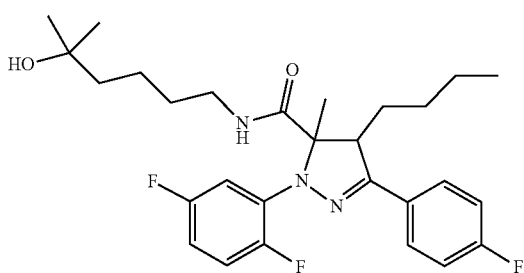 [SMILES: CCCCC1C(c2ccc(F)cc2)=NN(c2cc(F)ccc2F)C1(C)C(=O)NCCCCC(C)(C)O]

4-butyl-1-(2,5-difluorophenyl)-3-(4-fluorophenyl)-N-(5-hydroxy-5-methylhexyl)-5-methyl-4,5-dihydro-1H-pyrazole-5-carboxamide (Compound 9);

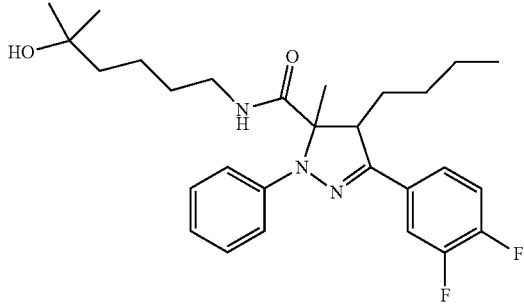 [SMILES: CCCCC1C(c2ccc(F)c(F)c2)=NN(c2ccccc2)C1(C)C(=O)NCCCCC(C)(C)O]

4-butyl-3-(3,4-difluorophenyl)-N-(5-hydroxy-5-methylhexyl)-5-methyl-1-phenyl-4,5-dihydro-1H-pyrazole-5-carboxamide (Compound 10);

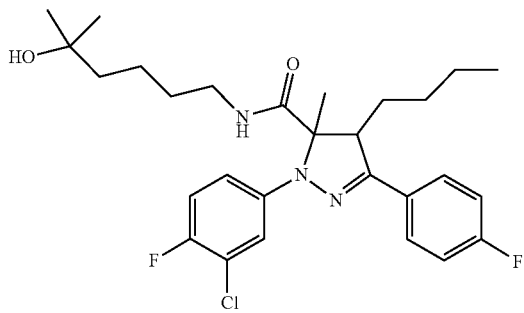 [SMILES: CCCCC1C(c2ccc(F)cc2)=NN(c2ccc(F)c(Cl)c2)C1(C)C(=O)NCCCCC(C)(C)O]

4-butyl-1-(3-chloro-4-fluorophenyl)-3-(4-fluorophenyl)-N-(5-hydroxy-5-methylhexyl)-5-methyl-4,5-dihydro-1H-pyrazole-5-carboxamide (Compound 11);

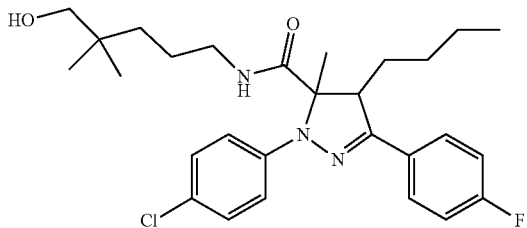 [SMILES: CCCCC1C(c2ccc(F)cc2)=NN(c2ccc(Cl)cc2)C1(C)C(=O)NCCCC(C)(C)CO]

4-butyl-1-(4-chlorophenyl)-3-(4-fluorophenyl)-N-(5-hydroxy-4,4-dimethylpentyl)-5-methyl-4,5-dihydro-1H-pyrazole-5-carboxamide (Compound 12);

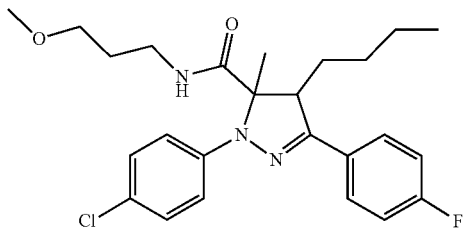

4-butyl-1-(4-chlorophenyl)-3-(4-fluorophenyl)-N-(3-methoxypropyl)-5-methyl-4,5-dihydro-1H-pyrazole-5-carboxamide (Compound 13);

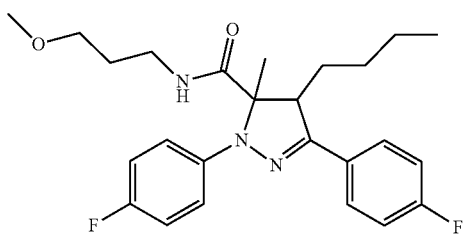 [SMILES: CCCCC1C(c2ccc(F)cc2)=NN(c2ccc(F)cc2)C1(C)C(=O)NCCCOC]

4-butyl-1,3-bis(4-fluorophenyl)-N-(3-methoxypropyl)-5-methyl-4,5-dihydro-1H-pyrazole-5-carboxamide (Compound 14);

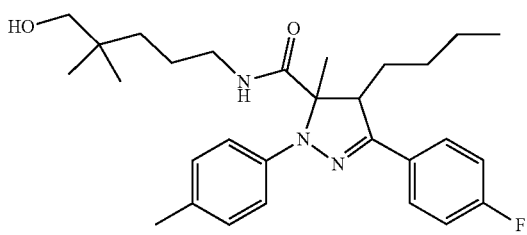

4-butyl-3-(4-fluorophenyl)-N-(5-hydroxy-4,4-dimethylpentyl)-5-methyl-1-p-tolyl-4,5-dihydro-1H-pyrazole-5-carboxamide (Compound 15);

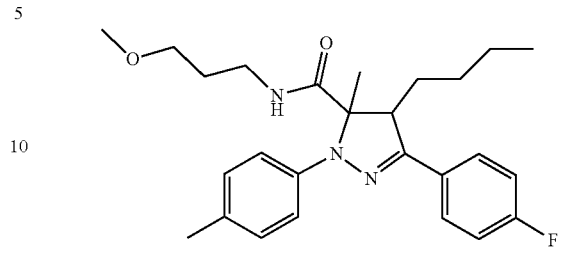

4-butyl-3-(4-fluorophenyl)-N-(3-methoxypropyl)-5-methyl-1-p-tolyl-4,5-dihydro-1H-pyrazole-5-carboxamide (Compound 16);

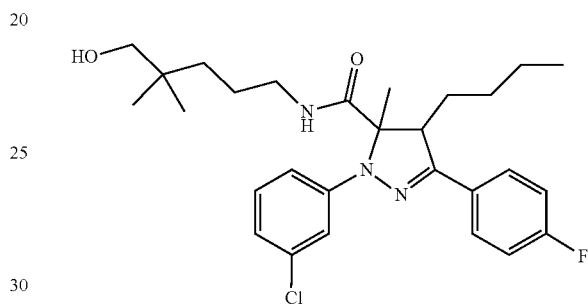

4-butyl-1-(3-chlorophenyl)-3-(4-fluorophenyl)-N-(5-hydroxy-4,4-dimethylpentyl)-5-methyl-4,5-dihydro-1H-pyrazole-5-carboxamide (Compound 17);

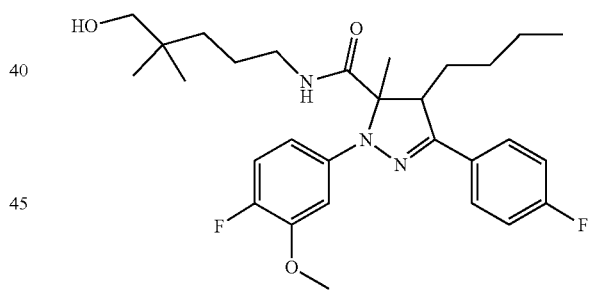

4-butyl-1-(4-fluoro-3-methoxyphenyl)-3-(4-fluorophenyl)-N-(5-hydroxy-4,4-dimethylpentyl)-5-methyl-4,5-dihydro-1H-pyrazole-5-carboxamide (Compound 18);

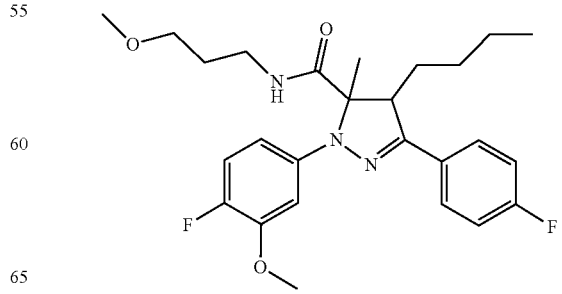

4-butyl-1-(4-fluoro-3-methoxyphenyl)-3-(4-fluorophenyl)-N-(3-methoxypropyl)-5-methyl-4,5-dihydro-1H-pyrazole-5-carboxamide (Compound 19);

4-butyl-1-(4-chloro-2-fluorophenyl)-3-(4-fluorophenyl)-N-(5-hydroxy-4,4-dimethylpentyl)-5-methyl-4,5-dihydro-1H-pyrazole-5-carboxamide (Compound 23);

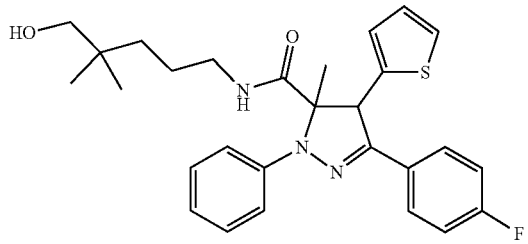 [SMILES: CC(C)(CO)CCCNC(=O)C1(C)C(c2cccs2)C(c2ccc(F)cc2)=NN1c1ccccc1]

3-(4-fluorophenyl)-N-(5-hydroxy-4,4-dimethylpentyl)-5-methyl-1-phenyl-4-(thiophen-2-yl)-4,5-dihydro-1H-pyrazole-5-carboxamide (Compound 20);

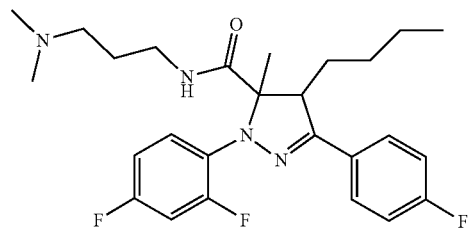

4-butyl-1-(2,4-difluorophenyl)-N-(3-(dimethylamino)propyl)-3-(4-fluorophenyl)-5-methyl-4,5-dihydro-1H-pyrazole-5-carboxamide (Compound 24);

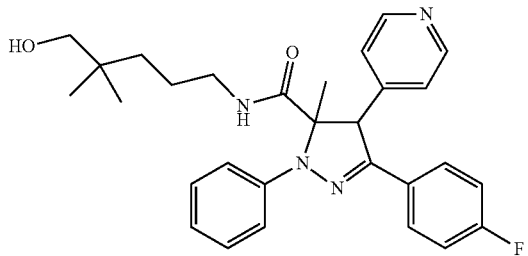 [SMILES: CC(C)(CO)CCCNC(=O)C1(C)C(c2ccncc2)C(c2ccc(F)cc2)=NN1c1ccccc1]

3-(4-fluorophenyl)-N-(5-hydroxy-4,4-dimethylpentyl)-5-methyl-1-phenyl-4-(pyridin-4-yl)-4,5-dihydro-1H-pyrazole-5-carboxamide (Compound 21);

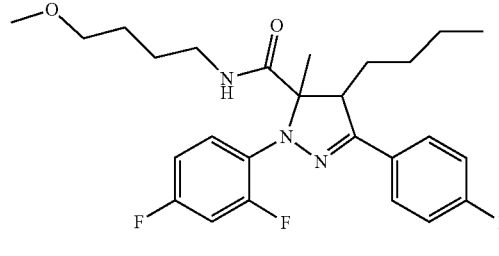

4-butyl-1-(2,4-difluorophenyl)-3-(4-fluorophenyl)-N-(4-methoxybutyl)-5-methyl-4,5-dihydro-1H-pyrazole-5-carboxamide (Compound 25);

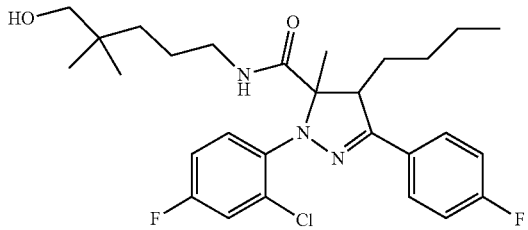 [SMILES: CCCCC1C(c2ccc(F)cc2)=NN(c2ccc(F)cc2Cl)C1(C)C(=O)NCCCC(C)(C)CO]

4-butyl-1-(2-chloro-4-fluorophenyl)-3-(4-fluorophenyl)-N-(5-hydroxy-4,4-dimethylpentyl)-5-methyl-4,5-dihydro-1H-pyrazole-5-carboxamide (Compound 22);

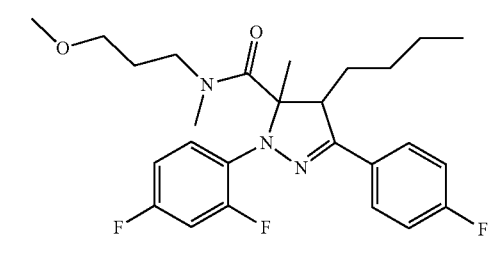

4-butyl-1-(2,4-difluorophenyl)-3-(4-fluorophenyl)-N-(3-methoxypropyl)-N,5-dimethyl-4,5-dihydro-1H-pyrazole-5-carboxamide (Compound 26);

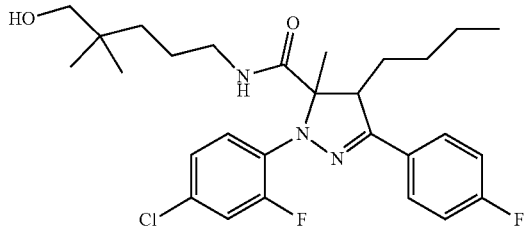 [SMILES: CCCCC1C(c2ccc(F)cc2)=NN(c2ccc(Cl)cc2F)C1(C)C(=O)NCCCC(C)(C)CO]

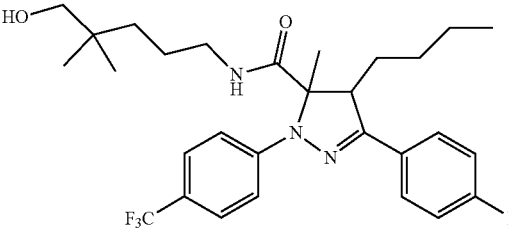

4-butyl-3-(4-fluorophenyl)-N-(5-hydroxy-4,4-dimethylpentyl)-5-methyl-1-(4-(trifluoromethyl)phenyl)-4,5-dihydro-1H-pyrazole-5-carboxamide (Compound 28);

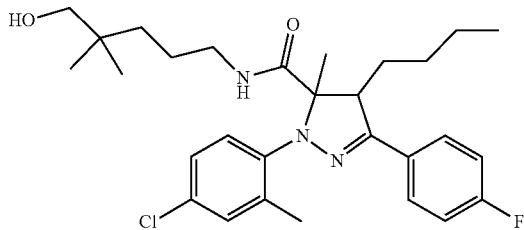 [SMILES: CCCCC1C(c2ccc(F)cc2)=NN(c2ccc(Cl)cc2C)C1(C)C(=O)NCCCC(C)(C)CO]

4-butyl-1-(4-chloro-2-methylphenyl)-3-(4-fluorophenyl)-N-(5-hydroxy-4,4-dimethylpentyl)-5-methyl-4,5-dihydro-1H-pyrazole-5-carboxamide (Compound 29);

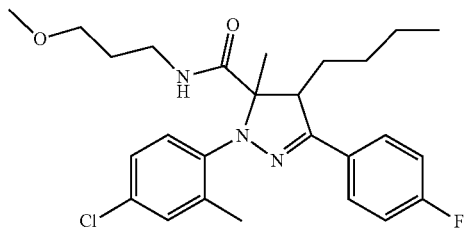 [SMILES: CCCCC1C(c2ccc(F)cc2)=NN(c2ccc(Cl)cc2C)C1(C)C(=O)NCCCOC]

4-butyl-1-(4-chloro-2-methylphenyl)-3-(4-fluorophenyl)-N-(3-methoxypropyl)-5-methyl-4,5-dihydro-1H-pyrazole-5-carboxamide (Compound 30);

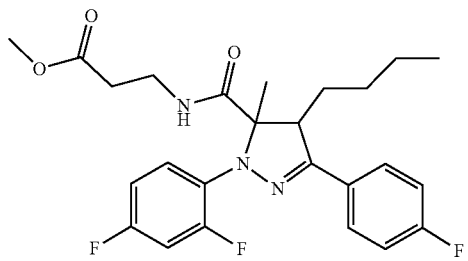 [SMILES: CCCCC1C(c2ccc(F)cc2)=NN(c2ccc(F)cc2F)C1(C)C(=O)NCCC(=O)OC]

methyl 3-(4-butyl-1-(2,4-difluorophenyl)-3-(4-fluorophenyl)-5-methyl-4,5-dihydro-1H-pyrazole-5-carboxamido)propanoate (Compound 31);

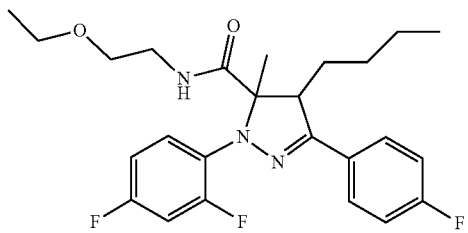 [SMILES: CCCCC1C(c2ccc(F)cc2)=NN(c2ccc(F)cc2F)C1(C)C(=O)NCCOCC]

4-butyl-1-(2,4-difluorophenyl)-N-(2-ethoxyethyl)-3-(4-fluorophenyl)-5-methyl-4,5-dihydro-1H-pyrazole-5-carboxamide (Compound 32);

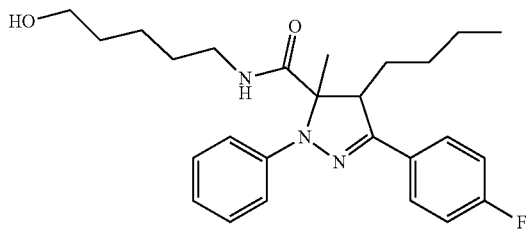 [SMILES: CCCCC1C(c2ccc(F)cc2)=NN(c2ccccc2)C1(C)C(=O)NCCCCCO]

4-butyl-3-(4-fluorophenyl)-N-(5-hydroxypentyl)-5-methyl-1-phenyl-4,5-dihydro-1H-pyrazole-5-carboxamide (Compound 33);

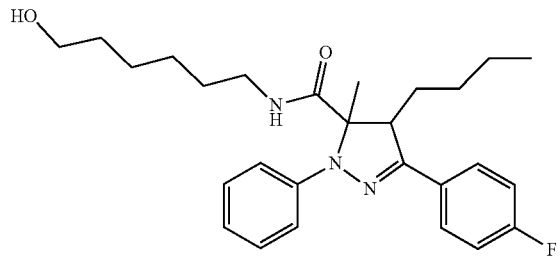 [SMILES: CCCCC1C(c2ccc(F)cc2)=NN(c2ccccc2)C1(C)C(=O)NCCCCCCO]

4-butyl-3-(4-fluorophenyl)-N-(6-hydroxyhexyl)-5-methyl-1-phenyl-4,5-dihydro-1H-pyrazole-5-carboxamide (Compound 34);

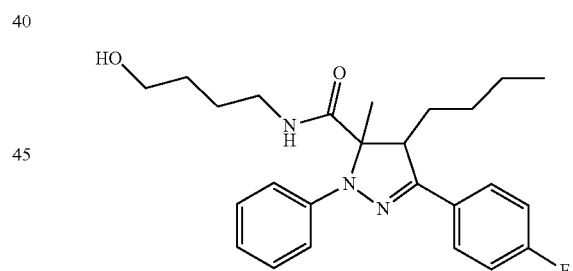

4-butyl-3-(4-fluorophenyl)-N-(4-hydroxybutyl)-5-methyl-1-phenyl-4,5-dihydro-1H-pyrazole-5-carboxamide (Compound 35);

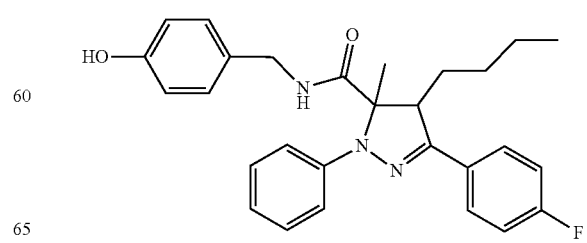

4-butyl-3-(4-fluorophenyl)-N-(4-hydroxybenzyl)-5-methyl-1-phenyl-4,5-dihydro-1H-pyrazole-5-carboxamide (Compound 36);

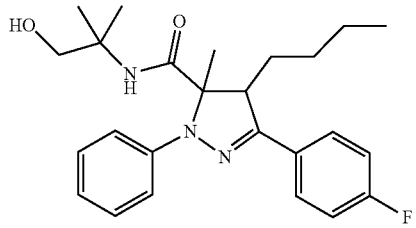 [SMILES: CCCCC1C(c2ccc(F)cc2)=NN(c2ccccc2)C1(C)C(=O)NC(C)(C)CO]

4-butyl-3-(4-fluorophenyl)-N-(1-hydroxy-2-methylpropan-2-yl)-5-methyl-1-phenyl-4,5-dihydro-1H-pyrazole-5-carboxamide (Compound 37);

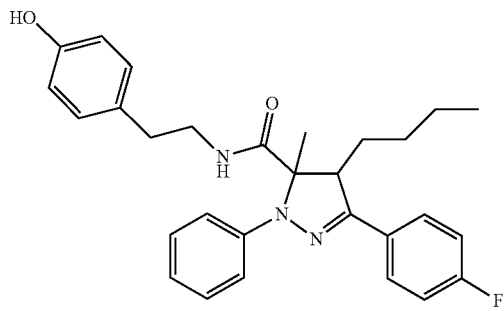 [SMILES: CCCCC1C(c2ccc(F)cc2)=NN(c2ccccc2)C1(C)C(=O)NCCc1ccc(O)cc1]

4-butyl-3-(4-fluorophenyl)-N-(4-hydroxyphenethyl)-5-methyl-1-phenyl-4,5-dihydro-1H-pyrazole-5-carboxamide (Compound 38);

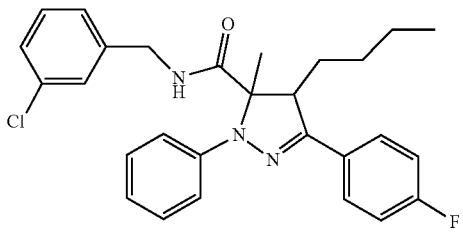 [SMILES: CCCCC1C(c2ccc(F)cc2)=NN(c2ccccc2)C1(C)C(=O)NCc1cccc(Cl)c1]

4-butyl-N-(3-chlorobenzyl)-3-(4-fluorophenyl)-5-methyl-1-phenyl-4,5-dihydro-1H-pyrazole-5-carboxamide (Compound 39);

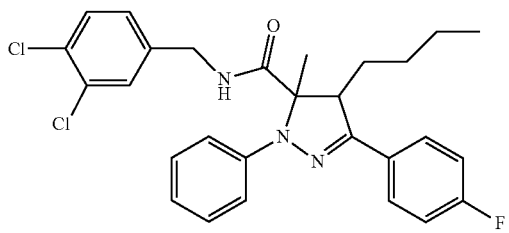 [SMILES: CCCCC1C(c2ccc(F)cc2)=NN(c2ccccc2)C1(C)C(=O)NCc1ccc(Cl)c(Cl)c1]

4-butyl-N-(3,4-dichlorobenzyl)-3-(4-fluorophenyl)-5-methyl-1-phenyl-4,5-dihydro-1H-pyrazole-5-carboxamide (Compound 40);

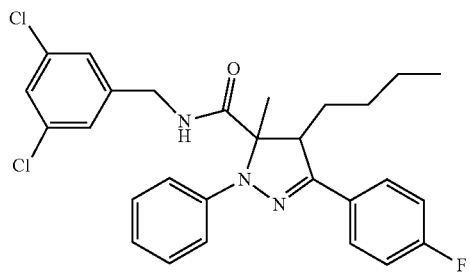 [SMILES: CCCCC1C(c2ccc(F)cc2)=NN(c2ccccc2)C1(C)C(=O)NCc1cc(Cl)cc(Cl)c1]

4-butyl-N-(3,5-dichlorobenzyl)-3-(4-fluorophenyl)-5-methyl-1-phenyl-4,5-dihydro-1H-pyrazole-5-carboxamide (Compound 41);

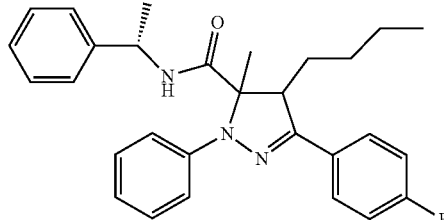

4-butyl-3-(4-fluorophenyl)-5-methyl-1-phenyl-N-((S)-1-phenylethyl)-4,5-dihydro-1H-pyrazole-5-carboxamide (Compound 42);

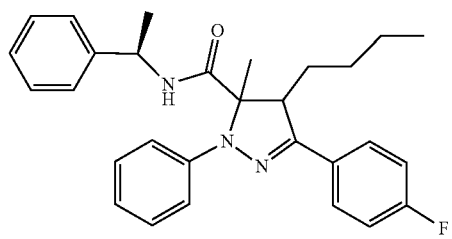 [SMILES: CCCCC1C(c2ccc(F)cc2)=NN(c2ccccc2)C1(C)C(=O)N[C@H](C)c1ccccc1]

4-butyl-3-(4-fluorophenyl)-5-methyl-1-phenyl-N-((R)-1-phenylethyl)-4,5-dihydro-1H-pyrazole-5-carboxamide (Compound 43);

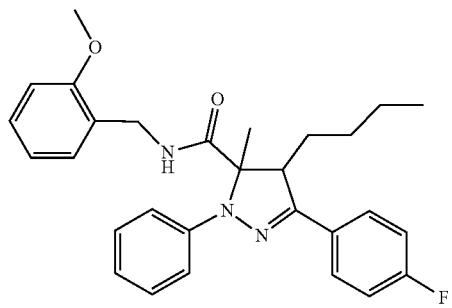 [SMILES: CCCCC1C(c2ccc(F)cc2)=NN(c2ccccc2)C1(C)C(=O)NCc1ccccc1OC]

4-butyl-3-(4-fluorophenyl)-N-(2-methoxybenzyl)-5-methyl-1-phenyl-4,5-dihydro-1H-pyrazole-5-carboxamide (Compound 44);

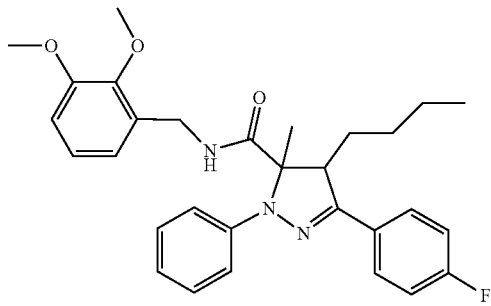 [SMILES: CCCCC1C(c2ccc(F)cc2)=NN(c2ccccc2)C1(C)C(=O)NCc1cccc(OC)c1OC]

4-butyl-N-(2,3-dimethoxybenzyl)-3-(4-fluorophenyl)-5-methyl-1-phenyl-4,5-dihydro-1H-pyrazole-5-carboxamide (Compound 45);

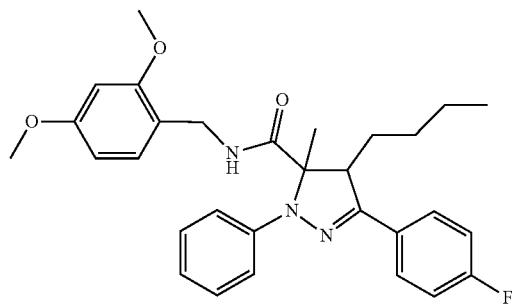 [SMILES: CCCCC1C(c2ccc(F)cc2)=NN(c2ccccc2)C1(C)C(=O)NCc1ccc(OC)cc1OC]

4-butyl-N-(2,4-dimethoxybenzyl)-3-(4-fluorophenyl)-5-methyl-1-phenyl-4,5-dihydro-1H-pyrazole-5-carboxamide (Compound 46);

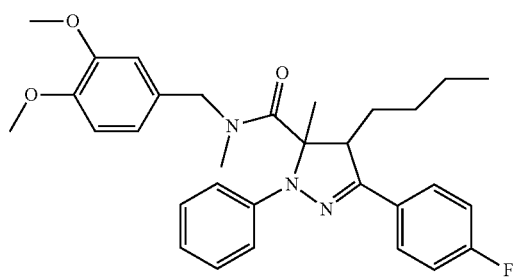 [SMILES: CCCCC1C(c2ccc(F)cc2)=NN(c2ccccc2)C1(C)C(=O)N(C)Cc1ccc(OC)c(OC)c1]

4-butyl-N-(3,4-dimethoxybenzyl)-3-(4-fluorophenyl)-N,5-dimethyl-1-phenyl-4,5-dihydro-1H-pyrazole-5-carboxamide (Compound 47);

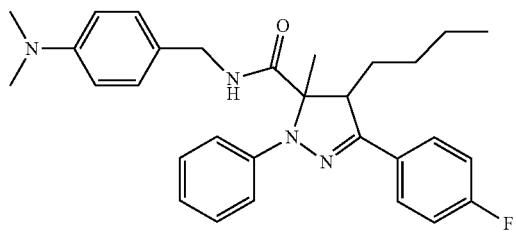 [SMILES: CCCCC1C(c2ccc(F)cc2)=NN(c2ccccc2)C1(C)C(=O)NCc1ccc(N(C)C)cc1]

4-butyl-N-(4-(dimethylamino)benzyl)-3-(4-fluorophenyl)-5-methyl-1-phenyl-4,5-dihydro-1H-pyrazole-5-carboxamide (Compound 48);

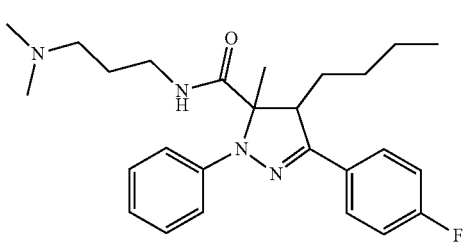 [SMILES: CCCCC1C(c2ccc(F)cc2)=NN(c2ccccc2)C1(C)C(=O)NCCCN(C)C]

4-butyl-N-(3-(dimethylamino)propyl)-3-(4-fluorophenyl)-5-methyl-1-phenyl-4,5-dihydro-1H-pyrazole-5-carboxamide (Compound 49);

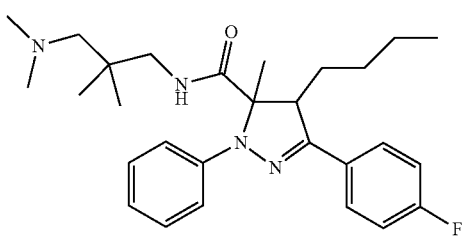 [SMILES: CCCCC1C(c2ccc(F)cc2)=NN(c2ccccc2)C1(C)C(=O)NCC(C)(C)CN(C)C]

4-butyl-N-(3-(dimethylamino)-2,2-dimethylpropyl)-3-(4-fluorophenyl)-5-methyl-1-phenyl-4,5-dihydro-1H-pyrazole-5-carboxamide (Compound 50);

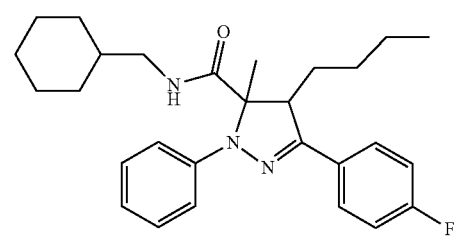 [SMILES: CCCCC1C(c2ccc(F)cc2)=NN(c2ccccc2)C1(C)C(=O)NCC1CCCCC1]

4-butyl-N-(cyclohexylmethyl)-3-(4-fluorophenyl)-5-methyl-1-phenyl-4,5-dihydro-1H-pyrazole-5-carboxamide (Compound 51);

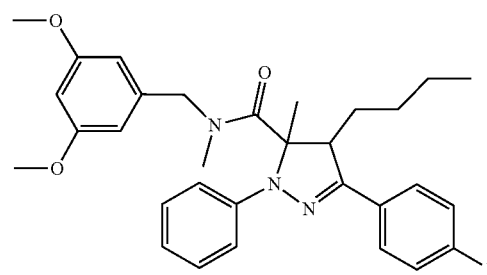

4-butyl-N-(3,5-dimethoxybenzyl)-3-(4-fluorophenyl)-N,5-dimethyl-1-phenyl-4,5-dihydro-1H-pyrazole-5-carboxamide (Compound 52);

4-butyl-3-(2,4-difluorophenyl)-N-(5-hydroxy-4,4-dimethylpentyl)-5-methyl-1-phenyl-4,5-dihydro-1H-pyrazole-5-carboxamide (Compound 56);

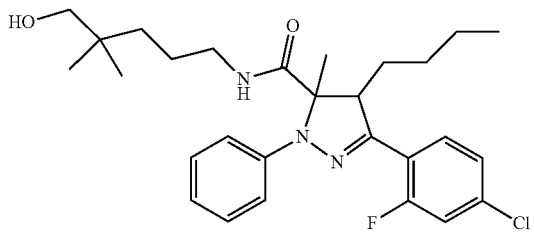 [SMILES: CCCCC1C(c2ccc(Cl)cc2F)=NN(c2ccccc2)C1(C)C(=O)NCCCC(C)(C)CO]

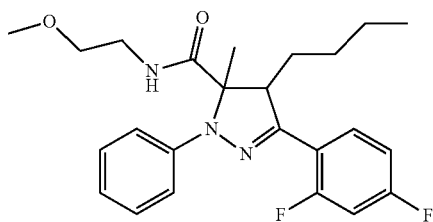

4-butyl-3-(4-chloro-2-fluorophenyl)-N-(5-hydroxy-4,4-dimethylpentyl)-5-methyl-1-phenyl-4,5-dihydro-1H-pyrazole-5-carboxamide (Compound 53);

4-butyl-3-(2,4-difluorophenyl)-N-(2-methoxyethyl)-5-methyl-1-phenyl-4,5-dihydro-1H-pyrazole-5-carboxamide (Compound 57);

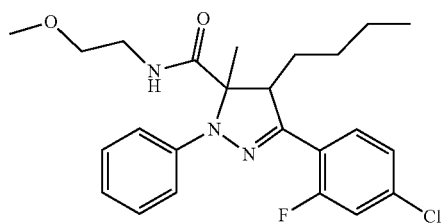 [SMILES: CCCCC1C(c2ccc(Cl)cc2F)=NN(c2ccccc2)C1(C)C(=O)NCCOC]

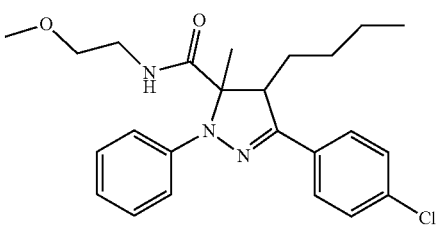

4-butyl-3-(4-chloro-2-fluorophenyl)-N-(2-methoxyethyl)-5-methyl-1-phenyl-4,5-dihydro-1H-pyrazole-5-carboxamide (Compound 54);

4-butyl-3-(4-chlorophenyl)-N-(2-methoxyethyl)-5-methyl-1-phenyl-4,5-dihydro-1H-pyrazole-5-carboxamide (Compound 58);

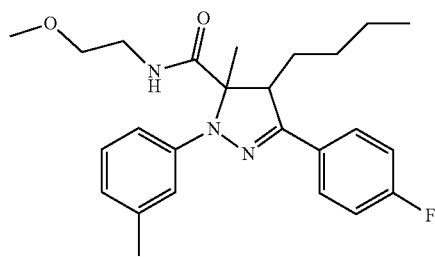 [SMILES: CCCCC1C(c2ccc(F)cc2)=NN(c2cccc(C)c2)C1(C)C(=O)NCCOC]

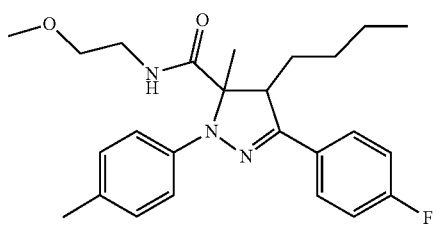

4-butyl-3-(4-fluorophenyl)-N-(2-methoxyethyl)-5-methyl-1-m-tolyl-4,5-dihydro-1H-pyrazole-5-carboxamide (Compound 55);

4-butyl-3-(4-fluorophenyl)-N-(2-methoxyethyl)-5-methyl-1-p-tolyl-4,5-dihydro-1H-pyrazole-5-carboxamide (Compound 59);

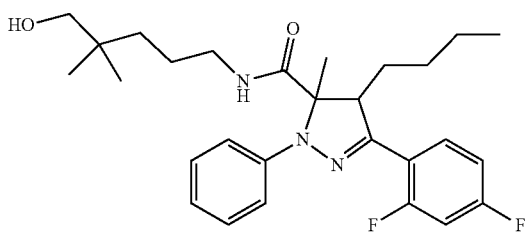 [SMILES: CCCCC1C(c2ccc(F)cc2F)=NN(c2ccccc2)C1(C)C(=O)NCCCC(C)(C)CO]

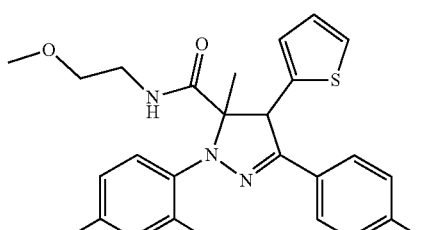

1-(2,4-difluorophenyl)-3-(4-fluorophenyl)-N-(2-methoxyethyl)-5-methyl-4-(thiophen-2-yl)-4,5-dihydro-1H-pyrazole-5-carboxamide (Compound 60);

4-butyl-1-(4-chloro-2-fluorophenyl)-3-(4-fluorophenyl)-N-(2-methoxyethyl)-5-methyl-4,5-dihydro-1H-pyrazole-5-carboxamide (Compound 64);

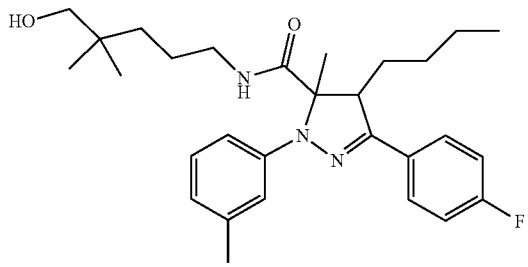 [SMILES: CCCCC1C(c2ccc(F)cc2)=NN(c2cccc(C)c2)C1(C)C(=O)NCCCC(C)(C)CO]

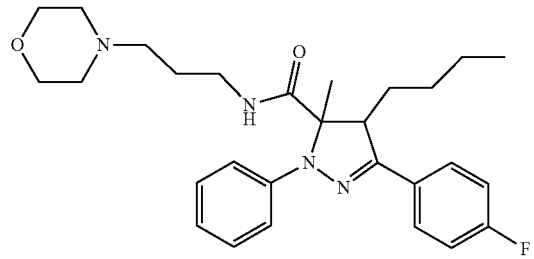 [SMILES: CCCCC1C(c2ccc(F)cc2)=NN(c2ccccc2)C1(C)C(=O)NCCCN1CCOCC1]

4-butyl-3-(4-fluorophenyl)-N-(5-hydroxy-4,4-dimethylpentyl)-5-methyl-1-m-tolyl-4,5-dihydro-1H-pyrazole-5-carboxamide (Compound 61);

4-butyl-3-(4-fluorophenyl)-5-methyl-N-(3-morpholinopropyl)-1-phenyl-4,5-dihydro-1H-pyrazole-5-carboxamide (Compound 65);

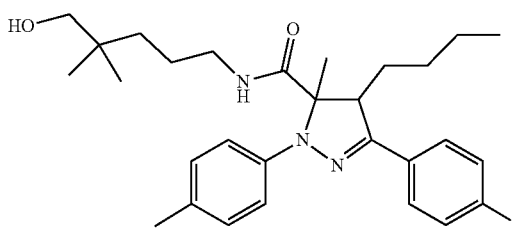

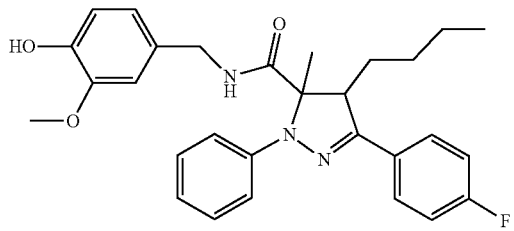 [SMILES: CCCCC1C(c2ccc(F)cc2)=NN(c2ccccc2)C1(C)C(=O)NCc1ccc(O)c(OC)c1]

4-butyl-3-(4-fluorophenyl)-N-(5-hydroxy-4,4-dimethylpentyl)-5-methyl-1-p-tolyl-4,5-dihydro-1H-pyrazole-5-carboxamide (Compound 62);

4-butyl-3-(4-fluorophenyl)-N-(4-hydroxy-3-methoxybenzyl)-5-methyl-1-phenyl-4,5-dihydro-1H-pyrazole-5-carboxamide (Compound 66);

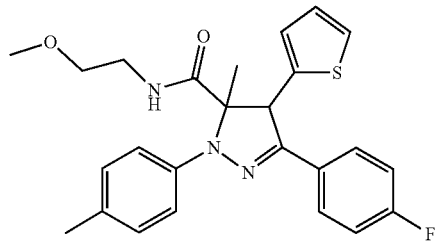

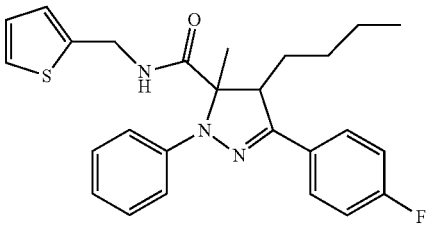 [SMILES: CCCCC1C(c2ccc(F)cc2)=NN(c2ccccc2)C1(C)C(=O)NCc1cccs1]

3-(4-fluorophenyl)-N-(2-methoxyethyl)-5-methyl-4-(thiophen-2-yl)-1-p-tolyl-4,5-dihydro-1H-pyrazole-5-carboxamide (Compound 63);

4-butyl-3-(4-fluorophenyl)-5-methyl-1-phenyl-N-(thiophen-2-ylmethyl)-4,5-dihydro-1H-pyrazole-5-carboxamide (Compound 67);

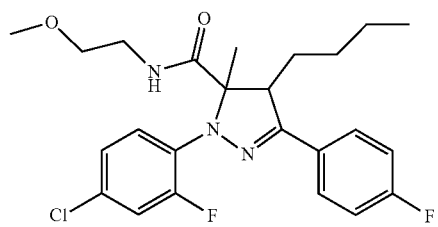

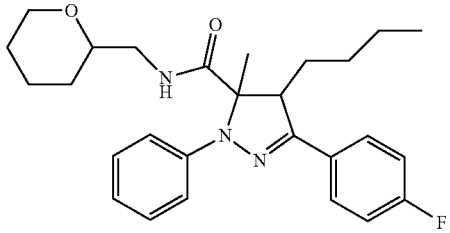 [SMILES: CCCCC1C(c2ccc(F)cc2)=NN(c2ccccc2)C1(C)C(=O)NCC1CCCCO1]

4-butyl-3-(4-fluorophenyl)-5-methyl-1-phenyl-N-((tetrahydro-2H-pyran-2-yl)methyl)-4,5-dihydro-1H-pyrazole-5-carboxamide (Compound 68);

4-butyl-3-(4-fluorophenyl)-5-methyl-N-neopentyl-1-phenyl-4,5-dihydro-1H-pyrazole-5-carboxamide (Compound 72);

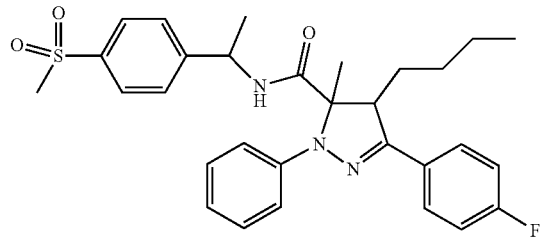 [SMILES: CCCCC1C(c2ccc(F)cc2)=NN(c2ccccc2)C1(C)C(=O)NC(C)c1ccc(S(C)(=O)=O)cc1]

4-butyl-3-(4-fluorophenyl)-5-methyl-N-(1-(4-(methylsulfonyl)phenyl)ethyl)-1-phenyl-4,5-dihydro-1H-pyrazole-5-carboxamide (Compound 69);

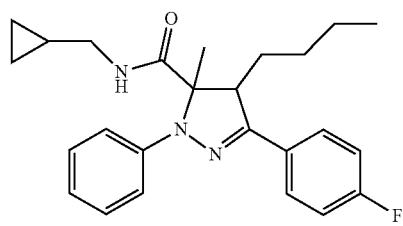

4-butyl-N-(cyclopropylmethyl)-3-(4-fluorophenyl)-5-methyl-1-phenyl-4,5-dihydro-1H-pyrazole-5-carboxamide (Compound 73);

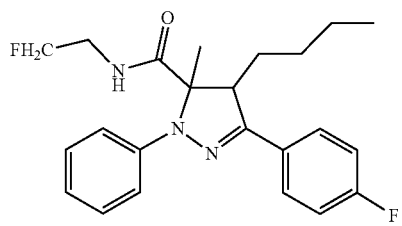

4-butyl-N-(2-fluoroethyl)-3-(4-fluorophenyl)-5-methyl-1-phenyl-4,5-dihydro-1H-pyrazole-5-carboxamide (Compound 70);

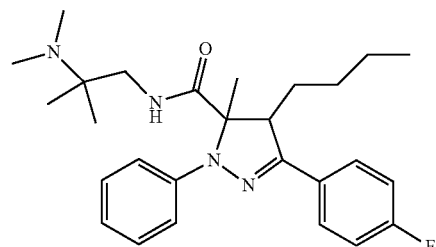

4-butyl-N-(2-(dimethylamino)-2-methylpropyl)-3-(4-fluorophenyl)-5-methyl-1-phenyl-4,5-dihydro-1H-pyrazole-5-carboxamide (Compound 74);

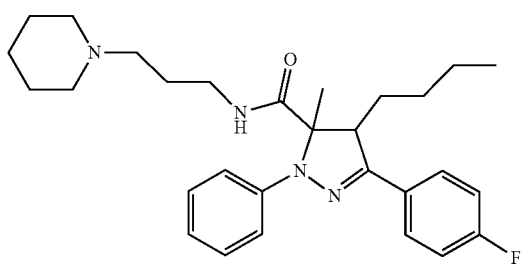 [SMILES: CCCCC1C(c2ccc(F)cc2)=NN(c2ccccc2)C1(C)C(=O)NCCCN1CCCCC1]

4-butyl-3-(4-fluorophenyl)-5-methyl-1-phenyl-N-(3-(piperidin-1-yl)propyl)-4,5-dihydro-1H-pyrazole-5-carboxamide (Compound 71);

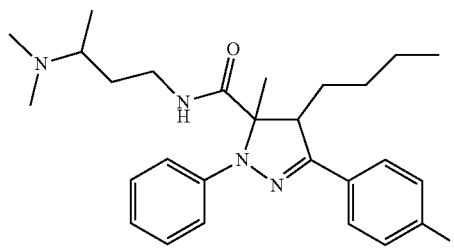

4-butyl-N-(3-(dimethylamino)butyl)-3-(4-fluorophenyl)-5-methyl-1-phenyl-4,5-dihydro-1H-pyrazole-5-carboxamide (Compound 75);

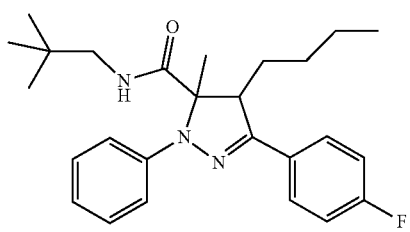 [SMILES: CCCCC1C(c2ccc(F)cc2)=NN(c2ccccc2)C1(C)C(=O)NCC(C)(C)C]

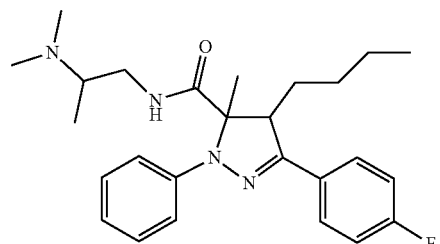

4-butyl-N-(2-(dimethylamino)propyl)-3-(4-fluorophenyl)-5-methyl-1-phenyl-4,5-dihydro-1H-pyrazole-5-carboxamide (Compound 76);

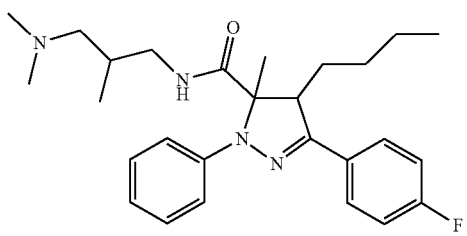 [SMILES: CCCCC1C(c2ccc(F)cc2)=NN(c2ccccc2)C1(C)C(=O)NCC(C)CN(C)C]

4-butyl-N-(3-(dimethylamino)-2-methylpropyl)-3-(4-fluorophenyl)-5-methyl-1-phenyl-4,5-dihydro-1H-pyrazole-5-carboxamide (Compound 77);

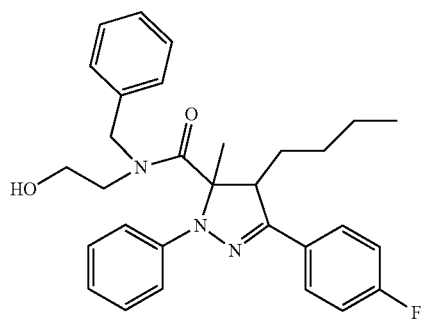 [SMILES: CCCCC1C(c2ccc(F)cc2)=NN(c2ccccc2)C1(C)C(=O)N(CCO)Cc1ccccc1]

N-benzyl-4-butyl-3-(4-fluorophenyl)-N-(2-hydroxyethyl)-5-methyl-1-phenyl-4,5-dihydro-1H-pyrazole-5-carboxamide (Compound 78);

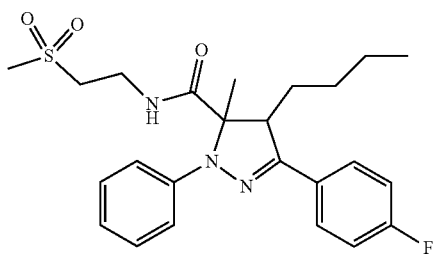 [SMILES: CCCCC1C(c2ccc(F)cc2)=NN(c2ccccc2)C1(C)C(=O)NCCS(C)(=O)=O]

4-butyl-3-(4-fluorophenyl)-5-methyl-N-(2-(methylsulfonyl)ethyl)-1-phenyl-4,5-dihydro-1H-pyrazole-5-carboxamide (Compound 79);

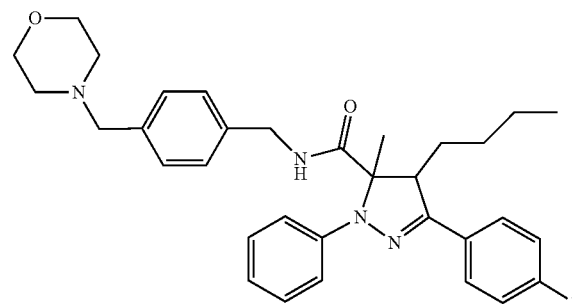

4-butyl-3-(4-fluorophenyl)-5-methyl-N-(4-(morpholinomethyl)benzyl)-1-phenyl-4,5-dihydro-1H-pyrazole-5-carboxamide (Compound 80);

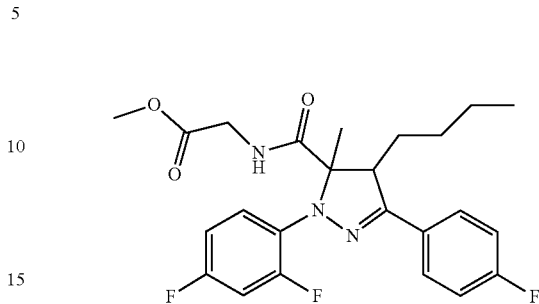

methyl 2-(4-butyl-1-(2,4-difluorophenyl)-3-(4-fluorophenyl)-5-methyl-4,5-dihydro-1H-pyrazole-5-carboxamido)acetate (Compound 81);

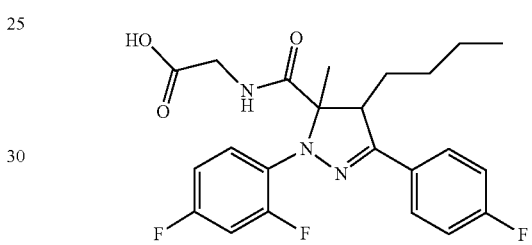

2-(4-butyl-1-(2,4-difluorophenyl)-3-(4-fluorophenyl)-5-methyl-4,5-dihydro-1H-pyrazole-5-carboxamido)acetic acid (Compound 82);

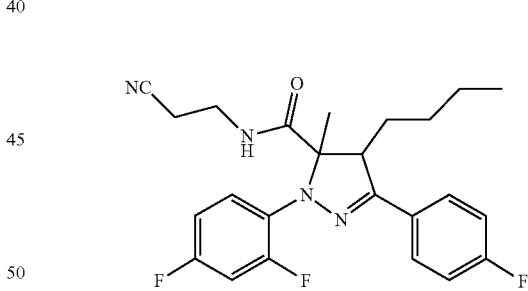

4-butyl-N-(2-cyanoethyl)-1-(2,4-difluorophenyl)-3-(4-fluorophenyl)-5-methyl-4,5-dihydro-1H-pyrazole-5-carboxamide (Compound 83);

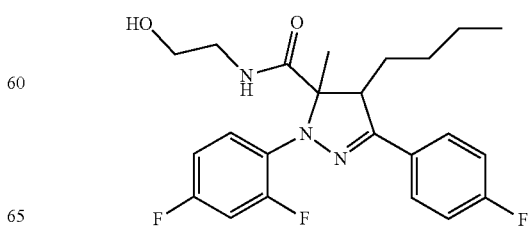

4-butyl-1-(2,4-difluorophenyl)-3-(4-fluorophenyl)-N-(2-hydroxyethyl)-5-methyl-4,5-dihydro-1H-pyrazole-5-carboxamide (Compound 84);

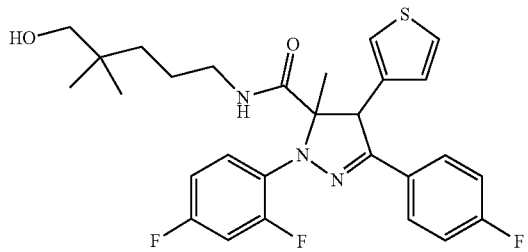 [SMILES: CC(C)(CO)CCCNC(=O)C1(C)C(c2ccsc2)C(c2ccc(F)cc2)=NN1c1ccc(F)cc1F]

1-(2,4-difluorophenyl)-3-(4-fluorophenyl)-N-(5-hydroxy-4,4-dimethylpentyl)-5-methyl-4-(thiophen-3-yl)-4,5-dihydro-1H-pyrazole-5-carboxamide (Compound 85);

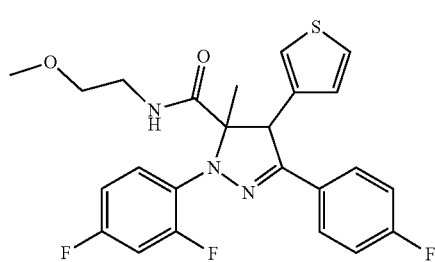 [SMILES: COCCNC(=O)C1(C)C(c2ccsc2)C(c2ccc(F)cc2)=NN1c1ccc(F)cc1F]

1-(2,4-difluorophenyl)-3-(4-fluorophenyl)-N-(2-methoxyethyl)-5-methyl-4-(thiophen-3-yl)-4,5-dihydro-1H-pyrazole-5-carboxamide (Compound 86);

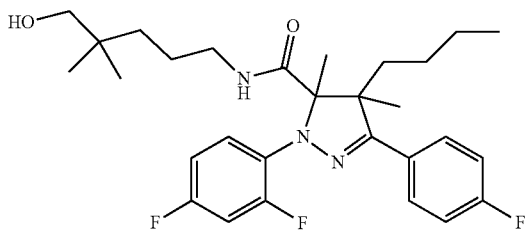 [SMILES: CCCCC1(C)C(c2ccc(F)cc2)=NN(c2ccc(F)cc2F)C1(C)C(=O)NCCCC(C)(C)CO]

4-butyl-1-(2,4-difluorophenyl)-3-(4-fluorophenyl)-N-(5-hydroxy-4,4-dimethylpentyl)-4,5-dimethyl-4,5-dihydro-1H-pyrazole-5-carboxamide (Compound 87);

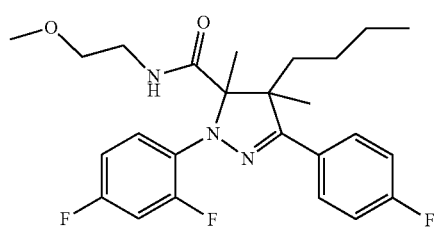 [SMILES: CCCCC1(C)C(c2ccc(F)cc2)=NN(c2ccc(F)cc2F)C1(C)C(=O)NCCOC]

4-butyl-1-(2,4-difluorophenyl)-3-(4-fluorophenyl)-N-(2-methoxyethyl)-4,5-dimethyl-4,5-dihydro-1H-pyrazole-5-carboxamide (Compound 88);

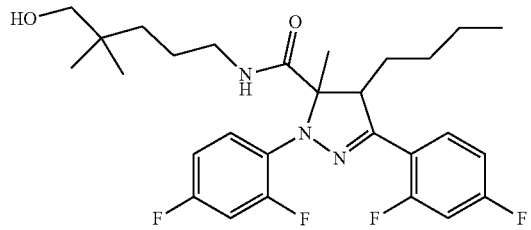 [SMILES: CCCCC1C(c2ccc(F)cc2F)=NN(c2ccc(F)cc2F)C1(C)C(=O)NCCCC(C)(C)CO]

4-butyl-1,3-bis(2,4-difluorophenyl)-N-(5-hydroxy-4,4-dimethylpentyl)-5-methyl-4,5-dihydro-1H-pyrazole-5-carboxamide (Compound 89);

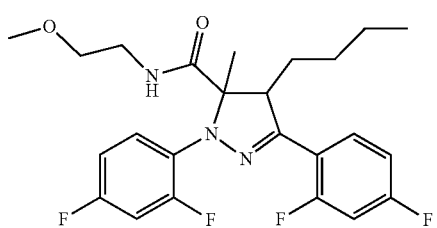 [SMILES: CCCCC1C(c2ccc(F)cc2F)=NN(c2ccc(F)cc2F)C1(C)C(=O)NCCOC]

4-butyl-1,3-bis(2,4-difluorophenyl)-N-(2-methoxyethyl)-5-methyl-4,5-dihydro-1H-pyrazole-5-carboxamide (Compound 90);

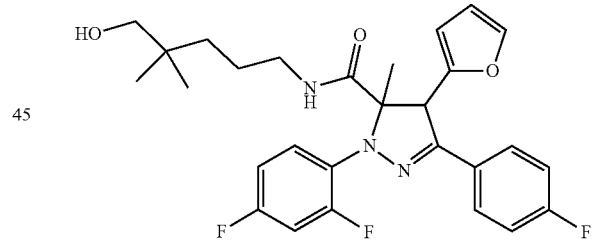

1-(2,4-difluorophenyl)-3-(4-fluorophenyl)-4-(furan-2-yl)-N-(5-hydroxy-4,4-dimethylpentyl)-5-methyl-4,5-dihydro-1H-pyrazole-5-carboxamide (Compound 91);

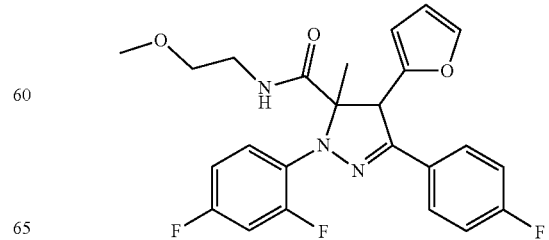

1-(2,4-difluorophenyl)-3-(4-fluorophenyl)-4-(furan-2-yl)-N-(2-methoxyethyl)-5-methyl-4,5-dihydro-1H-pyrazole-5-carboxamide (Compound 92);

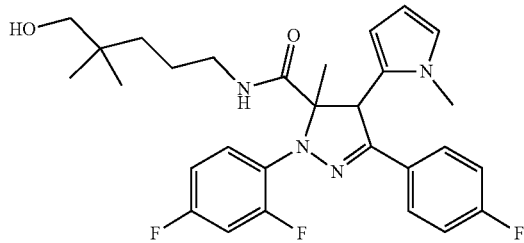 [SMILES: Cn1cccc1C1C(c2ccc(F)cc2)=NN(c2ccc(F)cc2F)C1(C)C(=O)NCCCC(C)(C)CO]

1-(2,4-difluorophenyl)-3-(4-fluorophenyl)-N-(5-hydroxy-4,4-dimethylpentyl)-5-methyl-4-(1-methyl-1H-pyrrol-2-yl)-4,5-dihydro-1H-pyrazole-5-carboxamide (Compound 93);

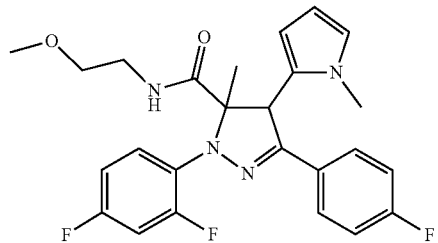 [SMILES: COCCNC(=O)C1(C)C(c2cccn2C)C(c2ccc(F)cc2)=NN1c1ccc(F)cc1F]

1-(2,4-difluorophenyl)-3-(4-fluorophenyl)-N-(2-methoxyethyl)-5-methyl-4-(1-methyl-1H-pyrrol-2-yl)-4,5-dihydro-1H-pyrazole-5-carboxamide (Compound 94);

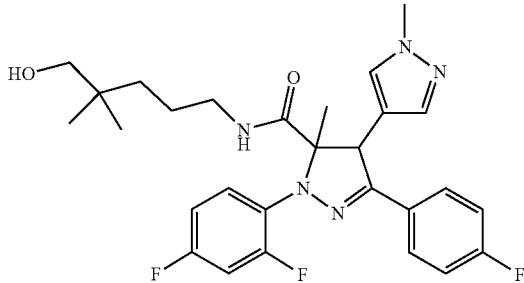 [SMILES: Cn1cc(C2C(c3ccc(F)cc3)=NN(c3ccc(F)cc3F)C2(C)C(=O)NCCCC(C)(C)CO)cn1]

1-(2,4-difluorophenyl)-3-(4-fluorophenyl)-N-(5-hydroxy-4,4-dimethylpentyl)-5-methyl-4-(1-methyl-1H-pyrazol-4-yl)-4,5-dihydro-1H-pyrazole-5-carboxamide (Compound 95);

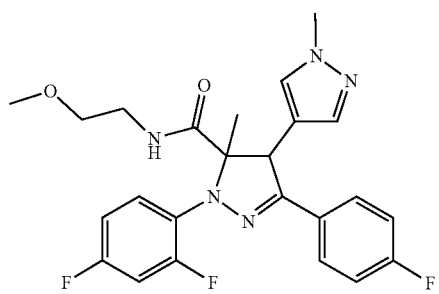 [SMILES: COCCNC(=O)C1(C)C(c2cnn(C)c2)C(c2ccc(F)cc2)=NN1c1ccc(F)cc1F]

1-(2,4-difluorophenyl)-3-(4-fluorophenyl)-N-(2-methoxyethyl)-5-methyl-4-(1-methyl-1H-pyrazol-4-yl)-4,5-dihydro-1H-pyrazole-5-carboxamide (Compound 96);

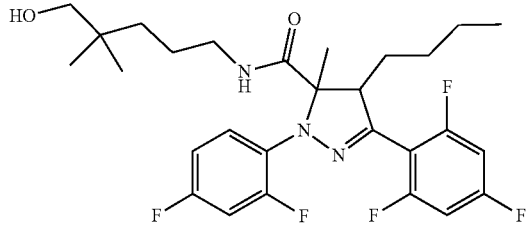 [SMILES: CCCCC1C(c2c(F)cc(F)cc2F)=NN(c2ccc(F)cc2F)C1(C)C(=O)NCCCC(C)(C)CO]

4-butyl-1-(2,4-difluorophenyl)-N-(5-hydroxy-4,4-dimethylpentyl)-5-methyl-3-(2,4,6-trifluorophenyl)-4,5-dihydro-1H-pyrazole-5-carboxamide (Compound 97);

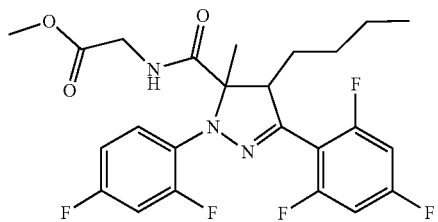 [SMILES: CCCCC1C(c2c(F)cc(F)cc2F)=NN(c2ccc(F)cc2F)C1(C)C(=O)NCC(=O)OC]

methyl 2-(4-butyl-1-(2,4-difluorophenyl)-5-methyl-3-(2,4,6-trifluorophenyl)-4,5-dihydro-1H-pyrazole-5-carboxamido)acetate (Compound 98);

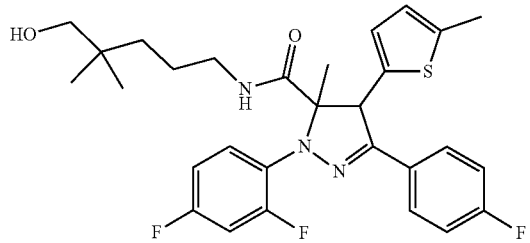 [SMILES: Cc1ccc(C2C(c3ccc(F)cc3)=NN(c3ccc(F)cc3F)C2(C)C(=O)NCCCC(C)(C)CO)s1]

1-(2,4-difluorophenyl)-3-(4-fluorophenyl)-N-(5-hydroxy-4,4-dimethylpentyl)-5-methyl-4-(5-methylthiophen-2-yl)-4,5-dihydro-1H-pyrazole-5-carboxamide (Compound 99);

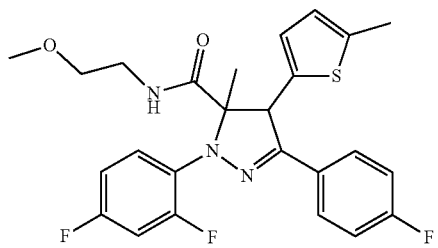 [SMILES: COCCNC(=O)C1(C)C(c2ccc(C)s2)C(c2ccc(F)cc2)=NN1c1ccc(F)cc1F]

1-(2,4-difluorophenyl)-3-(4-fluorophenyl)-N-(2-methoxyethyl)-5-methyl-4-(5-methylthiophen-2-yl)-4,5-dihydro-1H-pyrazole-5-carboxamide (Compound 100);

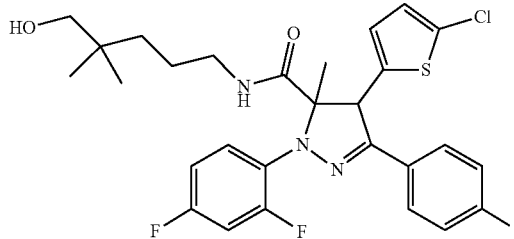

4-(5-chlorothiophen-2-yl)-1-(2,4-difluorophenyl)-3-(4-fluorophenyl)-N-(5-hydroxy-4,4-dimethylpentyl)-5-methyl-4,5-dihydro-1H-pyrazole-5-carboxamide (Compound 101);

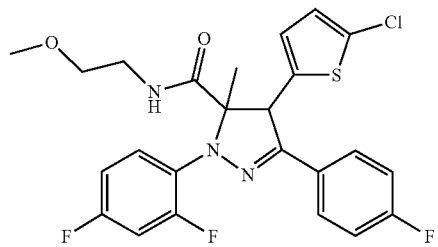 [SMILES: COCCNC(=O)C1(C)C(c2ccc(Cl)s2)C(c2ccc(F)cc2)=NN1c1ccc(F)cc1F]

4-(5-chlorothiophen-2-yl)-1-(2,4-difluorophenyl)-3-(4-fluorophenyl)-N-(2-methoxyethyl)-5-methyl-4,5-dihydro-1H-pyrazole-5-carboxamide (Compound 102);

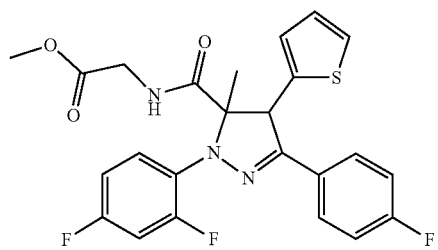 [SMILES: COC(=O)CNC(=O)C1(C)C(c2cccs2)C(c2ccc(F)cc2)=NN1c1ccc(F)cc1F]

methyl 2-(1-(2,4-difluorophenyl)-3-(4-fluorophenyl)-5-methyl-4-(thiophen-2-yl)-4,5-dihydro-1H-pyrazole-5-carboxamido)acetate (Compound 103);

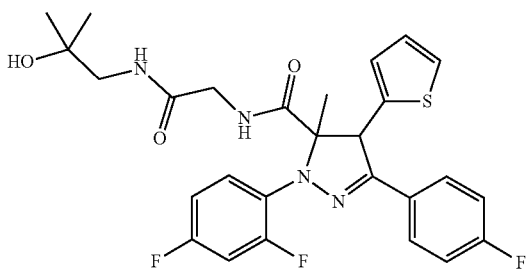 [SMILES: CC(C)(O)CNC(=O)CNC(=O)C1(C)C(c2cccs2)C(c2ccc(F)cc2)=NN1c1ccc(F)cc1F]

1-(2,4-difluorophenyl)-3-(4-fluorophenyl)-N-(2-(2-hydroxy-2-methylpropylamino)-2-oxoethyl)-5-methyl-4-(thiophen-2-yl)-4,5-dihydro-1H-pyrazole-5-carboxamide (Compound 104);

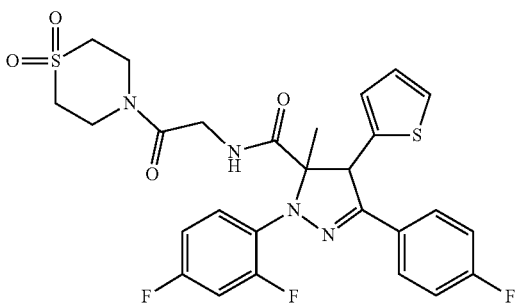 [SMILES: CC1(C(=O)NCC(=O)N2CCS(=O)(=O)CC2)C(c2cccs2)C(c2ccc(F)cc2)=NN1c1ccc(F)cc1F]

1-(2,4-difluorophenyl)-3-(4-fluorophenyl)-5-methyl-N-(1,1-dioxo-1-thiomorpholine-2-oxoethyl)-4-(thiophen-2-yl)-4,5-dihydro-1H-pyrazole-5-carboxamide (Compound 105);

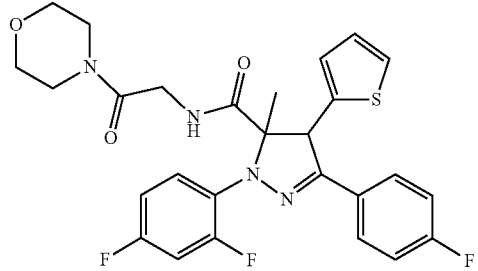 [SMILES: CC1(C(=O)NCC(=O)N2CCOCC2)C(c2cccs2)C(c2ccc(F)cc2)=NN1c1ccc(F)cc1F]

1-(2,4-difluorophenyl)-3-(4-fluorophenyl)-5-methyl-N-(2-morpholino-2-oxoethyl)-4-(thiophen-2-yl)-4,5-dihydro-1H-pyrazole-5-carboxamide (Compound 106);

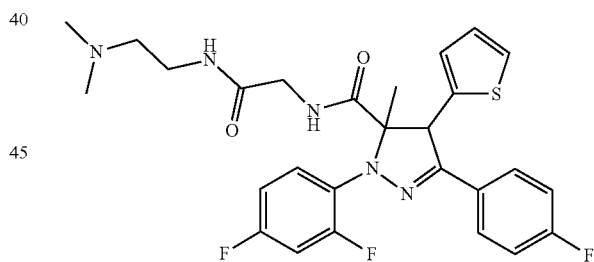

1-(2,4-difluorophenyl)-N-(2-(2-(dimethylamino)ethylamino)-2-oxoethyl)-3-(4-fluorophenyl)-5-methyl-4-(thiophen-2-yl)-4,5-dihydro-1H-pyrazole-5-carboxamide (Compound 107);

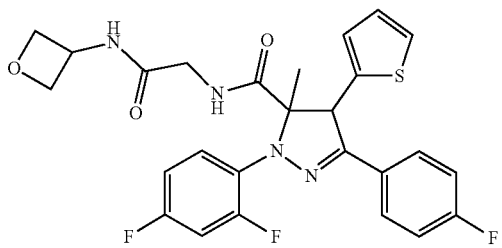 [SMILES: CC1(C(=O)NCC(=O)NC2COC2)C(c2cccs2)C(c2ccc(F)cc2)=NN1c1ccc(F)cc1F]

61

1-(2,4-difluorophenyl)-3-(4-fluorophenyl)-5-methyl-N-(2-(oxetan-3-ylamino)-2-oxoethyl)-4-(thiophen-2-yl)-4,5-dihydro-1H-pyrazole-5-carboxamide (Compound 108);

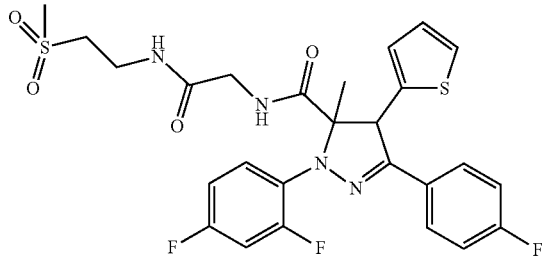 [SMILES: CC1(C(=O)NCC(=O)NCCS(C)(=O)=O)C(c2cccs2)C(c2ccc(F)cc2)=NN1c1ccc(F)cc1F]

1-(2,4-difluorophenyl)-3-(4-fluorophenyl)-5-methyl-N-(2-(2-(methylsulfonyl)ethylamino)-2-oxoethyl)-4-(thiophen-2-yl)-4,5-dihydro-1H-pyrazole-5-carboxamide (Compound 109);

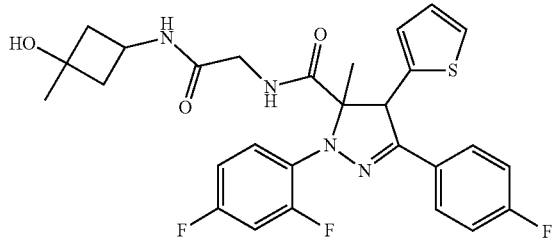 [SMILES: CC1(O)CC(NC(=O)CNC(=O)C2(C)C(c3cccs3)C(c3ccc(F)cc3)=NN2c2ccc(F)cc2F)C1]

1-(2,4-difluorophenyl)-3-(4-fluorophenyl)-N-(2-(3-hydroxy-3-methylcyclobutylamino)-2-oxoethyl)-5-methyl-4-(thiophen-2-yl)-4,5-dihydro-1H-pyrazole-5-carboxamide (Compound 110);

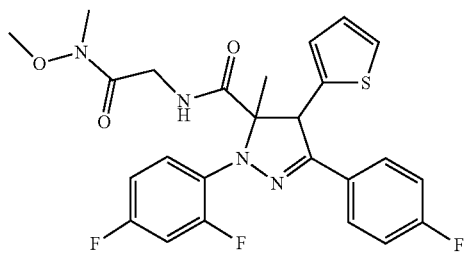 [SMILES: CON(C)C(=O)CNC(=O)C1(C)C(c2cccs2)C(c2ccc(F)cc2)=NN1c1ccc(F)cc1F]

1-(2,4-difluorophenyl)-3-(4-fluorophenyl)-N-(2-(methoxy(methyl)amino)-2-oxoethyl)-5-methyl-4-(thiophen-2-yl)-4,5-dihydro-1H-pyrazole-5-carboxamide (Compound 111);

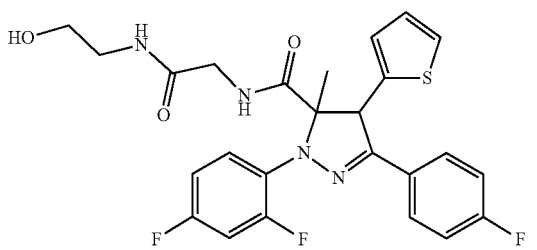 [SMILES: CC1(C(=O)NCC(=O)NCCO)C(c2cccs2)C(c2ccc(F)cc2)=NN1c1ccc(F)cc1F]

62

1-(2,4-difluorophenyl)-3-(4-fluorophenyl)-N-(2-(2-hydroxyethylamino)-2-oxoethyl)-5-methyl-4-(thiophen-2-yl)-4,5-dihydro-1H-pyrazole-5-carboxamide (Compound 112);

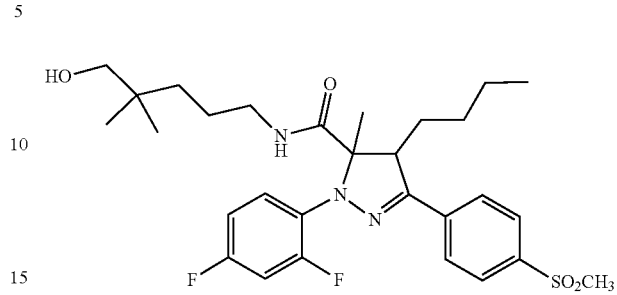

4-butyl-1-(2,4-difluorophenyl)-N-(5-hydroxy-4,4-dimethylpentyl)-5-methyl-3-(4-(methylsulfonyl)phenyl)-4,5-dihydro-1H-pyrazole-5-carboxamide (Compound 113);

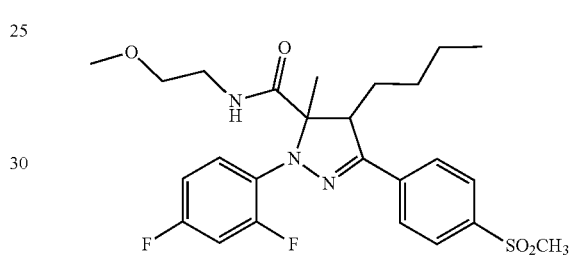

4-butyl-1-(2,4-difluorophenyl)-N-(2-methoxyethyl)-5-methyl-3-(4-(methylsulfonyl)phenyl)-4,5-dihydro-1H-pyrazole-5-carboxamide (Compound 114);

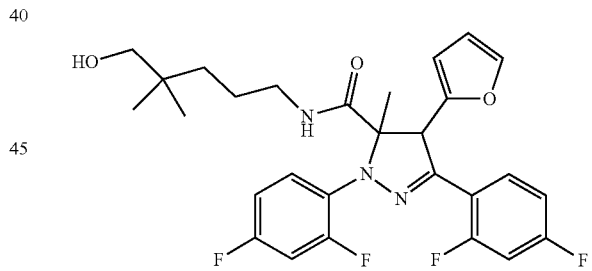

1,3-bis(2,4-difluorophenyl)-4-(furan-2-yl)-N-(5-hydroxy-4,4-dimethylpentyl)-5-methyl-4,5-dihydro-1H-pyrazole-5-carboxamide (Compound 115);

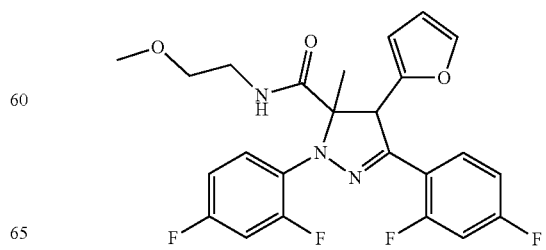

1,3-bis(2,4-difluorophenyl)-4-(furan-2-yl)-N-(2-methoxyethyl)-5-methyl-4,5-dihydro-1H-pyrazole-5-carboxamide (Compound 116);

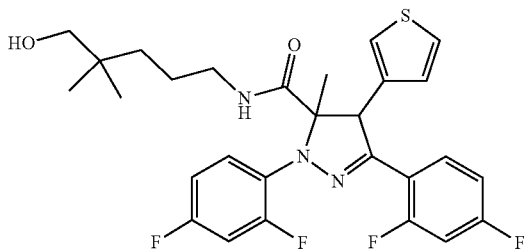

1,3-bis(2,4-difluorophenyl)-N-(5-hydroxy-4,4-dimethylpentyl)-5-methyl-4-(thiophen-3-yl)-4,5-dihydro-1H-pyrazole-5-carboxamide (Compound 117);

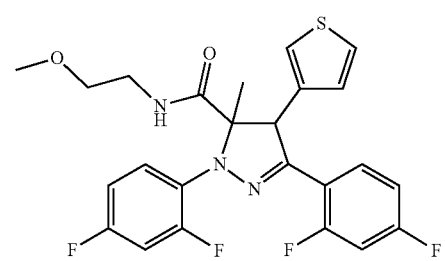

1,3-bis(2,4-difluorophenyl)-N-(2-methoxyethyl)-5-methyl-4-(thiophen-3-yl)-4,5-dihydro-1H-pyrazole-5-carboxamide (Compound 118);

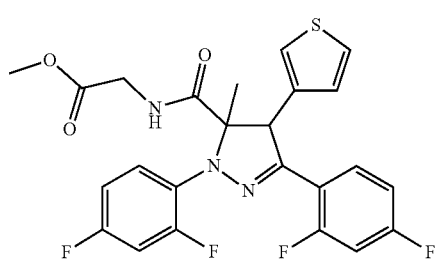 [SMILES: COC(=O)CNC(=O)C1(C)C(c2ccsc2)C(c2ccc(F)cc2F)=NN1c1ccc(F)cc1F]

methyl 2-(1,3-bis(2,4-difluorophenyl)-5-methyl-4-(thiophen-3-yl)-4,5-dihydro-1H-pyrazole-5-carboxamido)acetate (Compound 119);

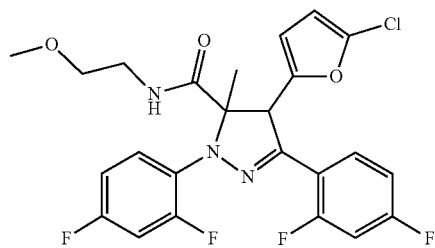 [SMILES: COCCNC(=O)C1(C)C(c2ccc(Cl)o2)C(c2ccc(F)cc2F)=NN1c1ccc(F)cc1F]

4-(5-chlorofuran-2-yl)-1,3-bis(2,4-difluorophenyl)-N-(2-methoxyethyl)-5-methyl-4,5-dihydro-1H-pyrazole-5-carboxamide (Compound 120);

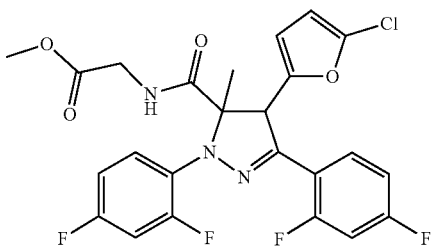 [SMILES: COC(=O)CNC(=O)C1(C)C(c2ccc(Cl)o2)C(c2ccc(F)cc2F)=NN1c1ccc(F)cc1F]

methyl 2-(4-(5-chlorofuran-2-yl)-1,3-bis(2,4-difluorophenyl)-5-methyl-4,5-dihydro-1H-pyrazole-5-carboxamido)acetate (Compound 121);

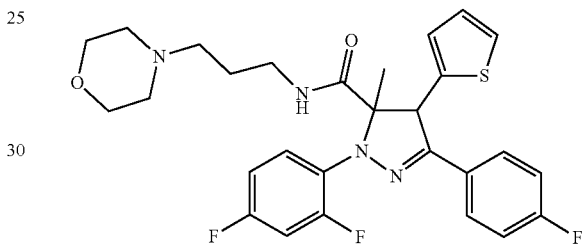

1-(2,4-difluorophenyl)-3-(4-fluorophenyl)-5-methyl-N-(3-morpholinopropyl)-4-(thiophen-2-yl)-4,5-dihydro-1H-pyrazole-5-carboxamide (Compound 122);

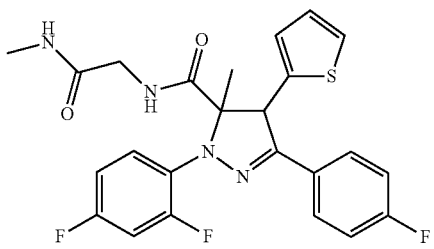 [SMILES: CNC(=O)CNC(=O)C1(C)C(c2cccs2)C(c2ccc(F)cc2)=NN1c1ccc(F)cc1F]

1-(2,4-difluorophenyl)-3-(4-fluorophenyl)-5-methyl-N-(2-(methylamino)-2-oxoethyl)-4-(thiophen-2-yl)-4,5-dihydro-1H-pyrazole-5-carboxamide (Compound 123);

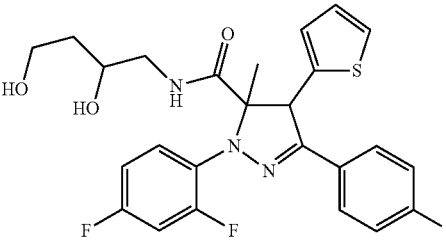

1-(2,4-difluorophenyl)-N-(2,4-dihydroxybutyl)-3-(4-fluoro-
phenyl)-5-methyl-4-(thiophen-2-yl)-4,5-dihydro-1H-
pyrazole-5-carboxamide (Compound 124);

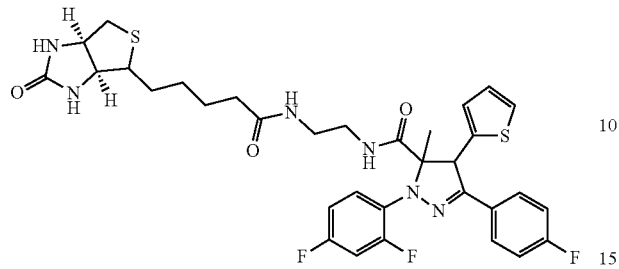

1-(2,4-difluorophenyl)-3-(4-fluorophenyl)-5-methyl-N-(2-
(5-((3aS,6aR)-2-oxohexahydro-1H-thieno[3,4-d]imida-
zol-4-yl)pentanamido)ethyl)-4-(thiophen-2-yl)-4,5-di-
hydro-1H-pyrazole-5-carboxamide (Compound 125);

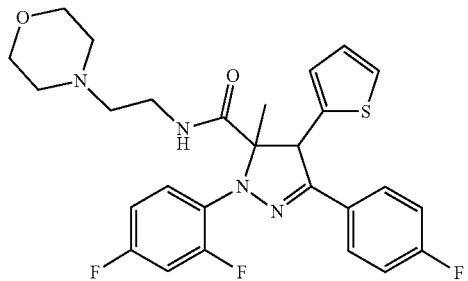 [SMILES: CC1(C(=O)NCCN2CCOCC2)C(c2cccs2)C(c2ccc(F)cc2)=NN1c1ccc(F)cc1F]

1-(2,4-difluorophenyl)-3-(4-fluorophenyl)-5-methyl-N-(2-
morpholinoethyl)-4-(thiophen-2-yl)-4,5-dihydro-1H-
pyrazole-5-carboxamide (Compound 126);

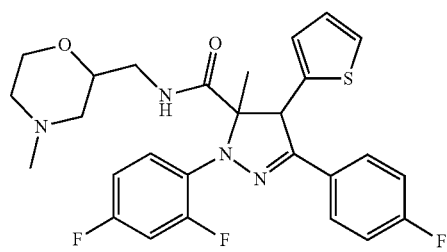 [SMILES: CN1CCOC(CNC(=O)C2(C)C(c3cccs3)C(c3ccc(F)cc3)=NN2c2ccc(F)cc2F)C1]

1-(2,4-difluorophenyl)-3-(4-fluorophenyl)-5-methyl-N-((4-
methylmorpholin-2-yl)methyl)-4-(thiophen-2-yl)-4,5-di-
hydro-1H-pyrazole-5-carboxamide (Compound 127);

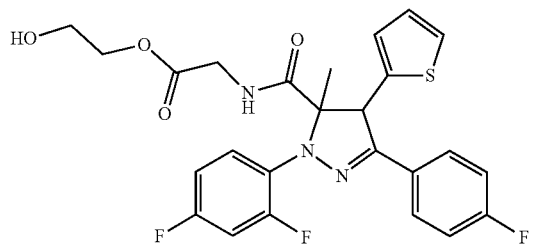 [SMILES: CC1(C(=O)NCC(=O)OCCO)C(c2cccs2)C(c2ccc(F)cc2)=NN1c1ccc(F)cc1F]

2-hydroxyethyl 2-(1-(2,4-difluorophenyl)-3-(4-fluorophe-
nyl)-5-methyl-4-(thiophen-2-yl)-4,5-dihydro-1H-pyra-
zole-5-carboxamido)acetate (Compound 128);

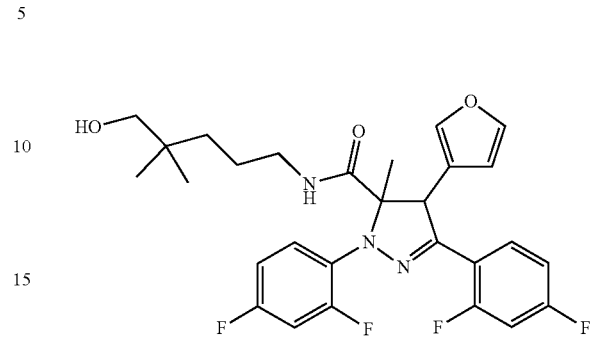

1,3-bis(2,4-difluorophenyl)-4-(furan-3-yl)-N-(5-hydroxy-4,
4-dimethylpentyl)-5-methyl-4,5-dihydro-1H-pyrazole-5-
carboxamide (Compound 129);

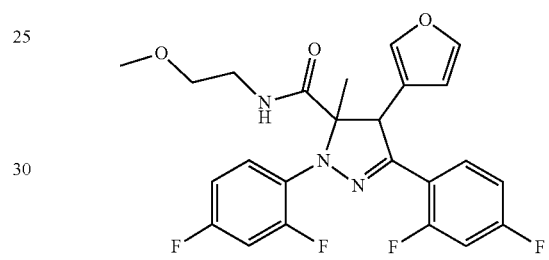

1,3-bis(2,4-difluorophenyl)-4-(furan-3-yl)-N-(2-methoxy-
ethyl)-5-methyl-4,5-dihydro-1H-pyrazole-5-carboxamide
(Compound 130);

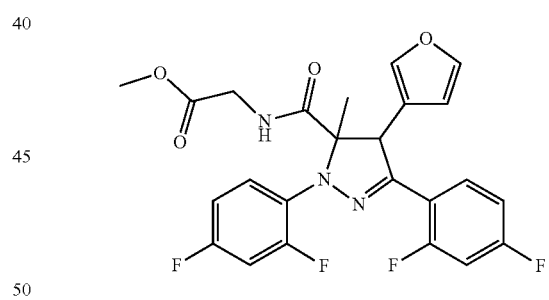

methyl 2-(1,3-bis(2,4-difluorophenyl)-4-(furan-3-yl)-5-
methyl-4,5-dihydro-1H-pyrazole-5-carboxamido)acetate
(Compound 131);

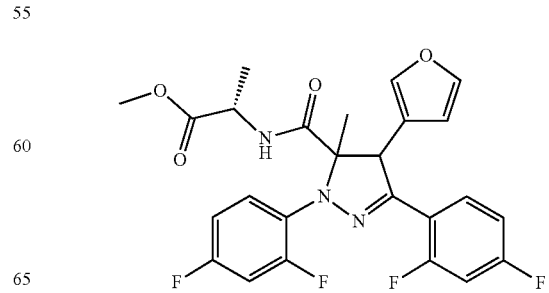

(2S)-methyl 2-(1,3-bis(2,4-difluorophenyl)-4-(furan-3-yl)-5-methyl-4,5-dihydro-1H-pyrazole-5-carboxamido)propanoate (Compound 132);

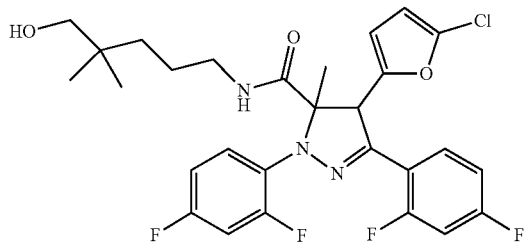 [SMILES: CC(C)(CO)CCCNC(=O)C1(C)C(c2ccc(Cl)o2)C(c2ccc(F)cc2F)=NN1c1ccc(F)cc1F]

4-(5-chlorofuran-2-yl)-1,3-bis(2,4-difluorophenyl)-N-(5-hydroxy-4,4-dimethylpentyl)-5-methyl-4,5-dihydro-1H-pyrazole-5-carboxamide (Compound 133);

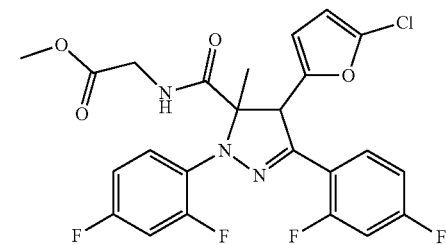 [SMILES: COC(=O)CNC(=O)C1(C)C(c2ccc(Cl)o2)C(c2ccc(F)cc2F)=NN1c1ccc(F)cc1F]

methyl 2-(4-(5-chlorofuran-2-yl)-1,3-bis(2,4-difluorophenyl)-5-methyl-4,5-dihydro-1H-pyrazole-5-carboxamido)acetate (Compound 134);

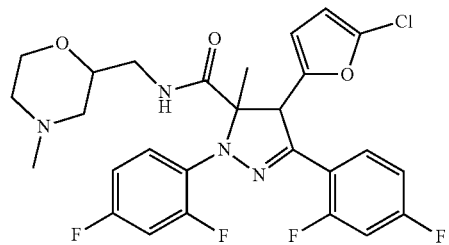 [SMILES: CN1CCOC(CNC(=O)C2(C)C(c3ccc(Cl)o3)C(c3ccc(F)cc3F)=NN2c2ccc(F)cc2F)C1]

4-(5-chlorofuran-2-yl)-1,3-bis(2,4-difluorophenyl)-5-methyl-N-((4-methylmorpholin-2-yl)methyl)-4,5-dihydro-1H-pyrazole-5-carboxamide (Compound 135);

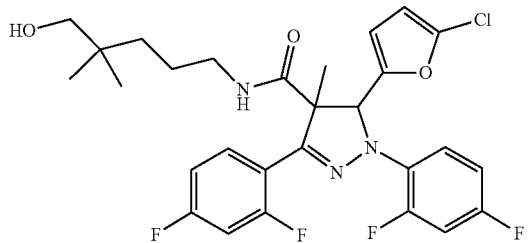 [SMILES: CC(C)(CO)CCCNC(=O)C1(C)C(c2ccc(F)cc2F)=NN(c2ccc(F)cc2F)C1c1ccc(Cl)o1]

5-(5-chlorofuran-2-yl)-1,3-bis(2,4-difluorophenyl)-N-(5-hydroxy-4,4-dimethylpentyl)-4-methyl-4,5-dihydro-1H-pyrazole-4-carboxamide (Compound 136);

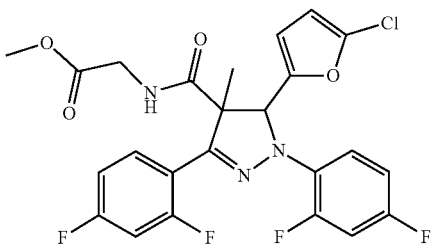 [SMILES: COC(=O)CNC(=O)C1(C)C(c2ccc(F)cc2F)=NN(c2ccc(F)cc2F)C1c1ccc(Cl)o1]

methyl 2-(5-(5-chlorofuran-2-yl)-1,3-bis(2,4-difluorophenyl)-4-methyl-4,5-dihydro-1H-pyrazole-4-carboxamido)acetate (Compound 137);

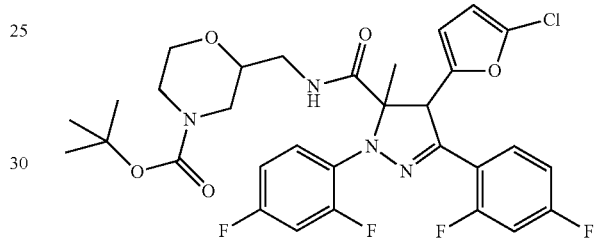

tert-butyl 2-((4-(5-chlorofuran-2-yl)-1,3-bis(2,4-difluorophenyl)-5-methyl-4,5-dihydro-1H-pyrazole-5-carboxamido)methyl)morpholine-4-carboxylate (Compound 138);

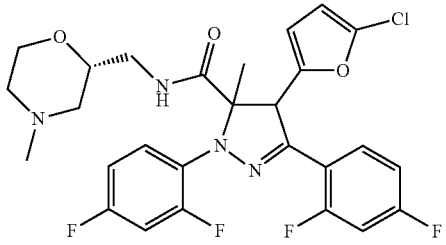

4-(5-chlorofuran-2-yl)-1,3-bis(2,4-difluorophenyl)-5-methyl-N-(((R)-4-methylmorpholin-2-yl)methyl)-4,5-dihydro-1H-pyrazole-5-carboxamide (Compound 139);

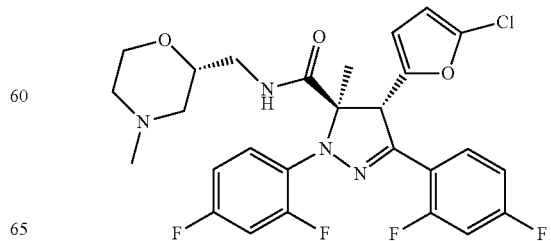

(4S,5R)-4-(5-chlorofuran-2-yl)-1,3-bis(2,4-difluorophenyl)-5-methyl-N-(((R)-4-methylmorpholin-2-yl)methyl)-4,5-dihydro-1H-pyrazole-5-carboxamide (Compound 140);

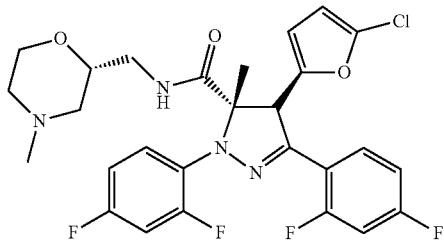

(4R,5S)-4-(5-chlorofuran-2-yl)-1,3-bis(2,4-difluorophenyl)-5-methyl-N-(((R)-4-methylmorpholin-2-yl)methyl)-4,5-dihydro-1H-pyrazole-5-carboxamide (Compound 141);

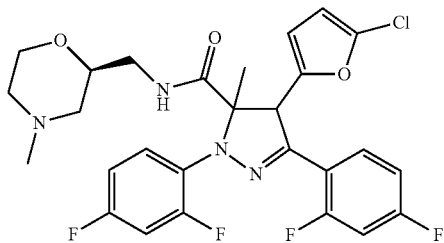 [SMILES: CN1CCO[C@@H](CNC(=O)C2(C)C(c3ccc(Cl)o3)C(c3ccc(F)cc3F)=NN2c2ccc(F)cc2F)C1]

4-(5-chlorofuran-2-yl)-1,3-bis(2,4-difluorophenyl)-5-methyl-N-(((S)-4-methylmorpholin-2-yl)methyl)-4,5-dihydro-1H-pyrazole-5-carboxamide (Compound 142);

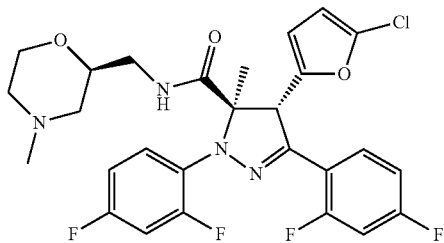 [SMILES: CN1CCO[C@@H](CNC(=O)[C@@]2(C)[C@H](c3ccc(Cl)o3)C(c3ccc(F)cc3F)=NN2c2ccc(F)cc2F)C1]

(4S,5R)-4-(5-chlorofuran-2-yl)-1,3-bis(2,4-difluorophenyl)-5-methyl-N-(((S)-4-methylmorpholin-2-yl)methyl)-4,5-dihydro-1H-pyrazole-5-carboxamide (Compound 143);

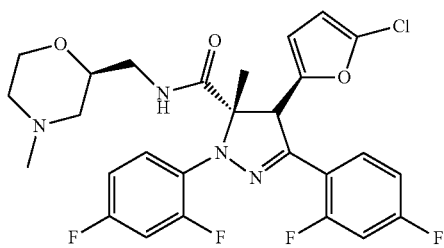

(4R,5S)-4-(5-chlorofuran-2-yl)-1,3-bis(2,4-difluorophenyl)-5-methyl-N-(((S)-4-methylmorpholin-2-yl)methyl)-4,5-dihydro-1H-pyrazole-5-carboxamide (Compound 144);

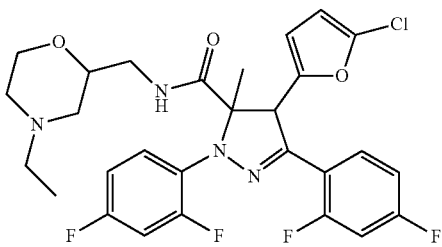 [SMILES: CCN1CCOC(CNC(=O)C2(C)C(c3ccc(Cl)o3)C(c3ccc(F)cc3F)=NN2c2ccc(F)cc2F)C1]

4-(5-chlorofuran-2-yl)-1,3-bis(2,4-difluorophenyl)-N-((4-ethylmorpholin-2-yl)methyl)-5-methyl-4,5-dihydro-1H-pyrazole-5-carboxamide (Compound 145);

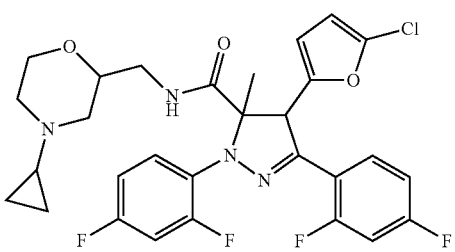 [SMILES: CC1(C(=O)NCC2CN(C3CC3)CCO2)C(c2ccc(Cl)o2)C(c2ccc(F)cc2F)=NN1c1ccc(F)cc1F]

4-(5-chlorofuran-2-yl)-N-((4-cyclopropylmorpholin-2-yl)methyl)-1,3-bis(2,4-difluorophenyl)-5-methyl-4,5-dihydro-1H-pyrazole-5-carboxamide (Compound 146);

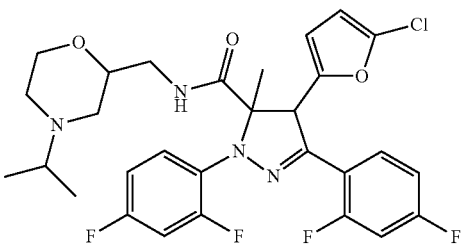 [SMILES: CC(C)N1CCOC(CNC(=O)C2(C)C(c3ccc(Cl)o3)C(c3ccc(F)cc3F)=NN2c2ccc(F)cc2F)C1]

4-(5-chlorofuran-2-yl)-1,3-bis(2,4-difluorophenyl)-N-((4-isopropylmorpholin-2-yl)methyl)-5-methyl-4,5-dihydro-1H-pyrazole-5-carboxamide (Compound 147);

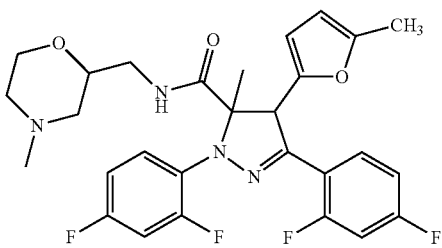

1,3-bis(2,4-difluorophenyl)-5-methyl-4-(5-methylfuran-2-yl)-N-((4-methylmorpholin-2-yl)methyl)-4,5-dihydro-1H-pyrazole-5-carboxamide (Compound 148);

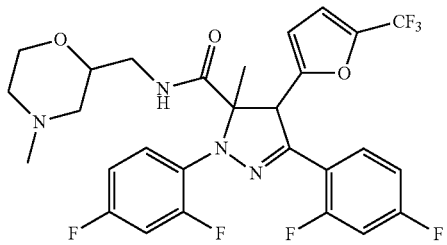 [SMILES: CN1CCOC(CNC(=O)C2(C)C(c3ccc(C(F)(F)F)o3)C(c3ccc(F)cc3F)=NN2c2ccc(F)cc2F)C1]

1,3-bis(2,4-difluorophenyl)-5-methyl-N-((4-methylmorpholin-2-yl)methyl)-4-(5-(trifluoromethyl)furan-2-yl)-4,5-dihydro-1H-pyrazole-5-carboxamide (Compound 149);

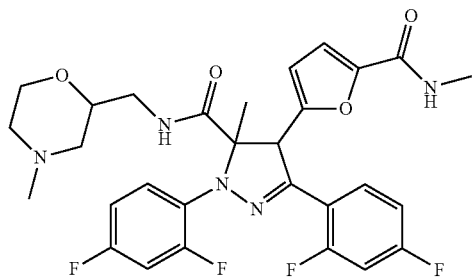 [SMILES: CNC(=O)c1ccc(C2C(c3ccc(F)cc3F)=NN(c3ccc(F)cc3F)C2(C)C(=O)NCC2CN(C)CCO2)o1]

1,3-bis(2,4-difluorophenyl)-5-methyl-4-(5-(methylcarbamoyl)furan-2-yl)-N-((4-methylmorpholin-2-yl)methyl)-4,5-dihydro-1H-pyrazole-5-carboxamide (Compound 150);

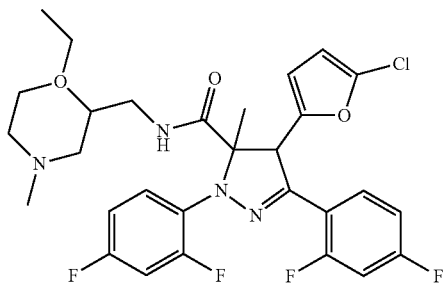

4-(5-chlorofuran-2-yl)-1,3-bis(2,4-difluorophenyl)-N-((4-methoxy-1-methylpiperidin-3-yl)methyl)-5-methyl-4,5-dihydro-1H-pyrazole-5-carboxamide (Compound 151);

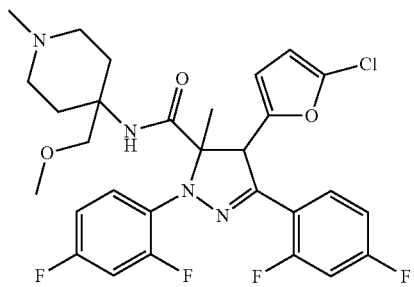 [SMILES: COCC1(NC(=O)C2(C)C(c3ccc(Cl)o3)C(c3ccc(F)cc3F)=NN2c2ccc(F)cc2F)CCN(C)CC1]

4-(5-chlorofuran-2-yl)-1,3-bis(2,4-difluorophenyl)-N-(4-(methoxymethyl)-1-methylpiperidin-4-yl)-5-methyl-4,5-dihydro-1H-pyrazole-5-carboxamide (Compound 152);

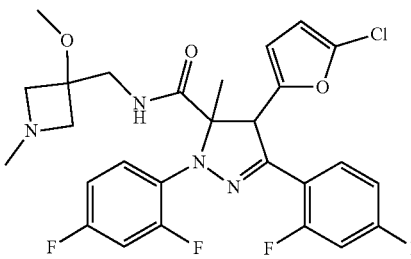

4-(5-chlorofuran-2-yl)-1,3-bis(2,4-difluorophenyl)-N-((3-methoxy-1-methylazetidin-3-yl)methyl)-5-methyl-4,5-dihydro-1H-pyrazole-5-carboxamide (Compound 153);

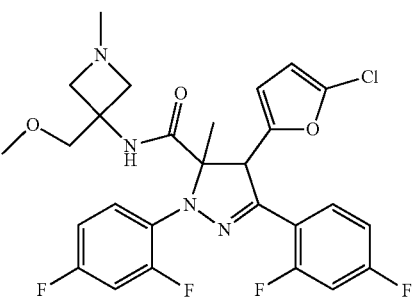 [SMILES: COCC1(NC(=O)C2(C)C(c3ccc(Cl)o3)C(c3ccc(F)cc3F)=NN2c2ccc(F)cc2F)CN(C)C1]

4-(5-chlorofuran-2-yl)-1,3-bis(2,4-difluorophenyl)-N-(3-(methoxymethyl)-1-methylazetidin-3-yl)-5-methyl-4,5-dihydro-1H-pyrazole-5-carboxamide (Compound 154);

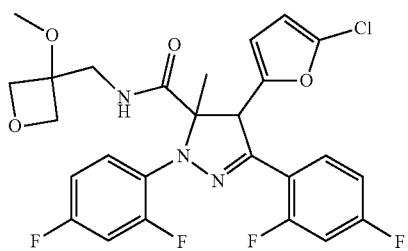 [SMILES: COC1(CNC(=O)C2(C)C(c3ccc(Cl)o3)C(c3ccc(F)cc3F)=NN2c2ccc(F)cc2F)COC1]

4-(5-chlorofuran-2-yl)-1,3-bis(2,4-difluorophenyl)-N-((3-methoxyoxetan-3-yl)methyl)-5-methyl-4,5-dihydro-1H-pyrazole-5-carboxamide (Compound 155);

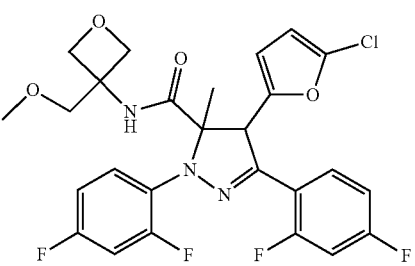 [SMILES: COCC1(NC(=O)C2(C)C(c3ccc(Cl)o3)C(c3ccc(F)cc3F)=NN2c2ccc(F)cc2F)COC1]

4-(5-chlorofuran-2-yl)-1,3-bis(2,4-difluorophenyl)-N-(3-(methoxymethyl)oxetan-3-yl)-5-methyl-4,5-dihydro-1H-pyrazole-5-carboxamide (Compound 156);

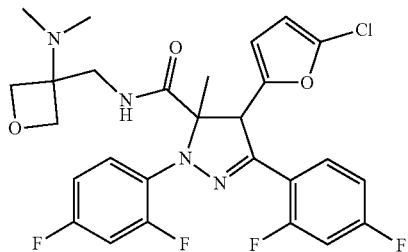 [SMILES: CN(C)C1(CNC(=O)C2(C)C(c3ccc(Cl)o3)C(c3ccc(F)cc3F)=NN2c2ccc(F)cc2F)COC1]

4-(5-chlorofuran-2-yl)-1,3-bis(2,4-difluorophenyl)-N-((3-(dimethylamino)oxetan-3-yl)methyl)-5-methyl-4,5-dihydro-1H-pyrazole-5-carboxamide (Compound 157);

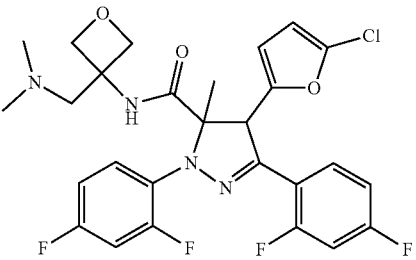 [SMILES: CN(C)CC1(NC(=O)C2(C)C(c3ccc(Cl)o3)C(c3ccc(F)cc3F)=NN2c2ccc(F)cc2F)COC1]

4-(5-chlorofuran-2-yl)-1,3-bis(2,4-difluorophenyl)-N-(3-((dimethylamino)methyl)oxetan-3-yl)-5-methyl-4,5-dihydro-1H-pyrazole-5-carboxamide (Compound 158);

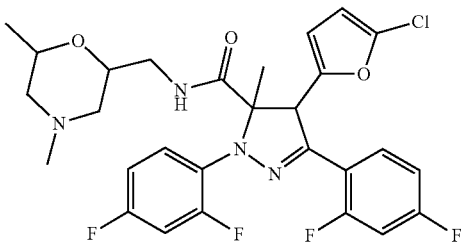 [SMILES: CC1CN(C)CC(CNC(=O)C2(C)C(c3ccc(Cl)o3)C(c3ccc(F)cc3F)=NN2c2ccc(F)cc2F)O1]

4-(5-chlorofuran-2-yl)-1,3-bis(2,4-difluorophenyl)-N-((4,6-dimethylmorpholin-2-yl)methyl)-5-methyl-4,5-dihydro-1H-pyrazole-5-carboxamide (Compound 159);

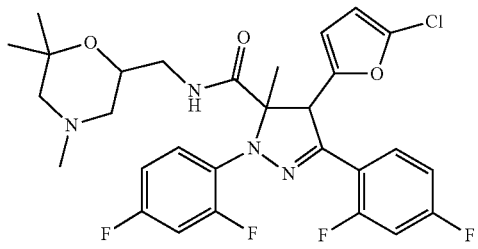 [SMILES: CN1CC(CNC(=O)C2(C)C(c3ccc(Cl)o3)C(c3ccc(F)cc3F)=NN2c2ccc(F)cc2F)OC(C)(C)C1]

4-(5-chlorofuran-2-yl)-1,3-bis(2,4-difluorophenyl)-5-methyl-N-((4,6,6-trimethylmorpholin-2-yl)methyl)-4,5-dihydro-1H-pyrazole-5-carboxamide (Compound 160);

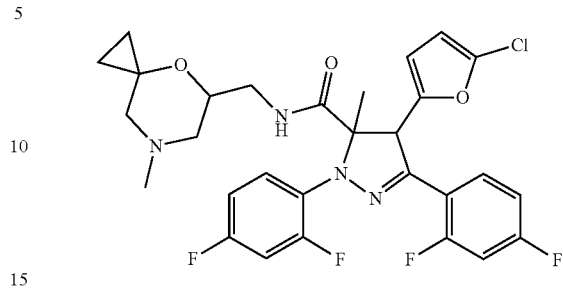

4-(5-chlorofuran-2-yl)-1,3-bis(2,4-difluorophenyl)-5-methyl-N-((7-methyl-4-oxa-7-azaspiro[2.5]octan-5-yl)methyl)-4,5-dihydro-1H-pyrazole-5-carboxamide (Compound 161);

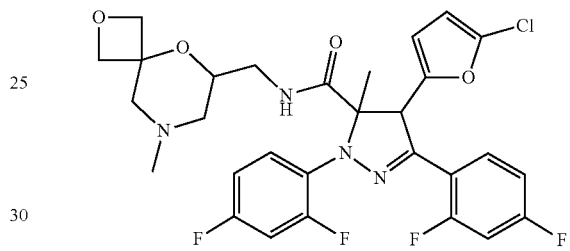

4-(5-chlorofuran-2-yl)-1,3-bis(2,4-difluorophenyl)-5-methyl-N-((8-methyl-2,5-dioxa-8-azaspiro[3.5]nonan-6-yl)methyl)-4,5-dihydro-1H-pyrazole-5-carboxamide (Compound 162);

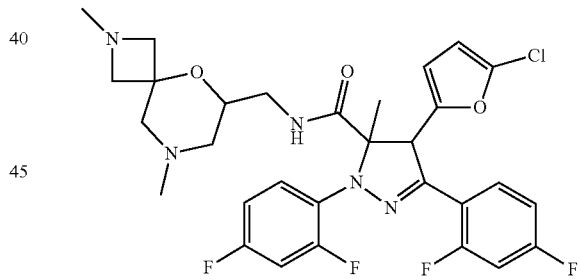

4-(5-chlorofuran-2-yl)-1,3-bis(2,4-difluorophenyl)-N-((2,8-dimethyl-5-oxa-2,8-diazaspiro[3.5]nonan-6-yl)methyl)-5-methyl-4,5-dihydro-1H-pyrazole-5-carboxamide (Compound 163);

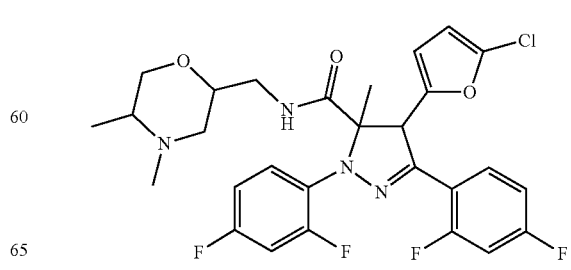

4-(5-chlorofuran-2-yl)-1,3-bis(2,4-difluorophenyl)-N-((4,5-dimethylmorpholin-2-yl)methyl)-5-methyl-4,5-dihydro-1H-pyrazole-5-carboxamide (Compound 164);

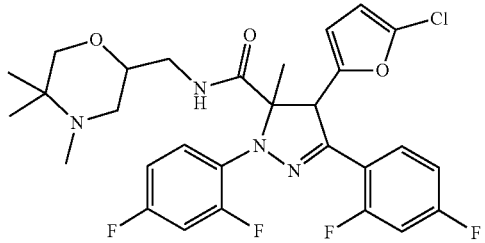 [SMILES: CN1CC(CNC(=O)C2(C)C(c3ccc(Cl)o3)C(c3ccc(F)cc3F)=NN2c2ccc(F)cc2F)OCC1(C)C]

4-(5-chlorofuran-2-yl)-1,3-bis(2,4-difluorophenyl)-5-methyl-N-((4,5,5-trimethylmorpholin-2-yl)methyl)-4,5-dihydro-1H-pyrazole-5-carboxamide (Compound 165);

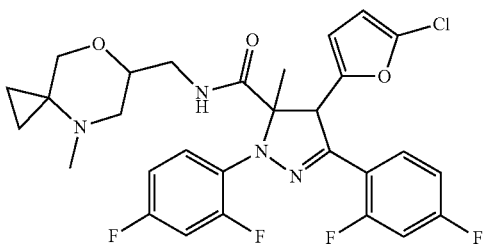 [SMILES: CN1CC(CNC(=O)C2(C)C(c3ccc(Cl)o3)C(c3ccc(F)cc3F)=NN2c2ccc(F)cc2F)OCC12CC2]

4-(5-chlorofuran-2-yl)-1,3-bis(2,4-difluorophenyl)-5-methyl-N-((4-methyl-7-oxa-4-azaspiro[2.5]octan-6-yl)methyl)-4,5-dihydro-1H-pyrazole-5-carboxamide (Compound 166);

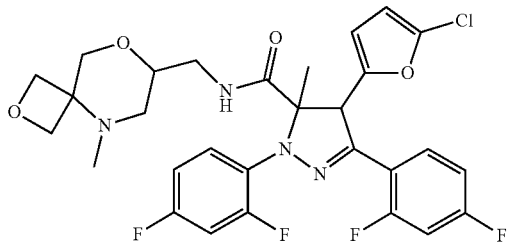 [SMILES: CN1CC(CNC(=O)C2(C)C(c3ccc(Cl)o3)C(c3ccc(F)cc3F)=NN2c2ccc(F)cc2F)OCC12COC2]

4-(5-chlorofuran-2-yl)-1,3-bis(2,4-difluorophenyl)-5-methyl-N-((5-methyl-2,8-dioxa-5-azaspiro[3.5]nonan-7-yl)methyl)-4,5-dihydro-1H-pyrazole-5-carboxamide (Compound 167);

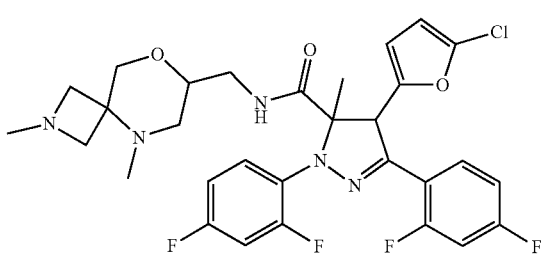 [SMILES: CN1CC2(COC(CNC(=O)C3(C)C(c4ccc(Cl)o4)C(c4ccc(F)cc4F)=NN3c3ccc(F)cc3F)CN2C)C1]

4-(5-chlorofuran-2-yl)-1,3-bis(2,4-difluorophenyl)-N-((2,5-dimethyl-8-oxa-2,5-diazaspiro[3.5]nonan-7-yl)methyl)-5-methyl-4,5-dihydro-1H-pyrazole-5-carboxamide (Compound 168);

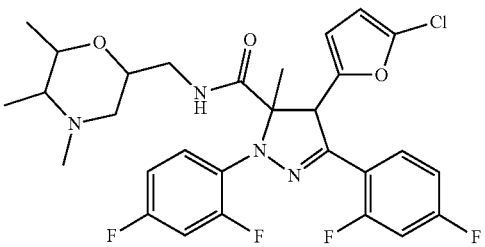 [SMILES: CC1OC(CNC(=O)C2(C)C(c3ccc(Cl)o3)C(c3ccc(F)cc3F)=NN2c2ccc(F)cc2F)CN(C)C1C]

4-(5-chlorofuran-2-yl)-1,3-bis(2,4-difluorophenyl)-5-methyl-N-((4,5,6-trimethylmorpholin-2-yl)methyl)-4,5-dihydro-1H-pyrazole-5-carboxamide (Compound 169);

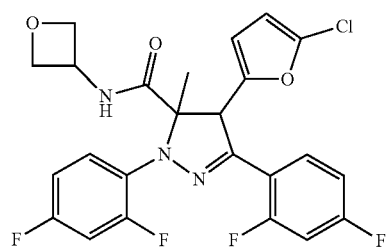 [SMILES: CC1(C(=O)NC2COC2)C(c2ccc(Cl)o2)C(c2ccc(F)cc2F)=NN1c1ccc(F)cc1F]

4-(5-chlorofuran-2-yl)-1,3-bis(2,4-difluorophenyl)-5-methyl-N-(oxetan-3-yl)-4,5-dihydro-1H-pyrazole-5-carboxamide (Compound 170);

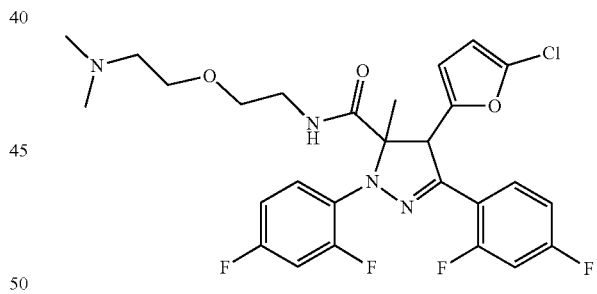

4-(5-chlorofuran-2-yl)-1,3-bis(2,4-difluorophenyl)-N-(2-(2-(dimethylamino)ethoxy)ethyl)-5-methyl-4,5-dihydro-1H-pyrazole-5-carboxamide (Compound 171);

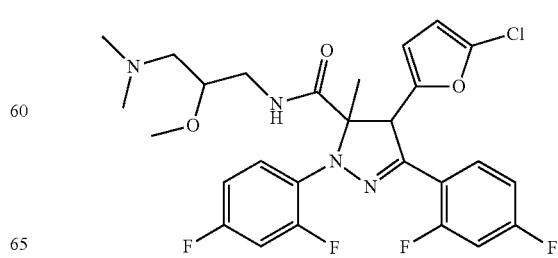

4-(5-chlorofuran-2-yl)-1,3-bis(2,4-difluorophenyl)-N-(3-(dimethylamino)-2-methoxypropyl)-5-methyl-4,5-dihydro-1H-pyrazole-5-carboxamide (Compound 172);

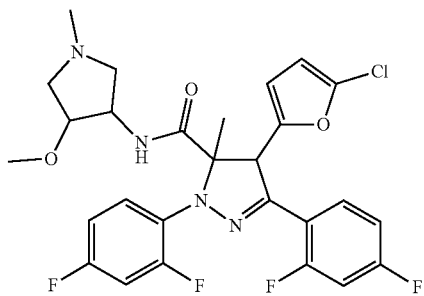 [SMILES: COC1CN(C)CC1NC(=O)C1(C)C(c2ccc(Cl)o2)C(c2ccc(F)cc2F)=NN1c1ccc(F)cc1F]

4-(5-chlorofuran-2-yl)-1,3-bis(2,4-difluorophenyl)-N-(4-methoxy-1-methylpyrrolidin-3-yl)-5-methyl-4,5-dihydro-1H-pyrazole-5-carboxamide (Compound 173);

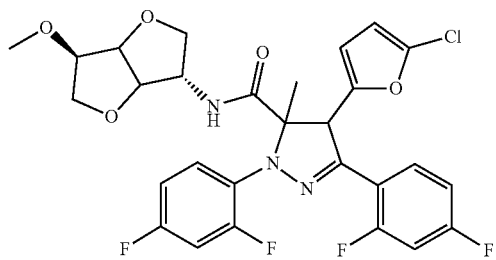 [SMILES: CO[C@@H]1COC2C1OC[C@@H]2NC(=O)C1(C)C(c2ccc(Cl)o2)C(c2ccc(F)cc2F)=NN1c1ccc(F)cc1F]

4-(5-chlorofuran-2-yl)-1,3-bis(2,4-difluorophenyl)-N-((3S,6R)-6-methoxyhexahydrofuro[3,2-b]furan-3-yl)-5-methyl-4,5-dihydro-1H-pyrazole-5-carboxamide (Compound 174);

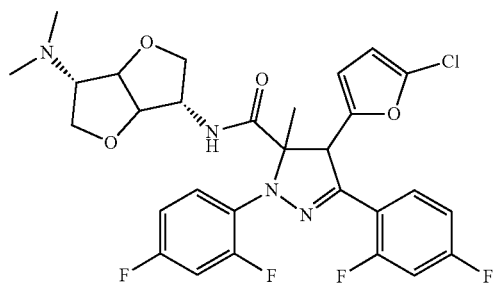 [SMILES: CN(C)[C@H]1COC2C1OC[C@@H]2NC(=O)C1(C)C(c2ccc(Cl)o2)C(c2ccc(F)cc2F)=NN1c1ccc(F)cc1F]

4-(5-chlorofuran-2-yl)-1,3-bis(2,4-difluorophenyl)-N-((3S,6S)-6-(dimethylamino)hexahydrofuro[3,2-b]furan-3-yl)-5-methyl-4,5-dihydro-1H-pyrazole-5-carboxamide (Compound 175);

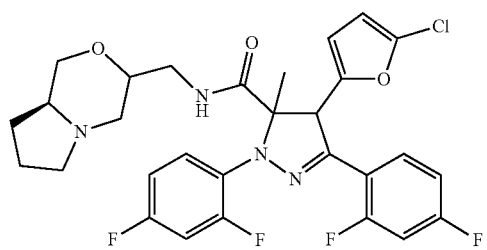 [SMILES: CC1(C(=O)NCC2CN3CCC[C@H]3CO2)C(c2ccc(Cl)o2)C(c2ccc(F)cc2F)=NN1c1ccc(F)cc1F]

4-(5-chlorofuran-2-yl)-1,3-bis(2,4-difluorophenyl)-N-(((8aS)-hexahydro-1H-pyrrolo[2,1-c][1,4]oxazin-3-yl)methyl)-5-methyl-4,5-dihydro-1H-pyrazole-5-carboxamide (Compound 176);

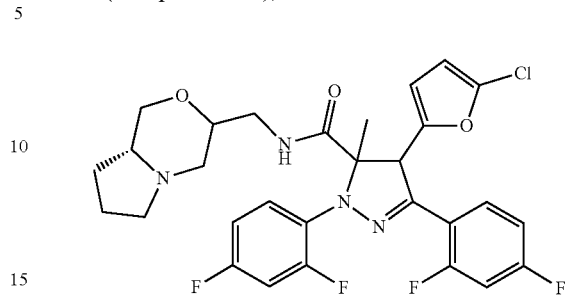

4-(5-chlorofuran-2-yl)-1,3-bis(2,4-difluorophenyl)-N-(((8aR)-hexahydro-1H-pyrrolo[2,1-c][1,4]oxazin-3-yl)methyl)-5-methyl-4,5-dihydro-1H-pyrazole-5-carboxamide (Compound 177);

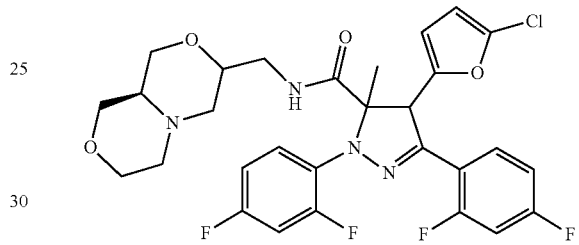

4-(5-chlorofuran-2-yl)-1,3-bis(2,4-difluorophenyl)-N-(((9aS)-hexahydro-1H-[1,4]oxazino[3,4-c][1,4]oxazin-3-yl)methyl)-5-methyl-4,5-dihydro-1H-pyrazole-5-carboxamide (Compound 178);

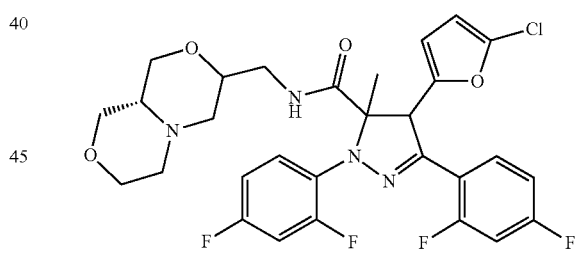

4-(5-chlorofuran-2-yl)-1,3-bis(2,4-difluorophenyl)-N-(((9aR)-hexahydro-1H-[1,4]oxazino[3,4-c][1,4]oxazin-3-yl)methyl)-5-methyl-4,5-dihydro-1H-pyrazole-5-carboxamide (Compound 179);

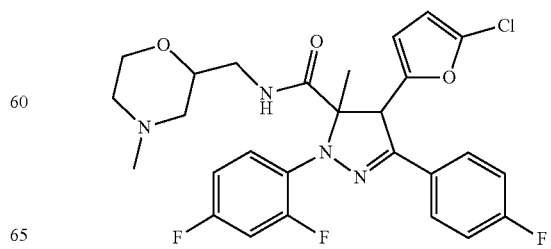

4-(5-chlorofuran-2-yl)-1-(2,4-difluorophenyl)-3-(4-fluorophenyl)-5-methyl-N-((4-methylmorpholin-2-yl)methyl)-4,5-dihydro-1H-pyrazole-5-carboxamide (Compound 180);

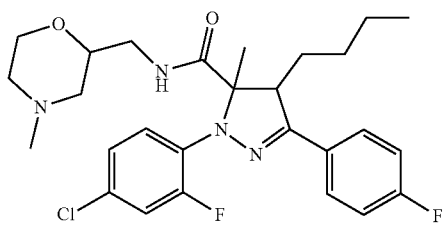 [SMILES: CCCCC1C(c2ccc(F)cc2)=NN(c2ccc(Cl)cc2F)C1(C)C(=O)NCC1CN(C)CCO1]

4-butyl-1-(4-chloro-2-fluorophenyl)-3-(4-fluorophenyl)-5-methyl-N-((4-methylmorpholin-2-yl)methyl)-4,5-dihydro-1H-pyrazole-5-carboxamide (Compound 181);

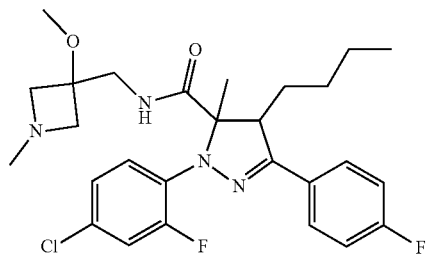 [SMILES: CCCCC1C(c2ccc(F)cc2)=NN(c2ccc(Cl)cc2F)C1(C)C(=O)NCC1(OC)CN(C)C1]

4-butyl-1-(4-chloro-2-fluorophenyl)-3-(4-fluorophenyl)-N-((3-methoxy-1-methylazetidin-3-yl)methyl)-5-methyl-4,5-dihydro-1H-pyrazole-5-carboxamide (Compound 182);

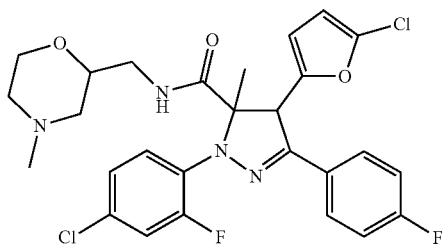 [SMILES: CN1CCOC(CNC(=O)C2(C)C(c3ccc(Cl)o3)C(c3ccc(F)cc3)=NN2c2ccc(Cl)cc2F)C1]

1-(4-chloro-2-fluorophenyl)-4-(5-chlorofuran-2-yl)-3-(4-fluorophenyl)-5-methyl-N-((4-methylmorpholin-2-yl)methyl)-4,5-dihydro-1H-pyrazole-5-carboxamide (Compound 183);

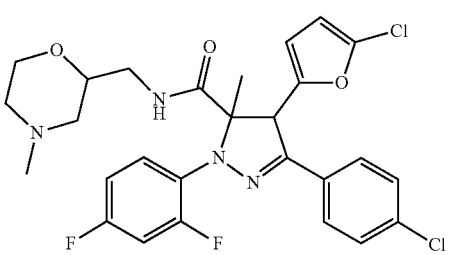 [SMILES: CN1CCOC(CNC(=O)C2(C)C(c3ccc(Cl)o3)C(c3ccc(Cl)cc3)=NN2c2ccc(F)cc2F)C1]

4-(5-chlorofuran-2-yl)-3-(4-chlorophenyl)-1-(2,4-difluorophenyl)-5-methyl-N-((4-methylmorpholin-2-yl)methyl)-4,5-dihydro-1H-pyrazole-5-carboxamide (Compound 184);

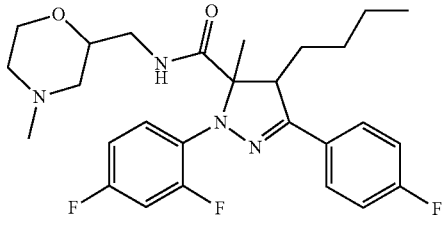 [SMILES: CCCCC1C(c2ccc(F)cc2)=NN(c2ccc(F)cc2F)C1(C)C(=O)NCC1CN(C)CCO1]

4-butyl-1-(2,4-difluorophenyl)-3-(4-fluorophenyl)-5-methyl-N-((4-methylmorpholin-2-yl)methyl)-4,5-dihydro-1H-pyrazole-5-carboxamide (Compound 185);

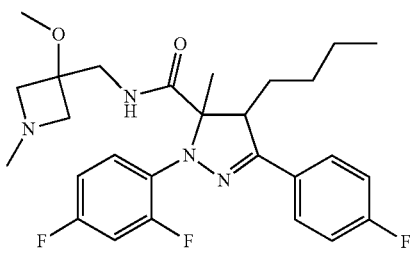 [SMILES: CCCCC1C(c2ccc(F)cc2)=NN(c2ccc(F)cc2F)C1(C)C(=O)NCC1(OC)CN(C)C1]

4-butyl-1-(2,4-difluorophenyl)-3-(4-fluorophenyl)-N-((3-methoxy-1-methylazetidin-3-yl)methyl)-5-methyl-4,5-dihydro-1H-pyrazole-5-carboxamide (Compound 186);

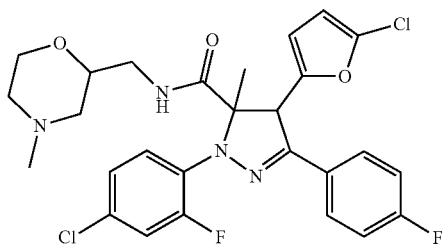 [SMILES: CN1CCOC(CNC(=O)C2(C)C(c3ccc(Cl)o3)C(c3ccc(F)cc3)=NN2c2ccc(Cl)cc2F)C1]

4-butyl-1-(2,4-difluorophenyl)-3-(4-fluorophenyl)-N-((3-methoxyoxetan-3-yl)methyl)-5-methyl-4,5-dihydro-1H-pyrazole-5-carboxamide (Compound 187);

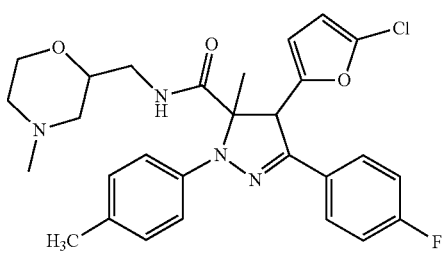 [SMILES: Cc1ccc(N2N=C(c3ccc(F)cc3)C(c3ccc(Cl)o3)C2(C)C(=O)NCC2CN(C)CCO2)cc1]

4-(5-chlorofuran-2-yl)-3-(4-fluorophenyl)-5-methyl-N-((4-methylmorpholin-2-yl)methyl)-1-(p-tolyl)-4,5-dihydro-1H-pyrazole-5-carboxamide (Compound 188);

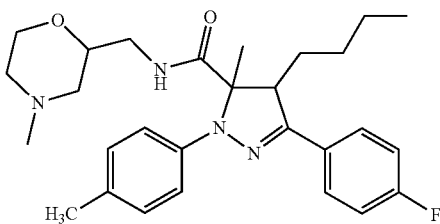 [SMILES: CCCCC1C(c2ccc(F)cc2)=NN(c2ccc(C)cc2)C1(C)C(=O)NCC1CN(C)CCO1]

4-butyl-3-(4-fluorophenyl)-5-methyl-N-((4-methylmorpholin-2-yl)methyl)-1-(p-tolyl)-4,5-dihydro-1H-pyrazole-5-carboxamide (Compound 189);

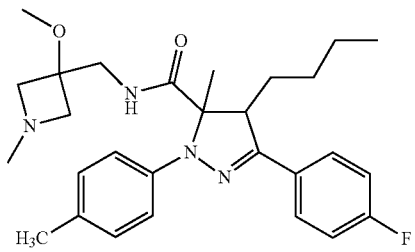 [SMILES: CCCCC1C(c2ccc(F)cc2)=NN(c2ccc(C)cc2)C1(C)C(=O)NCC1(OC)CN(C)C1]

4-butyl-3-(4-fluorophenyl)-N-((3-methoxy-1-methylazetidin-3-yl)methyl)-5-methyl-1-(p-tolyl)-4,5-dihydro-1H-pyrazole-5-carboxamide (Compound 190); and

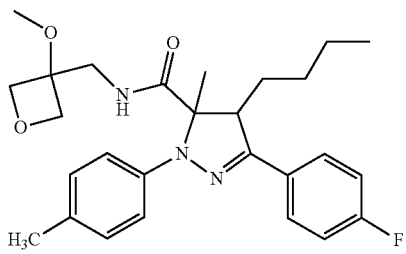 [SMILES: CCCCC1C(c2ccc(F)cc2)=NN(c2ccc(C)cc2)C1(C)C(=O)NCC1(OC)COC1]

4-butyl-3-(4-fluorophenyl)-N-((3-methoxyoxetan-3-yl)methyl)-5-methyl-1-(p-tolyl)-4,5-dihydro-1H-pyrazole-5-carboxamide (Compound 191).

Preparation of Compounds

Many general references providing commonly known chemical synthetic schemes and conditions useful for synthesizing the disclosed compounds are available (see, e.g., Smith and March, March's Advanced Organic Chemistry: Reactions, Mechanisms, and Structure, Fifth Edition, Wiley-Interscience, 2001; or Vogel, A Textbook of Practical Organic Chemistry, Including Qualitative Organic Analysis, Fourth Edition, New York: Longman, 1978). The compounds of the embodiments can be prepared according to standard chemical synthetic schemes. One of skill in the art will recognize that additional methods exist for the preparation of the compounds of the embodiments.

Compounds as described herein can be purified by any of the means known in the art, including chromatographic means, such as high performance liquid chromatography (HPLC), preparative thin layer chromatography, flash column chromatography and ion exchange chromatography. Any suitable stationary phase can be used, including normal and reversed phases as well as ionic resins. See, e.g., Introduction to Modern Liquid Chromatography, 2nd Edition, ed. L. R. Snyder and J. J. Kirkland, John Wiley and Sons, 1979; and Thin Layer Chromatography, ed E. Stahl, Springer-Verlag, New York, 1969.

During any of the processes for preparation of the compounds of the present disclosure, it may be necessary and/or desirable to protect sensitive or reactive groups on any of the molecules concerned. This can be achieved by means of conventional protecting groups as described in standard works, such as T. W. Greene and P. G. M. Wuts, "Protective Groups in Organic Synthesis", Fourth edition, Wiley, New York 2006. The protecting groups can be removed at a convenient subsequent stage using methods known from the art.

In certain embodiments, a compound of formula (I) comprises a label. Labels may be useful for detecting and testing the distribution of the compound after administration in vivo. For example, tritium (3H) can be used as a label in conventional pharmacokinetic/dynamic studies. A compound comprising a label can be detected by, for example, spectroscopic, photochemical, biochemical, immunochemical, chemical, or other physical means.

A compound of the embodiments may also contain unnatural proportions of atomic isotopes at one or more of the atoms that constitute such compounds. For example, the compounds may be radiolabeled with radioactive isotopes, such as for example deuterium ($^2$H), tritium ($^3$H), or carbon-14 ($^{14}$C). All isotopic variations of the compounds of the embodiments, whether radioactive or not, are intended to be encompassed within the scope of the embodiments.

An example of a process for preparing compounds of the present disclosure is described and illustrated in the reaction schemes shown below. The variables and substituents described and shown in the reaction schemes below (e.g., $R^3$, $R^5$, $R^6$, $R^7$, m, n, etc.) are the same as those described herein in relation to compounds of the present disclosure.

Scheme 1

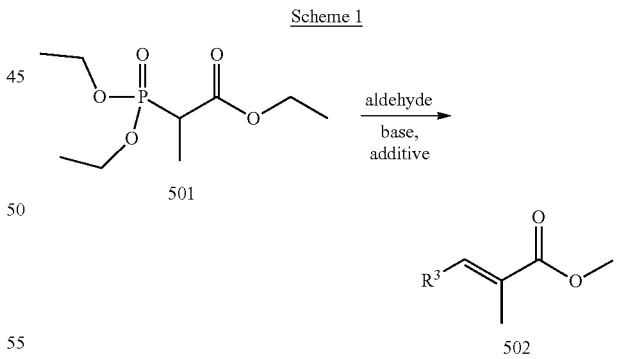

For the preparation of intermediate compounds (α-methyl-α,β-unsaturated esters) represented by formula 502 the Horner-Wadsworth-Emmons modification of the Wittig reaction may be used, which has a high preference for the formation of the thermodynamically more stable E-olefins. High yield and E-selective olefination can be achieved in the presence of lithium or magnesium halides and bases such as DBU, diisopropylethylamine or triethylamine using triethyl-2 phosphonopropionate (501) as the phosphonate and aliphatic or aromatic aldehydes.

Scheme 2

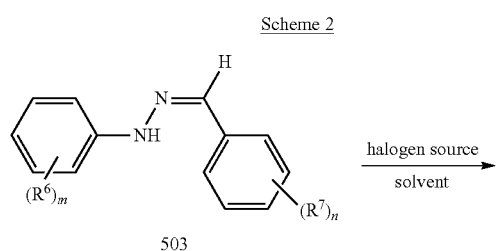

Hydrazonyl halides, represented by formula 504 (X=Cl or Br) can be precursors for nitrile imines, which may be used in 1,3-dipolar cycloaddition reactions for the formation of five-member heterocycles and may be prepared by reacting N'-aroyl-N-aryl-hydrazines with phosphorous pentachloride, Appel's reagent or dichlorotriphenylphosphorane, or from the corresponding hydrazones with Chloramine-T and used in situ. Electrophilic bromination of hydrazones may provide hydrazonyl bromides. Alternatively hydrazonyl halides may be prepared by the reaction of an optional hydrazone with the appropriate Core-Kim reagent (e.g., N-halosuccinimide-dimethyl sulfide complex).

Scheme 3

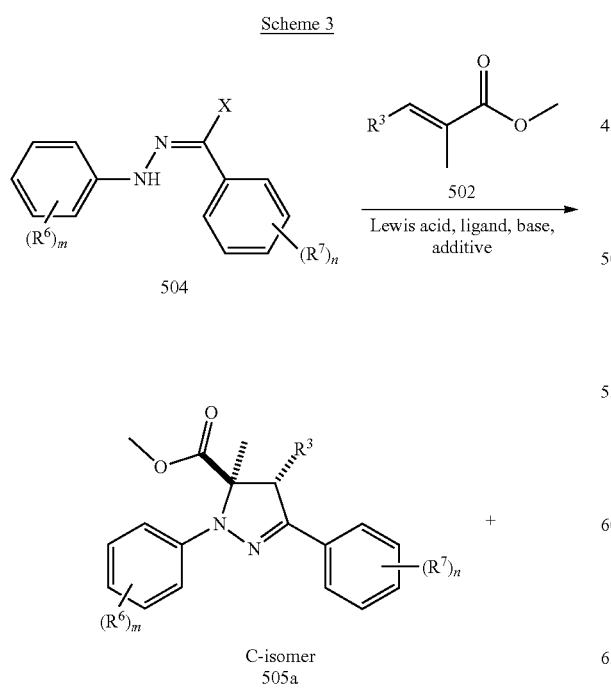

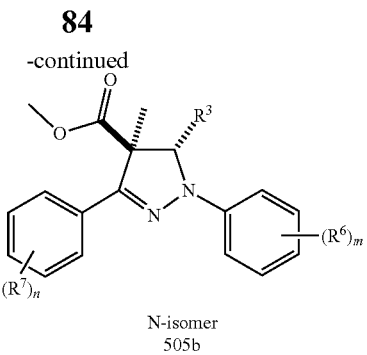

As shown in Scheme 3, 4,5-dihydropyrazole intermediates of formula 505a and 505b may be prepared using [3+2] cycloaddition reactions of nitrile imine dipoles of interest generated from their respected hydrazonyl chloride precursor in situ, with olefins (e.g., α,β-unsaturated-enoates), such as compounds of formula 502, as dipolarophiles. The E-geometry of the dipolarophile is translated into trans stereochemistry of the C4 and C5 positions of the 2-pyrazolines. In addition to the reaction condition, the regioselectivity of the reaction may also be influenced by the electronics of the dipole and the dipolarophile; α,β-disubstituted-α,β-unsaturated dipolarophiles promote the formation of C-regioisomer; electron withdrawing groups on the aryl rings may decrease regioselectivity. The regioisomers may be separated using conventional chromatographic methods. The use of an appropriate Lewis acid catalyst and ligand at low temperature may influence the enantioselectivity of the reaction.

Scheme 4

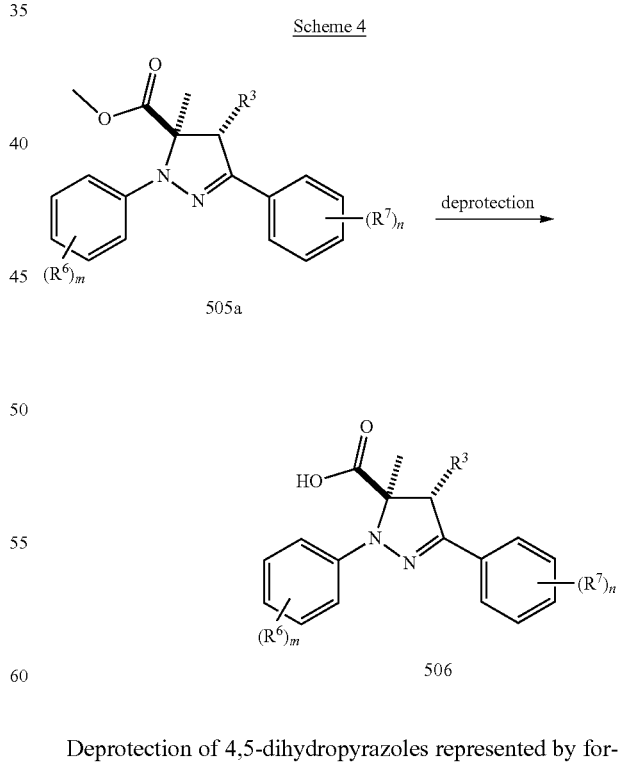

Deprotection of 4,5-dihydropyrazoles represented by formula 505a may be achieved under basic condition, using aqueous lithium, sodium, or potassium hydroxide solutions. The resulting salt may be converted to the free carboxylic acid (506) by treating the salt with dilute acid.

Scheme 5

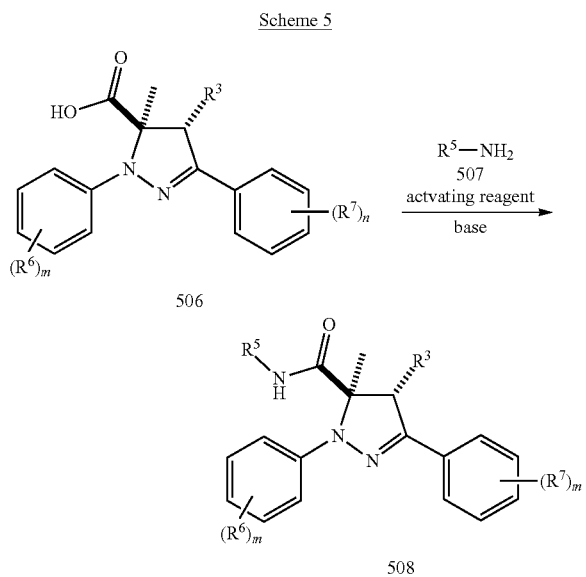

Compounds of formula 508 can be prepared from a carboxylic acid 506 and an amine 507, according to Scheme 5. The reaction may be carried out in the presence of an activating reagent, for example, N-(3-dimethylaminopropyl)-N'-ethylcarbodiimide hydrochloride (EDCI) or O-(7-azabenzotriazol-1-yl)-N,N,N',N'-tetramethyluronium hexafluorophosphate (HATU), in an organic solvent, for example, N,N-dimethylformamide or dichloromethane, optionally in the presence of a base, e.g., N,N-diisopropylethylamine or triethylamine, at a temperature, for example in the range from 0° C. to 60° C.

Enantiomer-Specific Activity

In certain embodiments, the compounds described herein may include two or more stereoisomers. As used herein, the term "stereoisomers" refers to compounds of the embodiments that possess asymmetric carbon atoms (optical centers) or double bonds. For example, the compounds described herein may include two enantiomers. As used herein, an "enantiomer" is one of two stereoisomers that are non-superimposable mirror images of each other. In some instances, a racemic mixture of enantiomers of a compound may be separated into individual enantiomers. For instance, enantiomers may be separated using separation techniques, such as, but not limited to high-performance liquid chromatography (HPLC) (e.g., chiral HPLC), crystallization, and the like. In other embodiments, individual enantiomers may be synthesized separately, for example by using chiral starting materials and asymmetric synthetic techniques.

In certain embodiments, individual enantiomers may be separated using chiral separation techniques (e.g., chiral HPLC), as described above. In some cases, the chiral separation technique is configured to provide substantially pure individual enantiomers. For example, an individual enantiomer may have a purity of 90% or more, such as 95% or more, or 96% or more, or 97% or more, or 98% or more, or 99% or more, or 99.5% or more, or 99.9% or more, or even 100% purity. In certain instances, an individual enantiomer has a purity of 98%, or 99%, or 99.9%. In some cases, the separated enantiomer has an enantiomeric excess of 90% or more, such as 95% or more, or 96% or more, or 97% or more, or 98% or more, or 99% or more, or 99.5% or more, or 99.9% or more.

In embodiments where chiral separation techniques (e.g., chiral HPLC) are used to separate the individual enantiomers, the different enantiomers may have significantly different retention times under the separation conditions used (see e.g., Example 16 below). For example, a first enantiomer may have a significantly shorter retention time than a second enantiomer. In these cases, the first enantiomer may be described as the "faster eluting" enantiomer, and the second enantiomer may be described as the "slower eluting" enantiomer. In some instances, the first and second enantiomers may have a difference in elution times of 0.1 min or more, including 0.2 min or more, such as 0.3 min or more, or 0.4 min or more, or 0.5 min or more, or 0.6 min or more, or 0.7 min or more, or 0.8 min or more, or 0.9 min or more, or 1 min or more, or 1.1 min or more, or 1.2 min or more, or 1.3 min or more, or 1.4 min or more, or 1.5 min or more, or 1.6 min or more, or 1.7 min or more, or 1.8 min or more, or 1.9 min or more, or 2 min or more or 2.5 min or more, or 3 min or more, or 3.5 min or more, or 4 min or more, or 4.5 min or more, or 5 min or more. In some embodiments, the first and second enantiomers have a difference in elution times ranging from 0.5 min to 2 min, such as 0.5 min to 1.5 min, or from 0.7 min to 1.2 min. For example, the first and second enantiomers may have a difference in elution times of 1 min.

In certain embodiments, one enantiomer may have an activity greater than the activity of the other enantiomer. For example, a first enantiomer may have an activity greater than the activity of a second enantiomer. Alternatively, the second enantiomer may have an activity greater than the activity of the first enantiomer. In some cases, as described above, the enantiomers may be distinguished from each other based on their retention times in a chiral separation technique (e.g., chiral HPLC). In these instances, the first enantiomer (e.g., the faster eluting enantiomer) may have an activity significantly different from the second enantiomer (e.g., the slower eluting enantiomer). For instance, the faster eluting enantiomer may have an activity greater than the slower eluting enantiomer. In other embodiments, the slower eluting enantiomer has an activity greater than the faster eluting enantiomer.

In some cases, the activity of a compound may be measured by its half-maximal inhibitor concentration ($IC_{50}$). The $IC_{50}$ is a measure of the effectiveness of a compound in inhibiting a biological process (or component of a process, e.g., an enzyme, cell, cell receptor, microorganism, etc.). This quantitative measure indicates how much of a compound is needed to inhibit the biological process by half. In certain embodiments, as described above, enantiomers of a compound may have significantly different activities. For example, a second enantiomer (e.g., the slower eluting enantiomer) may have an $IC_{50}$ less than a first enantiomer (e.g., the faster eluting enantiomer); i.e., the second enantiomer is more active than the first enantiomer. In some cases, the $IC_{50}$ of the second enantiomer is 75% or less of the $IC_{50}$ of the first enantiomer, such as 70% or less, including 65% or less, or 60% or less, or 55% or less, or 50% or less, or 45% or less, or 40% or less, or 35% or less, or 30% or less, or 25% or less, or 20% or less, or 15% or less, or 10% or less, or 5% or less, or 3% or less, or the $IC_{50}$ of the second enantiomer is 1% or less of the $IC_{50}$ of the first enantiomer.

In other embodiments, the first enantiomer (e.g., the faster eluting enantiomer) has an $IC_{50}$ less than the second enantiomer (e.g., the slower eluting enantiomer); i.e., the first enantiomer is more active than the second enantiomer. In certain instances, the $IC_{50}$ of the first enantiomer is 75% or less of the $IC_{50}$ of the second enantiomer, such as 70% or less, including 65% or less, or 60% or less, or 55% or less, or 50% or less, or 45% or less, or 40% or less, or 35% or less, or 30% or less, or 25% or less, or 20% or less, or 15% or less, or 10% or less, or 5% or less, or 3% or less, or the $IC_{50}$ of the first enantiomer is 1% or less of the $IC_{50}$ of the second enantiomer.

Testing of Compounds in Cell-Based Assays

A compound of the embodiments can be screened for activity in vitro and in vivo. For in vitro assays, the disclosure provides cell-based cytotoxicity assays, as described herein. For in vivo assays, the disclosure provides mouse xenograft assays as described herein.

Pharmaceutical Compositions

The disclosure provides a pharmaceutical composition or a medicament comprising at least one compound of formula (I) and optionally a pharmaceutically acceptable carrier. A pharmaceutical composition or medicament can be administered to a patient for the treatment of, for example, a condition, such as a cancer or a fibrosis.

Formulation and Administration

The compounds of the embodiments are useful in the manufacture of a pharmaceutical composition or a medicament comprising an effective amount thereof in conjunction or mixture with excipients or carriers suitable for either enteral or parenteral application. Pharmaceutical compositions or medicaments for use in the embodiments can be formulated by standard techniques using one or more physiologically acceptable carriers or excipients. Suitable pharmaceutical carriers are described herein and in "Remington's Pharmaceutical Sciences" by E. W. Martin. The compounds of embodiments and their physiologically acceptable salts and solvates can be formulated for administration by any suitable route, including via inhalation, topically, nasally, orally, parenterally, or rectally. Thus, the administration of the pharmaceutical composition may be made by intradermal, subdermal, intravenous, intramuscular, intranasal, intracerebral, intratracheal, intraarterial, intraperitoneal, intravesical, intrapleural, intracoronary or intratumoral injection, with a syringe or other devices. Transdermal administration is also contemplated, as are inhalation or aerosol administration. Tablets and capsules can be administered orally, rectally or vaginally.

For oral administration, a pharmaceutical composition or a medicament can take the form of, for example, a tablets or a capsule prepared by conventional means with a pharmaceutically acceptable carrier and/or pharmaceutically acceptable excipient. In certain embodiments, tablets and gelatin capsules comprise the active ingredient, i.e., a compound of the embodiments, together with (a) diluents or fillers, e.g., lactose, dextrose, sucrose, mannitol, sorbitol, cellulose (e.g., ethyl cellulose, microcrystalline cellulose), glycine, pectin, polyacrylates and/or calcium hydrogen phosphate, calcium sulfate; (b) lubricants, e.g., silica, talcum, stearic acid, its magnesium or calcium salt, metallic stearates, colloidal silicon dioxide, hydrogenated vegetable oil, corn starch, sodium benzoate, sodium acetate and/or polyethyleneglycol; for tablets also (c) binders, e.g., magnesium aluminum silicate, starch paste, gelatin, tragacanth, methylcellulose, sodium carboxymethylcellulose, polyvinylpyrrolidone and/or hydroxypropyl methylcellulose; if desired (d) disintegrants, e.g., starches (e.g., potato starch or sodium starch), glycolate, agar, alginic acid or its sodium salt, or effervescent mixtures; (e) wetting agents, e.g., sodium lauryl sulphate, and/or (f) absorbents, colorants, flavors and sweeteners.

Tablets may be either film coated or enteric coated according to methods known in the art. Liquid preparations for oral administration can take the form of, for example, solutions, syrups, or suspensions, or they can be presented as a dry product for constitution with water or other suitable vehicle before use. Such liquid preparations can be prepared by conventional means with pharmaceutically acceptable additives, for example, suspending agents, for example, sorbitol syrup, cellulose derivatives, or hydrogenated edible fats; emulsifying agents, for example, lecithin or acacia; non-aqueous vehicles, for example, almond oil, oily esters, ethyl alcohol, or fractionated vegetable oils; and preservatives, for example, methyl or propyl-p-hydroxybenzoates or sorbic acid. The preparations can also contain buffer salts, flavoring, coloring, and/or sweetening agents as appropriate. If desired, preparations for oral administration can be suitably formulated to give controlled release of the active compound.

For administration by inhalation, the compounds may be conveniently delivered in the form of an aerosol spray presentation from pressurized packs or a nebulizer, with the use of a suitable propellant, for example, dichlorodifluoromethane, trichlorofluoromethane, dichlorotetrafluoroethane, carbon dioxide, or other suitable gas. In the case of a pressurized aerosol, the dosage unit can be determined by providing a valve to deliver a metered amount. Capsules and cartridges of, for example, gelatin for use in an inhaler or insufflator can be formulated containing a powder mix of the compound and a suitable powder base, for example, lactose or starch.

The compounds of the embodiments can be formulated for parenteral administration by injection, for example by bolus injection or continuous infusion. Formulations for injection can be presented in unit dosage form, for example, in ampoules or in multi-dose containers, with an added preservative. In certain embodiments, injectable compositions are aqueous isotonic solutions or suspensions, and suppositories are prepared from fatty emulsions or suspensions. The compositions may be sterilized and/or contain adjuvants, such as preserving, stabilizing, wetting or emulsifying agents, solution promoters, salts for regulating the osmotic pressure and/or buffers. Alternatively, the active ingredient can be in powder form for constitution with a suitable vehicle, for example, sterile pyrogen-free water, before use. In addition, they may also contain other therapeutically valuable substances. The compositions are prepared according to conventional mixing, granulating or coating methods, respectively, and contain about 0.1 to 75%, or about 1 to 50%, of the active ingredient.

Suitable formulations for transdermal application include an effective amount of a compound of the embodiments with carrier. In certain embodiments, carriers include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and optionally an adhesive overlay to secure the device to the skin. Matrix transdermal formulations may also be used.

In certain embodiments, suitable formulations for topical application, e.g., to the skin and eyes, are aqueous solutions, ointments, creams or gels well-known in the art. Such may contain solubilizers, stabilizers, tonicity enhancing agents, buffers and preservatives.

The compounds can also be formulated in rectal compositions, for example, suppositories or retention enemas, for example, containing conventional suppository bases, for example, cocoa butter or other glycerides.

Furthermore, the compounds can be formulated as a depot preparation. Such long-acting formulations can be administered by implantation (for example, subcutaneously or intramuscularly) or by intramuscular injection. Thus, for example, the compounds can be formulated with suitable polymeric or hydrophobic materials (for example, as an emulsion in an acceptable oil) or ion exchange resins, or as sparingly soluble derivatives, for example, as a sparingly soluble salt.

The compositions can, if desired, be presented in a pack or dispenser device that can contain one or more unit dosage forms containing the active ingredient. The pack can, for example, comprise metal or plastic foil, for example, a blister pack. The pack or dispenser device can be accompanied by instructions for administration.

Combination Formulations

In certain embodiments, a pharmaceutical composition or medicament comprises an effective amount of a compound of the embodiments as defined herein, and another therapeutic agent, such as a chemotherapeutic agent.

Examples of chemotherapeutic agents include, but are not limited to, daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine (CA), 5-azacytidine, hydroxyurea, deoxycoformycin, 4-hydroxyperoxycyclophosphor-amide, 5-fluorouracil (5-FU), 5-fluorodeoxyuridine (5-FUdR), methotrexate (MTX), colchicine, taxol, vincristine, vinblastine, etoposide, trimetrexate, teniposide, cisplatin diethylstilbestrol (DES), vismodegib (GDC-0449), erlotinib (Tarceva®), pemetrexed (Alimta®), PI3K inhibitor LY294002, TGFβ inhibitor SB431542, and cisplatin. See, generally, The Merck Manual of Diagnosis and Therapy, 15th Ed. 1987, pp. 1206-1228, Berkow et al., eds., Rahway, N.J.

In certain embodiments, a pharmaceutical composition or medicament comprises a compound of the embodiments and another therapeutic agent selected from vismodegib (GDC-0449), erlotinib (Tarceva®), pemetrexed (Alimta®), LY294002, SB431542, and cisplatin. In certain embodiments, a pharmaceutical composition or medicament comprises a compound of the embodiments and vismodegib (GDC-0449). In certain embodiments, a pharmaceutical composition or medicament comprises a compound of the embodiments and erlotinib (Tarceva®). In certain embodiments, a pharmaceutical composition or medicament comprises a compound of the embodiments and pemetrexed (Alimta®). In certain embodiments, a pharmaceutical composition or medicament comprises a compound of the embodiments and LY294002. In certain embodiments, a pharmaceutical composition or medicament comprises a compound of the embodiments and SB431542. In certain embodiments, a pharmaceutical composition or medicament comprises a compound of the embodiments and cisplatin.

When used with a compound of the embodiments, such chemotherapeutic agent may be used individually (e.g., 5-FU and compound of the embodiments), sequentially (e.g., 5-FU and compound of the embodiments for a period of time followed by e.g., MTX and compound of the embodiments), or in combination with one or more other such chemotherapeutic agents (e.g., 5-FU, MTX and compound of the embodiments, or 5-FU, radiotherapy and compound of the embodiments). Administration may be by the same or different route of administration or together in the same pharmaceutical formulation.

In certain embodiments, a therapeutically effective amount of a compound of the embodiments is administered in combination with surgery, and optionally administration of another chemotherapeutic agent.

In certain embodiments, a pharmaceutical composition or medicament comprises a compound of the embodiments and another therapeutic agent, such as an antibody (e.g., a therapeutically effective antibody). Antibodies suitable for use in the embodiments of the present disclosure include antibodies that specifically bind to a Shh polypeptide, or an antigen binding fragment thereof. For example, antibodies suitable for use in the embodiments of the present disclosure are described in U.S. Provisional Application titled "Antibodies Specific to Sonic Hedgehog and Methods of Use Thereof", filed Jun. 29, 2016, the disclosure of which is incorporated herein by reference. As described herein, when used with a compound of the embodiments, such antibodies may be administered individually (e.g., a therapeutically effective antibody composition and a separate composition comprising a compound of the embodiments), sequentially (e.g., an antibody followed by a compound of the embodiments after a period of time, or vice versa), or in combination (e.g., a therapeutically effective composition comprising an antibody and a compound of the embodiments). Administration may be by the same or different route of administration or together in the same pharmaceutical formulation.

Also provided herein are combination formulations that include a compound of the present disclosure conjugated to an antibody (e.g., a therapeutically effective antibody). Antibodies suitable for use in the embodiments of the present disclosure include antibodies that specifically bind to a Shh polypeptide, or an antigen binding fragment thereof. For example, antibodies suitable for use in the embodiments of the present disclosure are described in U.S. Provisional Application titled "Antibodies Specific to Sonic Hedgehog and Methods of Use Thereof", filed Jun. 29, 2016, the disclosure of which is incorporated herein by reference. By "conjugate" is meant a first moiety (e.g., a compound of the present disclosure) that is stably associated with a second moiety (e.g., an antibody). By "stably associated" is meant that a moiety is bound to another moiety or structure under standard conditions. In certain embodiments, the first and second moieties are bound to each other through one or more covalent bonds. The compound of the present disclosure may be conjugated to any one or more Ig polypeptides (i.e., heavy chain or light chain) of the antibody.

The compound of the present disclosure may be attached to the antibody in any suitable manner, and in a manner compatible with the activity of the compound and/or the antibody, e.g., the therapeutic activity of the compound when administered to an individual to treat a cancer. Thus, in some cases, the compound of the present disclosure is attached non-covalently to the antibody. In some cases, the antibody is functionalized with a carrier, (e.g., a polymeric carrier, a liposome, etc.), and the compound may interact non-covalently with the carrier, to attach the compound to the antibody.

In some cases, the compound of the present disclosure is attached covalently to the antibody in an antibody conjugate. The antibody conjugate may then be represented schematically as: X-(L-)Y, where X is the antibody, L is an optional linking group, Y is the compound of the present disclosure, and "-" represent covalent bonds. The compound may be covalently attached to the antibody in the conjugate in any suitable manner. A compound may be attached, for example to reduced SH groups (e.g., of a cysteine residue) to form a disulfide bond between the compound and an Ig polypeptide of the antibody, and/or to carbohydrate side chains of an Ig polypeptide of the antibody, which may involve a secondary amine formed via reduction of an initial Schiff base (imine) linkage between an oxidized carbohydrate of the Ig polypeptide and a free amine group. A compound may be attached at the hinge region of a reduced antibody component via disulfide bond formation. Alternatively, such agents can be attached using a heterobifunctional cross-linker, such as N-succinyl 3-(2-pyridyldithio)propionate (SPDP). Thus, a suitable Ig polypeptide of an antibody included in the present antibody conjugates may be engineered to include a suitable conjugation site for attaching a payload and/or a linking group, e.g., by modifying one or more amino acids in the amino acid sequence of the Ig polypeptide compared to a parent Ig polypeptide which may lacked suitable sites for conjugation of the payload and/or linking group. The modification may include one or more of insertion, deletion, and substitution of one or more amino acids of the parent Ig polypeptide, as is appropriate to introduce a conjugation site that is accessible to the conjugation chemistry.

In some embodiments, the compound is conjugated via a carbohydrate moiety in the Fc region of the antibody. The Fc region may be absent if the antibody component of the antibody conjugate is an antibody fragment. However, it is possible to introduce a carbohydrate moiety into the light chain variable region of a full length antibody or antibody fragment.

In some embodiments, the compound is attached to an antibody or fragment through the use of click chemistry reactions. Any suitable click chemistry may be used, such as the Huisgen 1,3-dipolar cycloaddition copper catalyzed reaction, which links a conjugating moiety (e.g., the compound) to the antibody through a chemically stable 1,4-disubstituted 1,2,3-triazole group. Other alternatives include cycloaddition reactions such as the Diels-Alder, nucleophilic substitution reactions (such as to small strained rings like epoxy and aziridine compounds), carbonyl chemistry formation of urea compounds and reactions involving carbon-carbon double bonds, such as alkynes in thiol-yne reactions.

Any suitable linking group (L) may be used to conjugate the antibody (i.e., an Ig polypeptide of the antibody) with a compound of the present disclosure. The linking group may be a cleavable linking group, or a non-cleavable linking group.

For example, in some embodiments, the linking group is cleavable by a cleaving agent that is present in the intracellular environment (e.g., within a lysosome or endosome or caveolea). The linking group can be, e.g., a peptidyl linking group that is cleaved by an intracellular peptidase or protease enzyme, including, but not limited to, a lysosomal or endosomal protease. Typically, the peptidyl linking group is at least two amino acids long or at least three amino acids long. Cleaving agents can include cathepsins B and D and plasmin, which may hydrolyze the peptidyl linking group, resulting in the release of the payload, e.g., therapeutic agent, inside target cells. For example, a peptidyl linking group that is cleavable by the thiol-dependent protease cathepsin-B, which is highly expressed in cancerous tissue, can be used (e.g., a Phe-Leu or a Gly-Phe-Leu-Gly linking group). Other such linking groups are described, e.g., in U.S. Pat. No. 6,214,345. In specific embodiments, the peptidyl linking group cleavable by an intracellular protease is a Val-Cit linking group or a Phe-Lys linking group.

In other embodiments, the cleavable linking group is pH-sensitive, i.e., sensitive to hydrolysis at certain pH values. Typically, the pH-sensitive linking group hydrolyzable under acidic conditions. For example, an acid-labile linking group that is hydrolyzable in the lysosome (e.g., a hydrazone, semicarbazone, thiosemicarbazone, cis-aconitic amide, orthoester, acetal, ketal, or the like) can be used. Such linking groups are relatively stable under neutral pH conditions, such as those in the blood, but are unstable at below pH 5.5 or 5.0, the approximate pH of the lysosome. In certain embodiments, the hydrolyzable linking group is a thioether linking group (such as, e.g., a thioether attached to the therapeutic agent via an acylhydrazone bond (see, e.g., U.S. Pat. No. 5,622,929)).

In yet other embodiments, the linking group is cleavable under reducing conditions (e.g., a disulfide linking group). A variety of disulfide linking groups are known in the art, including, for example, those that can be formed using SATA (N-succinimidyl-S-acetylthioacetate), SPDP (N-succinimidyl-3-(2-pyridyldithio)propionate), SPDB (N-succinimidyl-3-(2-pyridyldithio)butyrate) and SMPT (N-succinimidyl-oxycarbonyl-alpha-methyl-alpha-(2-pyridyl-dithio) toluene), SPDB and SMPT.

In yet other specific embodiments, the linking group is a malonate linking group, a maleimidobenzoyl linking group, or a 3'-N-amide analog.

The linking group may not be substantially sensitive to the extracellular environment. As used herein, "not substantially sensitive to the extracellular environment," in the context of a linking group, means that about 20% or less, e.g., about 15% or less, about 10% or less, about 5% or less, about 3% or less, including about 1% or less of the linking groups, in a sample of antibody conjugate, are cleaved when the antibody conjugate is present in an extracellular environment (e.g., in plasma), in the absence of a cleaving agent or a cleaving condition(s), as described above.

In some cases, the linking group is non-cleavable. A non-cleavable linking group is substantially resistant to cleavage, such as acid-induced cleavage, light-induced cleavage, peptidase-induced cleavage, esterase-induced cleavage, or disulfide bond cleavage. Examples of such non-cleavable linking groups include, without limitation, those that are or can be derived from a haloacetyl-based moiety selected from the group consisting of N-succinimidyl-4-(iodoacetyl)-aminobenzoate (SIAB), N-succinimidyl iodoacetate (SIA), N-succinimidyl bromoacetate (SBA), and N-succinimidyl 3-(bromoacetamido)propionate (SBAP). Alternatively, the non-cleavable linking group is or is derived from, without limitation, a maleimido-based moiety selected from the group consisting of N-succinimidyl 4-(maleimidomethyl)cyclohexanecarboxylate (SMCC), N-succinimidyl-4-(N-maleimidomethyl)-cyclohexane-1-carboxy-(6-amidocaproate) (LC-SMCC), K-maleimidoundecanoic acid N-succinimidyl ester (KMUA), γ-maleimidobutyric acid N-succinimidyl ester (GMBS), ε-maleimidcaproic acid N-hydroxysuccinimide ester (EMCS), m-maleimidobenzoyl-N-hydroxysuccinimide ester (MBS), N-(a-maleimidoacetoxy)-succinimide ester (AMAS), succinimidyl-6-(p-maleimidopropionamido)hexanoate (SMPH), N-succinimidyl 4-(p-maleimidophenyl)-butyrate (SMPB), and N-(p-maleimidophenyl)isocyanate (PMPI); another non-cleavable linking group is maleimidocaproyl.

Therapeutically Effective Amount and Dosing

In certain embodiments, a pharmaceutical composition or medicament is administered to a patient at a therapeutically effective dose to prevent, treat, or control a cancer or a fibrosis in the patient. The pharmaceutical composition or medicament is administered to a patient in an amount sufficient to elicit an effective therapeutic response in the patient. An effective therapeutic response is a response that at least partially arrests or slows the symptoms or complications of the disease (e.g., cancer or fibrosis). An amount adequate to accomplish this is defined as "therapeutically effective dose."

The dosage of compound administered is dependent on the species of warm-blooded animal (mammal), the body weight, age, individual condition, surface area of the area to be treated and on the form of administration. The size of the dose also will be determined by the existence, nature, and extent of any adverse effects that accompany the administration of a particular compound in a particular subject. A unit dosage for oral administration to a mammal of about 50 to 70 kg may contain between about 5 and 500 mg of the active ingredient. Typically, a dosage of the compound of the embodiments, is a dosage that is sufficient to achieve the desired effect.

Optimal dosing schedules can be calculated from measurements of compound accumulation in the body of a subject. In general, dosage is from 1 ng to 1,000 mg per kg of body weight and may be given once or more daily, weekly, monthly, or yearly. Persons of ordinary skill in the art can determine optimum dosages, dosing methodologies and repetition rates.

In certain embodiments, a pharmaceutical composition or medicament that includes a compound of the embodiments is administered in a daily dose in the range from about 1 mg of compound per kg of subject weight (1 mg/kg) to about 1 g/kg for multiple days. In certain embodiments, the daily dose is a dose in the range of about 5 mg/kg to about 500 mg/kg. In certain embodiments, the daily dose is about 10 mg/kg to about 250 mg/kg. In certain embodiments, the daily dose is about 25 mg/kg to about 150 mg/kg. The daily dose can be administered once per day or divided into sub-doses and administered in multiple doses, e.g., twice, three times, or four times per day.

To achieve the desired therapeutic effect, a compound can be administered for multiple days at the therapeutically effective daily dose. Thus, therapeutically effective administration of a compound to treat cancer or fibrosis in a subject requires periodic (e.g., daily) administration that continues for a period ranging from three days to two weeks or longer. Typically, a compound will be administered for at least three consecutive days, often for at least five consecutive days, more often for at least ten, and sometimes for 20, 30, 40 or more consecutive days. While consecutive daily doses are a one route to achieve a therapeutically effective dose, a therapeutically beneficial effect can be achieved even if the compound is not administered daily, so long as the administration is repeated frequently enough to maintain a therapeutically effective concentration of the compound in the subject. For example, one can administer the compound every other day, every third day, or, if higher dose ranges are employed and tolerated by the subject, once a week.

Optimum dosages, toxicity, and therapeutic efficacy of such compounds may vary depending on the relative potency of individual compounds and can be determined by standard pharmaceutical procedures in cell cultures or experimental animals, for example, by determining the $LD_{50}$ (the dose lethal to 50% of the population) and the $ED_{50}$ (the dose therapeutically effective in 50% of the population). The dose ratio between toxic and therapeutic effects is the therapeutic index and can be expressed as the ratio, $LD_{50}/ED_{50}$. In certain embodiments, the disclosure provides compounds that exhibit large therapeutic indices. While compounds that exhibit toxic side effects can be used, care should be taken to design a delivery system that targets such compounds to the site of affected tissue to minimize potential damage to normal cells and, thereby, reduce side effects.

The data obtained from, for example, cell culture assays and animal studies can be used to formulate a dosage range for use in humans. In certain embodiments, the dosage of such compounds lies within a range of circulating concentrations that include the $ED_{50}$ with little or no toxicity. The dosage can vary within this range depending upon the dosage form employed and the route of administration. For any compound used in the methods of the embodiments, the therapeutically effective dose can be estimated initially from cell culture assays. A dose can be formulated in animal models to achieve a circulating plasma concentration range that includes the $IC_{50}$ (the concentration of the test compound that achieves a half-maximal inhibition of symptoms) as determined in cell culture. Such information can be used to more accurately determine useful doses in humans. Levels in plasma can be measured, for example, by high performance liquid chromatography (HPLC). In general, the dose equivalent of a small molecule compound is from about 1 ng/kg to 100 mg/kg for a typical subject.

Following successful treatment, it may be desirable to have the subject undergo maintenance therapy to prevent the recurrence of the condition treated, e.g., a cancer or a fibrosis.

Treating Cancer Using Compounds

The embodiments provide methods for using the compounds of formula (I) to, for example, treat a condition, such as a cancer. In some instances, the cancer is a cancer expressing a GLI polypeptide. For examples, any cell or tumor cell expressing a GLI polypeptide can be used to practice a method of the embodiments. In some instances, the cancer is a RAS-mutant cancer. For example, any cell or tumor cell expressing a mutant RAS polypeptide can be used to practice a method of the embodiments.

In certain embodiments, a method for treating a subject suffering from a cancerous condition is provided. This method comprises the step of administering to the subject a therapeutically effective amount of a compound of the embodiments, wherein the step of administering results in the treatment of the subject.

Further, the embodiments provide for a compound of formula (I) for use in medical therapy. Further, the embodiments provide for a compound of formula (I) for use in the treatment of a cancer. Further, the embodiments provide for the use of a compound of formula (I) in the manufacture of a medicament treatment of a cancer.

Certain cancers express a GLI polypeptide or a mutant RAS polypeptide. Thus, most cancerous conditions or cancers in a subject can be treated using a compound of the embodiments. In certain embodiments, a cancerous condition or cancer is selected from colon cancer, melanoma, mesothelioma, lung cancer (e.g., NSCLC), pancreatic cancer, renal cell carcinoma, breast cancer, prostate cancer, sarcoma, ovarian cancer, esophageal cancer, gastric cancer, hepatocellular cancer, nasopharyngeal cancer, and glioma.

In certain embodiments, a compound is used to treat a subject suffering from a colon cancer expressing a GLI polypeptide, such as a GLI1, GLI2, or GLI3 polypeptide. In certain embodiments, a compound is used to treat a subject suffering from a colon cancer expressing a mutant RAS polypeptide, such as a KRAS, NRAS, or HRAS polypeptide.

In certain embodiments, a compound is used to treat a subject suffering from a breast cancer expressing a GLI polypeptide, such as a GLI1, GLI2, or GLI3 polypeptide. In certain embodiments, a compound is used to treat a subject suffering from a breast cancer expressing a mutant RAS polypeptide, such as a KRAS, NRAS, or HRAS polypeptide.

In certain embodiments, a compound is used to treat a subject suffering from a nasopharyngeal cancer expressing a GLI polypeptide, such as a GLI1, GLI2, or GLI3 polypeptide. In certain embodiments, a compound is used to treat a subject suffering from a nasopharyngeal cancer expressing a mutant RAS polypeptide, such as a KRAS, NRAS, or HRAS polypeptide.

In certain embodiments, a compound is used to treat a subject suffering from a lung cancer expressing a GLI polypeptide, such as a GLI1, GLI2, or GLI3 polypeptide. In certain embodiments, a compound is used to treat a subject suffering from a lung cancer expressing a mutant RAS polypeptide, such as a KRAS, NRAS, or HRAS polypeptide. A lung cancer includes, but is not limited to, bronchogenic carcinoma [squamous cell, undifferentiated small cell, undifferentiated large cell, adenocarcinoma], alveolar [bronchiolar] carcinoma, bronchial adenoma, sarcoma, lymphoma, chondromatous hamartoma, mesothelioma, SCLC, and NSCLC.

In certain embodiments, a compound is used to treat a subject suffering from a pancreatic cancer expressing a GLI polypeptide, such as a GLI1, GLI2, or GLI3 polypeptide. In certain embodiments, a compound is used to treat a subject suffering from a pancreatic cancer expressing a mutant RAS polypeptide, such as a KRAS, NRAS, or HRAS polypeptide.

In certain embodiments, a compound is used to treat a subject suffering from a sarcoma expressing a GLI polypeptide, such as a GLI1, GLI2, or GLI3 polypeptide. In certain embodiments, a compound is used to treat a subject suffering from a sarcoma expressing a mutant RAS polypeptide, such as a KRAS, NRAS, or HRAS polypeptide. A sarcoma includes, but is not limited to, cancers such as angiosarcoma, fibrosarcoma, rhabdomyosarcoma, liposarcoma, myxoma, rhabdomyoma, fibroma, lipoma and teratoma.

In certain embodiments, a compound is used to treat a subject suffering from a gastrointestinal cancer expressing a GLI polypeptide, such as a GLI1, GLI2, or GLI3 polypeptide. In certain embodiments, a compound is used to treat a subject suffering from a gastrointestinal cancer expressing a mutant RAS polypeptide, such as a KRAS, NRAS, or HRAS polypeptide. A gastrointestinal cancer includes, but is not limited to cancers of esophagus [squamous cell carcinoma, adenocarcinoma, leiomyosarcoma, lymphoma], stomach [carcinoma, lymphoma, leiomyosarcoma], pancreas [ductal adenocarcinoma, insulinoma, glucagonoma, gastrinoma, carcinoid tumors, VIPoma], small bowel [adenocarcinoma, lymphoma, carcinoid tumors, Kaposi's sarcoma, leiomyoma, hemangioma, lipoma, neurofibroma, fibroma], and large bowel [adenocarcinoma, tubular adenoma, villous adenoma, hamartoma, leiomyoma].

In certain embodiments, a compound is used to treat a subject suffering from a cancer of the genitourinary tract expressing a GLI polypeptide, such as a GLI1, GLI2, or GLI3 polypeptide. In certain embodiments, a compound is used to treat a subject suffering from a cancer of the genitourinary tract expressing a mutant RAS polypeptide, such as a KRAS, NRAS, or HRAS polypeptide. Cancers of the genitourinary tract include, but are not limited to cancers of kidney [adenocarcinoma, Wilms tumor (nephroblastoma), lymphoma, leukemia, renal cell carcinoma], bladder and urethra [squamous cell carcinoma, transitional cell carcinoma, adenocarcinoma], prostate [adenocarcinoma, sarcoma], and testis [seminoma, teratoma, embryonal carcinoma, teratocarcinoma, choriocarcinoma, sarcoma, Leydig cell tumor, fibroma, fibroadenoma, adenomatoid tumors, lipoma].

In certain embodiments, a compound is used to treat a subject suffering from a liver cancer expressing a GLI polypeptide, such as a GLI1, GLI2, or GLI3 polypeptide. In certain embodiments, a compound is used to treat a subject suffering from a liver cancer expressing a mutant RAS polypeptide, such as a KRAS, NRAS, or HRAS polypeptide. A liver cancer includes, but is not limited to, hepatocellular carcinoma, cholangiocarcinoma, hepatoblastoma, angiosarcoma, hepatocellular adenoma, and hemangioma.

In certain embodiments, a compound is used to treat a subject suffering from a skin cancer expressing a GLI polypeptide, such as a GLI1, GLI2, or GLI3 polypeptide. In certain embodiments, a compound is used to treat a subject suffering from a skin cancer expressing a mutant RAS polypeptide, such as a KRAS, NRAS, or HRAS polypeptide. Skin cancer includes, but is not limited to, malignant melanoma, basal cell carcinoma, squamous cell carcinoma, Kaposi's sarcoma, nevi, dysplastic nevi, lipoma, angioma, dermatofibroma, keloids, and psoriasis.

In certain embodiments, a compound is used to treat a subject suffering from a gynecological cancer expressing a GLI polypeptide, such as a GLI1, GLI2, or GLI3 polypeptide. In certain embodiments, a compound is used to treat a subject suffering from a gynecological cancer expressing a mutant RAS polypeptide, such as a KRAS, NRAS, or HRAS polypeptide. Gynecological cancers include, but are not limited to, cancer of uterus [endometrial carcinoma], cervix [cervical carcinoma, pre-invasive cervical dysplasia], ovaries [ovarian carcinoma (serous cystadenocarcinoma, mucinous cystadenocarcinoma, endometrioid carcinoma, clear cell adenocarcinoma, unclassified carcinoma), granulosa-theca cell tumors, Sertoli-Leydig cell tumors, dysgerminoma, malignant teratoma and other germ cell tumors], vulva [squamous cell carcinoma, intraepithelial carcinoma, adenocarcinoma, fibrosarcoma, melanoma], vagina [clear cell carcinoma, squamous cell carcinoma, sarcoma botryoides (embryonal rhabdomyosarcoma), and fallopian tubes [carcinoma].

In certain embodiments, a compound is used to treat a subject suffering from a bone cancer expressing a GLI polypeptide, such as a GLI1, GLI2, or GLI3 polypeptide. In certain embodiments, a compound is used to treat a subject suffering from a bone cancer expressing a mutant RAS polypeptide, such as a KRAS, NRAS, or HRAS polypeptide. Bone cancer includes, but is not limited to, osteogenic sarcoma [osteosarcoma], fibrosarcoma, malignant fibrous histiocytoma, chondrosarcoma, Ewing's sarcoma, malignant lymphoma [reticulum cell sarcoma], multiple myeloma, malignant giant cell tumor, chordoma, osteochondroma [osteocartilaginous exostoses], benign chondroma, chondroblastoma, chondromyxoid fibroma, osteoid osteoma, and giant cell tumors.

In certain embodiments, a compound is used to treat a subject suffering from a cancer of the nervous system expressing a GLI polypeptide, such as a GLI1, GLI2, or GLI3 polypeptide. In certain embodiments, a compound is used to treat a subject suffering from a cancer of the nervous system expressing a mutant RAS polypeptide, such as a KRAS, NRAS, or HRAS polypeptide. Cancers of the nervous system include, but are not limited to cancers of skull [osteoma, hemangioma, granuloma, xanthoma, Paget's disease of bone], meninges [meningioma, meningiosarcoma, gliomatosis], brain [astrocytoma, medulloblastoma, glioma, ependymoma, germinoma (pinealoma), glioblastoma multiforme, oligodendroglioma, schwannoma, retinoblastoma, congenital tumors], and spinal cord [neurofibroma, meningioma, glioma, sarcoma].

In certain embodiments, a compound is used to treat a subject suffering from a hematologic cancer expressing a GLI polypeptide, such as a GLI1, GLI2, or GLI3 polypeptide. In certain embodiments, a compound is used to treat a subject suffering from a hematological cancer expressing a mutant RAS polypeptide, such as a KRAS, NRAS, or HRAS polypeptide. Hematologic cancers include, but are not limited to cancer of blood [myeloid leukemia (acute and chronic), acute lymphoblastic leukemia, chronic lymphocytic leukemia, myeloproliferative diseases, multiple myeloma, myelodysplastic syndrome], Hodgkin's disease, and non-Hodgkin's lymphoma (malignant lymphoma).

In certain embodiments, a compound is used to treat a subject suffering from a cancer of adrenal glands expressing a GLI polypeptide, such as a GLI1, GLI2, or GLI3 polypeptide. In certain embodiments, a compound is used to treat a subject suffering from a cancer of adrenal glands expressing a mutant RAS polypeptide, such as a KRAS, NRAS, or HRAS polypeptide. A cancer of adrenal glands includes, but is not limited to, neuroblastoma.

The disclosure provides a method for treatment or prevention of a cancer where a GLI polypeptide, such as a GLI1, GLI2, or GLI3 polypeptide is expressed. In addition, the disclosure provides a method for treatment or prevention of a cancer where a mutant RAS polypeptide, such as a KRAS, NRAS, or HRAS polypeptide is expressed. In certain embodiments, this method comprises the step of administering to a patient a pharmaceutical composition. Such pharmaceutical composition comprises, for example, a compound of formula (I) as described herein.

Pharmaceutical compositions of the embodiments are administered alone or in combination with one or more additional therapeutic compound or treatments. Examples of such therapeutic compounds or treatments include, but are not limited to, taxol, cyclophosphamide, tamoxifen, fluorouracil and doxorubicin. In certain embodiments, a pharmaceutical composition or medicament comprises a compound of the embodiments and another therapeutic agent selected from erlotinib (Tarceva®), pemetrexed (Alimta®), LY294002, SB431542, and cisplatin. In addition, other chemotherapeutic agents are described herein.

Methods for treating cancer may optionally comprise one or more of the following steps: obtaining a biological sample of tissue or fluid from an individual; screening the biological sample for the expression of a GLI polypeptide, such as a GLI1, GLI2, or GLI3 polypeptide, for example by contacting the biological sample with an antibody directed to GLI1, GLI2, or GLI3; or screening the biological sample for expression of a Gli1, Gli2, or Gli3 polynucleotide, for example by detecting a Gli1, Gli2, or Gli3 mRNA.

Methods for treating cancer may optionally comprise one or more of the following steps: obtaining a biological sample of tissue or fluid from an individual; screening the biological sample for the expression of a mutant RAS polypeptide, such as a KRAS, NRAS, or HRAS polypeptide, for example by contacting the biological sample with an antibody directed to a KRAS, NRAS, or HRAS polypeptide; or screening the biological sample for expression of a RAS polynucleotide, for example by detecting a Ras mRNA.

Many cancers are initially treated using chemotherapeutic agents as described herein. However, very often, cancers develop resistance against such chemotherapeutic agents which then are no longer effective. Thus, in one embodiment, the cancer is a multi-drug resistant cancer or a cancer that is otherwise refractory to treatment. Therefore, in certain embodiments, a compound of the embodiments is used to overcome resistance to chemotherapeutic agents in tumor cells. This method comprises the step of administering to a tumor cell resistant to at least one chemotherapeutic agent, a compound of the embodiments, where the administering results in subsequent tumor cell death. In certain embodiments, the compound is a compound of formula (I) as described herein.

In a certain embodiment, a compound of the embodiments for use in the treatment of a cancer is provided. In certain embodiments, the disclosure provides the use of a compound of the embodiments in the manufacture of a pharmaceutical composition or a medicament for the therapeutic and/or prophylactic treatment of a condition, e.g., cancer where a GLI polypeptide is expressed, or a cancer where a mutant RAS polypeptide is expressed.

In certain embodiments, the disclosure provides for the use of a compound in the manufacture of a pharmaceutical composition or medicament for use in combination with another chemotherapeutic anticancer agent for the treatment of a cancer expressing a GLI polypeptide or a RAS-mutant cancer. Pharmaceutical composition and medicaments provided by the disclosure are described herein.

Treating Fibrosis Using Compounds

The embodiments provide methods for using the compounds of formula (I) to, for example, treat a condition, such as a fibrosis. In some instances, the fibrosis is a fibrosis expressing a GLI polypeptide. For examples, any cell expressing a GLI polypeptide can be used to practice a method of the embodiments.

In certain embodiments, a method for treating a subject suffering from a fibrotic condition is provided. This method comprises the step of administering to the subject a therapeutically effective amount of a compound of the embodiments, wherein the step of administering results in the treatment of the subject.

Further, the embodiments provide for a compound of formula (I) for use in medical therapy. Further, the embodiments provide a compound of formula (I) for use in the treatment of a fibrosis. Further, the embodiments provide for the use of a compound of formula (I) in the manufacture of a medicament treatment of a fibrosis.

Certain fibrotic conditions express a GLI polypeptide. Thus, fibrotic conditions or fibrosis in a subject can be treated using a compound of the embodiments. In certain embodiments, the fibrotic condition or fibrosis is selected from, but not limited to, kidney fibrosis, pulmonary fibrosis, cirrhosis, endomyocardial fibrosis, arthofibrosis, Crohn's disease, mediastinal fibrosis, myelofibrosis, retroperitoneal fibrosis, and the like.

In certain embodiments, a compound is used to treat a subject suffering from a kidney fibrosis expressing a GLI polypeptide, such as a GLI1, GLI2, or GLI3 polypeptide. In certain embodiments, a compound is used to treat a subject suffering from a pulmonary fibrosis expressing a GLI polypeptide, such as a GLI1, GLI2, or GLI3 polypeptide. In certain embodiments, a compound is used to treat a subject suffering from cirrhosis expressing a GLI polypeptide, such as a GLI1, GLI2, or GLI3 polypeptide. In certain embodiments, a compound is used to treat a subject suffering from an endomyocardial fibrosis expressing a GLI polypeptide, such as a GLI1, GLI2, or GLI3 polypeptide. In certain embodiments, a compound is used to treat a subject suffering from an arthofibrosis expressing a GLI polypeptide, such as a GLI1, GLI2, or GLI3 polypeptide. In certain embodiments, a compound is used to treat a subject suffering from Crohn's disease expressing a GLI polypeptide, such as a GLI1, GLI2, or GLI3 polypeptide. In certain embodiments, a compound is used to treat a subject suffering from a mediastinal fibrosis expressing a GLI polypeptide, such as a GLI1, GLI2, or GLI3 polypeptide. In certain embodiments, a compound is used to treat a subject suffering from a myelofibrosis expressing a GLI polypeptide, such as a GLI1, GLI2, or GLI3 polypeptide. In certain embodiments, a compound is used to treat a subject suffering from a retroperitoneal fibrosis expressing a GLI polypeptide, such as a GLI1, GLI2, or GLI3 polypeptide.

The disclosure provides a method for treatment or prevention of a fibrosis where a GLI polypeptide, such as a GLI1, GLI2, or GLI3 polypeptide is expressed. In certain embodiments, this method comprises the step of administering to a patient a pharmaceutical composition. Such pharmaceutical composition comprises, for example, a compound of formula (I) as described herein.

Pharmaceutical compositions of the embodiments are administered alone or in combination with one or more additional therapeutic compound or treatments. Examples of such therapeutic compounds or treatments include, but are not limited to, nintedanib, pirfenidone, corticosteroids (e.g., prednisone), anti-inflammatory drugs, immune system suppressants (e.g., methotrexate, cyclosporine cyclophosphamide, azathioprine, methotrexate, penicillamine, etc.), acetylcysteine, non-steroidal anti-inflammatory drugs (NSAID), infliximab, adalimumab, certolizumab, natalizumab, and the like, and combinations thereof.

Methods for treating fibrosis may optionally comprise one or more of the following steps: obtaining a biological sample of tissue or fluid from an individual; screening the biological sample for the expression of a GLI polypeptide, such as a GLI1, GLI2, or GLI3 polypeptide, for example by contacting the biological sample with an antibody directed to GLI1, GLI2, or GLI3; or screening the biological sample for expression of a Gli1, Gli2, or Gli3 polynucleotide, for example by detecting a Gli1, Gli2, or Gli3 mRNA.

In a certain embodiment, a compound of the embodiments for use in the treatment of a fibrosis is provided. In certain embodiments, the disclosure provides the use of a compound of the embodiments in the manufacture of a pharmaceutical composition or a medicament for the therapeutic and/or prophylactic treatment of a condition, e.g., fibrosis where a GLI polypeptide is expressed.

In certain embodiments, the disclosure provides for the use of a compound in the manufacture of a pharmaceutical composition or medicament for use in combination with another therapeutic agent for the treatment of a fibrosis expressing a GLI polypeptide. Pharmaceutical composition and medicaments provided by the disclosure are described herein.

Kits

For use in diagnostic, research, and therapeutic applications suggested above, kits are also provided by the disclosure. In the diagnostic and research applications such kits may include any or all of the following: assay reagents, buffers, a compound of the embodiments, a GLI polypeptide, a RAS polypeptide, a Gli nucleic acid, a Ras nucleic acid, an anti-GLI antibody, an anti-RAS antibody, hybridization probes and/or primers, Gli expression constructs, Ras expression constructs, etc. A therapeutic product may include sterile saline or another pharmaceutically acceptable emulsion and suspension base.

In addition, the kits may include instructional materials containing directions (i.e., protocols) for the practice of the methods of the embodiments. The instructions may be present in the subject kits in a variety of forms, one or more of which may be present in the kit. While the instructional materials typically comprise written or printed materials they are not limited to such. Any medium capable of storing such instructions and communicating them to an end user is contemplated. Such media include, but are not limited to electronic storage media (e.g., magnetic discs, tapes, cartridges, chips, flash memory), optical media (e.g., CD-ROM, DVD, Blu-ray), and the like. Such media may include addresses to internet sites that provide such instructional materials.

A wide variety of kits and components can be prepared according to the embodiments, depending upon the intended user of the kit and the particular needs of the user.

In certain embodiments, the kit is a pharmaceutical kit and comprises a pharmaceutical composition comprising (i) a compound of the embodiments disclosed herein and (ii) a pharmaceutical acceptable carrier. Pharmaceutical kits optionally comprise an instruction stating that the pharmaceutical composition can or should be used for treating a cancer or fibrosis expressing a GLI polypeptide, a Gli nucleic acid, a RAS polypeptide, or a Ras nucleic acid.

Additional kit embodiments include optional functional components that would allow one of ordinary skill in the art to perform any of the method variations described herein.

The following examples are put forth so as to provide those of ordinary skill in the art with a complete disclosure and description of how to make and use the embodiments of the invention, and are not intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

In the examples below, unless otherwise indicated, all temperatures are set forth in degrees Celsius and all parts and percentages are by weight. Reagents may be purchased from commercial suppliers, such as Sigma-Aldrich Chemical Company, and may be used without further purification unless otherwise indicated. Reagents may also be prepared following standard literature procedures known to those skilled in the art. Solvents may be purchased from Sigma-Aldrich in Sure-Seal bottles and used as received. All solvents may be purified using standard methods known to those skilled in the art, unless otherwise indicated. The reactions set forth below were run generally at ambient temperature, unless otherwise indicated. The reaction vessels were fitted with rubber septa for introduction of substrates and reagents via syringe. Analytical thin layer chromatography (TLC) was performed using glass-backed silica gel pre-coated plates (Analtech TLC Uniplates™ with fluorescent indicator) and eluted with appropriate solvent ratios (v/v). Reactions were assayed by TLC or LC/MS, and terminated as judged by the consumption of starting material. Visualization of the TLC plates was done with UV light (254 nm wavelength) or with an appropriate TLC visualizing solvent, such as basic aqueous $KMnO_4$ solution, ninhydrin, cerium molybdate, or phosphomolybdic acid, activated with heat. Flash column chromatography (W. C. Still et al., J. Org. Chem., 43, 1978, 2923-2925) was performed using Biotage Isolera Prime automated flash purification system (220 and 254 nm wavelength) with ZIP Sphere-spherical Silica or KP Silica cartridges or various preparative HPLC systems. The compound structures in the examples below were confirmed by one or more of the following methods: proton magnetic resonance spectroscopy, mass spectrometry, and melting point. Proton magnetic resonance ($^1$HNMR) spectra were recorded using an NMR spectrometers operating at 330, 400 or 500 MHz field strength. Chemical shifts are reported in the form of delta (δ) values given in parts per million (ppm) relative to an internal standard, such as tetramethylsilane (TMS). Alternatively, $^1$HNMR spectra were referenced to signals from residual protons in deuterated solvents as follows: CDCl$_3$=7.25 ppm; DMSO-d$_6$=2.49 ppm; CD$_3$OD=3.30 ppm. Peak multiplicities are designated as follows: s, singlet; d, doublet; dd, doublet of doublets; t, triplet; dt, doublet of triplets; q, quartet; br, broadened; and m, multiplet. Coupling constants are given in Hertz (Hz). Mass spectrometric (MS) data were obtained using a mass spectrometer with APCI or ESI ionization.

EXAMPLES

Example A

N-(2,4-difluorophenyl)-4-fluorobenzohydrazonoyl chloride (704) was prepared as follows

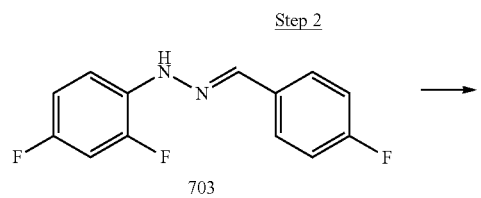

To a solution of 2,4-difluorophenylhydrazine (701) (7.46 g, 51.76 mmol) in ethanol (100 mL) was added 4-fluorobenzaldehyde (702) (5.55 mL, 51.76 mmol) dropwise and the mixture was stirred at room temperature for 18 hours. The solvent was concentrated and the precipitate was filtered off, washed with cold ethanol and hexanes, dried in vacuo to give 1-(2,4-difluorophenyl)-2-(4-fluorobenzylidene)hydrazine (703) (9.47 g, 73%).

MS (EI) for C$_{13}$H$_9$F$_3$N$_2$: 251 [MH$^+$]

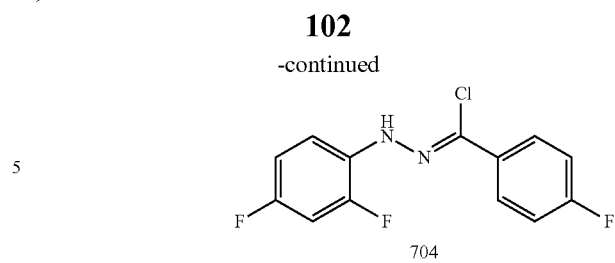

To a solution of 1-(2,4-difluorophenyl)-2-(4-fluorobenzylidene)hydrazine (703) (3.45 g, 13.80 mmol) in N,N-dimethylformamide (20.0 mL) was added N-chlorosuccinimide (1.88 g, 14.00 mmol) and the reaction mixture was stirred at room temperature for 18 hours. The mixture was partitioned with ethyl acetate (150 ml) and brine (50 mL). The organic layer was washed with brine (2×50 mL), dried over anhydrous sodium sulfate and concentrated. The resulting crude product was purified by gradient silica gel flash chromatography (1-10% ethyl acetate in hexanes) to give N-(2,4-difluorophenyl)-4-fluorobenzohydrazonoyl chloride (704) as a white solid (3.12 g, 79%).

MS (EI) for C$_{13}$H$_8$ClF$_3$N$_2$: 285 [MH$^+$].

Methyl (E)-2-methylhept-2-enoate (708) was prepared as follows

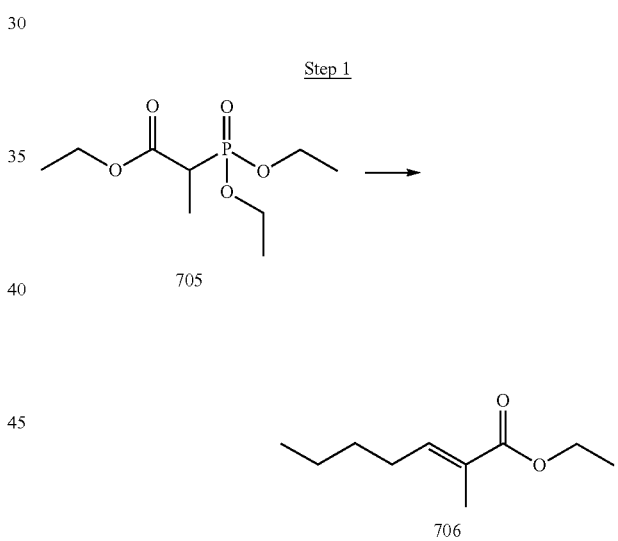

To a suspension of lithium chloride (4.30 g, 100.8 mmol) in dry acetonitrile (75.0 ml) was added triethyl-2-phosphonopropionate (705) (18.01 mL, 84.0 mmol) and 1,8-diazabicyclo[5.4.0]undec-7-ene (12.40 mL, 84.0 mmol) and the resulting solution was cooled to 0° C. followed by the addition of pentanal (8.40 mL, 80.0 mmol). The mixture was stirred at room temperature for 18 hours. The solvent was evaporated and the crude product was partitioned with ethyl acetate (300 mL) and 2M aqueous hydrochloric acid (100 ml). The organic layer was separated, washed with 2M aqueous hydrochloric acid (2×50 ml) and brine (2×150 mL), dried over anhydrous sodium sulfate and concentrated. The resulting crude ethyl (E)-2-methylhept-2-enoate (706) was used without further purification (14 g, quant.).

MS (EI) for C$_{10}$H$_{18}$O$_2$: 171 [MH$^+$].

Step 2

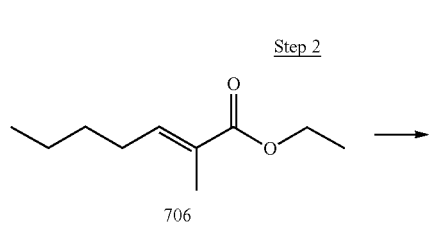

706

To a solution of ethyl (E)-2-methylhept-2-enoate (706) (14 g, 80.0 mmol) in a mixture of tetrahydrofuran (80.0 mL) and methanol (20.0 mL) at 0° C. was added potassium hydroxide (27.0 mL, 240.0 mmol, 50% aq. solution) and the reaction mixture was stirred at room temperature for 18 hours. The solvent was concentrated and the pH was adjusted to 2 by the addition of concentrated hydrochloric acid. The mixture was partitioned with ethyl acetate (300 mL) and the organic layer was separated, washed with brine (2×250 mL), dried over anhydrous sodium sulfate and concentrated to give crude (E)-2-methylhept-2-enoic acid (707) as white solid (quantitative). The crude was used without further purification.

MS (EI) for $C_8H_{14}O_2$: 141 [MH⁻].

Step 3

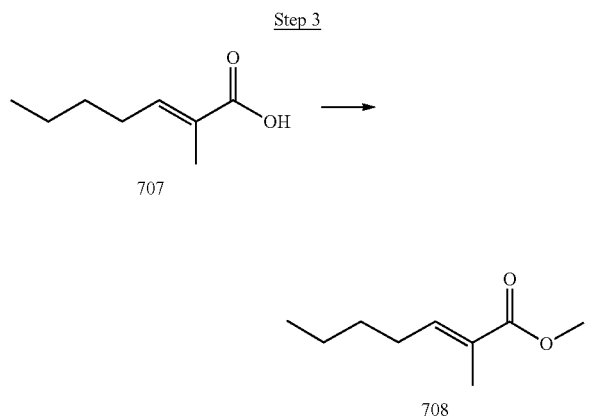

707

708

To a suspension of (E)-2-methylhept-2-enoic acid (707) in N,N-dimethylformamide (75.0 mL) and potassium carbonate (33.2 g, 240.0 mmol) at 0° C. was added iodomethane (6.0 mL, 96.0 mmol) and the reaction mixture was stirred at room temperature for 18 hours. The mixture was diluted with water (150 mL) and partitioned with ethyl acetate (300 mL). The organic layer was washed with 2M aqueous hydrochloric acid (2×150 ml) and brine (2×150 mL), dried over anhydrous sodium sulfate and concentrated. The resulting crude was purified by gradient silica gel flash chromatography (1-10% ethyl acetate in hexanes) to give methyl (E)-2-methylhept-2-enoate (708) (11.9 g, 95%).

MS (EI) for $C_9H_{16}O_2$: 157 [MH⁺].

4-butyl-1-(2,4-difluorophenyl)-3-(4-fluorophenyl)-N-(2-methoxyethyl)-5-methyl-4,5-dihydro-1H-pyrazole-5-carboxamide (Compound 6) was synthesized as follows

Step 1

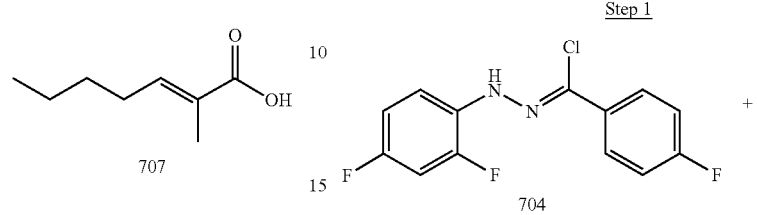

704

708

709

To a solution of N-(2,4-difluorophenyl)-4-fluorobenzohydrazonoyl chloride (704) (1.40 g, 5.0 mmol) and methyl (E)-2-methylhept-2-enoate (708) (1.60 g, 10.0 mmol) in tetrahydrofuran (10.0 mL) was added trimethylamine (2.10 mL, 15.0 mmol) and the reaction mixture was stirred at room temperature for 18 hours. The mixture was diluted with ethyl acetate (200 mL) and partitioned with 1M aqueous hydrochloric acid (50 mL). The organic layer was separated washed with 1M aqueous hydrochloric acid (2×50 mL), brine (2×100 mL), dried over anhydrous sodium sulfate and concentrated. The resulting crude product was purified by gradient silica gel flash chromatography (1-25% ethyl acetate in hexanes) to give methyl 4-butyl-1-(2,4-difluorophenyl)-3-(4-fluorophenyl)-5-methyl-4,5-dihydro-1H-pyrazole-5-carboxylate (709) (0.80 g, 40%).

MS (EI) for $C_{22}H_{23}F_3N_2O_2$: 405 [MH⁺].

Step 2

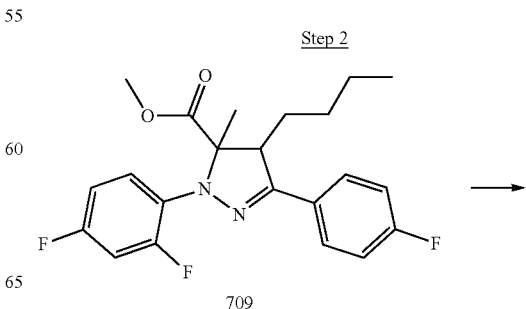

709

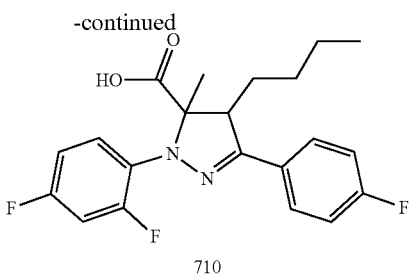

710

To a solution of methyl 4-butyl-1-(2,4-difluorophenyl)-3-(4-fluorophenyl)-5-methyl-4,5-dihydro-1H-pyrazole-5-carboxylate (709) (0.80 g, 1.98 mmol) in a mixture of tetrahydrofuran (10.0 mL), methanol (4.0 mL) and water (1.0 mL) was added potassium hydroxide (0.70 mL, 5.94 mmol, 50% aq. solution) and the reaction mixture was stirred at room temperature for 2 hours. The pH was adjusted to 2 by the addition of 2M aqueous hydrochloric acid. The mixture was partitioned with ethyl acetate (150 mL) and the organic layer was separated, washed with brine (2×50 mL), dried over anhydrous sodium sulfate and concentrated to give 4-butyl-1-(2,4-difluorophenyl)-3-(4-fluorophenyl)-5-methyl-4,5-dihydro-1H-pyrazole-5-carboxylic acid (710) (quantitative). The product was used without further purification.

MS (EI) for $C_{21}H_{21}F_3N_2O_2$: 389 [MH$^-$].

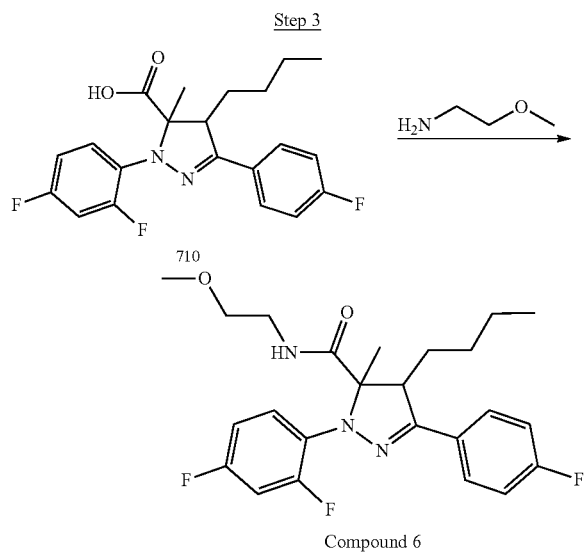

Compound 6

To a solution of 4-butyl-1-(2,4-difluorophenyl)-3-(4-fluorophenyl)-5-methyl-4,5-dihydro-1H-pyrazole-5-carboxylic acid (710) (0.77 g, 1.98 mmol) in N,N-dimethylformamide (5.0 mL) was added O-(7-azabenzotriazol-1-yl)-N,N,N',N'-tetramethyluronium hexafluorophosphate (HATU) (0.80 g, 2.08 mmol) and 4-methylmorpholine (0.65 mL, 5.94 mmol) and the reaction mixture was stirred at room temperature for thirty minutes, followed by the addition of 2-methoxyethylamine (0.17 mL, 1.98 mmol) and the stirring was continued for 18 hours. The mixture was partitioned with ethyl acetate (150 mL) and 1M aqueous hydrochloric acid (75 ml). The organic layer was separated and washed with 1M aqueous hydrochloric acid (50 ml) and brine (2×50 mL), dried over anhydrous sodium sulfate and concentrated. The resulting crude was purified by gradient silica gel flash chromatography (1-30% ethyl acetate in hexanes) to give 4-butyl-1-(2,4-difluorophenyl)-3-(4-fluorophenyl)-N-(2-methoxyethyl)-5-methyl-4,5-dihydro-1H-pyrazole-5-carboxamide (Compound 6) (0.81 g, 93%).

$^1$H-NMR (500 MHz, d$_6$-DMSO): 8.21 (t, 1H), 7.84 (m, 2H), 7.46 (m, 1H), 7.30 (m, 2H), 7.16 (m, 2H), 3.62 (m, 1H), 3.4 (m, 2H), 3.22 (m, 2H), 3.18 (s, 3H), 1.64-1.58 (m, 2H), 1.42 (s, 3H), 1.22 (m, 4H), 0.84 (m, 3H).

MS (EI) for $C_{24}H_{28}F_3N_3O_2$: 448 [MH$^+$].

Compounds of the present disclosure were prepared using similar procedures as described above for Compound 6.

Further examples are presented below.

Example 1

REAGENTS (R.1.x) The following reagents were prepared and used in the Examples described below.

Reagent 1.2. (R.1.2.)N-(2,4-difluorophenyl)-4-fluorobenzohydrazonoyl chloride was prepared according to the following scheme.

STEP 1

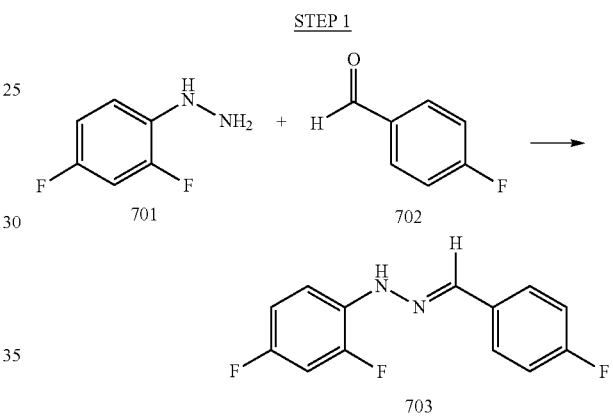

To a solution of 2,4-difluorophenylhydrazine (701) (7.46 g, 51.76 mmol) in ethanol (100 mL) was added 4-fluorobenzaldehyde (702) (5.55 mL, 51.76 mmol) dropwise and the mixture was stirred at room temperature for 18 hours. The solvent was concentrated and the precipitate was filtered off, washed with cold ethanol and hexanes, dried in vacuo to give 1-(2,4-difluorophenyl)-2-(4-fluorobenzylidene)hydrazine (703) (9.47 g, 73%). MS (EI) for $C_{13}H_9F_3N_2$: 251 [M+H]

STEP 2

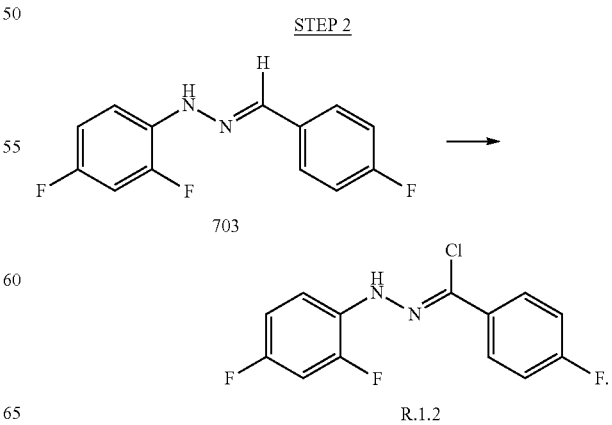

R.1.2

To a solution of 1-(2,4-difluorophenyl)-2-(4-fluorobenzylidene)hydrazine (703) (3.45 g, 13.80 mmol) in N,N-dimethylformamide (20.0 mL) was added N-chlorosuccinimide (1.88 g, 14.00 mmol) and the reaction mixture was stirred at room temperature for 18 hours. It was partitioned with ethyl acetate (150 ml) and brine (50 mL). The organic layer was washed with brine (2×50 mL), dried over anhydrous sodium sulfate and concentrated. The resulting crude product was purified by gradient silica gel flash chromatography (1-10% ethyl acetate in hexanes) to give N-(2,4-difluorophenyl)-4-fluorobenzohydrazonoyl chloride as white solid (R.1.2.) (3.12 g, 79%). MS (EI) for $C_{13}H_8ClF_3N_2$: 285 [M+H].

Reagent 1.1. (R.1.1.) 4-Fluoro-N-phenylbenzohydrazonoyl chloride was prepared using phenylhydrazine and 4-fluorobenzaldehyde in step 1. MS (EI) for $C_{13}H_{10}ClFN_2$: 249 [M+H].

Reagent 1.3. (R.1.3.) 4-Fluoro-N-(3-fluorophenyl)benzohydrazonoyl chloride was prepared using (3-fluorophenyl)hydrazine and 4-fluorobenzaldehyde in step 1. MS (EI) for $C_{13}H_9ClF_2N_2$: 267 [M+H].

Reagent 1.4. (R.1.4.) 4-Fluoro-N-(4-fluorophenyl)benzohydrazonoyl chloride was prepared using (4-fluorophenyl)hydrazine and 4-fluorobenzaldehyde in step 1. MS (EI) for $C_{13}H_9ClFN_2$: 267 [M+H].

Reagent 1.5. (R.1.5.)N-(4-Chlorophenyl)-4-fluorobenzohydrazonoyl chloride was prepared using (4-chlorophenyl)hydrazine and 4-fluorobenzaldehyde in step 1. MS (EI) for $C_{13}H_9Cl_2FN_2$: 284 [M+H].

Reagent 1.6. (R.1.6.)N-(3-Chlorophenyl)-4-fluorobenzohydrazonoyl chloride was prepared using (3-chlorophenyl)hydrazine and 4-fluorobenzaldehyde in step 1. MS (EI) for $C_{13}H_9Cl_2FN_2$: 284 [M+H].

Reagent 1.7. (R.1.7.) 4-Fluoro-N-(p-tolyl)benzohydrazonoyl chloride was prepared using p-tolylhydrazine and 4-fluorobenzaldehyde in step 1. MS (EI) for $C_{14}H_{12}ClFN_2$: 263 [M+H].

Reagent 1.8. (R.1.8.) 4-Fluoro-N-(m-tolyl)benzohydrazonoyl chloride was prepared using m-tolylhydrazine and 4-fluorobenzaldehyde in step 1. MS (EI) for $C_{14}H_{12}ClFN_2$: 263 [M+H].

Reagent 1.9. (R.1.9.) 4-Fluoro-N-(4-(trifluoromethyl)phenyl)benzohydrazonoyl chloride was prepared using (4-(trifluoromethyl)phenyl)hydrazine and 4-fluorobenzaldehyde in step 1. MS (EI) for $C_{14}H_9ClF_4N_2$: 317 [M+H].

Reagent 1.10. (R.1.10.)N-(2,5-Difluorophenyl)-4-fluorobenzohydrazonoyl chloride was prepared using (2,5-difluorophenyl)hydrazine and 4-fluorobenzaldehyde in step 1. MS (EI) for $C_{13}H_8ClF_3N_2$: 285 [M+H].

Reagent 1.11. (R.1.11.) 4-Fluoro-N-(4-fluoro-3-methoxyphenyl)benzohydrazonoyl chloride was prepared using (4-fluoro-3-methoxyphenyl)hydrazine and 4-fluorobenzaldehyde in step 1. MS (EI) for $C_{14}H_{11}ClF_2N_2O$: 297 [M+H].

Reagent 1.12. (R.1.12.)N-(3-Chloro-4-fluorophenyl)-4-fluorobenzohydrazonoyl chloride was prepared using (3-chloro-4-fluorophenyl)hydrazine and 4-fluorobenzaldehyde in step 1. MS (EI) for $C_{13}H_8Cl_2F_2N_2$: 302 [M+H].

Reagent 1.13. (R.1.13.)N-(2-Chloro-4-fluorophenyl)-4-fluorobenzohydrazonoyl chloride was prepared using (2-chloro-4-fluorophenyl)hydrazine and 4-fluorobenzaldehyde in step 1. MS (EI) for $C_{13}H_8Cl_2F_2N_2$: 302 [M+H].

Reagent 1.14. (R.1.14.)N-(4-Chloro-2-fluorophenyl)-4-fluorobenzohydrazonoyl chloride was prepared using (4-chloro-2-fluorophenyl)hydrazine and 4-fluorobenzaldehyde in step 1. MS (EI) for $C_{13}H_8Cl_2F_2N_2$: 302 [M+H].

Reagent 1.15. (R.1.15.)N-(4-Chloro-2-methylphenyl)-4-fluorobenzohydrazonoyl chloride was prepared using (4-chloro-2-methylphenyl)hydrazine and 4-fluorobenzaldehyde in step 1. MS (EI) for $C_{14}H_{11}Cl_2FN_2$: 298 [M+H].

Reagent 1.16. (R.1.16.) 4-Chloro-N-phenylbenzohydrazonoyl chloride was prepared using phenylhydrazine and 4-chlorobenzaldehyde in step 1. MS (EI) for $C_{13}H_{10}Cl_2N_2$: 266 [M+H].

Reagent 1.17. (R.1.17.) 3,4-Difluoro-N-phenylbenzohydrazonoyl chloride was prepared using phenylhydrazine and 3,4-difluorobenzaldehyde in step 1. MS (EI) for $C_{13}H_9ClF_2N_2$: 267 [M+H].

Reagent 1.18. (R.1.18.) 2,4-Difluoro-N-phenylbenzohydrazonoyl chloride was prepared using phenylhydrazine and 2,4-difluorobenzaldehyde in step 1. MS (EI) for $C_{13}H_9ClF_2N_2$: 267 [M+H].

Reagent 1.19. (R.1.19.) 4-Chloro-2-fluoro-N-phenylbenzohydrazonoyl chloride was prepared using phenylhydrazine and 4-chloro-2-fluorobenzaldehyde in step 1. MS (EI) for $C_{13}H_9Cl_2FN_2$: 284 [M+H].

Reagent 1.20. (R.1.20.)N-(2,4-Difluorophenyl)-2,4-difluorobenzohydrazonoyl chloride was prepared using (2,4-difluorophenyl)hydrazine and 2,4-difluorobenzaldehyde in step 1. MS (EI) for $C_{13}H_7ClF_4N_2$: 303 [M+H].

Reagent 1.21. (R.1.21.) 4-Chloro-N-(2,4-difluorophenyl)benzohydrazonoyl chloride was prepared using (2,4-difluorophenyl)hydrazine and 4-chlorobenzaldehyde in step 1. MS (EI) for $C_{13}H_8Cl_2F_2N_2$: 301 [M+H].

Reagent 2.1. Methyl (E)-2-methylhept-2-enoate was prepared as shown in the following scheme.

STEP 1.

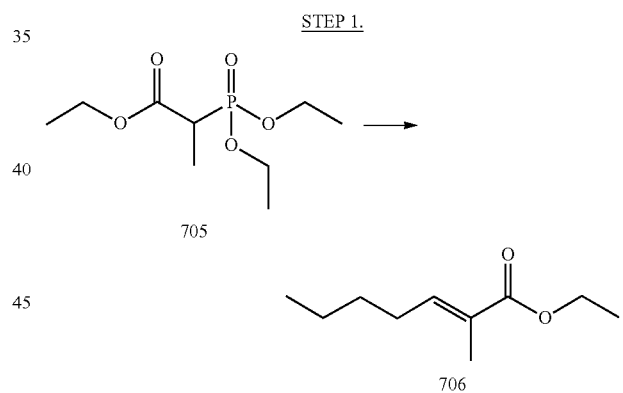

To a suspension of lithium chloride (4.30 g, 100.8 mmol) in dry acetonitrile (75.0 ml) was added triethyl-2-phosphonopropionate (705) (18.01 mL, 84.0 mmol) and 1,8-diazabicyclo[5.4.0]undec-7-ene (12.40 mL, 84.0 mmol) and the resulting solution was cooled to 0° C. followed by the addition of pentanal (8.40 mL, 80.0 mmol); it was stirred at room temperature for 18 hours. The solvent was evaporated and the crude was partitioned with ethyl acetate (300 mL) and 2M aqueous hydrochloric acid (100 ml). The organic layer was separated, washed with 2M aqueous hydrochloric acid (2×50 ml) and brine (2×150 mL), dried over anhydrous sodium sulfate and concentrated. The resulting crude, ethyl (E)-2-methylhept-2-enoate (706), was used without further purification (14 g, quant.). MS (EI) for $C_{10}H_{18}O_2$: 171 [M+H].

STEP 2.

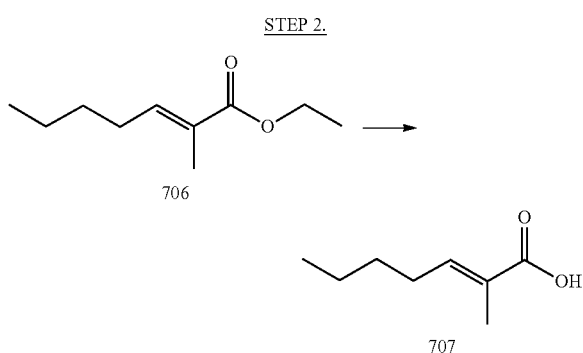

To a solution of ethyl (E)-2-methylhept-2-enoate (706) 14 g, 80.0 mmol) in a mixture of tetrahydrofuran (80.0 mL) and methanol (20.0 mL) at 0° C. was added potassium hydroxide (27.0 mL, 240.0 mmol, 50% aq. solution) and the reaction mixture was stirred at room temperature for 18 hours. The solvent was concentrated and the pH was adjusted to 2 by the addition of concentrated hydrochloric acid. The mixture was partitioned with ethyl acetate (300 mL) and the organic layer was separated, washed with brine (2×250 mL), dried over anhydrous sodium sulfate and concentrated to give crude (E)-2-methylhept-2-enoic acid (707) as white solid (quantitative). MS (EI) for $C_8H_{14}O_2$: 141 [M+H]. The crude was used without further purification.

STEP 3.

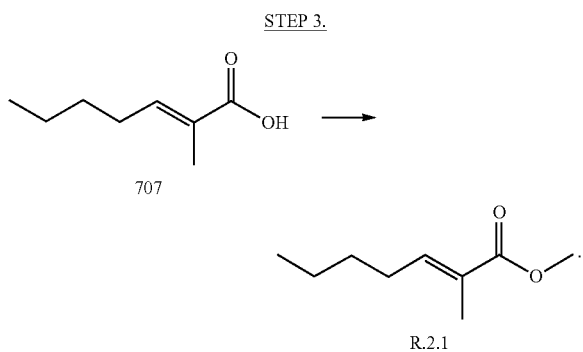

To a suspension of (E)-2-methylhept-2-enoic acid (707) in N,N-dimethylformamide (75.0 mL) and potassium carbonate (33.2 g, 240.0 mmol) at 0° C. was added iodomethane (6.0 mL, 96.0 mmol) and the reaction mixture was stirred at room temperature for 18 hours. It was diluted with water (150 mL) and partitioned with ethyl acetate (300 mL). The organic layer was washed with 2M aqueous hydrochloric acid (2×150 ml) and brine (2×150 mL), dried over anhydrous sodium sulfate and concentrated. The resulting crude was purified by gradient silica gel flash chromatography (1-10% ethyl acetate in hexanes) to give methyl (E)-2-methylhept-2-enoate (R.2.1.) (11.9 g, 95%). MS (EI) for $C_9H_{16}O_2$: 157 [M+H].

Reagent 2.2. Methyl (E)-2-methyl-3-(thiophen-3-yl)acrylate was prepared using (thiophene-3-carbaldehyde in step 1. MS (EI) for $C_9H_{10}O_2S$: 183 [M+H].

Reagent 2.3. Methyl (E)-2-methyl-3-(pyridin-4-yl)acrylate was prepared using isonicotinalde-hyde in step 1. MS (EI) for $C_{10}H_{11}NO_2$: 178 [M+H].

Reagent 2.4. Methyl (E)-2-methyl-3-(thiophen-2-yl)acrylate was prepared using thiophene-2carbaldehyde in step 1. MS (EI) for $C_9H_{10}O_2S$: 183 [M+H].

Reagent 2.5. Methyl (E)-3-(furan-3-yl)-2-methylacrylate was prepared using furan-3-carb-aldehyde in step 1. MS (EI) for $C_9H_{10}O_3$: 167 [M+H].

Reagent 2.6. Methyl (E)-2-methyl-3-(5-methylthiophen-2-yl)acrylate was prepared using 5-methylthiophene-2-carbaldehyde in step 1. MS (EI) for $C_{10}H_{12}O_2S$: 197 [M+H].

Reagent 2.7. Methyl (E)-3-(5-chlorothiophen-2-yl)-2-methylacrylate was prepared using 5-chlorothiophene-2-carbaldehyde in step 1. MS (EI) for $C_9H_9ClO_2S$: 217 [M+H].

Reagent 2.8. Methyl (E)-3-(furan-2-yl)-2-methylacrylate was prepared using furan-2-carbaldehyde in step 1. MS (EI) for $C_9H_{10}O_3$: 167 [M+H].

Reagent 2.9. Methyl (E)-3-(5-chlorofuran-2-yl)-2-methylacrylate was prepared using 5-chloro-furan-2-carbaldehyde in step 1. MS (EI) for $C_9H_9ClO_3$: 201 [M+H].

Reagent 2.10. Methyl (E)-2-methyl-3-(5-methylfuran-2-yl)acrylate was prepared using 5-methyl-furan-2-carbaldehyde in step 1. MS (EI) for $C_{10}H_{12}O_3$: 181 [M+H].

Reagent 2.11. Methyl (E)-2-methyl-3-(5-(trifluoromethyl)furan-2-yl)acrylate was prepared using 5-(trifluoromethyl)furan-2-carbaldehyde in step 1. MS (EI) for $C_{10}H_9F_3O_3$: 235 [M+H].

Reagent 2.12. Methyl (E)-2-methyl-3-(5-(methylcarbamoyl)furan-2-yl)acrylate was prepared using 5-formyl-N-methylfuran-2-carboxamide in step 1. MS (EI) for $C_{11}H_{13}NO_4$: 224 [M+H].

The following reagents were also used in the Examples described below.

Reagent 3.1. tert-Butyl 4-(aminomethyl)-4-methoxypiperidine-1-carboxylate. MS (EI) for $C_{12}H_{24}N_2O_3$: 245 [M+H].

Reagent 3.2. tert-Butyl 4-amino-4-(methoxymethyl)piperidine-1-carboxylate. MS (EI) for $C_{12}H_{24}N_2O_3$: 245 [M+H].

Reagent 3.3. tert-Butyl 3-(aminomethyl)-3-methoxyazetidine-1-carboxylate. MS (EI) for $C_{10}H_{20}N_2O_3$: 217 [M+H].

Reagent 3.4. tert-Butyl 3-amino-3-(methoxymethyl)azetidine-1-carboxylate. MS (EI) for $C_{10}H_{20}N_2O_3$: 217 [M+H].

Reagent 3.5. (3-Methoxyoxetan-3-yl)methanamine. MS (EI) for $C_5H_{11}NO_2$: 118 [M+H].

Reagent 3.6. 3-(Methoxymethyl)oxetan-3-amine. MS (EI) for $C_5H_{11}NO_2$: 118 [M+H].

Reagent 3.7. 3-(Aminomethyl)-N,N-dimethyloxetan-3-amine. MS (EI) for $C_6H_{14}N_2O$: 131 [M+H].

Reagent 3.8. 3-((Dimethylamino)methyl)oxetan-3-amine. MS (EI) for $C_6H_{14}N_2O$: 131 [M+H].

Reagent 3.9. (4,6-Dimethylmorpholin-2-yl)methanamine. MS (EI) for $C_7H_{16}N_2O$: 145 [M+H].

Reagent 3.10. (4,6,6-Trimethylmorpholin-2-yl)methanamine. MS (EI) for $C_8H_{18}N_2O$: 159 [M+H].

Reagent 3.11. (7-Methyl-4-oxa-7-azaspiro[2.5]octan-5-yl)methanamine. MS (EI) for $C_8H_{16}N_2O$: 157 [M+H].

Reagent 3.12. (8-Methyl-2,5-dioxa-8-azaspiro[3.5]nonan-6-yl)methanamine. MS (EI) for $C_6H_{16}N_2O_2$: 173 [M+H].

Reagent 3.13. tert-Butyl 6-(aminomethyl)-2-methyl-5-oxa-2,8-diazaspiro[3.5]nonane-8-carboxylate. MS (EI) for $C_{13}H_{25}N_3O_3$: 272 [M+H].

Reagent 3.14. (4,5-Dimethylmorpholin-2-yl)methanamine. MS (EI) for $C_7H_{16}N_2O$: 145 [M+H].

Reagent 3.15. (4,5,5-Trimethylmorpholin-2-yl)methanamine. MS (EI) for $C_8H_{18}N_2O$: 159 [M+H].

Reagent 3.16. (4-Methyl-7-oxa-4-azaspiro[2.5]octan-6-yl)methanamine. MS (EI) for $C_8H_{16}N_2O$: 157 [M+H].

Reagent 3.17. (5-Methyl-2,8-dioxa-5-azaspiro[3.5]nonan-7-yl)methanamine. MS (EI) for $C_8H_{16}N_2O_2$: 173 [M+H].

Reagent 3.18. tert-Butyl 7-(aminomethyl)-2-methyl-8-oxa-2,5-diazaspiro[3.5]nonane-5-carboxylate. MS (EI) for $C_{13}H_{25}N_3O_3$: 272 [M+H].

Reagent 3.19. (4,5,6-Trimethylmorpholin-2-yl)methanamine. MS (EI) for $C_8H_{18}N_2O$: 159 [M+H].

Reagent 3.20. (3-Amino-2-methoxypropyl)dimethylamine. MS (EI) for $C_6H_{16}N_2O$: 133 [M+H].

Reagent 3.21. tert-Butyl 3-amino-4-methoxypyrrolidine-1-carboxylate. MS (EI) for $C_{10}H_{20}N_2O_3$: 217 [M+H].

Reagent 3.22. (3S,6R)-6-Nethoxyhexahydrofuro[3,2-b]furan-3-amine. MS (EI) for $C_7H_{13}NO_3$: 131 [M+H].

Reagent 3.23. (3S,6S)—$N_3,N_3$-dimethylhexahydrofuro[3,2-b]furan-3,6-diamine. MS (EI) for $C_8H_{16}N_2O_2$: 173 [M+H].

Reagent 3.24.
R.3.24.1 ((8aS)-hexahydro-1H-pyrrolo[2,1-c][1,4]oxazin-3-yl)methanamine. MS (EI) for $C_8H_{16}N_2O$: 157 [M+H].
R.3.24.2. ((8aR)-hexahydro-1H-pyrrolo[2,1-c][1,4]oxazin-3-yl)methanamine. MS (EI) for $C_8H_{16}N_2O$: 157 [M+H].

Reagent 3.25.
R.3.25.1. ((9aS)-hexahydro-1H-[1,4]oxazino[3,4-c][1,4]oxazin-3-yl)methanamine. MS (EI) for $C_8H_{16}N_2O_2$: 172 [M+H].
R.3.25.2. ((9aR)-hexahydro-1H-[1,4]oxazino[3,4-c][1,4]oxazin-3-yl)methanamine. MS (EI) for $C_8H_{16}N_2O_2$: 172 [M+H].

Reagent 3.26. (3-methoxy-1-methylazetidin-3-yl)methanamine. MS (EI) for $C_6H_{14}N_2O$: 131 [M+H].

INTERMEDIATE 1 (I.1.x) COMPOUNDS

Intermediate 1.2. (I.1.2) 4-Butyl-1-(2,4-difluorophenyl)-3-(4-fluorophenyl)-5-methyl-4,5-dihydro-1H-pyrazole-5-carboxylate was synthesized according to the following scheme.

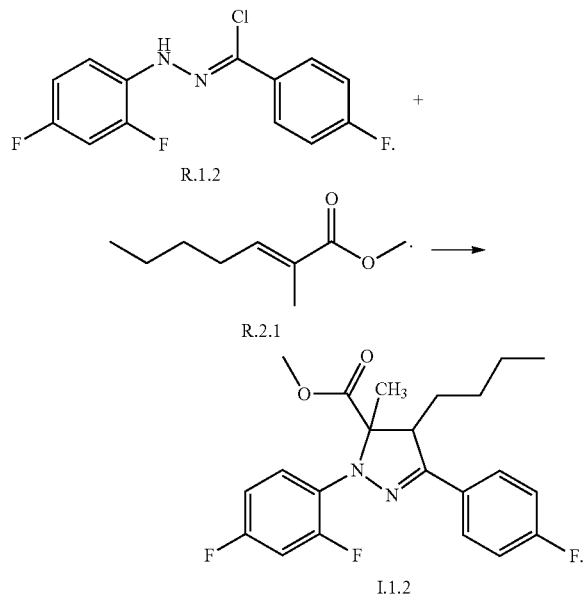

To a solution of N-(2,4-difluorophenyl)-4-fluorobenzohydrazonoyl chloride (R.1.2.) (1.40 g, 5.0 mmol) and methyl (E)-2-methylhept-2-enoate (1.60 g, 10.0 mmol) (R.2.1.) in anhydrous tetrahydrofuran (10.0 mL) was added trimethylamine (2.10 mL, 15.0 mmol) and the reaction mixture was stirred at room temperature for 18 hours. It was diluted with ethyl acetate (200 mL) and partitioned with 1M aqueous hydrochloric acid (50 mL). The organic layer was separated washed with 1M aqueous hydrochloric acid (2×50 mL), brine (2×100 mL), dried over anhydrous sodium sulfate and concentrated. The resulting crude product was purified by gradient silica gel flash chromatography (1-25% ethyl acetate in hexanes) to give methyl 4-butyl-1-(2,4-difluorophenyl)-3-(4-fluorophenyl)-5-methyl-4,5-dihydro-1H-pyrazole-5-carboxylate (I.1.2.) (0.80 g, 40%). MS (EI) for $C_{22}H_{23}F_3N_2O_2$: 405 [MH$^+$].

Intermediate 1.1. Methyl 4-butyl-3-(4-fluorophenyl)-5-methyl-1-phenyl-4,5-dihydro-1H-pyrazole-5-carboxylate was prepared according to the procedures used for I.1.2. using 4-fluoro-N-phenylbenzohydrazonoyl chloride (R.1.1.) and methyl (E)-2-methylhept-2-enoate (R.2.1.). 1H-NMR (300 MHz, d-chloroform): 7.64 (dd, 2H), 7.30 (2t, 2H), 7.16-7.07 (m, 4H), 6.97 (t, 1H), 3.70 (dd, 1H), 3.66 (s, 3H), 1.72 (m, 2H), 1.54 (s, 3H), 1.28 (m, 4H), 0.83 (t, 3H). MS (EI) for $C_{22}H_{25}FN_2O_2$: 369 [M+H].

Intermediate 1.3. Methyl 4-butyl-1-(3-fluorophenyl)-3-(4-fluorophenyl)-5-methyl-4,5-dihydro-1H-pyrazole-5-carboxylate was prepared according to the procedures used for I.1.2. using 4-fluoro-N-(3-fluorophenyl)benzohydrazonoyl chloride (R.1.3.) and methyl (E)-2-methylhept-2-enoate (R.2.1.). MS (EI) for $C_{22}H_{24}F_2N_2O_2$: 387 [M+H].

Intermediate 1.4. Methyl 4-butyl-1,3-bis(4-fluorophenyl)-5-methyl-4,5-dihydro-1H-pyrazole-5-carboxylate was prepared according to the procedures used for 1.1.2. using 4-fluoro-N-(4-fluorophenyl)benzohydrazonoyl chloride (R.1.4.) and methyl (E)-2-methylhept-2-enoate (R.2.1.). MS (EI) for $C_{22}H_{24}F_2N_2O_2$: 387 [M+H].

Intermediate 1.5. Methyl 4-butyl-1-(4-chlorophenyl)-3-(4-fluorophenyl)-5-methyl-4,5-dihydro-1H-pyrazole-5-carboxylate was prepared according to the procedures used for 1.1.2. using N-(4-chlorophenyl)-4-fluorobenzohydrazonoyl chloride (R.1.5.) and methyl (E)-2-methylhept-2-enoate (R.2.1.). MS (EI) for $C_{22}H_{24}ClFN_2O_2$: 404 [M+H].

Intermediate 1.6. Methyl 4-butyl-1-(3-chlorophenyl)-3-(4-fluorophenyl)-5-methyl-4,5-dihydro-1H-pyrazole-5-carboxylate was prepared according to the procedures used for 1.1.2. using N-(3-chlorophenyl)-4-fluorobenzohydrazonoyl chloride (R.1.6.) and methyl (E)-2-methylhept-2-enoate (R.2.1.). MS (EI) for $C_{22}H_{24}ClFN_2O_2$: 404 [M+H].

Intermediate 1.7. Methyl 4-butyl-3-(4-fluorophenyl)-5-methyl-1-(p-tolyl)-4,5-dihydro-1H-pyrazole-5-carboxylate was prepared according to the procedures used for 1.1.2. using 4-fluoro-N-(p-tolyl)benzohydrazonoyl chlorid (R.1.7.) and methyl (E)-2-methylhept-2-enoate (R.2.1.). 1H-NMR (300 MHz, $d_6$-DMSO): 7.64 (q, 2H), 7.28 (t, 2H), 7.08-6.94 (m, 4H), 3.80 (q, 1H), 3.64 (s, 3H), 2.22 (s, 3H), 1.72 (m, 1H), 1.52 (m, 1H), 1.22 (m, 4H), 1.18 (s, 3H), 0.81 (s, 3H). MS (EI) for $C_{23}H_{27}FN_2O_2$: 383 [M+H].

Intermediate 1.8. Methyl 4-butyl-3-(4-fluorophenyl)-5-methyl-1-(m-tolyl)-4,5-dihydro-1H-pyrazole-5-carboxylate was prepared according to the procedures used for 1.1.2. using 4-fluoro-N-(m-tolyl)benzohydrazonoyl chloride R.1.8.) and methyl (E)-2-methylhept-2-enoate (R.2.1.). 1H-NMR (300 MHz, $d_6$-DMSO): 7.65 (dd, 2H), 7.25 (t, 2H), 7.14 (t, 1H), 6.96 (s, 1H), 6.82 (d, 1H), 6.69 (d, 1H), 3.80 (q, 1H), 3.66 (s, 3H), 2.26 (s, 3H), 1.74 (m, 1H), 1.54 (m, 1H), 1.22 (m, 4H), 1.20 (s, 3H), 0.80 (s, 3H). MS (EI) for $C_{23}H_{27}FN_2O_2$: 383 [M+H].

Intermediate 1.9. Methyl 4-butyl-3-(4-fluorophenyl)-5-methyl-1-(4-(trifluoromethyl)phenyl)-4,5-dihydro-1H-pyrazole-5-carboxylate was prepared according to the procedures used for I.1.2. using 4-fluoro-N-(4-(trifluoromethyl)phenyl) benzohydrazonoyl chloride (R.1.9.) and methyl (E)-2-methylhept-2-enoate (R.2.1.). MS (EI) for $C_{23}H_{24}F_4N_2O_2$: 437 [M+H].

Intermediate 1.10. Methyl 4-butyl-1-(2,5-difluorophenyl)-3-(4-fluorophenyl)-5-methyl-4,5-dihydro-1H-pyrazole-5-carboxylate was prepared according to the procedures used for I.1.2. using N-(2,5-difluorophenyl)-4-fluorobenzo-hydrazonoyl chloride (R.1.10.) and methyl (E)-2-methylhept-2-enoate (R.2.1.). MS (EI) for $C_{22}H_{23}F_3N_2O_2$: 405 [M+H].

Intermediate 1.11. Methyl 4-butyl-1-(4-fluoro-3-methoxyphenyl)-3-(4-fluorophenyl)-5-methyl-4,5-dihydro-1H-pyrazole-5-carboxylate was prepared according to the procedures used for 1.1.2. using 4-fluoro-N-(4-fluoro-3-methoxy-phenyl)benzohydrazonoyl chloride (R.1.11.) and methyl (E)-2-methylhept-2-enoate (R.2.1.). MS (EI) for $C_{23}H_{26}F_2N_2O_2$: 417 [M+H].

Intermediate 1.12. Methyl 4-butyl-1-(3-chloro-4-fluorophenyl)-3-(4-fluorophenyl)-5-methyl-4,5-dihydro-1H-pyrazole-5-carboxylate was prepared according to the procedures used for 1.1.2. using N-(3-chloro-4-fluorophenyl)-4-fluoro-benzohydrazonoyl chloride (R.1.12.) and methyl (E)-2-methylhept-2-enoate (R.2.1.). MS (EI) for $C_{22}H_{23}ClFN_2O_2$: 421 [M+H].

Intermediate 1.13. Methyl 4-butyl-1-(2-chloro-4-fluorophenyl)-3-(4-fluorophenyl)-5-methyl-4,5-dihydro-1H-pyrazole-5-carboxylate was prepared according to the procedures used for I.1.2. using N-(2-chloro-4-fluorophenyl)-4-fluoro-benzohydrazonoyl chloride (R.1.13.) and methyl (E)-2-methylhept-2-enoate (R.2.1.). MS (EI) for $C_{22}H_{23}ClF_2N_2O_2$: 421 [M+H].

Intermediate 1.14. Methyl 4-butyl-1-(4-chloro-2-fluorophenyl)-3-(4-fluorophenyl)-5-methyl-4,5-dihydro-1H-pyrazole-5-carboxylate was prepared according to the procedures used for I.1.2. using N-(4-chloro-2-fluorophenyl)-4-fluoro-benzohydrazonoyl chloride (R.1.14.) and methyl (E)-2-methylhept-2-enoate (R.2.1.). 1H-NMR (300 MHz, $d_6$-DMSO): 7.74 (m, 2H), 7.41 (dd, 1H), 7.39 (t, 1H), 7.28 (2t, 2H), 7.21 (dd, 1H), 3.80 (t, 1H), 3.64 (s, 3H), 1.54 (m, 2H), 1.20 (s, 3H), 1.18 (m, 4H), 0.78 (s, 3H). MS (EI) for $C_{22}H_{23}ClF_2N_2O_2$: 421 [M+H].

Intermediate 1.15. Methyl 4-butyl-1-(4-chloro-2-methylphenyl)-3-(4-fluorophenyl)-5-methyl-4,5-dihydro-1H-pyrazole-5-carboxylate was prepared according to the procedures used for I.1.2. using N-(4-chloro-2-methylphenyl)-4-fluoro-benzohydrazonoyl chloride (R.1.15.) and methyl (E)-2-methylhept-2-enoate (R.2.1.). MS (EI) for $C_{23}H_{26}ClFN_2O_2$: 417 [M+H].

Intermediate 1.16. Methyl 4-butyl-3-(4-chlorophenyl)-5-methyl-1-phenyl-4,5-dihydro-1H-pyrazole-5-carboxylate was prepared according to the procedures used for 1.1.2. using 4-chloro-N-phenylbenzohydrazonoyl chloride (R.1.16.) and methyl (E)-2-methylhept-2-enoate (R.2.1.). MS (EI) for $C_{22}H_{25}ClN_2O_2$: 385 [M+H].

Intermediate 1.17. Methyl 4-butyl-3-(3,4-difluorophenyl)-5-methyl-1-phenyl-4,5-dihydro-1H-pyrazole-5-carboxylate was prepared according to the procedures used for 1.1.2. using 3,4-difluoro-N-phenylbenzohydrazonoyl chloride (R.1.17.) and methyl (E)-2-methylhept-2-enoate (R.2.1.). MS (EI) for $C_{22}H_{24}F_2N_2O_2$: 387 [M+H].

Intermediate 1.18. Methyl 4-butyl-3-(2,4-difluorophenyl)-5-methyl-1-phenyl-4,5-dihydro-1H-pyrazole-5-carboxylate was prepared according to the procedures used for 1.1.2. using 2,4-difluoro-N-phenylbenzohydrazonoyl chloride (R.1.18.) and methyl (E)-2-methylhept-2-enoate (R.2.1.). 1H-NMR (300 MHz, $d_6$-DMSO): 7.40 (q, 1H), 7.38 (m, 1H), 7.32 (m, 4H), 7.06 (m, 1H), 6.82 (t, 1H), 3.80 (t, 1H), 3.66 (s, 3H), 1.44 (m, 2H), 1.20 (m, 4H), 1.14 (s, 3H), 0.78 (t, 3H). MS (EI) for $C_{22}H_{24}F_2N_2O_2$: 387 [M+H].

Intermediate 1.19. Methyl 4-butyl-3-(4-chloro-2-fluorophenyl)-5-methyl-1-phenyl-4,5-dihydro-1H-pyrazole-5-carboxylate was prepared according to the procedures used for 1.1.2. using 4-chloro-2-fluoro-N-phenylbenzohydrazonoyl chloride (R.1.19.) and methyl (E)-2-methylhept-2-enoate (R.2.1.). MS (EI) for $C_{22}H_{23}ClFN_2O_2$: 403 [M+H].

Intermediate 1.20. Methyl 3-(4-fluorophenyl)-5-methyl-1-phenyl-4-(thiophen-2-yl)-4,5-dihydro-1H-pyrazole-5-carboxylate was prepared according to the procedures used for 1.1.2. using 4-fluoro-N-phenylbenzohydrazonoyl chloride (R.1.1.) and methyl (E)-2-methyl-3-(thiophen-2-yl)acrylate (R.2.2.). 1H-NMR (300 MHz, $d_6$-DMSO): 7.64 (dd, 2H), 7.44 (m, 1H), 7.26 (t, 2H), 7.21 (t, 2H), 7.07 (d, 2H), 6.98 (m, 1H), 6.90 (m, 1H), 6.82 (t, 1H), 5.20 (s, 1H), 3.68 (s, 3H), 0.84 (m, 3H). MS (EI) for $C_{22}H_{19}FN_2O_2S$: 395 [M+H].

Intermediate 1.21. Methyl 3-(4-fluorophenyl)-5-methyl-4-(thiophen-2-yl)-1-(p-tolyl)-4,5-dihydro-1H-pyrazole-5-carboxylate was prepared according to the procedures used for 1.1.2. using 4-fluoro-N-(p-tolyl)benzohydrazonoyl chloride (R.1.7.) and methyl (E)-2-methyl-3-(thiophen-2-yl)acrylate (R.2.2.). 1H-NMR (R.2.2.). 1H-NMR (300 MHz, $d_6$-DMSO): 7.64 (dd, 2H), 7.42 (m, 1H), 7.28 (t, 2H), 7.07-7.01 (q, 4H), 6.98 (m, 1H), 6.90 (m, 1H), 5.20 (s, 1H), 3.66 (s, 3H), 2.24 (s, 3H), 0.88 (s, 3H). MS (EI) for $C_{23}H_{21}FN_2O_2S$: 409 [M+H].

Intermediate 1.22. Methyl 3-(4-fluorophenyl)-5-methyl-1-phenyl-4-(pyridin-4-yl)-4,5-dihydro-1H-pyrazole-5-carboxylate was prepared according to the procedures used for 1.1.2. using 4-fluoro-N-phenylbenzohydrazonoyl chloride (R.1.1.) and methyl (E)-2-methyl-3-(pyridin-4-yl)acrylate (R.2.3.). MS (EI) for $C_{23}H_{20}FN_3O_2$: 390 [M+H].

Interm according to the procedures used for I.1.2. ediate 1.23. Methyl 1-(2,4-difluorophenyl)-3-(4-fluorophenyl)-5-methyl-4-(thiophen-3-yl)-4,5-dihydro-1H-pyrazole-5-carboxylate was prepared according to the procedures used for 1.1.2. using N-(2,4-difluorophenyl)-4-fluoro-benzohydrazonoyl chloride (R.1.2.) and methyl (E)-2-methyl-3-(thiophen-3-yl)acrylate (R.2.2.). 1H-NMR (300 MHz, $d_6$-DMSO): 7.62 (dd, 2H), 7.54 (m, 1H), 7.48 (dd, 1H), 7.34 (m, 1H), 7.28 (m, 1H), 7.18 (t, 2H), 7.08 (m, 1H), 6.78 (m, 1H), 5.08 (s, 1H), 3.64 (s, 3H), 0.78 (s, 3H). MS (EI) for $C_{22}H_{17}F_3N_2O_2S$: 431 [M+H].

Intermediate 1.24. Methyl 4-butyl-1,3-bis(2,4-difluorophenyl)-5-methyl-4,5-dihydro-1H-pyrazole-5-carboxylate was prepared according to the procedures used for 1.1.2. using N-(2,4-difluorophenyl)-2,4-difluorobenzohydrazonoyl chloride (R.1.20.) and methyl (E)-2-methylhept-2-enoate (R.2.1.). 1H-NMR (300 MHz, $d_6$-DMSO): 7.76 (q, 1H), 7.42 (q, 1H), 7.38 (m, 1H), 7.22 (m, 1H), 720 (m, 1H), 7.06 (m, 1H), 3.80 (t, 1H), 3.64 (s, 3H), 1.44 (m, 2H), 1.18 (m, 4H), 1.09 (s, 3H), 0.76 (s, 3H). MS (EI) for $C_{22}H_{22}F_4N_2O_2$: 423 [M+H].

Intermediate 1.25. Methyl 1-(2,4-difluorophenyl)-3-(4-fluorophenyl)-5-methyl-4-(thiophen-2-yl)-4,5-dihydro-1H-pyrazole-5-carboxylate was prepared according to the procedures used for I.1.2. using N-(2,4-difluorophenyl)-4-fluoro-benzohydrazonoyl chloride (R.1.2.) and methyl (E)-2-methyl-3-(thiophen-2-yl)acrylate (R.2.4). 1H-NMR (300 MHz, $d_6$-DMSO): 7.64 (dd, 2H), 7.44 (m, 2H), 7.28 (m, 1H), 7.19 (t, 2H), 7.10 (m, 1H), 6.98 (m, 1H), 6.92 (m, 1H), 5.23 (s, 1H), 3.66 (s, 3H), 0.84 (s, 3H). MS (EI) for $C_{22}H_{17}F_3N_2O_2S$: 431 [M+H].

Intermediate 1.26. Methyl 1,3-bis(2,4-difluorophenyl)-5-methyl-4-(thiophen-3-yl)-4,5-dihydro-1H-pyrazole-5-carboxylate was prepared according to the procedures used for 1.1.2. using N-(2,4-difluorophenyl)-2,4-difluoro-benzohydrazonoyl chloride (R.1.20.) and methyl (E)-2-methyl-3-(thiophen-3-yl)acrylate (R.2.2.). 1H-NMR (300 MHz, d$_6$-DMSO): 7.82 (q, 1H), 7.56 (q, 1H), 7.44 (dd, 1H), 7.28 (m, 1H), 7.22 (m, 1H), 7.19 (d, 1H), 7.11 (m, 2H), 6.78 (d, 1H), 5.08 (s, 1H), 3.68 (s, 3H), 0.74 (s, 3H). MS (EI) for $C_{22}H_{16}F_4N_2O_2S$: 449 [M+H].

Intermediate 1.27. Methyl 1,3-bis(2,4-difluorophenyl)-4-(furan-3-yl)-5-methyl-4,5-dihydro-1H-pyrazole-5-carboxylate was prepared according to the procedures used for 1.1.2. using N-(2,4-difluorophenyl)-2,4-difluorobenzohydrazonoyl chloride (R.1.20.) and methyl (E)-3-(furan-3-yl)-2-methylacrylate (R.2.5.). 1H-NMR (300 MHz, d$_6$-DMSO): 7.84 (q, 1H), 7.56 (s, 1H), 7.50 (m, 1H), 7.49 (s, 1H), 7.26 (m, 2H), 7.09 (m, 2H), 6.18 (s, 1H), 4.88 (s, 1H), 3.65 (s, 3H), 0.86 (s, 3H). MS (EI) for $C_{22}H_{16}F_4N_2O_3$: 433 [M+H].

Intermediate 1.28. Methyl 1-(2,4-difluorophenyl)-3-(4-fluorophenyl)-5-methyl-4-(5-methyl-thiophen-2-yl)-4,5-dihydro-1H-pyrazole-5-carboxylate was prepared according to the procedures used for I.1.2. using N-(2,4-difluorophenyl)-4-fluorobenzohydrazonoyl chloride (R.1.2.) and methyl (E)-2-methyl-3-(5-methylthiophen-2-yl)acrylate (R.2.6.). MS (EI) for $C_{23}H_{19}F_3N_2O_2S$: 445 [M+H].

Intermediate 1.29. Methyl 4-(5-chlorothiophen-2-yl)-1-(2,4-difluorophenyl)-3-(4-fluorophenyl)-5-methyl-4,5-dihydro-1H-pyrazole-5-carboxylate was prepared according to the procedures used for I.1.2. using N-(2,4-difluorophenyl)-4-fluorobenzohydrazonoyl chloride (R.1.2.) and methyl (E)-3-(5-chlorothiophen-2-yl)-2-methylacrylate (R.2.7.). MS (EI) for $C_{22}H_{16}ClF_3N_2O_2S$: 465 [M+H].

Intermediate 1.30. Methyl 1-(2,4-difluorophenyl)-3-(4-fluorophenyl)-4-(furan-2-yl)-5-methyl-4,5-dihydro-1H-pyrazole-5-carboxylate was prepared according to the procedures used for I.1.2. using N-(2,4-difluorophenyl)-4-fluoro-benzohydrazonoyl chloride (R.1.2.) and methyl (E)-3-(furan-2-yl)-2-methylacrylate (R.2.8.). MS (EI) for $C_{22}H_{17}F_3N_2O_3$: 415 [M+H].

Intermediate 1.31. Methyl 1,3-bis(2,4-difluorophenyl)-4-(furan-2-yl)-5-methyl-4,5-dihydro-1H-pyrazole-5-carboxylate was prepared according to the procedures used for 1.1.2. using N-(2,4-difluorophenyl)-2,4-difluorobenzohydrazonoyl chloride (R.1.20.) and methyl (E)-3-(furan-2-yl)-2-methylacrylate (R.2.8.). MS (EI) for $C_{22}H_{16}F_4N_2O_3$: 433 [M+H].

Intermediate 1.32. Methyl 4-(5-chlorofuran-2-yl)-1,3-bis(2,4-difluorophenyl)-5-methyl-4,5-dihydro-1H-pyrazole-5-carboxylate was prepared according to the procedures used for I.1.2. using N-(2,4-difluorophenyl)-2,4-difluoro-benzohydrazonoyl chloride (R.1.20.) and methyl (E)-3-(5-chlorofuran-2-yl)-2-methylacrylate (R.2.9.). 1H-NMR (300 MHz, d$_6$-DMSO): 7.91 (q, 1H), 7.54 (q, 1H), 7.30 (m, 2H), 7.16 (m, 2H), 6.38 (d, 1H), 6.33 (d, 1H), 5.20 (s, 1H), 3.64 (s, 3H), 0.92 (s, 3H). MS (EI) for $C_{22}H_{15}F_4N_2O_3$: 467 [M+H].

Intermediate 1.33. Methyl 1,3-bis(2,4-difluorophenyl)-5-methyl-4-(5-methylfuran-2-yl)-4,5-dihydro-1H-pyrazole-5-carboxylate was prepared according to the procedures used for 1.1.2. using N-(2,4-difluorophenyl)-2,4-difluoro-benzohydrazonoyl chloride (R.1.20.) and methyl (E)-2-methyl-3-(5-methylfuran-2-yl)acrylate (R.2.10.). MS (EI) for $C_{23}H_{18}F_4N_2O_3$: 447 [M+H].

Intermediate 1.34. Methyl 1,3-bis(2,4-difluorophenyl)-5-methyl-4-(5-(trifluoromethyl)furan-2-yl)-4,5-dihydro-1H-pyrazole-5-carboxylate was prepared according to the procedures used for 1.1.2. using N-(2,4-difluorophenyl)-2,4-difluorobenzohydrazonoyl chloride (R.1.20.) and methyl (E)-2-methyl-3-(5-(trifluoromethyl)furan-2-yl)acrylate (R.2.11.). MS (EI) for $C_{23}H_{15}F_7N_2O_3$: 501 [M+H].

Intermediate 1.35. Methyl 1,3-bis(2,4-difluorophenyl)-5-methyl-4-(5-(methylcarbamoyl)furan-2-yl)-4,5-dihydro-1H-pyrazole-5-carboxylate was prepared according to the procedures used for I.1.2. using N-(2,4-difluorophenyl)-2,4-difluorobenzohydrazonoyl chloride (R.1.20.) and methyl (E)-2-methyl-3-(5-(methylcarbamoyl)furan-2-yl)acrylate (R.2.13.). MS (EI) for $C_{24}H_{19}F_4N_3O_4$: 490 [M+H].

Intermediate 1.36. Methyl 4-(5-chlorofuran-2-yl)-1-(2,4-difluorophenyl)-3-(4-fluorophenyl)-5-methyl-4,5-dihydro-1H-pyrazole-5-carboxylate was prepared according to the procedures used for I.1.2. using N-(2,4-difluorophenyl)-4-fluorobenzohydrazonoyl chloride (R.1.2.) and methyl (E)-3-(5-chlorofuran-2-yl)-2-methylacrylate (R.2.9.). MS (EI) for $C_{22}H_{16}ClF_3N_2O_3$: 449 [M+H].

Intermediate 1.37. Methyl 1-(4-chloro-2-fluorophenyl)-4-(5-chlorofuran-2-yl)-3-(4-fluorophenyl)-5-methyl-4,5-dihydro-1H-pyrazole-5-carboxylate was prepared according to the procedures used for I.1.2. using N-(4-chloro-2-fluorophenyl)-4-fluorobenzohydrazonoyl chloride (R.1.14.) and methyl (E)-3-(5-chlorofuran-2-yl)-2-methylacrylate (R.2.9.). MS (EI) for $C_{22}H_{16}Cl_2F_2N_2O_3$: 465 [M+H].

Intermediate 1.38. Methyl 4-(5-chlorofuran-2-yl)-3-(4-chlorophenyl)-1-(2,4-difluorophenyl)-5-methyl-4,5-dihydro-1H-pyrazole-5-carboxylate was prepared according to the procedures used for I.1.2. using 4-chloro-N-(2,4-difluorophenyl)benzohydrazonoyl chloride (R.1.21.) and methyl (E)-3-(5-chlorofuran-2-yl)-2-methylacrylate (R.2.9.). MS (EI) for $C_{22}H_{16}Cl_2F_2N_2O_3$: 465 [M+H].

Intermediate 1.39. Methyl 4-(5-chlorofuran-2-yl)-3-(4-fluorophenyl)-5-methyl-1-(p-tolyl)-4,5-dihydro-1H-pyrazole-5-carboxylate was prepared according to the procedures used for 1.1.2. using 4-fluoro-N-(p-tolyl)benzohydrazonoyl chloride (R.1.7.) and methyl (E)-3-(5-chlorofuran-2-yl)-2-methylacrylate (R.2.9.). MS (EI) for $C_{23}H_{20}ClFN_2O_3$: 428 [M+H].

Example 1 Compounds

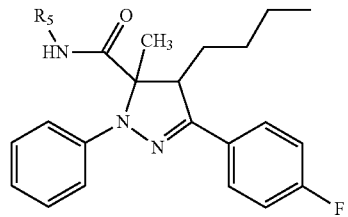

Example 1.4. (E.1.4.) 4-Butyl-3-(4-fluorophenyl)-N-(5-hydroxypentyl)-5-methyl-1-phenyl-4,5-dihydro-1H-pyrazole-5-carboxamide was synthesized according to the following scheme.

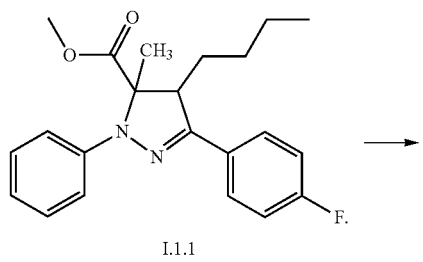

I.1.1

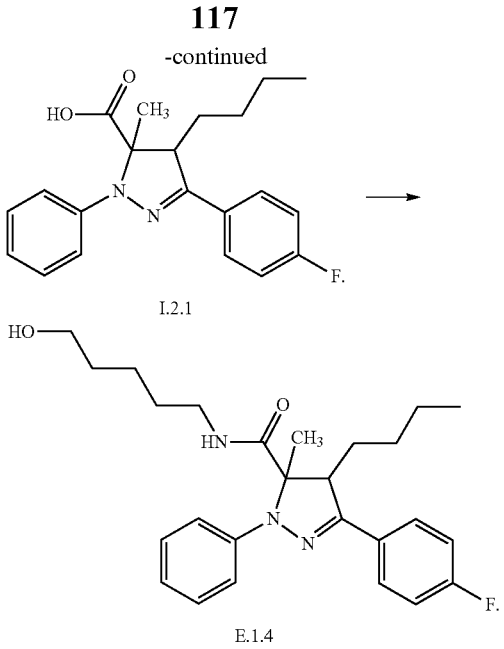

I.2.1

E.1.4

STEP 1. To a solution of methyl 4-butyl-3-(4-fluorophenyl)-5-methyl-1-phenyl-4,5-dihydro-1H-pyrazole-5-carboxylate (I.1.1.) (1.11 g, 3.00 mmol) in a mixture of tetrahyrofuran (18 mL), and water (2 mL) was added potassium hydroxide (1.0 mL, 9.00 mmol, 50% aq. solution) and the reaction mixture was stirred at room temperature for two hours. The progress of reaction was monitored by TLC (10% ethyl acetate in hexanes). The pH was adjusted to 4 by the addition of 2M aqueous hydrochloric acid and it was partitioned with ethyl acetate (250 mL) and water (50 mL), the organic layer was separated, washed with brine (2×50 mL), dried over anhydrous sodium sulfate and concentrated. The precipitated 4-butyl-3-(4-fluorophenyl)-5-methyl-1-phenyl-4,5-dihydro-1H-pyrazole-5-carboxylic acid (I.2.1.) was collected by filtration as a white solid (1.01 g, 95%) and used without further purification. MS (EI) for $C_{21}H_{23}FN_2O_2$: 353 [M−H].

STEP 2. To a solution of 4-butyl-3-(4-fluorophenyl)-5-methyl-1-phenyl-4,5-dihydro-1H-pyrazole-5-carboxylic acid (I.2.1.) (0.050 g, 0.15 mmol) in N,N-dimethylformamide (3 mL) was added 4-methylmorpholine (0.05 mL, 0.45 mmol) and O-(7-azabenzotriazol-1-yl)-N,N,N',N'-tetramethyluronium hexafluoro-phosphate (0.06 g, 0.17 mmol) and the reaction mixture was stirred at room temperature for ten minutes, followed by the addition of 5-amino-1-pentanol (0.02 mL, 0.16 mmol) and the stirring was continued for 18 hours. The mixture was partitioned with ethyl acetate (100 mL) and 1M aqueous hydrochloric acid (25 ml). The organic layer was separated and washed with 1M aqueous hydrochloric acid (25 ml) and brine (2×25 mL), dried over anhydrous sodium sulfate and concentrated. The resulting crude was purified by gradient silica gel flash chromatography (1-50% ethyl acetate in hexanes) to 4-butyl-3-(4-fluorophenyl)-N-(5-hydroxypentyl)-5-methyl-1-phenyl-4,5-dihydro-1H-pyrazole-5-carboxamide (E.1.4.) (0.06 g, 91%). 1H-NMR (300 MHz, d-chloroform): 7.64 (dd, 2H), 7.30 (2t, 2H), 7.16-7.07 (m, 4H), 6.97 (t, 1H), 6.56 (t, 1H), 3.70 (dd, 1H), 3.53 (t, 2H), 3.25 (m, 2H), 1.70 (m, 2H), 1.54 (s, 3H), 1.50 (m, 5H), 1.27 (m, 6H), 0.83 (t, 3H). MS (EI) for $C_{26}H_{34}FN_3O_2$: 440 [M+H].

Example 1.1. 4-Butyl-3-(4-fluorophenyl)-N-(5-hydroxy-4,4-dimethylpentyl)-5-methyl-1-phenyl-4,5-dihydro-1H-pyrazole-5-carboxamide was prepared using 5-amino-2,2-dimethylpentan-1-ol in step 2. 1H-NMR (500 MHz, $d_6$-DMSO): 8.19 (t, 1H), 7.62 (dd, 2H), 7.28 (t, 2H), 7.22 (t, 2H), 7.06 (d, 2H), 6.84 (t, 1H), 4.39 (t, 1H), 3.82 (dd, 1H), 3.10 (q, 2H), 3.02 (d, 2H), 1.74 (m, 1H), 1.56 (m, 1H), 1.36 (m, 4H), 1.24 (s, 3H), 1.23 (m, 2H), 1.08 (m, 1H), 0.80 (m, 4H), 0.68 (s, 6H). 13C-NMR ($d_6$-DMSO): 174.2, 163.8, 161.9, 150.2, 144.1, 129.2, 128.8, 120.2, 116.0, 115.9, 73.8, 70.2, 56.4, 36.6, 35.4, 29.6, 26.2, 24.2, 23.8, 22.6, 13.9, 13.2. MS (EI) for $C_{28}H_{38}FN_3O_2$: 468 [M+H].

Example 1.2. 4-Butyl-3-(4-fluorophenyl)-N-(5-hydroxy-5-methylhexyl)-5-methyl-1-phenyl-4,5-dihydro-1H-pyrazole-5-carboxamide was prepared using 6-amino-2-methylhexan-2-ol in step 2. MS (EI) for $C_{28}H_{38}FN_3O_2$: 468 [M+H].

Example 1.3. 4-Butyl-3-(4-fluorophenyl)-N-(6-hydroxyhexyl)-5-methyl-1-phenyl-4,5-dihydro-1H-pyrazole-5-carboxamide was prepared using 6-aminohexan-1-ol in step 2. 1H-NMR (300 MHz, d-chloroform): 7.64 (m, 2H), 7.28 (m, 2H), 7.16-7.07 (m, 4H), 6.97 (t, 1H), 6.54 (t, 1H), 3.68 (dd, 1H), 3.56 (t, 2H), 2.26 (m, 2H), 1.71 (m, 2H), 1.50 (s, 3H), 1.45 (m, 5H), 1.25 (m, 8H), 0.83 (t, 3H). MS (EI) for $C_{27}H_{36}FN_3O_2$: 454 [M+H].

Example 1.5. 4-Butyl-3-(4-fluorophenyl)-N-(4-hydroxybutyl)-5-methyl-1-phenyl-4,5-dihydro-1H-pyrazole-5-carboxamide was prepared using 4-aminobutan-1-ol in step 2. 1H-NMR (300 MHz, d-chloroform): 7.65 (dd, 2H), 7.28 (2t, 2H), 7.18-7.07 (m, 4H), 6.97 (t, 1H), 6.73 (t, 1H), 3.70 (dd, 1H), 3.54 (m, 2H), 3.28 (m, 2H), 1.70 (m, 2H), 1.54 (s, 3H), 1.48 (m, 4H), 1.39 (m, 1H), 1.26 (m, 4H), 0.83 (t, 3H). MS (EI) for $C_{25}H_{32}FN_3O_2$: 426 [M+H].

Example 1.6. 4-Butyl-3-(4-fluorophenyl)-N-(1-hydroxy-2-methylpropan-2-yl)-5-methyl-1-phenyl-4,5-dihydro-1H-pyrazole-5-carboxamide was prepared using 2-amino-2-methylpropan-1-ol in step 2. 1H-NMR (300 MHz, d-chloroform): 7.64 (dd, 2H), 7.31 (2t, 2H), 7.14 (m, 4H), 6.99 (t, 1H), 6.52 (br s, 1H), 4.59 (t, 1H), 3.68 (dd, 1H), 3.61 (dd, 2H), 1.71 (m, 2H), 1.57 (s, 3H), 1.44 (m, 3H), 1.28 (m, 1H), 1.26 (s, 3H), 1.22 (s, 3H), 0.85 (t, 3H). MS (EI) for $C_{25}H_{32}FN_3O_2$: 426 [M+H].

Example 1.7. 4-Butyl-3-(4-fluorophenyl)-5-methyl-1-phenyl-N-((tetrahydro-2H-pyran-2-yl)methyl)-4,5-dihydro-1H-pyrazole-5-carboxamide was prepared using 2-aminomethyl-tetrahydro-2H-pyran in step 2. 1H-NMR (300 MHz, d-chloroform): 7.64 (dd, 2H), 7.28 (1t, 2H), 7.17 (m, 2H), 7.09 (m, 2H), 6.99 (t, 1H), 3.80 (m, 1H), 3.70 (m, 1H), 3.49 (m, 1H), 3.29 (m, 1H), 3.20 (m, 1H), 3.06 (m, 1H), 1.72 (m, 3H), 1.49 (s, 3H), 1.48 (m, 1H), 1.40 (m, 4H), 1.24 (m, 4H), 0.83 (t, 3H). MS (EI) for $C_{27}H_{34}FN_3O_2$: 452 [M+H].

Example 1.8. 4-Butyl-3-(4-fluorophenyl)-5-methyl-N-(2-(methylsulfonyl)ethyl)-1-phenyl-4,5-dihydro-1H-pyrazole-5-carboxamide was prepared using 2-(methylsulfonyl)ethan-1-amine in step 2. 1H-NMR (300 MHz, d-chloroform): 7.63 (m, 2H), 7.27 (m, 2H), 7.15-7.06 (m, 4H), 6.98 (t, 1H), 3.78 (m, 3H), 3.20 (m, 2H), 3.86 (s, 3H), 1.70 (m, 2H), 1.51 (s, 3H), 1.38 (m, 1H), 1.25 (m, 3H), 0.84 (t, 3H). MS (EI) for $C_{24}H_{30}FN_3O_3S$: 460 [M+H].

Example 1.9. 4-Butyl-N-(3-(dimethylamino)propyl)-3-(4-fluorophenyl)-5-methyl-1-phenyl-4,5-dihydro-1H-pyrazole-5-carboxamide was prepared using 3-(dimethylamino)-1-propylamine in step 2. 1H-NMR (300 MHz, d-chloroform): 7.64 (m, 2H), 7.26 (m, 2H), 7.15-7.06 (m, 4H), 6.92 (t, 1H), 3.70 (dd, 1H), 3.33 (q, 2H), 2.27 (t, 2H), 1.97 (s, 6H), 1.71 (m, 2H), 1.60 (m, 2H), 1.51 (s, 3H), 1.38 (m, 1H), 1.25 (m, 4H), 0.83 (t, 3H). MS (EI) for $C_{26}H_{35}FN_4O$: 439 [M+H].

Example 1.10. 4-Butyl-3-(4-fluorophenyl)-5-methyl-N-(3-morpholinopropyl)-1-phenyl-4,5-dihydro-1H-pyrazole-5-carboxamide was prepared using 3-morpholinopropan-1-amine in step 2. 1H-NMR (300 MHz, d-chloroform): 7.62 (m, 3H), 7.27 (m, 1H), 7.14 (m, 2H), 7.10 (t, 1H), 6.94 (t, 2H), 3.66 (dd, 1H), 3.42 (m, 3H), 3.37 (m, 3H), 2.28 (t, 2H), 2.18 (m, 4H), 1.69 (m, 4H), 1.50 (s, 3H), 1.42 (m, 1H), 1.25 (m, 4H), 0.84 (t, 3H). MS (EI) for $C_{28}H_{37}FN_4O_2$: 481 [M+H].

Example 1.11. 4-Butyl-3-(4-fluorophenyl)-5-methyl-1-phenyl-N-(3-(piperidin-1-yl)propyl)-4,5-dihydro-1H-pyrazole-5-carboxamide was prepared using 3-(piperidin-1-yl)propan-1-amine in step 2. MS (EI) for $C_{29}H_{39}FN_4O$: 479 [M+H].

Example 1.12. 4-Butyl-N-(3-(dimethylamino)butyl)-3-(4-fluorophenyl)-5-methyl-1-phenyl-4,5-dihydro-1H-pyrazole-5-carboxamide was prepared using N-(3-amino-1-methylpropyl)-N,N-dimethylamine in step 2. MS (EI) for $C_{27}H_{37}FN_4O$: 453 [M+H].

Example 1.13. 4-Butyl-N-(3-(dimethylamino)-2-methylpropyl)-3-(4-fluorophenyl)-5-methyl-1-phenyl-4,5-dihydro-1H-pyrazole-5-carboxamide was prepared using (3-amino-2-methylpropyl)dimethylamine in step 2. MS (EI) for $C_{27}H_{37}FN_4O$: 453 [M+H].

Example 1.14. 4-Butyl-N-(3-(dimethylamino)-2,2-dimethylpropyl)-3-(4-fluorophenyl)-5-methyl-1-phenyl-4,5-dihydro-1H-pyrazole-5-carboxamide was prepared using (3-amino-2,2-dimethylpropyl)dimethylamine in step 2. 1H-NMR (300 MHz, d-chloroform): 9.22 (br s, 1H), 7.63 (m, 3H), 7.26 (m, 1H), 7.14 (m, 1H), 7.07 (m, 3H), 6.88 (t, 1H), 3.72 (t, 1H), 3.20 (q, 2H), 2.03 (s, 2H), 1.77 (s, 6H), 1.70 (m, 1H), 1.53 (s, 3H), 1.23 (m, 5H), 0.82 (t, 3H), 0.75 (s, 3H), 0.73 (s, 3H). MS (EI) for $C_{28}H_{39}FN_4O$: 467 [M+H].

Example 1.15. 4-Butyl-N-(2-(dimethylamino)propyl)-3-(4-fluorophenyl)-5-methyl-1-phenyl-4,5-dihydro-1H-pyrazole-5-carboxamide was prepared using N-(2-amino-1-methylethyl)-N,N-dimethylamine in step 2. MS (EI) for $C_{26}H_{35}FN_4O$: 439 [M+H].

Example 1.16. 4-Butyl-N-(2-(dimethylamino)-2-methylpropyl)-3-(4-fluorophenyl)-5-methyl-1-phenyl-4,5-dihydro-1H-pyrazole-5-carboxamide was prepared using N-(2-amino-1,1-dimethylethyl)-N,N-dimethylamine in step 2. 1H-NMR (300 MHz, d-chloroform): 7.65 (m, 2H), 7.25 (m, 1H), 7.19 (m, 2H), 7.09 (m, 3H), 6.93 (t, 1H), 3.73 (dd, 1H), 3.15 (d, 2H), 1.97 (s, 6H), 1.72 (m, 4H), 1.24 (m 5H), 0.88 (s, 6H), 0.83 (t, 3H). MS (EI) for $C_{27}H_{37}FN_4O$: 453 [M+H].

Example 1.17. 4-Butyl-N-(2-fluoroethyl)-3-(4-fluorophenyl)-5-methyl-1-phenyl-4,5-dihydro-1H-pyrazole-5-carboxamide was prepared 3-fluoropropan-1-amine in step 2. 1H-NMR (300 MHz, d-chloroform): 7.63 (m, 2H), 7.30 (m, 2H), 7.17-7.07 (m, 4H), 6.98 (t, 1H), 6.94 (t, 1H), 4.55 (t, 1H), 4.38 (t, 1H), 3.71 (m, 1H), 3.62 (m, 2H), 1.72 (m, 2H), 1.49 (s, 3H), 1.42 (m, 1H), 1.26 (m, 3H), 0.84 (t, 3H). MS (EI) for $C_{23}H_{27}F_2N_3O$: 400 [M+H].

Example 1.18. 4-Butyl-3-(4-fluorophenyl)-5-methyl-N-neopentyl-1-phenyl-4,5-dihydro-1H-pyrazole-5-carboxamide was prepared 2,2-dimethylpropan-1-amine in step 2. MS (EI) for $C_{26}H_{34}FN_3O$: 424 [M+H].

Example 1.19. 4-Butyl-N-(cyclopropylmethyl)-3-(4-fluorophenyl)-5-methyl-1-phenyl-4,5-dihydro-1H-pyrazole-5-carboxamide was prepared using cyclopropylmethylamine in step 2. 1H-NMR (300 MHz, d-chloroform): 7.64 (m, 2H), 7.27 (m, 2H), 7.20-7.07 (m, 4H), 6.97 (t, 1H), 6.67 (t, 1H), 3.71 (dd, 1H), 3.11 (m, 2H), 1.71 (m, 2H), 1.50 (s, 3H), 1.44 (m, 1H), 1.22 (m, 4H), 0.84 (t, 3H), 0.42 (m, 2H), 0.17 (m, 2H). MS (EI) for $C_{25}H_{30}FN_3O$: 408 [M+H].

Example 1.20. 4-Butyl-N-(cyclohexylmethyl)-3-(4-fluorophenyl)-5-methyl-1-phenyl-4,5-dihydro-1H-pyrazole-5-carboxamide was prepared using cyclohexylmethylamine in step 2. MS (EI) for $C_{28}H_{36}FN_3O$: 450 [M+H].

Example 1.21. 4-Butyl-3-(4-fluorophenyl)-N-(4-hydroxybenzyl)-5-methyl-1-phenyl-4,5-dihydro-1H-pyrazole-5-carboxamide was prepared using 4-hydroxybenzylamine in step 2. 1H-NMR (300 MHz, $d_6$-DMSO): 9.23 (s, 1H), 8.67 (t, 1H), 7.63 (m, 2H), 7.27 (m, 2H), 7.16 (m, 2H), 7.01 (m, 4H), 6.2 (m, 1H), 6.16 (m, 2H), 4.19 (m, 2H), 3.79 (m, 1H), 1.74 (m, 1H), 1.53 (m, 1H), 1.23 (s, 3H), 1.17 (m, 4H), 0.76 (t, 3H). MS (EI) for $C_{28}H_{30}FN_3O_2$: 460 [M+H].

Example 1.22. 4-Butyl-3-(4-fluorophenyl)-N-(4-hydroxyphenethyl)-5-methyl-1-phenyl-4,5-dihydro-1H-pyrazole-5-carboxamide was prepared using 4-(2-aminoethyl)phenol in step 2. MS (EI) for $C_{29}H_{32}FN_3O_2$: 474 [M+H].

Example 1.23. 4-Butyl-N-(3-chlorobenzyl)-3-(4-fluorophenyl)-5-methyl-1-phenyl-4,5-dihydro-1H-pyrazole-5-carboxamide was prepared using 3-chlorobenzylamine in step 2. MS (EI) for $C_{28}H_{29}ClFN_3O$: 479 [M+H].

Example 1.24. 4-Butyl-N-(3,4-dichlorobenzyl)-3-(4-fluorophenyl)-5-methyl-1-phenyl-4,5-dihydro-1H-pyrazole-5-carboxamide was prepared using 3,4-dichlorobenzylamine in step 2. 1H-NMR (300 MHz, $d_6$-DMSO): 7.60 (m, 2H), 7.25 (m, 1H), 7.22 (m, 2H), 7.10 (m, 1H), 7.08 (m, 4H), 6.97 (m, 2H), 4.47 (m, 2H), 3.65 (dd, 1H), 1.68 (m, 2H), 1.50 (s, 3H), 1.36 (m, 1H), 1.21 (m, 3H), 0.82 (t, 3H). MS (EI) for $C_{28}H_{28}ClFN_3O$: 513 [M+H].

Example 1.25. 4-Butyl-N-(3,5-dichlorobenzyl)-3-(4-fluorophenyl)-5-methyl-1-phenyl-4,5-dihydro-1H-pyrazole-5-carboxamide was prepared using 3,5-dichlorobenzylamine in step 2. MS (EI) for $C_{28}H_{28}ClFN_3O$: 513 [M+H].

Example 1.26. 4-Butyl-3-(4-fluorophenyl)-5-methyl-1-phenyl-N-((S)-1-phenylethyl)-4,5-dihydro-1H-pyrazole-5-carboxamide was prepared using (S)-phenylethylamine in step 2. MS (EI) for $C_{29}H_{32}FN_3O$: 458 [M+H].

Example 1.27. 4-Butyl-3-(4-fluorophenyl)-5-methyl-1-phenyl-N-((R)-1-phenylethyl)-4,5-dihydro-1H-pyrazole-5-carboxamide carboxamide was prepared using (R)-phenylethylamine in step 2. MS (EI) for $C_{29}H_{32}FN_3O$: 458 [M+H].

Example 1.28. 4-Butyl-3-(4-fluorophenyl)-N-(4-hydroxy-3-methoxybenzyl)-5-methyl-1-phenyl-4,5-dihydro-1H-pyrazole-5-carboxamide was prepared using 4-hydroxy-2-methoxybenzylamine in step 2. 1H-NMR (300 MHz, d-chloroform): 7.64 (m, 2H), 7.27 (m, 2H), 7.12-7.06 (m, 4H), 6.95 (t, 1H), 6.82 (t, 1H), 6.77 (m, 1H), 6.64 (m, 2H), 5.52 (s, 1H), 4.36 (d, 2H), 3.70 (m, 1H), 3.67 (s, 3H), 1.71 (m, 2H), 1.53 (s, 3H), 1.41 (m, 1H), 1.25 (m, 3H), 0.84 (t, 3H). MS (EI) for $C_{29}H_{32}FN_3O_3$: 490 [M+H].

Example 1.29. 4-Butyl-3-(4-fluorophenyl)-N-(2-methoxybenzyl)-5-methyl-1-phenyl-4,5-dihydro-1H-pyrazole-5-carboxamide was prepared using 2-methoxybenzylamine in step 2. MS (EI) for $C_{29}H_{32}FN_3O_2$: 474 [M+H].

Example 1.30. 4-Butyl-N-(2,3-dimethoxybenzyl)-3-(4-fluorophenyl)-5-methyl-1-phenyl-4,5-dihydro-1H-pyrazole-5-carboxamide was prepared using 2,3-dimethoxybenzylamine in step 2. 1H-NMR (300 MHz, d-chloroform): 7.59 (m, 2H), 7.22 (m, 2H), 7.08 (m, 4H), 6.91 (m, 3H), 6.78 (m, 2H), 4.45 (m, 2H), 3.80 (s, 3H), 3.70 (dd, 1H), 3.68 (s, 3H), 1.69 (m, 2H), 1.50 (s, 3H), 1.39 (m, 1H), 1.24 (m, 3H), 0.84 (t, 3H). MS (EI) for $C_{30}H_{34}FN_3O_3$: 504 [M+H].

Example 1.31. 4-Butyl-N-(2,4-dimethoxybenzyl)-3-(4-fluorophenyl)-5-methyl-1-phenyl-4,5-dihydro-1H-pyrazole-5-carboxamide was prepared using 2,4-dimethoxybenzylamine in step 2. MS (EI) for $C_{30}H_{34}FN_3O_3$: 504 [M+H].

Example 1.32. 4-Butyl-N-(3,4-dimethoxybenzyl)-3-(4-fluorophenyl)-N,5-dimethyl-1-phenyl-4,5-dihydro-1H- pyrazole-5-carboxamide was prepared using 3,4-dimethoxybenzylamine in step 2. MS (EI) for $C_{30}H_{34}FN_3O_3$: 504 [M+H].

Example 1.33. 4-Butyl-N-(3,5-dimethoxybenzyl)-3-(4-fluorophenyl)-N,5-dimethyl-1-phenyl-4,5-dihydro-1H-pyrazole-5-carboxamide was prepared using 3,5-dimethoxybenzylamine in step 2. 1H-NMR (300 MHz, d-chloroform): 7.61 (m, 2H), 7.25 (m, 2H), 7.15-7.06 (m, 4H), 6.95 (t, 1H), 6.87 (t, 1H), 6.39 (s, 3H), 3.90 (m, 2H), 3.72 (d, 1H), 3.63 (s, 6H), 1.70 (m, 2H), 1.55 (s, 3H), 1.42 (m, 1H), 1.26 (m, 3H), 0.84 (t, 3H). MS (EI) for $C_{30}H_{34}FN_3O_3$: 504 [M+H].

Example 1.34. 4-Butyl-3-(4-fluorophenyl)-5-methyl-N-(1-(4-(methylsulfonyl)phenyl)ethyl)-1-phenyl-4,5-dihydro-1H-pyrazole-5-carboxamide was prepared using(4-(methylsulfonyl)benzylamine in step 2. MS (EI) for $C_{29}H_{32}FN_3O_3S$: 522 [M+H].

Example 1.35. 4-Butyl-N-(4-(dimethylamino)benzyl)-3-(4-fluorophenyl)-5-methyl-1-phenyl-4,5-dihydro-1H-pyrazole-5-carboxamide was prepared using 4-dimethylaminobenzyla mine in step 2. MS (EI) for $C_{30}H_{35}FN_4O$: 487 [M+H].

Example 1.36. 4-Butyl-3-(4-fluorophenyl)-5-methyl-N-(4-(morpholinomethyl)benzyl)-1-phenyl-4,5-dihydro-1H-pyrazole-5-carboxamide was prepared using 4-(morpholinomethyl)benzylamine in step 2. MS (EI) for $C_{33}H_{39}FN_4O_2$: 543 [M+H].

Example 1.37. 4-Butyl-3-(4-fluorophenyl)-5-methyl-1-phenyl-N-(thiophen-2-ylmethyl)-4,5-dihydro-1H-pyrazole-5-carboxamide was prepared using 2-(aminomethyl)thiophene in step 2. 1H-NMR (300 MHz, d-chloroform): 7.61 (m, 2H), 7.26 (m, 2H), 7.17 (m, 1H), 7.13-7.06 (m, 4H), 6.95 (m, 3H), 6.88 (t, 1H), 4.64 (m, 2H), 3.72 (dd, 1H), 1.72 (m, 2H), 1.51 (s, 3H), 1.42 (m, 1H), 1.26 (m, 3H), 0.84 (t, 3H). MS (EI) for $C_{26}H_{28}FN_3OS$: 450 [M+H].

Example 1.38. N-Benzyl-4-butyl-3-(4-fluorophenyl)-N-(2-hydroxyethyl)-5-methyl-1-phenyl-4,5-dihydro-1H-pyrazole-5-carboxamide was prepared using 2-(benzylamino)ethan-1-ol in step 2. MS (EI) for $C_{30}H_{34}FN_3O_2$: 488 [M+H].

Example 2

Example 2 Compounds

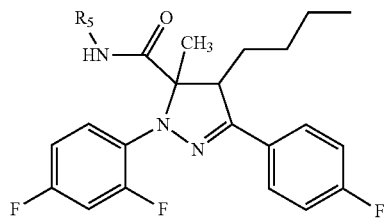

Example 2.6. 4-Butyl-1-(2,4-difluorophenyl)-3-(4-fluorophenyl)-N-(2-methoxyethyl)-5-methyl-4,5-dihydro-1H-pyrazole-5-carboxamide was prepared according to the following scheme.

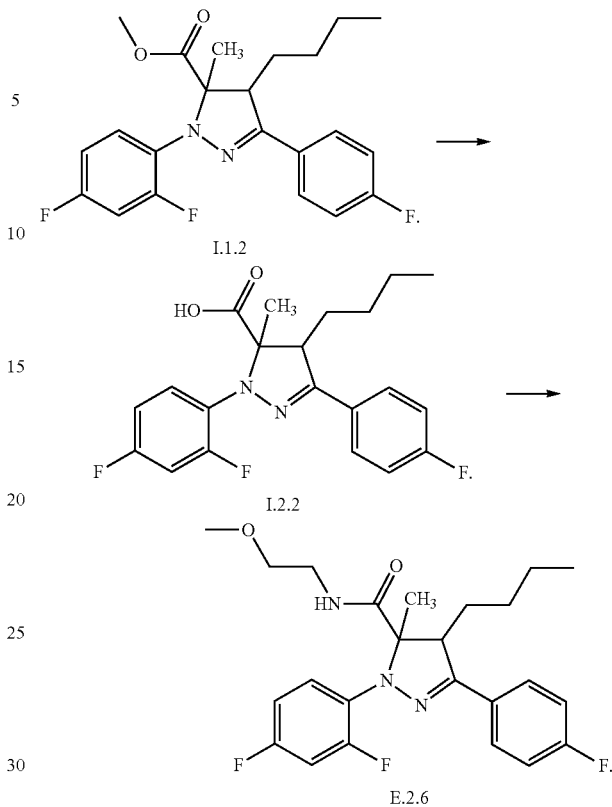

STEP 1. To a solution of methyl 4-butyl-1-(2,4-difluorophenyl)-3-(4-fluorophenyl)-5-methyl-4,5-dihydro-1H-pyrazole-5-carboxylate (I.1.2.) (0.80 g, 1.98 mmol) in a mixture of tetrahydrofuran (15 mL), methanol (4 mL) and water (1 mL) was added potassium hydroxide (0.70 mL, 5.94 mmol, 50% aq. solution) and the reaction mixture was stirred at room temperature for two hours. The pH was adjusted to 4 by the addition of 2M aqueous hydrochloric acid. It was partitioned with ethyl acetate (200 mL) and water (50 mL), the organic layer was separated, washed with brine (2×50 mL), dried over anhydrous sodium sulfate and concentrated to give 4-butyl-1-(2,4-difluorophenyl)-3-(4-fluorophenyl)-5-methyl-4,5-dihydro-1H-pyrazole-5-carboxylic acid as white solid (I.2.2.) (quantitative). MS (EI) for $C_{21}H_{21}F_3N_2O_2$: 389 [M–H]. It was used without further purification.

STEP 2. To a solution of 4-butyl-1-(2,4-difluorophenyl)-3-(4-fluorophenyl)-5-methyl-4,5-dihydro-1H-pyrazole-5-carboxylic acid (I.2.2.) (0.77 g, 1.98 mmol) in N,N-dimethylformamide (5 mL) was added 4-methylmorpholine (0.65 mL, 5.94 mmol) and O-(7-azabenzotriazol-1-yl)-N,N,N',N'-tetramethyluronium hexafluoro-phosphate (0.85 g, 2.18 mmol) and the reaction mixture was stirred at room temperature for ten minutes, followed by the addition of 2-methoxyethylamine (0.18 mL, 2.08 mmol) and the stirring was continued for 18 hours. The mixture was partitioned with ethyl acetate (250 mL) and 1M aqueous hydrochloric acid (50 ml). The organic layer was separated and washed with 1M aqueous hydrochloric acid (50 ml) and brine (2×50 mL), dried over anhydrous sodium sulfate and concentrated. The resulting crude was purified by gradient silica gel flash chromatography (1-30% ethyl acetate in hexanes) to give 4-butyl-1-(2,4-difluorophenyl)-3-(4-fluorophenyl)-N-(2-methoxyethyl)-5-methyl-4,5-dihydro-1H-pyrazole-5-carboxamide (E.2.6.) (0.81 g, 93%). 1H-NMR (500 MHz, d-acetone): 7.56 (t, 1H), 7.28 (dd, 2H), 6.90 (m, 1H), 6.80 (m, 3H), 6.59 (m, 1H), 3.68 (dd, 1H), 2.90 (m, 2H), 2.88 (s, 3H), 2.79 (m, 2H), 1.12 (m, 2H), 0.78 (m, 4H), 0.68 (s, 3H), 0.28 (t, 3H). MS (EI) for $C_{24}H_{28}F_3N_3O_2$: 448 [MH+].

Example 2.1. 4-Butyl-1-(2,4-difluorophenyl)-3-(4-fluorophenyl)-N-(5-hydroxy-4,4-dimethylpentyl)-5-methyl-4,5-dihydro-1H-pyrazole-5-carboxamide was prepared using 5-amino-2,2-dimethylpentan-1-ol in step 2. 1H-NMR (300 MHz, $d_6$-DMSO): 8.16 (t, 1H), 7.66 (dd, 2H), 7.49 (m, 1H), 7.31 (m, 1H), 7.20 (t, 2H), 7.08 (m, 1H), 4.42 (t, 1H), 3.80 (q, 1H), 3.10 (d, 2H), 3.01 (d, 2H), 1.72 (m 1H), 1.48 (m, 1H), 1.36 (m, 2H), 1.19 (m, 4H), 1.10 (s, 3H), 1.09 (m, 2H), 0.78 (t, 1H), 0.68 (s, 6H). MS (EI) for $C_{28}H_{36}F_3N_3O_2$: 504 [M+H].

Example 2.2. 4-Butyl-1-(2,4-difluorophenyl)-3-(4-fluorophenyl)-N-(5-hydroxy-5-methylhexyl)-5-methyl-4,5-dihydro-1H-pyrazole-5-carboxamide was prepared using 6-amino-2-methylhexan-2-ol in step 2. MS (EI) for $C_{28}H_{36}F_3N_3O_2$: 504 [M+H].

Example 2.3. 4-Butyl-1-(2,4-difluorophenyl)-3-(4-fluorophenyl)-N-(4-methoxybutyl)-5-methyl-4,5-dihydro-1H-pyrazole-5-carboxamide was prepared using 4-methoxybutylamine in step 2. MS (EI) for $C_{26}H_{32}F_3N_3O_2$: 476 [M+H].

Example 2.4. 4-Butyl-1-(2,4-difluorophenyl)-3-(4-fluorophenyl)-N-(3-methoxypropyl)-5-methyl-4,5-dihydro-1H-pyrazole-5-carboxamide was prepared using 3-methoxypropylamine in step 2. MS (EI) for $C_{25}H_{30}F_3N_3O_2$: 462 [M+H].

Example 2.5. Methyl 3-(4-butyl-1-(2,4-difluorophenyl)-3-(4-fluorophenyl)-5-methyl-4,5-dihydro-1H-pyrazole-5-carboxamido)propanoate was prepared using methyl 3-aminopropanoate in step 2. MS (EI) for $C_{25}H_{28}F_3N_3O_3$: 476 [M+H].

Example 2.7. 4-Butyl-1-(2,4-difluorophenyl)-N-(2-ethoxyethyl)-3-(4-fluorophenyl)-5-methyl-4,5-dihydro-1H-pyrazole-5-carboxamide was prepared using 2-ethoxyethylamine in step 2. MS (EI) for $C_{25}H_{30}F_3N_3O_2$: 462 [M+H].

Example 2.8. Methyl 2-(4-butyl-1-(2,4-difluorophenyl)-3-(4-fluorophenyl)-5-methyl-4,5-dihydro-1H-pyrazole-5-carboxamido)acetate was prepared using methyl glycinate in step 2. 1H-NMR (300 MHz, $d_6$-DMSO): 8.16 (t, 1H), 7.65 (dd, 2H), 7.48 (m, 1H), 7.30 (m, 1H), 7.18 (t, 2H), 7.06 (m, 1H), 3.80 (t, 1H), 3.92 (q, 2H), 3.65 (s, 3H), 1.44 (m, 2H), 1.16 (m, 4H), 1.10 (s, 3H), 0.78 (t, 3H). MS (EI) for $C_{24}H_{26}F_3N_3O_3$: 462 [M+H].

Example 2.9. 2-(4-Butyl-1-(2,4-difluorophenyl)-3-(4-fluorophenyl)-5-methyl-4,5-dihydro-1H-pyrazole-5-carboxamido)acetic acid was prepared as follows.

To a solution of methyl 2-(4-butyl-1-(2,4-difluorophenyl)-3-(4-fluorophenyl)-5-methyl-4,5-dihydro-1H-pyrazole-5-carboxamido)acetate (E.2.8.) (0.50 g,0.11 mmol) in a mixture of methanol (4 mL) and water (1 mL) was added lithium hydroxide (0.17 mL, 0.33 mmol, 2M aq. solution) and the reaction mixture was stirred at room temperature for two hours. The pH was adjusted to 2 by the addition of 2M aqueous hydrochloric acid. It was partitioned with ethyl acetate (100 mL) and water (50 mL), the organic layer was separated, washed with brine (2×50 mL), dried over anhydrous sodium sulfate and concentrated to give 2-(4-butyl-1-(2,4-difluorophenyl)-3-(4-fluorophenyl)-5-methyl-4,5-dihydro-1H-pyrazole-5-carboxamido)acetic acid (0.041 g, 83%). MS (EI) for $C_{23}H_{24}F_3N_3O_3$: 446 [M−H].

Example 2.10. 4-Butyl-1-(2,4-difluorophenyl)-3-(4-fluorophenyl)-N-(2-hydroxyethyl)-5-methyl-4,5-dihydro-1H-pyrazole-5-carboxamide was prepared using 2-aminoethan-1-ol in step 2. MS (EI) for $C_{23}H_{26}F_3N_3O_2$: 434 [M+H].

Example 2.11. 4-Butyl-N-(2-cyanoethyl)-1-(2,4-difluorophenyl)-3-(4-fluorophenyl)-5-methyl-4,5-dihydro-1H-pyrazole-5-carboxamide was prepared using 3-aminopropionitrile in step 2. MS (EI) for $C_{24}H_{25}F_3N_4O$: 443 [M+H].

Example 2.12. 4-Butyl-1-(2,4-difluorophenyl)-N-(3-(dimethylamino)propyl)-3-(4-fluorophenyl)-5-methyl-4,5-dihydro-1H-pyrazole-5-carboxamide was prepared using 3-(dimethylamino)-1-propylamine in step 2. MS (EI) for $C_{26}H_{33}F_3N_4O$: 475 [M+H].

Example 2.13. 4-Butyl-1-(2,4-difluorophenyl)-3-(4-fluorophenyl)-N-(3-methoxypropyl)-N,5-dimethyl-4,5-dihydro-1H-pyrazole-5-carboxamide was prepared using (3-methoxypropyl)(methyl)amine in step 2. MS (EI) for $C_{26}H_{32}F_3N_3O_2$: 476 [M+H].

Example 2.14. 4-Butyl-1-(2,4-difluorophenyl)-3-(4-fluorophenyl)-5-methyl-N-((4-methylmorpholin-2-yl)methyl)-4,5-dihydro-1H-pyrazole-5-carboxamide was prepared using (4-methylmorpholin-2-yl)methanamine in step 2. 1H-NMR (300 MHz, $d_6$-DMSO): 8.16 (t, 1H), 7.65 (dd, 2H), 7.48 (m, 1H), 7.30 (m, 1H), 7.18 (t, 2H), 7.06 (m, 1H), 3.80 (q, 1H), 3.68 (d, 1H), 3.46 (m, 1H), 3.40 (m, 1H), 3.18 (m, 2H), 2.54 (m, 2H), 2.03 (s, 3H), 1.82 (m, 1H), 1.60 (m, 1H), 1.43 (m, 2H), 1.16 (m, 4H), 1.12 (s, 3H), 0.78 (t, 3H). MS (EI) for $C_{27}H_{33}F_3N_4O_2$: 503 [M+H].

Example 2.15. 4-Butyl-1-(2,4-difluorophenyl)-3-(4-fluorophenyl)-N-((3-methoxy-1-methylazetidin-3-yl)methyl)-5-methyl-4,5-dihydro-1H-pyrazole-5-carboxamide is prepared using (3-methoxy-1-methylazetidin-3-yl)methanamine (R.3.26.) in step 2. MS (EI) for $C_{27}H_{33}F_3N_4O_2$: 503 [M+H].

Example 2.16. 4-Butyl-1-(2,4-difluorophenyl)-3-(4-fluorophenyl)-N-((3-methoxyoxetan-3-yl)methyl)-5-methyl-4,5-dihydro-1H-pyrazole-5-carboxamide is prepared using (3-methoxyoxetan-3-yl)methanamine (R.3.5.) in step 2. MS (EI) for $C_{26}H_{30}F_3N_3O_3$: 40 [M+H].

Example 3

Example 3 Compounds

4-$R^3$-1-($R^6$)$_m$-phenyl-3-($R^7$)$_n$-phenyl-N-($R^5$)-5-methyl-4,5-dihydro-1H-pyrazole-5-carboxamides

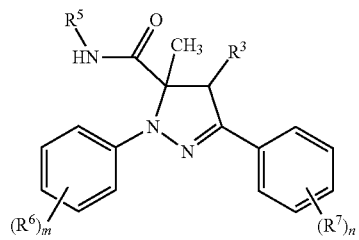

Example 3.8. 4-Butyl-3-(4-fluorophenyl)-N-(5-hydroxy-4,4-dimethylpentyl)-5-methyl-1-p-tolyl-4,5-dihydro-1H-pyrazole-5-carboxamide was prepared according to the following scheme.

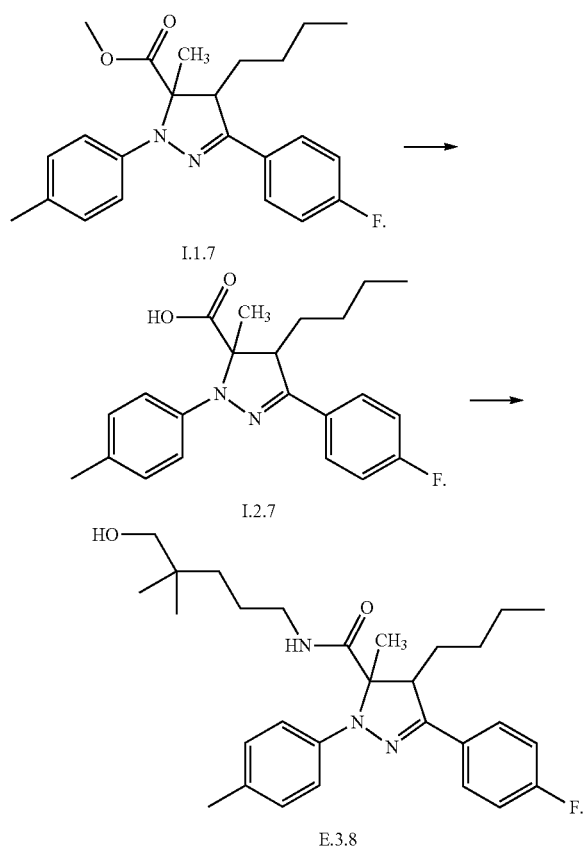

STEP 1. To a solution of methyl 4-butyl-3-(4-fluorophenyl)-5-methyl-1-(p-tolyl)-4,5-dihydro-1H-pyrazole-5-carboxylate (I.1.7.) (0.16 g, 0.42 mmol) in a mixture of tetrahydrofuran (12 mL), methanol (2 mL) and water (1 mL) was added potassium hydroxide (0.15 mL, 1.25 mmol, 50% aq. solution) and the reaction mixture was stirred at room temperature for one hour. The disappearance of starting material was monitored by TLC (10% ethyl acetate in hexanes). The pH was adjusted to 4 by the addition of 2M aqueous hydrochloric acid and the mixture was partitioned with ethyl acetate (150 mL) and water (25 mL). The organic layer was separated, washed with brine (2×50 mL), dried over anhydrous sodium sulfate and concentrated to give 4-butyl-3-(4-fluorophenyl)-5-methyl-1-(p-tolyl)-4,5-dihydro-1H-pyrazole-5-carboxylic acid (I.2.7.) and was used without further purification. MS (EI) for $C_{22}H_{25}FN_2O_2$: 367 [M−H].

STEP 2. To a solution of 4-butyl-3-(4-fluorophenyl)-5-methyl-1-(p-tolyl)-4,5-dihydro-1H-pyrazole-5-carboxylic acid (I.2.7.) (0.07 g, 0.20 mmol) in N,N-dimethylformamide (5 mL) was added 4-methylmorpholine (0.07 mL, 0.60 mmol) and O-(7-azabenzotriazol-1-yl)-N,N,N',N'-tetramethyluronium hexafluoro-phosphate (0.09 g, 0.24 mmol) and the reaction mixture was stirred at room temperature for ten minutes, followed by the addition of 5-amino-2,2-dimethylpentan-1-ol (0.03 g, 0.21 mmol) and the stirring was continued for 18 hours. The reaction mixture was partitioned with ethyl acetate (150 mL) and 1M aqueous hydrochloric acid (50 ml). The organic layer was separated and washed with 1M aqueous hydrochloric acid (50 ml) and brine (2×50 mL), dried over anhydrous sodium sulfate and concentrated. The resulting crude was purified by gradient silica gel flash chromatography (1-50% ethyl acetate in hexanes) to give to give 4-butyl-3-(4-fluorophenyl)-N-(5-hydroxy-4,4-dimethylpentyl)-5-methyl-1-p-tolyl-4,5-dihydro-1H-pyrazole-5-carboxamide (E.3.8) (0.078 g, 81%). 1H-NMR (300 MHz, $d_6$-DMSO): 8.18 (t, 1H), 7.64 (dd, 2H), 7.26 (t, 2H), 7.00 (q, 4H), 4.41 (t, 1H), 3.80 (q, 1H), 3.10 (m, 2H), 3.02 (d, 2H), 2.23 (s, 3H), 1.74 (m, 1H), 1.52 (m, 1H), 1.34 (m, 2H), 1.24 (m, 4H), 1.18 (s, 3H), 1.09 (m, 2H), 0.81 (s, 3H), 0.65 (s, 6H). MS (EI) for $C_{29}H_{40}FN_3O_2$: 482 [M+H].

Example 3.1. 4-Butyl-1-(3-fluorophenyl)-3-(4-fluorophenyl)-N-(5-hydroxy-5-methylhexyl)-5-methyl-4,5-dihydro-1H-pyrazole-5-carboxamide was prepared using methyl 4-butyl-1-(3-fluorophenyl)-3-(4-fluorophenyl)-5-methyl-4,5-dihydro-1H-pyrazole-5-carboxylate (I.1.3.) in step 1 and 6-amino-2-methylhexan-2-ol in step 2. MS (EI) for $C_{28}H_{37}F_2N_3O_2$: 468 [M+H].

Example 3.2. 4-Butyl-1-(3-fluorophenyl)-3-(4-fluorophenyl)-N-(3-methoxypropyl)-5-methyl-4,5-dihydro-1H-pyrazole-5-carboxamide was prepared using methyl 4-butyl-1-(3-fluorophenyl)-3-(4-fluorophenyl)-5-methyl-4,5-dihydro-1H-pyrazole-5-carboxylate (I.1.3.) in step 1 and 3-methoxypropylamine in step 2. MS (EI) for $C_{25}H_{31}F_2N_3O_2$: 444 [M+H].

Example 3.3. 4-Butyl-1,3-bis(4-fluorophenyl)-N-(3-methoxypropyl)-5-methyl-4,5-dihydro-1H-pyrazole-5-carboxamide was prepared using methyl 4-butyl-1,3-bis(4-fluorophenyl)-5-methyl-4,5-dihydro-1H-pyrazole-5-carboxylate (I.1.4.) in step 1 and 3-methoxypropylamine in step 2. MS (EI) for $C_{25}H_{31}F_2N_3O_2$: 444 [M+H].

Example 3.4. 4-Butyl-1-(4-chlorophenyl)-3-(4-fluorophenyl)-N-(5-hydroxy-4,4-dimethylpentyl)-5-methyl-4,5-dihydro-1H-pyrazole-5-carboxamide was prepared using methyl 4-butyl-1-(4-chlorophenyl)-3-(4-fluorophenyl)-5-methyl-4,5-dihydro-1H-pyrazole-5-carboxylate (I.1.5.) in step 1 and 5-amino-2,2-dimethylpentan-1-ol in step 2. MS (EI) for $C_{28}H_{37}ClFN_3O_2$: 503 [M+H].

Example 3.5. 4-Butyl-1-(4-chlorophenyl)-3-(4-fluorophenyl)-N-(3-methoxypropyl)-5-methyl-4,5-dihydro-1H-pyrazole-5-carboxamide was prepared using methyl 4-butyl-1-(4-chlorophenyl)-3-(4-fluorophenyl)-5-methyl-4,5-dihydro-1H-pyrazole-5-carboxylate (I.1.5.) in step 1 and 3-methoxypropylamine in step 2. MS (EI) for $C_{25}H_{31}ClFN_3O_2$: 460 [M+H].

Example 3.6. 4-Butyl-1-(4-chloro-2-fluorophenyl)-3-(4-fluorophenyl)-N-(2-methoxyethyl)-5-methyl-4,5-dihydro-1H-pyrazole-5-carboxamide was prepared using methyl 4-butyl-1-(4-chlorophenyl)-3-(4-fluorophenyl)-5-methyl-4,5-dihydro-1H-pyrazole-5-carboxylate (I.1.5.) in step 1 and 2-methoxyethylamine in step 2. 1H-NMR (300 MHz, $d_6$-DMSO): 8.18 (t, 1H), 7.64 (dd, 2H), 7.38 (d, 2H), 7.26 (t, 2H), 6.98 (d, 2H), 3.80 (q, 1H), 3.32 (m, 4H), 3.20 (s, 3H), 1.74 (m, 1H), 1.52 (m, 1H), 1.22 (m, 4H), 1.20 (s, 3H), 0.82 (s, 3H). MS (EI) for $C_{24}H_{29}ClFN_3O_2$: 447 [M+H].

Example 3.7. 4-Butyl-1-(3-chlorophenyl)-3-(4-fluorophenyl)-N-(5-hydroxy-4,4-dimethylpentyl)-5-methyl-4,5-dihydro-1H-pyrazole-5-carboxamide was prepared using methyl 4-butyl-1-(3-chlorophenyl)-3-(4-fluorophenyl)-5-methyl-4,5-dihydro-1H-pyrazole-5-carboxylate (I.1.6.) in step 1 and 5-amino-2,2-dimethylpentan-1-ol in step 2. MS (EI) for $C_{28}H_{37}ClFN_3O_2$: 503 [M+H].

Example 3.9. 4-Butyl-3-(4-fluorophenyl)-N-(3-methoxypropyl)-5-methyl-1-p-tolyl-4,5-dihydro-1H-pyrazole-5-carboxamide was prepared using methyl 4-butyl-3-(4-fluorophenyl)-5-methyl-1-(p-tolyl)-4,5-dihydro-1H-pyrazole-5-carboxylate (I.1.7.) in step 1 and 3-methoxypropylamine in step 2. MS (EI) for $C_{26}H_{34}FN_3O_2$: 440 [M+H].

Example 3.10. 4-Butyl-3-(4-fluorophenyl)-N-(2-methoxyethyl)-5-methyl-1-p-tolyl-4,5-dihydro-1H-pyrazole-5-carboxamide was prepared using methyl 4-butyl-3-(4-fluorophenyl)-5-methyl-1-(p-tolyl)-4,5-dihydro-1H-pyrazole-5-carboxylate (I.1.7.) in step 1 and 3-methoxyethylamine in step 2. 1H-NMR (300 MHz, d$_6$-DMSO): 8.19 (t, 1H), 7.65 (dd, 2H), 7.27 (t, 2H), 7.01 (q, 4H), 3.80 (q, 1H), 3.32 (m, 4H), 3.21 (s, 3H), 2.22 (s, 3H), 1.73 (m, 1H), 1.53 (m, 1H), 1.24 (m, 4H), 1.18 (s, 3H), 0.80 (s, 3H). MS (EI) for $C_{25}H_{32}FN_3O_2$: 426 [M+H].

Example 3.11. 4-Butyl-3-(4-fluorophenyl)-N-(5-hydroxy-4,4-dimethylpentyl)-5-methyl-1-m-tolyl-4,5-dihydro-1H-pyrazole-5-carboxamide was prepared using methyl 4-butyl-3-(4-fluorophenyl)-5-methyl-1-(m-tolyl)-4,5-dihydro-1H-pyrazole-5-carboxylate (I.1.8.) in step 1 and 5-amino-2,2-dimethylpentan-1-ol in step 2. 1H-NMR (300 MHz, d$_6$-DMSO): 8.16 (t, 1H), 7.68 (dd, 2H), 7.26 (t, 2H), 7.12 (t, 1H), 6.97 (s, 1H), 6.81 (d, 1H), 6.66 (d, 1H), 4.42 (t, 1H), 3.78 (q, 1H), 3.09 (m, 2H), 3.02 (d, 2H), 2.26 (s, 3H), 1.74 (m, 1H), 1.52 (m, 1H), 1.34 (m, 2H), 1.24-1.22 (m, 4H), 1.20 (s, 3H), 1.08 (m, 2H), 0.82 (s, 3H), 0.66 (s, 6H). MS (EI) for $C_{29}H_{40}FN_3O_2$: 482 [M+H].

Example 3.12. 4-Butyl-3-(4-fluorophenyl)-N-(2-methoxyethyl)-5-methyl-1-m-tolyl-4,5-dihydro-1H-pyrazole-5-carboxamide was prepared using methyl 4-butyl-3-(4-fluorophenyl)-5-methyl-1-(m-tolyl)-4,5-dihydro-1H-pyrazole-5-carboxylate (I.1.8.) in step 1 and 3-methoxyethylamine in step 2. 1H-NMR (300 MHz, d$_6$-DMSO): 8.18 (t, 1H), 7.66 (dd, 2H), 7.28 (t, 2H), 7.12 (t, 1H), 6.96 (s, 1H), 6.82 (d, 1H), 6.68 (d, 1H), 3.80 (q, 1H), 3.30 (m, 4H), 3.19 (s, 3H), 2.26 (s, 3H), 1.74 (m, 1H), 1.54 (m, 1H), 1.23 (m, 4H), 1.22 (s, 3H), 0.81 (s, 3H). MS (EI) for $C_{25}H_{32}FN_3O_2$: 426 [M+H].

Example 3.13. 4-Butyl-3-(4-fluorophenyl)-N-(5-hydroxy-4,4-dimethylpentyl)-5-methyl-1-(4-(trifluoromethyl)phenyl)-4,5-dihydro-1H-pyrazole-5-carboxamide was prepared using methyl 4-butyl-3-(4-fluorophenyl)-5-methyl-1-(4-(trifluoromethyl)phenyl)-4,5-dihydro-1H-pyrazole-5-carboxylate (I.1.9.) in step 1 and 5-amino-2,2-dimethylpentan-1-ol in step 2. MS (EI) for $C_{29}H_{37}FN_3O_2$: 536 [M+H].

Example 3.14. 4-Butyl-1-(2,5-difluorophenyl)-3-(4-fluorophenyl)-N-(5-hydroxy-5-methylhexyl)-5-methyl-4,5-dihydro-1H-pyrazole-5-carboxamide was prepared using methyl 4-butyl-1-(2,5-difluorophenyl)-3-(4-fluorophenyl)-5-methyl-4,5-dihydro-1H-pyrazole-5-carboxylate (I.1.10.) in step 1 and 6-amino-2-methylhexan-2-ol in step 2. MS (EI) for $C_{28}H_{36}F_3N_3O_2$: 504 [M+H].

Example 3.15. 4-Butyl-1-(4-fluoro-3-methoxyphenyl)-3-(4-fluorophenyl)-N-(5-hydroxy-4,4-dimethylpentyl)-5-methyl-4,5-dihydro-1H-pyrazole-5-carboxamide was prepared using methyl 4-butyl-1-(4-fluoro-3-methoxyphenyl)-3-(4-fluorophenyl)-5-methyl-4,5-dihydro-1H-pyrazole-5-carboxylate (I.1.11.) in step 1 and 5-amino-2,2-dimethylpentan-1-ol in step 2. MS (EI) for $C_{29}H_{39}F_2N_3O_3$: 516 [M+H].

Example 3.16. 4-Butyl-1-(4-fluoro-3-methoxyphenyl)-3-(4-fluorophenyl)-N-(3-methoxypropyl)-5-methyl-4,5-dihydro-1H-pyrazole-5-carboxamide was prepared using methyl 4-butyl-1-(4-fluoro-3-methoxyphenyl)-3-(4-fluorophenyl)-5-methyl-4,5-dihydro-1H-pyrazole-5-carboxylate (I.1.11.) in step 1 and 3-methoxypropylamine in step 2. MS (EI) for $C_{26}H_{33}F_2N_3O_3$: 474 [M+H].

Example 3.17. 4-Butyl-1-(3-chloro-4-fluorophenyl)-3-(4-fluorophenyl)-N-(5-hydroxy-5-methylhexyl)-5-methyl-4,5-dihydro-1H-pyrazole-5-carboxamide was prepared using methyl 4-butyl-1-(3-chloro-4-fluorophenyl)-3-(4-fluorophenyl)-5-methyl-4,5-dihydro-1H-pyrazole-5-carboxylate (I.1.12.) in step 1 and 6-amino-2-methylhexan-2-ol in step 2. MS (EI) for $C_{28}H_{36}ClF_2N_3O_2$: 521 [M+H].

Example 3.18. 4-Butyl-1-(2-chloro-4-fluorophenyl)-3-(4-fluorophenyl)-N-(5-hydroxy-4,4-dimethylpentyl)-5-methyl-4,5-dihydro-1H-pyrazole-5-carboxamide was prepared using methyl 4-butyl-1-(2-chloro-4-fluorophenyl)-3-(4-fluorophenyl)-5-methyl-4,5-dihydro-1H-pyrazole-5-carboxylate (I.1.13.) in step 1 and 5-amino-2,2-dimethylpentan-1-ol in step 2. MS (EI) for $C_{28}H_{36}ClF_2N_3O_2$: 521 [M+H].

Example 3.19. 4-Butyl-1-(4-chloro-2-fluorophenyl)-3-(4-fluorophenyl)-N-(5-hydroxy-4,4-dimethylpentyl)-5-methyl-4,5-dihydro-1H-pyrazole-5-carboxamide was prepared using methyl 4-butyl-1-(4-chloro-2-fluorophenyl)-3-(4-fluorophenyl)-5-methyl-4,5-dihydro-1H-pyrazole-5-carboxylate (I.1.14.) in step 1 and 5-amino-2,2-dimethylpentan-1-ol in step 2. 1H-NMR (300 MHz, d$_6$-DMSO): 7.932 (t, 1H), 7.76 (m 2H), 7.41 (m, 2H), 7.24 (m, 3H), 4.42 (t, 1H), 3.78 (m, 1H), 3.10 (m, 2H), 3.02 (m, 2H), 1.58 (m, 2H), 1.38 (m, 2H), 1.20 (s, 3H), 1.18 (m, 4H), 1.10 (m, 2H), 0.78 (t, 3H), 0.66 (s, 6H). MS (EI) for $C_{28}H_{36}ClF_2N_3O_2$: 521 [M+H].

Example 3.20. 4-Butyl-1-(4-chloro-2-fluorophenyl)-3-(4-fluorophenyl)-N-(2-methoxyethyl)-5-methyl-4,5-dihydro-1H-pyrazole-5-carboxamide was prepared using methyl 4-butyl-1-(4-chloro-2-fluorophenyl)-3-(4-fluorophenyl)-5-methyl-4,5-dihydro-1H-pyrazole-5-carboxylate (I.1.14.) in step 1 and 2-methoxyethylamine in step 2. 1H-NMR (300 MHz, d$_6$-DMSO): 7.93 (t, 1H), 7.74 (m 2H), 7.40 (m, 2H), 7.24 (t, 1H), 7.21 (t, 2H), 3.79 (m, 1H), 3.28 (m, 4H), 3.20 (s, 3H), 1.58 (m, 2H), 1.20 (s, 3H), 1.18 (m, 4H), 0.78 (t, 3H). MS (EI) for $C_{24}H_{28}ClF_2N_3O_2$: 464 [M+H].

Example 3.21. 4-Butyl-1-(4-chloro-2-methylphenyl)-3-(4-fluorophenyl)-N-(5-hydroxy-4,4-dimethylpentyl)-5-methyl-4,5-dihydro-1H-pyrazole-5-carboxamide was prepared using methyl 4-butyl-1-(4-chloro-2-methylphenyl)-3-(4-fluorophenyl)-5-methyl-4,5-dihydro-1H-pyrazole-5-carboxylate (I.1.15.) in step 1 and 5-amino-2,2-dimethylpentan-1-ol in step 2. MS (EI) for $C_{29}H_{39}ClFN_3O_2$: 517 [M+H].

Example 3.22. 4-Butyl-1-(4-chloro-2-methylphenyl)-3-(4-fluorophenyl)-N-(3-methoxypropyl)-5-methyl-4,5-dihydro-1H-pyrazole-5-carboxamide was prepared using methyl 4-butyl-1-(4-chloro-2-methylphenyl)-3-(4-fluorophenyl)-5-methyl-4,5-dihydro-1H-pyrazole-5-carboxylate (I.1.15.) in step 1 and 3-methoxypropylamine in step 2. MS (EI) for $C_{26}H_{33}ClFN_3O_2$: 475 [M+H].

Example 3.23. 4-Butyl-3-(4-chlorophenyl)-N-(2-methoxyethyl)-5-methyl-1-phenyl-4,5-dihydro-1H-pyrazole-5-carboxamide was prepared using methyl 4-butyl-3-(4-chlorophenyl)-5-methyl-1-phenyl-4,5-dihydro-1H-pyrazole-5-carboxylate (I.1.16.) in step 1 and 3-methoxethylamine in step 2. MS (EI) for $C_{24}H_{30}ClN_3O_2$: 429 [M+H].

Example 3.24. 4-Butyl-3-(3,4-difluorophenyl)-N-(5-hydroxy-5-methylhexyl)-5-methyl-1-phenyl-4,5-dihydro-1H-pyrazole-5-carboxamide was prepared using methyl 4-butyl-3-(3,4-difluorophenyl)-5-methyl-1-phenyl-4,5-dihydro-1H-pyrazole-5-carboxylate (I.1.17.) in step 1 and 6-amino-2-methylhexan-2-ol in step 2. MS (EI) for $C_{28}H_{37}F_2N_3O_2$: 486 [M+H].

Example 3.25. 4-Butyl-3-(2,4-difluorophenyl)-N-(5-hydroxy-4,4-dimethylpentyl)-5-methyl-1-phenyl-4,5-dihydro-1H-pyrazole-5-carboxamide was prepared using methyl 4-butyl-3-(2,4-difluorophenyl)-5-methyl-1-phenyl-4,5-dihydro-1H-pyrazole-5-carboxylate (I.1.18.) in step 1 and 5-amino-2,2-dimethylpentan-1-ol in step 2. MS (EI) for $C_{28}H_{37}F_2N_3O_2$: 486 [M+H].

Example 3.26. 4-Butyl-3-(2,4-difluorophenyl)-N-(2-methoxyethyl)-5-methyl-1-phenyl-4,5-dihydro-1H-pyrazole-5-carboxamide was prepared using methyl 4-butyl-3-(2,4-difluorophenyl)-5-methyl-1-phenyl-4,5-dihydro-1H-pyrazole-5-carboxylate (I.1.18.) in step 1 and 2-methoxyethylamine in step 2. 1H-NMR (300 MHz, $d_6$-DMSO): 8.14 (t, 1H), 7.40 (q, 1H), 7.38 (m, 1H), 7.32 (m, 4H), 7.06 (m, 1H), 6.82 (t, 1H), 3.80 (t, 1H), 3.36 (m, 3H), 3.26 (m, 1H), 3.21 (s, 3H), 1.46 (m, 2H), 1.18 (m, 4H), 1.11 (s, 3H), 0.78 (t, 3H). MS (EI) for $C_{24}H_{29}F_2N_3O_2$: 430 [M+H].

Example 3.27. 4-Butyl-3-(4-chloro-2-fluorophenyl)-N-(5-hydroxy-4,4-dimethylpentyl)-5-methyl-1-phenyl-4,5-dihydro-1H-pyrazole-5-carboxamide was prepared using methyl 4-butyl-3-(4-chloro-2-fluorophenyl)-5-methyl-1-phenyl-4,5-dihydro-1H-pyrazole-5-carboxylate (I.1.19.) in step 1 and 5-amino-2,2-dimethylpentan-1-ol in step 2. MS (EI) for $C_{28}H_{37}ClFN_3O_2$: 503 [M+H].

Example 3.28. 4-Butyl-3-(4-chloro-2-fluorophenyl)-N-(2-methoxyethyl)-5-methyl-1-phenyl-4,5-dihydro-1H-pyrazole-5-carboxamide was prepared using methyl 4-butyl-3-(4-chloro-2-fluorophenyl)-5-methyl-1-phenyl-4,5-dihydro-1H-pyrazole-5-carboxylate (I.1.19.) in step 1 and 2-methoxyethylamine in step 2. MS (EI) for $C_{24}H_{29}ClFN_3O_2$: 446 [M+H].

Example 3.29. 3-(4-Fluorophenyl)-N-(5-hydroxy-4,4-dimethylpentyl)-5-methyl-1-phenyl-4-(thiophen-2-yl)-4,5-dihydro-1H-pyrazole-5-carboxamide was prepared using methyl 3-(4-fluorophenyl)-5-methyl-1-phenyl-4-(thiophen-2-yl)-4,5-dihydro-1H-pyrazole-5-carboxylate (I.1.20.) in step 1 and 5-amino-2,2-dimethylpentan-1-ol in step 2. 1H-NMR (300 MHz, $d_6$-DMSO): 8.14 (t, 1H), 7.63 (dd, 2H), 7.44 (m, 1H), 7.28 (t, 2H), 7.22 (t, 2H), 7.07 (d, 2H), 6.99 (m, 1H), 6.90 (m, 1H), 6.83 (t, 1H), 5.21 (s, 1H), 4.40 (t, 1H), 3.10 (q, 2H), 3.02 (d, 2H), 1.36 (m, 2H), 1.08 (m, 2H), 0.84 (m, 3H), 0.68 (s, 6H). MS (EI) for $C_{28}H_{32}FN_3O_2S$: 494 [M+H].

Example 3.30. 3-(4-fluorophenyl)-N-(2-methoxyethyl)-5-methyl-4-(thiophen-2-yl)-1-p-tolyl-4,5-dihydro-1H-pyrazole-5-carboxamide was prepared using methyl 3-(4-fluorophenyl)-5-methyl-4-(thiophen-2-yl)-1-(p-tolyl)-4,5-dihydro-1H-pyrazole-5-carboxylate (I.1.21.) in step 1 and 2-methoxyethylamine in step 2. 1H-NMR (300 MHz, $d_6$-DMSO): 8.18 (t, 1H), 7.64 (dd, 2H), 7.43 (m, 1H), 7.28 (t, 2H), 7.02 (q, 4H), 6.98 (m, 1H), 6.92 (m, 1H), 5.21 (s, 1H), 3.38 (m, 3H), 3.28 (m, 1H), 3.21 (s, 3H), 2.22 (s, 3H), 0.88 (s, 3H). MS (EI) for $C_{25}H_{26}FN_3O_2S$: 452 [M+H].

Example 3.31. 3-(4-Fluorophenyl)-N-(5-hydroxy-4,4-dimethylpentyl)-5-methyl-1-phenyl-4-(pyridin-4-yl)-4,5-dihydro-1H-pyrazole-5-carboxamide was prepared using methyl 3-(4-fluorophenyl)-5-methyl-1-phenyl-4-(pyridin-4-yl)-4,5-dihydro-1H-pyrazole-5-carboxylate (I.1.22.) in step 1 and 5-amino-2,2-dimethylpentan-1-ol in step 2. MS (EI) for $C_{29}H_{33}FN_4O_2S$: 489 [M+H].

Example 3.32. 4-Butyl-1,3-bis(2,4-difluorophenyl)-N-(5-hydroxy-4,4-dimethylpentyl)-5-methyl-4,5-dihydro-1H-pyrazole-5-carboxamide was prepared using methyl 4-butyl-1,3-bis(2,4-difluorophenyl)-5-methyl-4,5-dihydro-1H-pyrazole-5-carboxylate (I.1.24.) in step 1 and 5-amino-2,2-dimethylpentan-1-ol in step 2. 1H-NMR (300 MHz, $d_6$-DMSO): 8.11 (t, 1H), 7.78 (q, 1H), 7.40 (m, 2H), 7.22 (m, 2H), 7.08 (m, 1H), 4.42 (t, 1H), 3.78 (m, 1H), 3.09 (m, 2H), 3.02 (d, 2H), 1.74 (m, 1H), 1.52 (m, 1H), 1.44 (m, 2H), 1.34 (m, 2H), 1.20 (m, 2H), 1.09 (m, 2H), 1.08 (s, 3H), 0.78 (s, 3H), 0.66 (s, 6H). MS (EI) for $C_{28}H_{35}F_4N_3O_2$: 522 [M+H].

Example 3.33. 4-Butyl-1,3-bis(2,4-difluorophenyl)-N-(2-methoxyethyl)-5-methyl-4,5-dihydro-1H-pyrazole-5-carboxamide was prepared using methyl 4-butyl-1,3-bis(2,4-difluorophenyl)-5-methyl-4,5-dihydro-1H-pyrazole-5-carboxylate (I.1.24.) in step 1 and 2-methoxyethylamine in step 2. 1H-NMR (300 MHz, $d_6$-DMSO): 8.10 (t, 1H), 7.77 (q, 1H), 7.42 (q, 1H), 7.38 (m, 1H), 7.22 (m, 1H), 7.20 (m, 1H), 7.06 (m, 1H), 3.80 (t, 1H), 3.38 (m, 3H), 3.28 (m, 1H), 3.21 (s, 3H), 1.44 (m, 2H), 1.18 (m, 4H), 1.10 (s, 3H), 0.78 (s, 3H). MS (EI) for $C_{24}H_{27}F_4N_3O_2$: 466 [M+H].

Example 3.34. 4-Butyl-1-(4-chloro-2-fluorophenyl)-3-(4-fluorophenyl)-5-methyl-N-((4-methylmorpholin-2-yl)methyl)-4,5-dihydro-1H-pyrazole-5-carboxamide is prepared using methyl 4-butyl-1-(4-chloro-2-fluorophenyl)-3-(4-fluorophenyl)-5-methyl-4,5-dihydro-1H-pyrazole-5-carboxylate (I.1.14.) in step 1 and (4-methylmorpholin-2-yl)methanamine in step 2. MS (EI) for $C_{27}H_{33}ClF_2N_4O_2$: 519 [M+H].

Example 3.35. 4-Butyl-1-(4-chloro-2-fluorophenyl)-3-(4-fluorophenyl)-N-((3-methoxy-1-methylazetidin-3-yl)methyl)-5-methyl-4,5-dihydro-1H-pyrazole-5-carboxamide is prepared using methyl 4-butyl-1-(4-chloro-2-fluorophenyl)-3-(4-fluorophenyl)-5-methyl-4,5-dihydro-1H-pyrazole-5-carboxylate (I.1.14.) in step 1 and (3-methoxy-1-methylazetidin-3-yl)methanamine (R.3.26.) in step 2. MS (EI) for $C_{27}H_{33}ClF_2N_4O_2$: 519 [M+H].

Example 3.36. 1-(4-Chloro-2-fluorophenyl)-4-(5-chlorofuran-2-yl)-3-(4-fluorophenyl)-5-methyl-N-((4-methylmorpholin-2-yl)methyl)-4,5-dihydro-1H-pyrazole-5-carboxamide is prepared using methyl 1-(4-chloro-2-fluorophenyl)-4-(5-chlorofuran-2-yl)-3-(4-fluorophenyl)-5-methyl-4,5-dihydro-1H-pyrazole-5-carboxylate (I.1.37.) and (4-methylmorpholin-2-yl) methanamine in step 2. MS (EI) for $C_{27}H_{26}ClF_2N_4O_3$: 563 [M+H].

Example 3.37. 4-(5-Chlorofuran-2-yl)-3-(4-chlorophenyl)-1-(2,4-difluorophenyl)-5-methyl-N-((4-methylmorpholin-2-yl)methyl)-4,5-dihydro-1H-pyrazole-5-carboxamide is prepared using methyl 4-(5-chlorofuran-2-yl)-3-(4-chlorophenyl)-1-(2,4-difluorophenyl)-5-methyl-4,5-dihydro-1H-pyrazole-5-carboxylate (I.1.38.) and (4-methylmorpholin-2-yl) methanamine in step 2. MS (EI) for $C_{27}H_{26}ClF_2N_4O_3$: 563 [M+H].

Example 3.38. 4-(5-Chlorofuran-2-yl)-3-(4-fluorophenyl)-5-methyl-N-((4-methylmorpholin-2-yl)methyl)-1-(p-tolyl)-4,5-dihydro-1H-pyrazole-5-carboxamide is prepared using methyl 4-(5-chlorofuran-2-yl)-3-(4-fluorophenyl)-5-methyl-1-(p-tolyl)-4,5-dihydro-1H-pyrazole-5-carboxylate (I.1.39.) and (4-methylmorpholin-2-yl)methanamine in step 2. MS (EI) for $C_{28}H_{30}ClFN_4O_3$: 525 [M+H].

Example 3.39. 4-Butyl-3-(4-fluorophenyl)-5-methyl-N-((4-methylmorpholin-2-yl)methyl)-1-(p-tolyl)-4,5-dihydro-1H-pyrazole-5-carboxamide is prepared using methyl 4-butyl-3-(4-fluorophenyl)-5-methyl-1-(p-tolyl)-4,5-dihydro-1H-pyrazole-5-carboxylate (I.1.7.) and (4-methylmorpholin-2-yl)methanamine in step 2. MS (EI) for $C_{28}H_{37}FN_4O_2$: 481 [M+H].

Example 3.40. 4-Butyl-3-(4-fluorophenyl)-N-((3-methoxy-1-methylazetidin-3-yl)methyl)-5-methyl-1-(p-tolyl)-4,5-dihydro-1H-pyrazole-5-carboxamide is prepared using methyl 4-butyl-3-(4-fluorophenyl)-5-methyl-1-(p-tolyl)-4,5-dihydro-1H-pyrazole-5-carboxylate (I.1.7.) and (3-methoxy-1-methylazetidin-3-yl)methanamine (R.3.26.) in step 2. MS (EI) for $C_{28}H_{37}FN_4O_2$: 481 [M+H].

Example 3.41. 4-Butyl-3-(4-fluorophenyl)-N-((3-methoxyoxetan-3-yl)methyl)-5-methyl-1-(p-tolyl)-4,5-dihydro-1H-pyrazole-5-carboxamide is prepared using methyl 4-butyl-3-(4-fluorophenyl)-5-methyl-1-(p-tolyl)-4,5-dihydro-1H-pyrazole-5-carboxylate (I.1.7.) and (3-methoxyoxetan-3-yl)methanamine (R.3.5.) in step 2. MS (EI) for $C_{27}H_{34}FN_3O_3$: 468 [M+H].

Example 4

Example 4 Compounds 1-(2,4-Difluorophenyl)-3-((2),4-(di)fluorophenyl) 5-methyl-N-($R^5$)-4-(5-$R^6$-thiophen-3-yl or 5-$R^6$-furan-3-yl)-4,5-dihydro-1H-pyrazole-5-carboxamide, where X is O or S

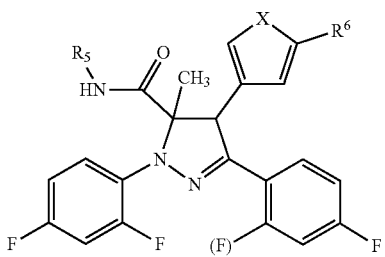

Example 4.2. 1-(2,4-Difluorophenyl)-3-(4-fluorophenyl)-N-(2-methoxyethyl)-5-methyl-4-(thiophen-3-yl)-4,5-dihydro-1H-pyrazole-5-carboxamide was prepared according to the following scheme.

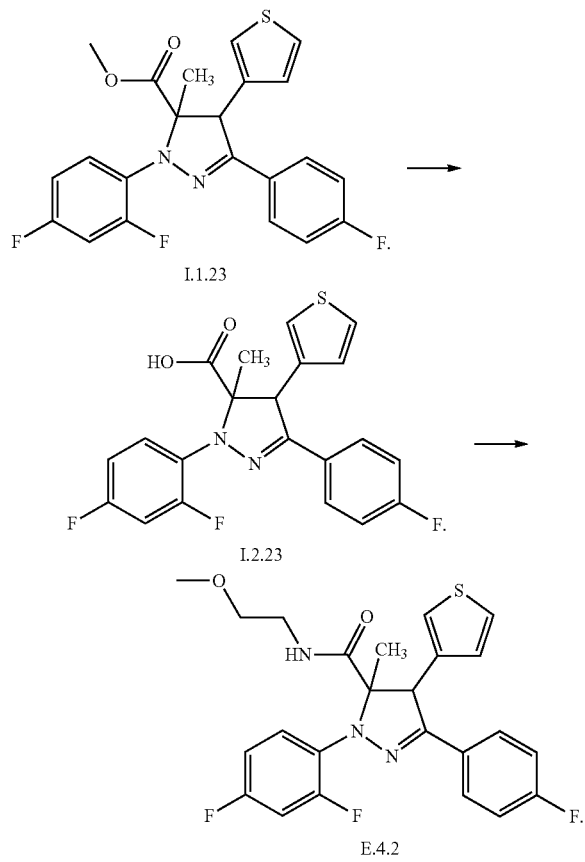

STEP 1. To a solution of methyl 1-(2,4-difluorophenyl)-3-(4-fluorophenyl)-5-methyl-4-(thiophen-3-yl)-4,5-dihydro-1H-pyrazole-5-carboxylate (I.1.23.) (0.22 g, 0.50 mmol) in a mixture of tetrahydrofuran (16 mL), methanol (3 mL) and water (1 mL) was added potassium hydroxide (0.17 mL, 1.50 mmol, 50% aq. solution) and the reaction mixture was stirred at room temperature for one hour. The reaction was monitored by TLC (10% ethyl acetate in hexanes). The pH was adjusted to 4 by the addition of 2M aqueous hydrochloric acid and the mixture was partitioned with ethyl acetate (200 mL) and water (50 mL). The organic layer was separated, washed with brine (2×50 mL), dried over anhydrous sodium sulfate and concentrated to give 1-(2,4-difluorophenyl)-3-(4-fluorophenyl)-5-methyl-4-(thiophen-3-yl)-4,5-dihydro-1H-pyrazole-5-carboxylic acid (I.2.23.); it was used without further purification. MS (EI) for $C_{21}H_{15}F_3N_2O_2S$: 415 [M–H].

STEP 2. To a solution of 1-(2,4-difluorophenyl)-3-(4-fluorophenyl)-5-methyl-4-(thiophen-3-yl)-4,5-dihydro-1H-pyrazole-5-carboxylic acid (I.2.23.) (0.10 g, 0.25 mmol) in N,N-dimethylformamide (5 mL) was added 4-methylmorpholine (0.08 mL, 0.75 mmol) and O-(7-azabenzotriazol-1-yl)-N,N,N',N'-tetramethyluronium hexafluoro-phosphate (0.10 g, 0.28 mmol) and the reaction mixture was stirred at room temperature for ten minutes, followed by the addition of 2-methoxyethylamine (0.02 mL, 0.26 mmol) and the stirring was continued for 18 hours. The reaction mixture was partitioned with ethyl acetate (150 mL) and 1M aqueous hydrochloric acid (50 ml). The organic layer was separated and washed with 1M aqueous hydrochloric acid (50 ml) and brine (2×50 mL), dried over anhydrous sodium sulfate and concentrated. The resulting crude was purified by gradient silica gel flash chromatography (1-30% ethyl acetate in hexanes) to give 1-(2,4-difluorophenyl)-3-(4-fluorophenyl)-N-(2-methoxyethyl)-5-methyl-4-(thiophen-3-yl)-4,5-dihydro-1H-pyrazole-5-carboxamide (E.4.2.) (0.11 g, 94%). 1H-NMR (500 MHz, $d_6$-DMSO): 8.08 (t, 1H), 7.62 (dd, 2H), 7.54 (m, 1H), 7.46 (dd, 1H), 7.32 (m, 1H), 7.29 (m, 1H), 7.17 (t, 2H), 7.08 (m, 1H), 6.79 (m, 1H), 5.06 (s, 1H), 3.38 (m, 3H), 3.24 (m, 1H), 3.19 (s, 3H), 0.78 (s, 3H). MS (EI) for $C_{24}H_{22}F_3N_3O_2S$: 474 [M–H].

Example 4.1. 1-(2,4-Difluorophenyl)-3-(4-fluorophenyl)-N-(5-hydroxy-4,4-dimethylpentyl)-5-methyl-4-(thiophen-3-yl)-4,5-dihydro-1H-pyrazole-5-carboxamide was prepared using methyl 1-(2,4-difluorophenyl)-3-(4-fluorophenyl)-5-methyl-4-(thiophen-3-yl)-4,5-dihydro-1H-pyrazole-5-carboxylate (I.1.23.) in step 1 and 5-amino-2,2-dimethylpentan-1-ol in step 2. 1H-NMR (500 MHz, $d_6$-DMSO): 8.08 (t, 1H), 7.62 (dd, 2H), 7.52 (m, 1H), 7.46 (dd, 1H), 7.29 (m, 1H), 7.27 (m, 1H), 7.16 (t, 2H), 7.06 (m, 1H), 6.78 (m, 1H), 5.06 (s, 1H), 4.0 (t, 1H), 3.10 (m, 2H), 3.02 (d, 2H), 1.36 (m, 2H), 1.08 (m, 2H), 0.78 (s, 3H), 0.68 (s, 6H). MS (EI) for $C_{28}H_{30}F_3N_3O_2S$: 530 [M+H].

Example 4.3. 1,3-Bis(2,4-difluorophenyl)-N-(5-hydroxy-4,4-dimethylpentyl)-5-methyl-4-(thiophen-3-yl)-4,5-dihydro-1H-pyrazole-5-carboxamide was prepared using methyl 1,3-bis(2,4-difluorophenyl)-5-methyl-4-(thiophen-3-yl)-4,5-dihydro-1H-pyrazole-5-carboxylate (I.1.26.) in step 1 and 5-amino-2,2-dimethylpentan-1-ol in step 2. 1H-NMR (300 MHz, $d_6$-DMSO): 8.15 (t, 1H), 7.85 (q, 1H), 7.58 (q, 1H), 7.44 (dd, 1H), 7.31 (m, 1H), 7.22 (m, 1H), 7.20 (d, 1H), 7.09 (m, 2H), 6.78 (d, 1H), 5.08 (s, 1H), 4.40 (t, 1H), 3.10 (m, 2H), 3.02 (d, 2H), 1.35 (m, 2H), 1.09 (m, 2H), 0.75 (s, 3H), 0.66 (s, 6H). MS (EI) for $C_{28}H_{29}F_4N_3O_2S$: 548 [M+H].

Example 4.4. 1,3-bis(2,4-Difluorophenyl)-N-(2-methoxyethyl)-5-methyl-4-(thiophen-3-yl)-4,5-dihydro-1H-pyrazole-5-carboxamide was prepared using methyl 1,3-bis(2,4-difluorophenyl)-5-methyl-4-(thiophen-3-yl)-4,5-dihydro-1H-pyrazole-5-carboxylate (I.1.26.) in step 1 and 2-metoxyethylamine in step 2. 1H-NMR (500 MHz, $d_6$-DMSO): 8.16 (t, 1H), 7.84 (q, 1H), 7.58 (q, 1H), 7.44 (dd, 1H), 7.32 (m, 1H), 7.22 (m, 1H), 7.20 (d, 1H), 7.10 (m, 2H), 6.78 (d, 1H), 5.10 (s, 1H), 3.38 (m, 2H), 3.34 (m, 2H), 3.22 (s, 3H), 0.74 (s, 3H). MS (EI) for $C_{24}H_{21}F_4N_3O_2S$: 492 [M+H].

Example 4.5. Methyl 2-(1,3-bis(2,4-difluorophenyl)-5-methyl-4-(thiophen-3-yl)-4,5-dihydro-1H-pyrazole-5-carboxamido)acetate was prepared using methyl 1,3-bis(2,4-difluorophenyl)-5-methyl-4-(thiophen-3-yl)-4,5-dihydro-1H-pyrazole-5-carboxylate (I.1.26.) in step 1 and methyl glycinate in step 2. 1H-NMR (300 MHz, $d_6$-DMSO): 8.16 (t, 1H), 7.83 (q, 1H), 7.59 (q, 1H), 7.46 (dd, 1H), 7.30 (m, 1H), 7.21 (m, 1H), 7.19 (d, 1H), 7.09 (m, 2H), 6.77 (d, 1H), 5.09 (s, 1H), 3.88 (q, 2H), 3.62 (s, 3H), 0.75 (s, 3H). MS (EI) for $C_{24}H_{19}F_4N_3O_3S$: 506 [M+H].

Example 4.6. 1,3-Bis(2,4-difluorophenyl)-4-(furan-3-yl)-N-(5-hydroxy-4,4-dimethylpentyl)-5-methyl-4,5-dihydro-1H-pyrazole-5-carboxamide was prepared using methyl 1,3-bis(2,4-difluorophenyl)-4-(furan-3-yl)-5-methyl-4,5-dihydro-1H-pyrazole-5-carboxylate (I.1.27.) in step 1 and 5-amino-2,2-dimethylpentan-1-ol in step 2. 1H-NMR (300 MHz, $d_6$-DMSO): 8.18 (t, 1H), 7.84 (q, 1H), 7.58 (s, 1H), 7.52 (dd, 1H), 7.49 (s, 1H), 7.29 (m, 2H), 7.09 (m, 2H), 6.17 (s, 1H), 4.95 (s, 1H), 4.40 (t, 1H), 3.08 (m, 2H), 3.02 (d, 2H), 1.38 (m, 2H), 1.09 (m, 2H), 0.84 (s, 3H), 0.68 (s, 6H). MS (EI) for $C_{28}H_{29}F_4N_3O_3$: 532 [M+H].

Example 4.7. 1,3-Bis(2,4-difluorophenyl)-4-(furan-3-yl)-N-(2-methoxyethyl)-5-methyl-4,5-dihydro-1H-pyrazole-5-carboxamide was prepared using methyl 1,3-bis(2,4-difluorophenyl)-4-(furan-3-yl)-5-methyl-4,5-dihydro-1H-pyrazole-5-carboxylate (I.1.27.) in step 1 and 2-metoxyethylamine in step 2. 1H-NMR (500 MHz, $d_6$-DMSO): 8.18 (t, 1H), 7.84 (q, 1H), 7.58 (s, 1H), 7.52 (dd, 1H), 7.48 (s, 1H), 7.28 (m, 2H), 7.10 (m, 2H), 6.16 (s, 1H), 4.94 (s, 1H), 3.28 (m, 3H), 3.18 (m, 1H), 3.16 (s, 3H), 0.88 (s, 3H). MS (EI) for $C_{24}H_{21}F_4N_3O_3$: 476 [M+H].

Example 4.8. Methyl 2-(1,3-bis(2,4-difluorophenyl)-4-(furan-3-yl)-5-methyl-4,5-dihydro-1H-pyrazole-5-carboxamido)acetate was prepared using methyl 1,3-bis(2,4-difluorophenyl)-4-(furan-3-yl)-5-methyl-4,5-dihydro-1H-pyrazole-5-carboxylate (I.1.27.) in step 1 and methyl glycinate in step 2. 1H-NMR (300 MHz, $d_6$-DMSO): 8.18 (t, 1H), 7.83 (q, 1H), 7.56 (s, 1H), 7.50 (m, 1H), 7.49 (s, 1H), 7.26 (m, 2H), 7.09 (m, 2H), 6.16 (s, 1H), 4.94 (s, 1H), 3.94 (q, 2H), 3.62 (s, 3H), 0.84 (s, 3H). MS (EI) for $C_{24}H_{19}F_4N_3O_4$: 490 [M+H].

Example 4.9. (2S)-Methyl 2-(1,3-bis(2,4-difluorophenyl)-4-(furan-3-yl)-5-methyl-4,5-dihydro-1H-pyrazole-5-carboxamido)propanoate was prepared using methyl 1,3-bis(2,4-difluorophenyl)-4-(furan-3-yl)-5-methyl-4,5-dihydro-1H-pyrazole-5-carboxylate (I.1.27.) in step 1 and L-alanine methyl ester in step 2. MS (EI) for $C_{25}H_{21}F_4N_3O_3$: 504 [M+H].

Example 5

Example 5 Compounds 1-(2,4-Difluorophenyl)-3-(4-fluorophenyl)-5-methyl-N-($R^5$)-4-(5-$R^6$-thiophen-2-yl)-4,5-dihydro-1H-pyrazole-5-carboxamide

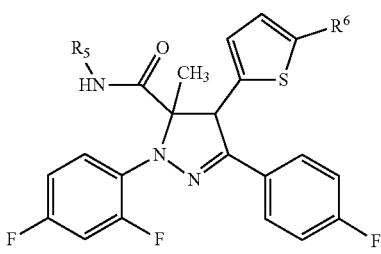

Example 5.2. 1-(2,4-Difluorophenyl)-3-(4-fluorophenyl)-N-(2-methoxyethyl)-5-methyl-4-(thiophen-2-yl)-4,5-dihydro-1H-pyrazole-5-carboxamide was prepared according to the following scheme.

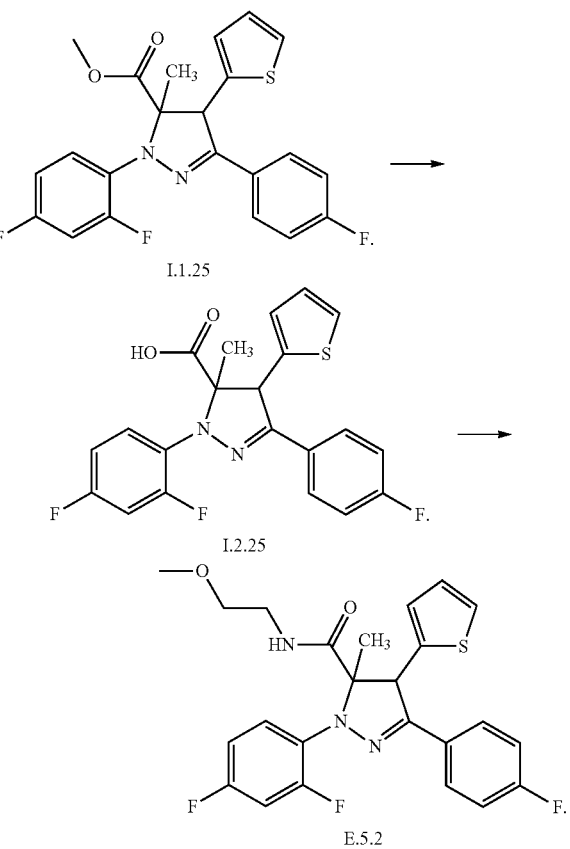

STEP 1. To a solution of methyl 1-(2,4-difluorophenyl)-3-(4-fluorophenyl)-5-methyl-4-(thiophen-2-yl)-4,5-dihydro-1H-pyrazole-5-carboxylate (I.1.25.) (1.22 g, 2.83 mmol) in a mixture of tetrahydrofuran (48 mL), methanol (11 mL) and water (1 mL) was added potassium hydroxide (0.95 mL, 8.50 mmol, 50% aq. solution) and the reaction mixture was stirred at room temperature for two hours. The reaction was monitored by TLC (10% ethyl acetate in hexanes). Upon completion, the pH was adjusted to 4 by the addition of 2M aqueous hydrochloric acid and the mixture was partitioned with ethyl acetate (350 mL) and water (100 mL). The organic layer was separated, washed with brine (2×100 mL), dried over anhydrous sodium sulfate and concentrated to give 1-(2,4-difluorophenyl)-3-(4-fluorophenyl)-5-methyl-4-(thiophen-2-yl)-4,5-dihydro-1H-pyrazole-5-carboxylic acid (I.2.25.) (1.15 g, 97%); it was used without further purification. MS (EI) for $C_{21}H_{15}F_3N_2O_2S$: 415 [M–H].

STEP 2. To a solution of 1-(2,4-difluorophenyl)-3-(4-fluorophenyl)-5-methyl-4-(thiophen-2-yl)-4,5-dihydro-1H-pyrazole-5-carboxylic acid (I.2.25.) (0.12 g, 0.28 mmol) in N,N-dimethylformamide (5 mL) was added 4-methylmorpholine (0.09 mL, 0.84 mmol) and O-(7-azabenzotriazol-1-yl)-N,N,N',N'-tetramethyluronium hexafluoro-phosphate (0.12 g, 0.31 mmol) and the reaction mixture was stirred at room temperature for ten minutes, followed by the addition of 2-methoxyethylamine (0.025 mL, 0.29 mmol) and the stirring was continued for 18 hours. The reaction mixture was partitioned with ethyl acetate (200 mL) and 1M aqueous hydrochloric acid (50 ml). The organic layer was separated and washed with 1M aqueous hydrochloric acid (50 ml) and brine (2×50 mL), dried over anhydrous sodium sulfate and concentrated. The resulting crude was purified by gradient silica gel flash chromatography (1-30% ethyl acetate in hexanes) to give 1-(2,4-difluorophenyl)-3-(4-fluorophenyl)-N-(2-methoxyethyl)-5-methyl-4-(thiophen-2-yl)-4,5-dihydro-1H-pyrazole-5-carboxamide (E.5.2.) (0.12 g, 91%). 1H-NMR (300 MHz, $d_6$-DMSO): 8.14 (t, 1H), 7.64 (dd, 2H), 7.46 (m, 2H), 7.32 (m, 1H), 7.18 (t, 2H), 7.08 (m, 1H), 6.98 (m, 1H), 6.92 (m, 1H), 5.21 (s, 1H), 3.28 (m, 3H), 3.22 (m, 1H), 3.20 (s, 3H), 0.86 (s, 3H). MS (EI) for $C_{24}H_{22}F_3N_3O_2S$: 474 [M–H].

Example 5.1. 1-(2,4-Difluorophenyl)-N-(2,4-dihydroxybutyl)-3-(4-fluorophenyl)-5-methyl-4-(thiophen-2-yl)-4,5-dihydro-1H-pyrazole-5-carboxamide was prepared using 4-aminobutane-1,3-diol in step 2. MS (EI) for $C_{25}H_{24}F_3N_3O_3S$: 504 [M+H].

Example 5.3. 1-(2,4-Difluorophenyl)-3-(4-fluorophenyl)-5-methyl-N-(2-morpholinoethyl)-4-(thiophen-2-yl)-4,5-dihydro-1H-pyrazole-5-carboxamide was prepared using 4-(2-aminoethyl)morpholine in step 2. MS (EI) for $C_{27}H_{27}F_3N_4O_2S$: 529 [M+H].

Example 5.4. 1-(2,4-Difluorophenyl)-3-(4-fluorophenyl)-5-methyl-N-(3-morpholinopropyl)-4-(thiophen-2-yl)-4,5-dihydro-1H-pyrazole-5-carboxamide was prepared using 4-(3-aminopropyl)morpholine in step 2. MS (EI) for $C_{28}H_{29}F_3N_4O_2S$: 543 [M+H].

Example 5.5. 1-(2,4-Difluorophenyl)-3-(4-fluorophenyl)-5-methyl-N-((4-methylmorpholin-2-yl)methyl)-4-(thiophen-2-yl)-4,5-dihydro-1H-pyrazole-5-carboxamide was prepared using (4-methylmorpholin-2-yl)methanamine in step 2. 1H-NMR (500 MHz, $d_6$-DMSO): 8.16 (t, 1H), 7.68 (dd, 2H), 7.46 (m, 2H), 7.30 (m, 1H), 7.18 (t, 2H), 7.10 (m, 1H), 6.98 (m, 1H), 6.90 (m, 1H), 5.23 (s, 1H), 3.68 (d, 1H), 3.45 (m, 1H), 3.39 (m, 1H), 3.19 (m, 2H), 2.49 (m, 2H), 2.01 (s, 3H), 1.81 (m, 1H), 1.58 (m, 1H), 0.88 (s, 3H). MS (EI) for $C_{27}H_{27}F_3N_4O_2S$: 529 [M+H].

Example 5.6. Methyl 2-(1-(2,4-difluorophenyl)-3-(4-fluorophenyl)-5-methyl-4-(thiophen-2-yl)-4,5-dihydro-1H-pyrazole-5-carboxamido)acetate was prepared as follows.

To a solution of 1-(2,4-difluorophenyl)-3-(4-fluorophenyl)-5-methyl-4-(thiophen-2-yl)-4,5-dihydro-1H-pyrazole-5-carboxylic acid (I.2.25.) (1.02 g, 2.44 mmol) in N,N-dimethylformamide (25 mL) was added 4-methylmorpholine (1.34 mL, 12.20 mmol) and O-(7-azabenzotriazol-1-yl)-N,N,N',N'-tetramethyluronium hexafluoro-phosphate (0.97 g, 2.56 mmol) and the reaction mixture was stirred at room temperature for ten minutes, followed by the addition of methyl glycinate (0.32 g, 2.56 mmol) and the stirring was continued for 18 hours. The reaction mixture was partitioned with ethyl acetate (350 mL) and 1M aqueous hydrochloric acid (100 ml). The organic layer was separated and washed with 1M aqueous hydrochloric acid (2×100 ml) and brine (2×100 mL), dried over anhydrous sodium sulfate and concentrated. The resulting crude was purified by gradient silica gel flash chromatography (1-30% ethyl acetate in hexanes) to give methyl 2-(1-(2,4-difluorophenyl)-3-(4-fluorophenyl)-5-methyl-4-(thiophen-2-yl)-4,5-dihydro-1H-pyrazole-5-carboxamido)acetate. (E.5.6.) (1.08 g, 92%). 1H-NMR (300 MHz, $d_6$-DMSO): 8.14 (t, 1H), 7.66 (dd, 2H), 7.46 (m, 2H), 7.31 (m, 1H), 7.19 (t, 2H), 7.12 (m, 1H), 6.99 (m, 1H), 6.91 (m, 1H), 5.21 (s, 1H), 3.90 (q, 2H), 3.62 (s, 3H), 0.88 (s, 3H). MS (EI) for $C_{24}H_{20}F_3N_3O_3S$: 488 [M+H].

Example 5.7. 1-(2,4-Difluorophenyl)-3-(4-fluorophenyl)-5-methyl-N-(2-(methylamino)-2-oxoethyl)-4-(thiophen-2-yl)-4,5-dihydro-1H-pyrazole-5-carboxamide was prepared as follows.

STEP 1. To a solution of methyl 2-(1-(2,4-difluorophenyl)-3-(4-fluorophenyl)-5-methyl-4-(thiophen-2-yl)-4,5-dihydro-1H-pyrazole-5-carboxamido)acetate (E.5.6.) in (0.94 g, 1.93 mmol) in a mixture of tetrahydrofuran (10 mL), methanol (5 mL) and water (1 mL) was added potassium hydroxide (0.65 mL, 5.79 mmol, 50% aq. solution) and the reaction mixture was stirred at room temperature for two hours. Upon completion of the reaction, the pH was adjusted to 2 by the addition of 2M aqueous hydrochloric acid and the mixture was partitioned with ethyl acetate (350 mL) and water (100 mL). The organic layer was separated, washed with brine (2×100 mL), dried over anhydrous sodium sulfate and concentrated to give 1-(2,4-difluorophenyl)-3-(4-fluorophenyl)-5-methyl-4-(thiophen-2-yl)-4,5-dihydro-1H-pyrazole-5-carbonyl)glycine (0.90 g, 98%) as white solid. The acid was used without further purification. MS (EI) for $C_{23}H_{18}F_3N_3O_3S$: 472 [M–H].

STEP 2. To a solution of 1-(2,4-difluorophenyl)-3-(4-fluorophenyl)-5-methyl-4-(thiophen-2-yl)-4,5-dihydro-1H-pyrazole-5-carbonyl)glycine (0.10 g, 0.21 mmol) in N,N-dimethylformamide (5 mL) was added 4-methylmorpholine (0.07 mL, 0.63 mmol) and O-(7-azabenzotriazol-1-yl)-N,N,N',N'-tetramethyluronium hexafluoro-phosphate (0.09 g, 0.23 mmol) and the reaction mixture was stirred at room temperature for ten minutes, followed by the addition of methylamine (0.12 mL, 0.23 mmol, 2M solution in tetrahydrofuran) and the stirring was continued for 18 hours. The reaction mixture was partitioned with ethyl acetate (150 mL) and 1M aqueous hydrochloric acid (50 ml). The organic layer was separated and washed with 1M aqueous hydrochloric acid (50 ml) and brine (2×50 mL), dried over anhydrous sodium sulfate and concentrated. The resulting crude was purified by gradient silica gel flash chromatography (1-35% ethyl acetate in hexanes) to give 1-(2,4-difluorophenyl)-3-(4-fluorophenyl)-5-methyl-N-(2-(methylamino)-2-oxoethyl)-4-(thiophen-2-yl)-4,5-dihydro-1H-pyrazole-5-carboxamide (E.5.7.) (0.09 g, 92%). MS (EI) for $C_{24}H_{21}F_3N_4O_2S$: 487 [M+H]. Example 5.8. 1-(2,4-Difluorophenyl)-3-(4-fluorophenyl)-N-(2-(methoxy(methyl)amino)-2-oxoethyl)-5-methyl-4-(thiophen-2-yl)-4,5-dihydro-1H-pyrazole-5-carboxamide was prepared using 1-(2,4-difluorophenyl)-3-(4-fluorophenyl)-5-methyl-4-(thiophen-2-yl)-4,5-dihydro-1H-pyrazole-5-carbonyl)

glycine and N,O-dimethylhydroxylamine. MS (EI) for $C_{25}H_{23}F_3N_4O_3S$: 517 [M+H].

Example 5.9. 1-(2,4-Difluorophenyl)-3-(4-fluorophenyl)-N-(2-(2-hydroxy-2-methylpropylamino)-2-oxoethyl)-5-methyl-4-(thiophen-2-yl)-4,5-dihydro-1H-pyrazole-5-carboxamide was prepared using 1-(2,4-difluorophenyl)-3-(4-fluorophenyl)-5-methyl-4-(thiophen-2-yl)-4,5-dihydro-1H-pyrazole-5-carbonyl)glycine and 1-amino-2-methylpropan-2-ol. MS (EI) for $C_{27}H_{27}F_3N_4O_3S$: 544 [M+H].

Example 5.10. 1-(2,4-Difluorophenyl)-N-(2-(1,1-dioxidothiomorpholino)-2-oxoethyl)-3-(4-fluorophenyl)-5-methyl-4-(thiophen-2-yl)-4,5-dihydro-1H-pyrazole-5-carboxamide was prepared using 1-(2,4-difluorophenyl)-3-(4-fluorophenyl)-5-methyl-4-(thiophen-2-yl)-4,5-dihydro-1H-pyrazole-5-carbonyl)glycine and thiomorpholine 1,1-dioxide. MS (EI) for $C_{27}H_{25}F_3N_4O_4S_2$: 517 [M+H].

Example 5.11. 1-(2,4-Difluorophenyl)-3-(4-fluorophenyl)-5-methyl-N-(2-morpholino-2-oxoethyl)-4-(thiophen-2-yl)-4,5-dihydro-1H-pyrazole-5-carboxamide was prepared using 1-(2,4-difluorophenyl)-3-(4-fluorophenyl)-5-methyl-4-(thiophen-2-yl)-4,5-dihydro-1H-pyrazole-5-carbonyl)glycine and morpholine. MS (EI) for $C_{27}H_{25}F_3N_4O_3S$: 543 [M+H].

Example 5.12. 1-(2,4-Difluorophenyl)-N-(2-(2-(dimethylamino)ethylamino)-2-oxoethyl)-3-(4-fluorophenyl)-5-methyl-4-(thiophen-2-yl)-4,5-dihydro-1H-pyrazole-5-carboxamide was prepared using 1-(2,4-difluorophenyl)-3-(4-fluorophenyl)-5-methyl-4-(thiophen-2-yl)-4,5-dihydro-1H-pyrazole-5-carbonyl)glycine and 2-dimethylaminoethylamine. MS (EI) for $C_{27}H_{28}F_3N_5O_2S$: 544 [M+H].

Example 5.13. 1-(2,4-Difluorophenyl)-3-(4-fluorophenyl)-5-methyl-N-(2-(oxetan-3-ylamino)-2-oxoethyl)-4-(thiophen-2-yl)-4,5-dihydro-1H-pyrazole-5-carboxamide was prepared using 1-(2,4-difluorophenyl)-3-(4-fluorophenyl)-5-methyl-4-(thiophen-2-yl)-4,5-dihydro-1H-pyrazole-5-carbonyl)glycine and oxetan-3-amine. MS (EI) for $C_{26}H_{23}F_3N_4O_3S$: 529 [M+H].

Example 5.14. 1-(2,4-Difluorophenyl)-3-(4-fluorophenyl)-5-methyl-N-(2-(2-(methylsulfonyl)ethylamino)-2-oxoethyl)-4-(thiophen-2-yl)-4,5-dihydro-1H-pyrazole-5-carboxamide was prepared using 1-(2,4-difluorophenyl)-3-(4-fluorophenyl)-5-methyl-4-(thiophen-2-yl)-4,5-dihydro-1H-pyrazole-5-carbonyl)glycine and 2-(methylsulfonyl)ethan-1-amine. MS (EI) for $C_{26}H_{25}F_3N_4O_4S_2$: 579 [M+H].

Example 5.15. 1-(2,4-Difluorophenyl)-3-(4-fluorophenyl)-N-(2-(3-hydroxy-3-methylcyclobutylamino)-2-oxoethyl)-5-methyl-4-(thiophen-2-yl)-4,5-dihydro-1H-pyrazole-5-carboxamide was prepared using 1-(2,4-difluorophenyl)-3-(4-fluorophenyl)-5-methyl-4-(thiophen-2-yl)-4,5-dihydro-1H-pyrazole-5-carbonyl)glycine and 3-amino-1-methylcyclobutan-1-ol MS (EI) for $C_{28}H_{27}F_3N_4O_3S$: 557 [M+H].

Example 5.16. 1-(2,4-Difluorophenyl)-3-(4-fluorophenyl)-N-(2-(2-hydroxyethylamino)-2-oxoethyl)-5-methyl-4-(thiophen-2-yl)-4,5-dihydro-1H-pyrazole-5-carboxamide was prepared using 1-(2,4-difluorophenyl)-3-(4-fluorophenyl)-5-methyl-4-(thiophen-2-yl)-4,5-dihydro-1H-pyrazole-5-carbonyl)glycine and 2-aminoethan-1-ol. MS (EI) for $C_{25}H_{23}F_3N_4O_3S$: 517 [M+H].

Example 5.17. 1-(2,4-Difluorophenyl)-3-(4-fluorophenyl)-N-(5-hydroxy-4,4-dimethylpentyl)-5-methyl-4-(5-methylthiophen-2-yl)-4,5-dihydro-1H-pyrazole-5-carboxamide was prepared using methyl 1-(2,4-difluorophenyl)-3-(4-fluorophenyl)-5-methyl-4-(5-methylthiophen-2-yl)-4,5-dihydro-1H-pyrazole-5-carboxylate (I.1.28.) in step 1 and 5-amino-2,2-dimethylpentan-1-ol in step 2. MS (EI) for $C_{29}H_{32}F_3N_3O_2S$: 544 [M+H].

Example 5.18. 1-(2,4-Difluorophenyl)-3-(4-fluorophenyl)-N-(2-methoxyethyl)-5-methyl-4-(5-methylthiophen-2-yl)-4,5-dihydro-1H-pyrazole-5-carboxamide was prepared using methyl 1-(2,4-difluorophenyl)-3-(4-fluorophenyl)-5-methyl-4-(5-methylthiophen-2-yl)-4,5-dihydro-1H-pyrazole-5-carboxylate (I.1.28.) in step 1 and 2-methoxyethylamine in step 2. MS (EI) for $C_{25}H_{24}F_3N_3O_2S$: 488 [M+H].

Example 5.19. 4-(5-Chlorothiophen-2-yl)-1-(2,4-difluorophenyl)-3-(4-fluorophenyl)-N-(5-hydroxy-4,4-dimethylpentyl)-5-methyl-4,5-dihydro-1H-pyrazole-5-carboxamide was prepared using methyl 4-(5-chlorothiophen-2-yl)-1-(2,4-difluorophenyl)-3-(4-fluorophenyl)-5-methyl-4,5-dihydro-1H-pyrazole-5-carboxylate (I.1.29.) in step 1 and 5-amino-2,2-dimethylpentan-1-ol in step 2. MS (EI) for $C_{28}H_{29}ClF_3N_3O_2S$: 565 [M+H].

Example 5.20. 4-(5-Chlorothiophen-2-yl)-1-(2,4-difluorophenyl)-3-(4-fluorophenyl)-N-(2-methoxyethyl)-5-methyl-4,5-dihydro-1H-pyrazole-5-carboxamide was prepared methyl 4-(5-chlorothiophen-2-yl)-1-(2,4-difluorophenyl)-3-(4-fluorophenyl)-5-methyl-4,5-dihydro-1H-pyrazole-5-carboxylate (I.1.29.) in step 1 and 2-methoxyethylamine in step 2. MS (EI) for $C_{24}H_{21}ClF_3N_3O_2S$: 508 [M+H].

Example 6

Example 6 Compounds 4-(5-$R^6$-furan-2-yl)-(2,4-Difluorophenyl)-3-((2),4-(di)fluorophenyl)-N-($R^5$)-5-methyl-4,5-dihydro-1H-pyrazole-5-carboxamide

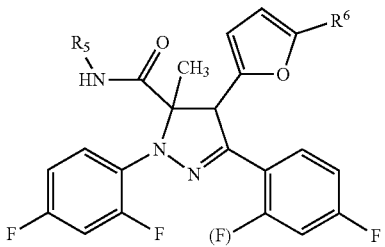

Example 6.6. 4-(5-Chlorofuran-2-yl)-1,3-bis(2,4-difluorophenyl)-N-(2-methoxyethyl)-5-methyl-4,5-dihydro-1H-pyrazole-5-carboxamide was prepared according to the following scheme.

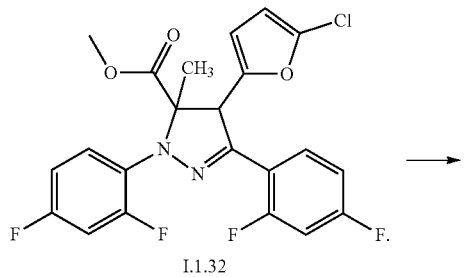

I.1.32

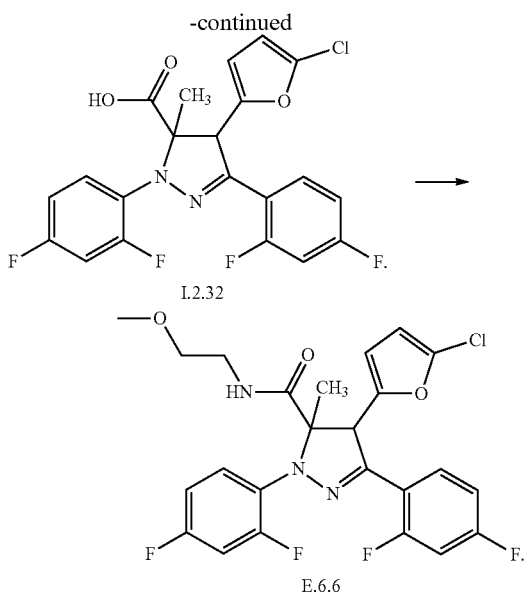

I.2.32

E.6.6

STEP 1. To a solution of methyl 4-(5-chlorofuran-2-yl)-1,3-bis(2,4-difluorophenyl)-5-methyl-4,5-dihydro-1H-pyrazole-5-carboxylate (I.1.32.) (0.28 g, 0.58 mmol) in a mixture of tetrahydrofuran (8 mL), methanol (1 mL) and water (1 mL) was added potassium hydroxide (0.20 mL, 1.74 mmol, 50% aq. solution) and the reaction mixture was stirred at room temperature for two hours, monitored by TLC (10% ethyl acetate in hexanes. Upon completion, the pH was adjusted to 4 by the addition of 2M aqueous hydrochloric acid and the mixture was partitioned with ethyl acetate (150 mL) and water (50 mL). The organic layer was separated, washed with brine (2×100 mL), dried over anhydrous sodium sulfate and concentrated to give 4-(5-chlorofuran-2-yl)-1,3-bis(2,4-difluorophenyl)-5-methyl-4,5-dihydro-1H-pyrazole-5-carboxylic acid (I.2.32.) as white solid (0.25 g, 96%); it was used without further purification. MS (EI) for $C_{21}H_{13}ClF_4N_2O_3$: 451 [M−H].

STEP 2. To a solution of 4-(5-chlorofuran-2-yl)-1,3-bis(2,4-difluorophenyl)-5-methyl-4,5-dihydro-1H-pyrazole-5-carboxylic acid (I.2.32.) (0.13 g, 0.28 mmol) in N,N-dimethylformamide (5 mL) was added 4-methylmorpholine (0.09 mL, 0.84 mmol) and O-(7-azabenzotriazol-1-yl)-N,N,N',N'-tetramethyluronium hexafluoro-phosphate (0.12 g, 0.31 mmol) and the reaction mixture was stirred at room temperature for ten minutes, followed by the addition of 2-methoxyethylamine (0.027 mL, 0.31 mmol) and the stirring was continued for 18 hours. The reaction mixture was partitioned with ethyl acetate (200 mL) and 1M aqueous hydrochloric acid (50 ml). The organic layer was separated and washed with 1M aqueous hydrochloric acid (50 ml) and brine (2×50 mL), dried over anhydrous sodium sulfate and concentrated. The resulting crude was purified by gradient silica gel flash chromatography (1-30% ethyl acetate in hexanes) to give 4-(5-chlorofuran-2-yl)-1,3-bis(2,4-difluorophenyl)-N-(2-methoxyethyl)-5-methyl-4,5-dihydro-1H-pyrazole-5-carboxamide (E.6.6.) (0.14 g, 95%). 1H-NMR (500 MHz, $d_6$-DMSO): 8.20 (t, 1H), 7.89 (q, 1H), 7.48 (q, 1H), 7.32 (m, 2H), 7.12 (m, 2H), 6.38 (d, 1H), 6.32 (d, 1H), 5.12 (s, 1H), 3.38 (m, 3H), 3.24 (m, 1H), 3.21 (s, 3H), 0.84 (s, 3H). MS (EI) for $C_{24}H_{20}ClF_4N_3O_3$: 510 [M+H].

Example 6.1. 1-(2,4-Difluorophenyl)-3-(4-fluorophenyl)-4-(furan-2-yl)-N-(5-hydroxy-4,4-dimethylpentyl)-5-methyl-4,5-dihydro-1H-pyrazole-5-carboxamide was prepared using methyl 1-(2,4-difluorophenyl)-3-(4-fluorophenyl)-4-(furan-2-yl)-5-methyl-4,5-dihydro-1H-pyrazole-5-carboxylate (I.1.30.) in step 1 and 5-amino-2,2-dimethylpentan-1-ol in step 2. 1H-NMR (300 MHz, $d_6$-DMSO): 8.12 (t, 1H), 7.64 (dd, 2H), 7.56 (s, 1H), 7.46 (m, 1H), 7.29 (m, 1H), 7.18 (t, 2H), 7.09 (m, 1H), 6.40 (d, 1H), 6.36 (d, 1H), 5.18 (s, 1H), 4.40 (t, 1H), 3.10 (m, 2H), 3.04 (d, 2H), 1.36 (m, 2H), 1.10 (m, 2H), 0.841 (s, 3H), 0.68 (s, 6H). MS (EI) for $C_{28}H_{30}F_3N_3O_3$: 514 [M+H].

Example 6.2. 1-(2,4-Difluorophenyl)-3-(4-fluorophenyl)-4-(furan-2-yl)-N-(2-methoxyethyl)-5-methyl-4,5-dihydro-1H-pyrazole-5-carboxamide was prepared using methyl 1-(2,4-difluorophenyl)-3-(4-fluorophenyl)-4-(furan-2-yl)-5-methyl-4,5-dihydro-1H-pyrazole-5-carboxylate (I.1.30.) in step 1 and 2-methoxyethylamine in step 2. 1H-NMR (500 MHz, $d_6$-DMSO): 8.14 (t, 1H), 7.64 (dd, 2H), 7.57 (s, 1H), 7.48 (m, 1H), 7.30 (m, 1H), 7.18 (t, 2H), 7.08 (m, 1H), 6.39 (d, 1H), 6.37 (d, 1H), 5.18 (s, 1H), 3.36 (m, 3H), 3.20 (m, 1H), 3.18 (s, 3H), 0.81 (s, 3H). MS (EI) for $C_{24}H_{22}F_3N_3O_3$: 458 [M+H].

Example 6.3. 1,3-Bis(2,4-difluorophenyl)-4-(furan-2-yl)-N-(5-hydroxy-4,4-dimethylpentyl)-5-methyl-4,5-dihydro-1H-pyrazole-5-carboxamide was prepared using methyl 1,3-bis(2,4-difluorophenyl)-4-(furan-2-yl)-5-methyl-4,5-dihydro-1H-pyrazole-5-carboxylate (I.1.31.) in step 1 and 5-amino-2,2-dimethylpentan-1-ol in step 2. MS (EI) for $C_{28}H_{29}F_4N_3O_3$: 532 [M+H].

Example 6.4. 1,3-Bis(2,4-difluorophenyl)-4-(furan-2-yl)-N-(2-methoxyethyl)-5-methyl-4,5-dihydro-1H-pyrazole-5-carboxamide was prepared using methyl 1,3-bis(2,4-difluorophenyl)-4-(furan-2-yl)-5-methyl-4,5-dihydro-1H-pyrazole-5-carboxylate (I.1.31.) in step 1 and 2-methoxyethylamine in step 2. 1H-NMR (500 MHz, $d_6$-DMSO): 8.18 (t, 1H), 7.82 (q, 1H), 7.58 (s, 1H), 7.49 (q, 1H), 7.29 (m, 2H), 7.12 (m, 2H), 6.36 (d, 1H), 6.20 (d, 1H), 5.16 (s, 1H), 3.38 (m, 3H), 3.28 (m, 1H), 3.21 (s, 3H), 0.81 (s, 3H). MS (EI) for $C_{24}H_{21}F_4N_3O_3$: 476 [M+H].

Example 6.5. 4-(5-Chlorofuran-2-yl)-1,3-bis(2,4-difluorophenyl)-N-(5-hydroxy-4,4-dimethylpentyl)-5-methyl-4,5-dihydro-1H-pyrazole-5-carboxamide was prepared using methyl 4-(5-chlorofuran-2-yl)-1,3-bis(2,4-difluorophenyl)-5-methyl-4,5-dihydro-1H-pyrazole-5-carboxylate (I.1.32.) in step 1 and 5-amino-2,2-dimethylpentan-1-ol in step 2. 1H-NMR (500 MHz, $d_6$-DMSO): 8.19 (t, 1H), 7.88 (q, 1H), 7.48 (m, 1H), 7.30 (m, 2H), 7.18 (m, 1H), 7.08 (m, 1H), 6.38 (d, 1H), 6.32 (d, 1H), 5.10 (s, 1H), 4.41 (t, 1H), 3.08 (m, 2H), 3.02 (d, 2H), 1.36 (m, 2H), 1.08 (m, 2H), 0.84 (s, 3H), 0.66 (s, 6H). MS (EI) for $C_{28}H_{28}ClF_4N_3O_3$: 567 [M+H].

Example 6.7. Methyl 2-(4-(5-chlorofuran-2-yl)-1,3-bis(2,4-difluorophenyl)-5-methyl-4,5-dihydro-1H-pyrazole-5-carboxamido)acetate was prepared using methyl 4-(5-chlorofuran-2-yl)-1,3-bis(2,4-difluorophenyl)-5-methyl-4,5-dihydro-1H-pyrazole-5-carboxylate (I.1.32.) in step 1 and methyl glycinate in step 2. 1H-NMR (500 MHz, $d_6$-DMSO): 8.64 (t, 1H), 7.88 (q, 1H), 7.58 (m, 1H), 7.30 (m, 2H), 7.18 (m, 1H), 7.12 (m, 1H), 6.38 (d, 1H), 6.32 (, 1H), 5.09 (s, 1H), 3.90 (q, 2H), 3.62 (s, 3H), 0.88 (s, 3H). MS (EI) for $C_{24}H_{18}ClF_4N_3O_4$: 524 [M+H].

Example 6.8. 4-(5-Chlorofuran-2-yl)-1,3-bis(2,4-difluorophenyl)-5-methyl-N-((4-methylmorpholin-2-yl)methyl)-4,5-dihydro-1H-pyrazole-5-carboxamide.

STEP 1. To a solution of 4-(5-chlorofuran-2-yl)-1,3-bis(2,4-difluorophenyl)-5-methyl-4,5-dihydro-1H-pyrazole-5-carboxylic acid (I.2.32.) (0.35 g, 0.77 mmol) in N,N-dimethylformamide (10 mL) was added 4-methylmorpholine (0.25 mL, 2.31 mmol) and O-(7-azabenzotriazol-1-yl)-N,N,N',N'-tetramethyluronium hexafluoro-phosphate (0.31 g, 0.81 mmol) and the reaction mixture was stirred at room temperature for ten minutes, followed by the addition of teri-butyl 2-(aminonethyl)morpholine-4-carboxylate (0.18 g, 0.81 mmol) and the stirring was continued for 18 hours. The reaction mixture was partitioned with ethyl acetate (250 mL) and 1M aqueous hydrochloric acid (50 ml). The organic layer was separated and washed with 1M aqueous hydrochloric acid (50 ml) and brine (2×100 mL), dried over anhydrous sodium sulfate and concentrated. The resulting crude was purified by gradient silica gel flash chromatography (1-30% ethyl acetate in hexanes) to give tert-butyl-((4-(5-chlorofuran-2-yl)-1,3-bis(2,4-difluorophenyl)-5-methyl-4,5-dihydro-1H-pyrazole-5-carboxamido)methyl) morpholine-4-carboxylate (0.48 g, 97%). MS (EI) for $C_{31}H_{31}ClF_4N_4O_5$: 652 [M+H].

STEP 2. To a solution of tert-butyl-((4-(5-chlorofuran-2-yl)-1,3-bis(2,4-difluorophenyl)-5-methyl-4,5-dihydro-1H-pyrazole-5-carboxamido)methyl)morpholine-4-carboxylate (0.31 g, 0.48 mmol) in methanol (10 mL) was added hydrochloric acid (1.50 mL, 6.0 mmol, 4M solution in 1,4-dioxane) and the reaction mixture was heated to reflux until the full conversion of the staring material (TLC 20% ethyl acetate in hexanes). The reaction mixture was cooled to room temperature and partitioned with ethyl acetate (250 mL) and saturated aqueous sodium hydrogen carbonate (50 mL). The organic layer was separated and washed with saturated aqueous sodium hydrogen carbonate (50 ml) and brine (2×100 mL), dried over anhydrous sodium sulfate and concentrated to give 4-(5-chlorofuran-2-yl)-1,3-bis(2,4-difluorophenyl)-5-methyl-N-(morpholin-2-ylmethyl)-4,5-dihydro-1H-pyrazole-5-carboxamide; the crude was used without further purification. MS (EI) for $C_{26}H_{23}ClF_4N_4O_3$: 552 [M+H].

STEP 3. To a solution of 4-(5-chlorofuran-2-yl)-1,3-bis (2,4-difluorophenyl)-5-methyl-N-(morpholin-2-ylmethyl)-4,5-dihydro-1H-pyrazole-5-carboxamide 0.26 g, 0.48 mmol) in tetrahydrofuran (10 mL) was added formaldehyde (0.18 mL, 2.50 mmol, 37 wt %, aqueous) at 0° C., followed by the addition of sodium triacetoxyborohydride (0.20 g, 0.96 mmol) and the stirring was continued for 18 hours. The reaction mixture was quenched with water and partitioned with ethyl acetate (250 mL) and water (50 mL). The organic layer was separated and washed with brine (2×100 mL), dried over anhydrous sodium sulfate and concentrated. The crude product was purified by gradient silica gel flash chromatography (1-20% 7N ammonia in methanol in chloroform) to give 4-(5-chlorofuran-2-yl)-1,3-bis(2,4-difluorophenyl)-5-methyl-N-((4-methylmorpholin-2-yl)methyl)-4,5-dihydro-1H-pyrazole-5-carboxamide (E.6.8.) (0.23 g, 85%). 1H-NMR (500 MHz, $d_6$-DMSO): 8.20 (2t, 1H), 7.88 (q, 1H), 7.46 (q, 1H), 7.29 (m, 2H), 7.18 (m, 1H), 7.14 (m, 1H), 6.38 (d, 1H), 6.32 (d, 1H), 5.12 (s, 1H), 3.68 (d, 1H), 3.48 (m, 1H), 3.42 (m, 1H), 3.18 (m, 2H), 2.58 (m, 1H), 2.12 (m, 1H), 2.04 (s, 3H), 1.84 (m, 1H), 1.62 (m, 1H), 0.85 (s, 3H). MS (EI) for $C_{27}H_{25}ClF_4N_4O_3$: 565 [M+H].

Example 6.9. 4-(5-Chlorofuran-2-yl)-1,3-bis(2,4-difluorophenyl)-5-methyl-N-(((R)-4-methylmorpholin-2-yl) methyl)-4,5-dihydro-1H-pyrazole-5-carboxamide was prepared as described for E.6.8., using 4-(5-chlorofuran-2-yl)-1,3-bis(2,4-difluorophenyl)-5-methyl-4,5-dihydro-1H-pyrazole-5-carboxylic acid (I.2.32.) and (R)-tert-butyl 2-(aminomethyl)morpholine-4-carboxylate in step 1 and formaldehyde in step 3. S (EI) for $C_{27}H_{25}ClF_4N_4O_3$: 565 [M+H].

Example 6.10. (4S,5R)-4-(5-Chlorofuran-2-yl)-1,3-bis(2,4-difluorophenyl)-5-methyl-N-(((R)-4-methylmorpholin-2-yl)methyl)-4,5-dihydro-1H-pyrazole-5-carboxamide is separated on a Chiralpak AD-H column (Chiral Technologies, Exton, PA), column size 25 cm×4.6 mm i.d., with a CSP particle size of 5 microns using 5% 2-propanol (0.1% N,N-Diisopropylethylamine) in hexanes. MS (EI) for $C_{27}H_{25}ClF_4N_4O_3$: 565 [M+H].

Example 6.11. (4R,5S)-4-(5-Chlorofuran-2-yl)-1,3-bis(2, 4-difluorophenyl)-5-methyl-N-(((R)-4-methylmorpholin-2-yl)methyl)-4,5-dihydro-1H-pyrazole-5-carboxamide is separated on a Chiralpak AD-H column (Chiral Technologies, Exton, PA), column size 25 cm×4.6 mm i.d., with a CSP particle size of 5 microns using 5% 2-propanol (0.1% N,N-Diisopropylethylamine) in hexanes. MS (EI) for $C_{27}H_{25}ClF_4N_4O_3$: 565 [M+H].

Example 6.12. 4-(5-Chlorofuran-2-yl)-1,3-bis(2,4-difluorophenyl)-5-methyl-N-(((S)-4-methylmorpholin-2-yl) methyl)-4,5-dihydro-1H-pyrazole-5-carboxamide was prepared as described for E.6.8., using 4-(5-chlorofuran-2-yl)-1,3-bis(2,4-difluorophenyl)-5-methyl-4,5-dihydro-1H-pyrazole-5-carboxylic acid (I.2.32.) and (S)-tert-butyl2-aminomethyl)morpholine-4-carboxylate in step 1 and formaldehyde in step 3. MS (EI) for $C_{27}H_{25}ClF_4N_4O_3$: 565 [M+H].

Example 6.13. (4S,5R)-4-(5-Chlorofuran-2-yl)-1,3-bis(2, 4-difluorophenyl)-5-methyl-N-(((S)-4-methylmorpholin-2-yl)methyl)-4,5-dihydro-1H-pyrazole-5-carboxamide is separated on a Chiralpak AD-H column (Chiral Technologies, Exton, PA), column size 25 cm×4.6 mm i.d., with a CSP particle size of 5 microns using 5% 2-propanol (0.1% N,N-Diisopropylethylamine) in hexanes. MS (EI) for $C_{27}H_{25}ClF_4N_4O_3$: 565 [M+H].

Example 6.14. (4R,5S)-4-(5-Chlorofuran-2-yl)-1,3-bis(2, 4-difluorophenyl)-5-methyl-N-(((S)-4-methylmorpholin-2-yl)methyl)-4,5-dihydro-1H-pyrazole-5-carboxamide is separated on a Chiralpak AD-H column (Chiral Technologies, Exton, PA), column size 25 cm×4.6 mm i.d., with a CSP particle size of 5 microns using 5% 2-propanol (0.1% N,N-Diisopropylethylamine) in hexanes. MS (EI) for $C_{27}H_{25}ClF_4N_4O_3$: 565 [M+H].

Example 6.15. 4-(5-Chlorofuran-2-yl)-1,3-bis(2,4-difluorophenyl)-N-((4-ethylmorpholin-2-yl)methyl)-5-methyl-4, 5-dihydro-1H-pyrazole-5-carboxamide is prepared as described for E.6.8., using 4-(5-chlorofuran-2-yl)-1,3-bis(2, 4-difluorophenyl)-5-methyl-4,5-dihydro-1H-pyrazole-5-carboxylic acid (I.2.32.) and tert-butyl 2-(aminomethyl) morpholine-4-carboxylate in step 1 and acetaldehyde in step 3. MS (EI) for $C_{28}H_{27}ClF_4N_4O_3$: 579 [M+H].

Example 6.16. 4-(5-Chlorofuran-2-yl)-N-((4-cyclopropylmorpholin-2-yl)methyl)-1,3-bis(2,4-difluorophenyl)-5-methyl-4,5-dihydro-1H-pyrazole-5-carboxamide is prepared as described for E.6.8., using 4-(5-chlorofuran-2-yl)-1,3-bis(2,4-difluorophenyl)-5-methyl-4,5-dihydro-1H-pyrazole-5-carboxylic acid (I.2.32.) and tert-butyl 2-(aminomethyl)morpholine-4-carboxylate in step 1 and cyclopropanecarbaldehyde in step 3. MS (EI) for $C_{29}H_{27}ClF_4N_4O_3$: 591 [M+H].

Example 6.17. 4-(5-Chlorofuran-2-yl)-1,3-bis(2,4-difluorophenyl)-N-((4-isopropylmorpholin-2-yl)methyl)-5-methyl-4,5-dihydro-1H-pyrazole-5-carboxamide is prepared as described for E.6.8., using 4-(5-chlorofuran-2-yl)-1,3-bis(2,4-difluorophenyl)-5-methyl-4,5-dihydro-1H-pyrazole-5-carboxylic acid (I.2.32.) and tert-butyl 2-(aminomethyl)morpholine-4-carboxylate in step 1 and acetone in step 3. MS (EI) for $C_{29}H_{29}ClF_4N_4O_3$: 593 [M+H].

Example 6.18. 1,3-Bis(2,4-difluorophenyl)-5-methyl-4-(5-methylfuran-2-yl)-N-((4-methylmorpholin-2-yl)methyl)-4,5-dihydro-1H-pyrazole-5-carboxamide is prepared using methyl 1,3-bis(2,4-difluorophenyl)-5-methyl-4-(5-methyl-furan-2-yl)-4,5-dihydro-1H-pyrazole-5-carboxylate (I.1.33.) in step 1 and (4-methylmorpholin-2-yl)methanamine in step 2. MS (EI) for $C_{28}H_{28}F_4N_4O_3$: 545 [M+H].

Example 6.19. 1,3-Bis(2,4-difluorophenyl)-5-methyl-N-((4-methylmorpholin-2-yl)methyl)-4-(5-(trifluoromethyl)furan-2-yl)-4,5-dihydro-1H-pyrazole-5-carboxamide is prepared using methyl 1,3-bis(2,4-difluorophenyl)-5-methyl-4-(5-(trifluoromethyl)furan-2-yl)-4,5-dihydro-1H-pyrazole-5-carboxylate (I.1.34.) in step 1 and (4-methylmorpholin-2-yl)methanamine in step 2. MS (EI) for $C_{28}H_{25}F_7N_4O_3$: 599 [M+H].

Example 6.20. 1,3-Bis(2,4-difluorophenyl)-5-methyl-4-(5-(methylcarbamoyl)furan-2-yl)-N-((4-methylmorpholin-2-yl)methyl)-4,5-dihydro-1H-pyrazole-5-carboxamide is prepared using methyl 1,3-bis(2,4-difluorophenyl)-5-methyl-4-(5-(methylcarbamoyl)furan-2-yl)-4,5-dihydro-1H-pyrazole-5-carboxylate (I.1.35.) in step 1 and (4-methylmorpholin-2-yl)methanamine in step 2. MS (EI) for $C_{29}H_{29}F_4N_5O_4$: 588 [M+H].

Example 6.21. 4-(5-Chlorofuran-2-yl)-1,3-bis(2,4-difluorophenyl)-N-((4-methoxy-1-methyl-piperidin-4-yl)methyl)-5-methyl-4,5-dihydro-1H-pyrazole-5-carboxamide is prepared as described for E.6.8., using 4-(5-chlorofuran-2-yl)-1,3-bis(2,4-difluorophenyl)-5-methyl-4,5-dihydro-1H-pyrazole-5-carboxylic acid (I.2.32.) and tert-butyl 4-(aminomethyl)-4-methoxypiperidine-1-carboxylate (R.3.1.) in step 1 and formaldehyde in step 3. MS (EI) for $C_{29}H_{29}ClF_4N_4O_3$: 593 [M+H].

Example 6.22. 4-(5-Chlorofuran-2-yl)-1,3-bis(2,4-difluorophenyl)-N-(4-(methoxymethyl)-1-methylpiperidin-4-yl)-5-methyl-4,5-dihydro-1H-pyrazole-5-carboxamide is prepared as described for E.6.8., using 4-(5-chlorofuran-2-yl)-1,3-bis(2,4-difluorophenyl)-5-methyl-4,5-dihydro-1H-pyrazole-5-carboxylic acid (I.2.32.) and tert-butyl 4-amino-4-(methoxymethyl)piperidine-1-carboxylate (R.3.2.) in step 1 and formaldehyde in step 3. MS (EI) for $C_{29}H_{29}ClF_4N_4O_3$: 593 [M+H].

Example 6.23. 4-(5-Chlorofuran-2-yl)-1,3-bis(2,4-difluorophenyl)-N-((3-methoxy-1-methyl-azetidin-3-yl)methyl)-5-methyl-4,5-dihydro-1H-pyrazole-5-carboxamide is prepared as described for E.6.8., using 4-(5-chlorofuran-2-yl)-1,3-bis(2,4-difluorophenyl)-5-methyl-4,5-dihydro-1H-pyrazole-5-carboxylic acid (I.2.32.) and tert-butyl 3-(aminomethyl)-3-methoxy-azetidine-1-carboxylate (R.3.3.) in step 1 and formaldehyde in step 3. MS (EI) for $C_{27}H_{25}ClF_4N_4O_3$: 565 [M+H].

Example 6.24. 4-(5-Chlorofuran-2-yl)-1,3-bis(2,4-difluorophenyl)-N-(3-(methoxymethyl)-1-methylazetidin-3-yl)-5-methyl-4,5-dihydro-1H-pyrazole-5-carboxamide is prepared as described for E.6.8., using 4-(5-chlorofuran-2-yl)-1,3-bis(2,4-difluorophenyl)-5-methyl-4,5-dihydro-1H-pyrazole-5-carboxylic acid (I.2.32.) and tert-butyl 3-amino-3-(methoxymethyl)azetidine-1-carboxylate (R.3.4.) in step 1 and formaldehyde in step 3. MS (EI) for $C_{27}H_{25}ClF_4N_4O_3$: 565 [M+H].

Example 6.25. 4-(5-Chlorofuran-2-yl)-1,3-bis(2,4-difluorophenyl)-N-((3-methoxyoxetan-3-yl)methyl)-5-methyl-4,5-dihydro-1H-pyrazole-5-carboxamide is prepared methyl 4-(5-chloro-furan-2-yl)-1,3-bis(2,4-difluorophenyl)-5-methyl-4,5-dihydro-1H-pyrazole-5-carboxylate (I.1.32.) in step 1 and (3-methoxyoxetan-3-yl)methanamine (R.3.5.) in step 2. MS (EI) for $C_{26}H_{22}ClF_4N_3O_4$: 552 [M+H].

Example 6.26. 4-(5-Chlorofuran-2-yl)-1,3-bis(2,4-difluorophenyl)-N-(3-(methoxymethyl)oxetan-3-yl)-5-methyl-4,5-dihydro-1H-pyrazole-5-carboxamide is prepared methyl 4-(5-chlorofuran-2-yl)-1,3-bis(2,4-difluorophenyl)-5-methyl-4,5-dihydro-1H-pyrazole-5-carboxylate (I.1.32.) in step 1 and 3-(methoxymethyl)oxetan-3-amine (R.3.6.) in step 2. MS (EI) for $C_{26}H_{22}ClF_4N_3O_4$: 552 [M+H].

Example 6.27. 4-(5-Chlorofuran-2-yl)-1,3-bis(2,4-difluorophenyl)-N-((3-(dimethylamino) oxetan-3-yl)methyl)-5-methyl-4,5-dihydro-1H-pyrazole-5-carboxamide is prepared methyl 4-(5-chlorofuran-2-yl)-1,3-bis(2,4-difluorophenyl)-5-methyl-4,5-dihydro-1H-pyrazole-5-carboxylate (I.1.32.) in step 1 and 3-(aminomethyl)-N,N-dimethyloxetan-3-amine (R.3.7.) in step 2. MS (EI) for $C_{27}H_{25}ClF_4N_3O_4$: 565 [M+H].

Example 6.28. 4-(5-Chlorofuran-2-yl)-1,3-bis(2,4-difluorophenyl)-N-(3-((dimethylamino) methyl)oxetan-3-yl)-5-methyl-4,5-dihydro-1H-pyrazole-5-carboxamide is prepared methyl 4-(5-chlorofuran-2-yl)-1,3-bis(2,4-difluorophenyl)-5-methyl-4,5-dihydro-1H-pyrazole-5-carboxylate (I.1.32.) in step 1 and 3-((dimethylamino)methyl)oxetan-3-amine (R.3.8.) in step 2. MS (EI) for $C_{27}H_{25}ClF_4N_3O_4$: 565 [M+H].

Example 6.29. 4-(5-Chlorofuran-2-yl)-1,3-bis(2,4-difluorophenyl)-N-((4,6-dimethylmorpholin-2-yl)methyl)-5-methyl-4,5-dihydro-1H-pyrazole-5-carboxamide is prepared methyl 4-(5-chloro-furan-2-yl)-1,3-bis(2,4-difluorophenyl)-5-methyl-4,5-dihydro-1H-pyrazole-5-carboxylate (I.1.32.) in step 1 and (4,6-dimethylmorpholin-2-yl)methanamine (R.3.9.) in step 2. MS (EI) for $C_{28}H_{27}ClF_4N_4O_3$: 579 [M+H].

Example 6.30. 4-(5-Chlorofuran-2-yl)-1,3-bis(2,4-difluorophenyl)-5-methyl-N-((4,6,6-trimethyl-morpholin-2-yl)methyl)-4,5-dihydro-1H-pyrazole-5-carboxamide is prepared methyl 4-(5-chlorofuran-2-yl)-1,3-bis(2,4-difluorophenyl)-5-methyl-4,5-dihydro-1H-pyrazole-5-carboxylate (I.1.32.) in step 1 and (4,6,6-trimethylmorpholin-2-yl)methanamine (R.3.10.) in step 2. MS (EI) for $C_{29}H_{29}ClF_4N_4O_3$: 593 [M+H].

Example 6.31. 4-(5-Chlorofuran-2-yl)-1,3-bis(2,4-difluorophenyl)-5-methyl-N-((7-methyl-4-oxa-7-azaspiro[2.5]octan-5-yl)methyl)-4,5-dihydro-1H-pyrazole-5-carboxamide is prepared methyl 4-(5-chlorofuran-2-yl)-1,3-bis(2,4-difluorophenyl)-5-methyl-4,5-dihydro-1H-pyrazole-5-carboxylate (I.1.32.) in step 1 and (7-methyl-4-oxa-7-azaspiro[2.5]octan-5-yl)methanamine (R.3.11.) in step 2. MS (EI) for $C_{29}H_{27}ClF_4N_4O_3$: 591 [M+H].

Example 6.32. 4-(5-Chlorofuran-2-yl)-1,3-bis(2,4-difluorophenyl)-5-methyl-N-((8-methyl-2,5-dioxa-8-azaspiro[3.5]nonan-6-yl)methyl)-4,5-dihydro-1H-pyrazole-5-carboxamide is prepared methyl 4-(5-chlorofuran-2-yl)-1,3-bis(2,4-difluorophenyl)-5-methyl-4,5-dihydro-1H-pyrazole-5-carboxylate (I.1.32.) in step 1 and (8-methyl-2,5-dioxa-8-azaspiro[3.5]nonan-6-yl)methanamine (R.3.12.) in step 2. MS (EI) for $C_{29}H_{27}ClF_4N_4O_3$: 607 [M+H].

Example 6.33. 4-(5-Chlorofuran-2-yl)-1,3-bis(2,4-difluorophenyl)-N-((2,8-dimethyl-5-oxa-2,8-diazaspiro[3.5]nonan-6-yl)methyl)-5-methyl-4,5-dihydro-1H-pyrazole-5-carboxamide is prepared as described for E.6.8., using 4-(5-chlorofuran-2-yl)-1,3-bis(2,4-difluorophenyl)-5-methyl-4,5-dihydro-1H-pyrazole-5-carboxylic acid (I.2.32.) and tert-butyl 6-(aminomethyl)-2-methyl-5-oxa-2,8-diazaspiro[3.5]nonane-8-carboxylate (R.3.13.) in step 1 and formaldehyde in step 3. MS (EI) for $C_{30}H_{30}ClF_4N_5O_3$: 620 [M+H].

Example 6.34. 4-(5-Chlorofuran-2-yl)-1,3-bis(2,4-difluorophenyl)-N-((4,5-dimethylmorpholin-2-yl)methyl)-5-methyl-4,5-dihydro-1H-pyrazole-5-carboxamide is prepared methyl 4-(5-chloro-furan-2-yl)-1,3-bis(2,4-difluorophenyl)-5-methyl-4,5-dihydro-1H-pyrazole-5-carboxylate (I.1.32.) in step 1 and (4,5-dimethylmorpholin- 2-yl)methanamine (R.3.14.) in step 2. MS (EI) for $C_{28}H_{27}ClF_4N_4O_3$: 579 [M+H].

Example 6.35. 4-(5-Chlorofuran-2-yl)-1,3-bis(2,4-difluorophenyl)-5-methyl-N-((4,5,5-trimethyl-morpholin-2-yl)methyl)-4,5-dihydro-1H-pyrazole-5-carboxamide is prepared methyl 4-(5-chloro-furan-2-yl)-1,3-bis(2,4-difluorophenyl)-5-methyl-4,5-dihydro-1H-pyrazole-5-carboxylate (I.1.32.) in step 1 and ((4,5,5-trimethylmorpholin-2-yl)methanamine (R.3.15.) in step 2. MS (EI) for $C_{29}H_{29}ClF_4N_4O_3$: 593 [M+H].

Example 6.36. 4-(5-Chlorofuran-2-yl)-1,3-bis(2,4-difluorophenyl)-5-methyl-N-((4-methyl-7-oxa-4-azaspiro[2.5]octan-6-yl)methyl)-4,5-dihydro-1H-pyrazole-5-carboxamide is prepared methyl 4-(5-chlorofuran-2-yl)-1,3-bis(2,4-difluorophenyl)-5-methyl-4,5-dihydro-1H-pyrazole-5-carboxylate (I.1.32.) in step 1 and (4-methyl-7-oxa-4-azaspiro[2.5]octan-6-yl)methanamine (R.3.16.) in step 2. MS (EI) for $C_{29}H_{27}ClF_4N_4O_3$: 591 [M+H].

Example 6.37. 4-(5-Chlorofuran-2-yl)-1,3-bis(2,4-difluorophenyl)-5-methyl-N-((5-methyl-2,8-dioxa-5-azaspiro[3.5]nonan-7-yl)methyl)-4,5-dihydro-1H-pyrazole-5-carboxamide is prepared methyl 4-(5-chlorofuran-2-yl)-1,3-bis(2,4-difluorophenyl)-5-methyl-4,5-dihydro-1H-pyrazole-5-carboxylate (I.1.32.) in step 1 and (5-methyl-2,8-dioxa-5-azaspiro[3.5]nonan-7-yl)methanamine (R.3.17.) in step 2. MS (EI) for $C_{29}H_{27}ClF_4N_4O_3$: 607 [M+H].

Example 6.38. 4-(5-chlorofuran-2-yl)-1,3-bis(2,4-difluorophenyl)-N-((2,5-dimethyl-8-oxa-2,5-diazaspiro[3.5]nonan-7-yl)methyl)-5-methyl-4,5-dihydro-1H-pyrazole-5-carboxamide is prepared as described for E.6.8., using 4-(5-chlorofuran-2-yl)-1,3-bis(2,4-difluorophenyl)-5-methyl-4,5-dihydro-1H-pyrazole-5-carboxylic acid (I.2.32.) and tert-butyl 7-(aminomethyl)-2-methyl-8-oxa-2,5-diazaspiro[3.5]nonane-5-carboxylate (R.3.18.) in step 1 and formaldehyde in step 3. MS (EI) for $C_{30}H_{30}ClF_4N_5O_3$: 620 [M+H].

Example 6.39. 4-(5-Chlorofuran-2-yl)-1,3-bis(2,4-difluorophenyl)-5-methyl-N-((4,5,6-trimethyl-morpholin-2-yl)methyl)-4,5-dihydro-1H-pyrazole-5-carboxamide is prepared methyl 4-(5-chlorofuran-2-yl)-1,3-bis(2,4-difluorophenyl)-5-methyl-4,5-dihydro-1H-pyrazole-5-carboxylate (I.1.32.) in step 1 and (4,5,6-trimethylmorpholin-2-yl)methanamine (R.3.19.) in step 2. MS (EI) for $C_{29}H_{29}ClF_4N_4O_3$: 592 [M+H].

Example 6.40. 4-(5-Chlorofuran-2-yl)-1,3-bis(2,4-difluorophenyl)-5-methyl-N-(oxetan-3-yl)-4,5-dihydro-1H-pyrazole-5-carboxamide is prepared methyl 4-(5-chlorofuran-2-yl)-1,3-bis(2,4-difluorophenyl)-5-methyl-4,5-dihydro-1H-pyrazole-5-carboxylate (I.1.32.) in step 1 and oxetan-3-amine in step 2. MS (EI) for $C_{24}H_{18}ClF_4N_3O_3$: 508 [M+H].

Example 6.41. 4-(5-Chlorofuran-2-yl)-1,3-bis(2,4-difluorophenyl)-N-(2-(2-(dimethylamino)ethoxy)ethyl)-5-methyl-4,5-dihydro-1H-pyrazole-5-carboxamide is prepared methyl 4-(5-chlorofuran-2-yl)-1,3-bis(2,4-difluorophenyl)-5-methyl-4,5-dihydro-1H-pyrazole-5-carboxylate (I.1.32.) in step 1 and 2-(2-aminoethoxy)-N,N-dimethylethan-1-amine in step 2. MS (EI) for $C_{27}H_{27}ClF_4N_3O_3$: 567 [M+H].

Example 6.42. 4-(5-Chlorofuran-2-yl)-1,3-bis(2,4-difluorophenyl)-N-(3-(dimethylamino)-2-methoxypropyl)-5-methyl-4,5-dihydro-1H-pyrazole-5-carboxamide is prepared methyl 4-(5-chlorofuran-2-yl)-1,3-bis(2,4-difluorophenyl)-5-methyl-4,5-dihydro-1H-pyrazole-5-carboxylate (I.1.32.) in step 1 and (3-amino-2-methoxypropyl)dimethylamine (R.3.20.) in step 2. MS (EI) for $C_{27}H_{27}ClF_4N_3O_3$: 567 [M+H].

Example 6.43. 4-(5-Chlorofuran-2-yl)-1,3-bis(2,4-difluorophenyl)-N-(4-methoxy-1-methyl-pyrrolidin-3-yl)-5-methyl-4,5-dihydro-1H-pyrazole-5-carboxamide is prepared as described for E.6.8., using 4-(5-chlorofuran-2-yl)-1,3-bis(2,4-difluorophenyl)-5-methyl-4,5-dihydro-1H-pyrazole-5-carboxylic acid (I.2.32.) and tert-butyl 3-amino-4-methoxypyrrolidine-1-carboxylate (R.3.21.) in step 1 and formaldehyde in step 3. MS (EI) for $C_{27}H_{25}ClF_4N_4O_3$: 565 [M+H].

Example 6.44. 4-(5-Chlorofuran-2-yl)-1,3-bis(2,4-difluorophenyl)-N-((3S,6R)-6-methoxyhexa-hydrofuro[3,2-b]furan-3-yl)-5-methyl-4,5-dihydro-1H-pyrazole-5-carboxamide is prepared methyl 4-(5-chlorofuran-2-yl)-1,3-bis(2,4-difluorophenyl)-5-methyl-4,5-dihydro-1H-pyrazole-5-carboxylate (I.1.32.) in step 1 and (3S,6R)-6-methoxyhexahydrofuro[3,2-b]furan-3-amine (R.3.22.) in step 2. MS (EI) for $C_{28}H_{24}ClF_4N_3O_5$: 594 [M+H].

Example 6.45. 4-(5-Chlorofuran-2-yl)-1,3-bis(2,4-difluorophenyl)-N-((3S,6S)-6-(dimethylamino) hexahydrofuro[3,2-b]furan-3-yl)-5-methyl-4,5-dihydro-1H-pyrazole-5-carboxamide is prepared methyl 4-(5-chlorofuran-2-yl)-1,3-bis(2,4-difluorophenyl)-5-methyl-4,5-dihydro-1H-pyrazole-5-carboxylate (I.1.32.) in step 1 and (3S,6S)-N,N-dimethylhexahydrofuro[3,2-b]furan-3,6-diamine (R.3.23.) in step 2. MS (EI) for $C_{29}H_{27}ClF_4N_4O_4$: 607 [M+H].

Example 6.46. 4-(5-Chlorofuran-2-yl)-1,3-bis(2,4-difluorophenyl)-N-(((8aS)-hexahydro-1H-pyrrolo[2,1-c][1,4]oxazin-3-yl)methyl)-5-methyl-4,5-dihydro-1H-pyrazole-5-carboxamide is prepared methyl 4-(5-chlorofuran-2-yl)-1,3-bis(2,4-difluorophenyl)-5-methyl-4,5-dihydro-1H-pyrazole-5-carboxylate (I.1.32.) in step 1 and ((8aS)-hexahydro-1H-pyrrolo[2,1-c][1,4]oxazin-3-yl)methanamine (R.3.24.1.) in step 2. MS (EI) for $C_{29}H_{27}ClF_4N_4O_3$: 591 [M+H].

Example 6.47. 4-(5-Chlorofuran-2-yl)-1,3-bis(2,4-difluorophenyl)-N-(((8aR)-hexahydro-1H-pyrrolo[2,1-c][1,4]oxazin-3-yl)methyl)-5-methyl-4,5-dihydro-1H-pyrazole-5-carboxamide is prepared methyl 4-(5-chlorofuran-2-yl)-1,3-bis(2,4-difluorophenyl)-5-methyl-4,5-dihydro-1H-pyrazole-5-carboxylate (I.1.32.) in step 1 and ((8aR)-hexahydro-1H-pyrrolo[2,1-c][1,4]oxazin-3-yl)methanamine (R.3.24.2.) in step 2. MS (EI) for $C_{29}H_{27}ClF_4N_4O_3$: 591 [M+H].

Example 6.48. 4-(5-Chlorofuran-2-yl)-1,3-bis(2,4-difluorophenyl)-N-(((9aS)-hexahydro-1H-[1,4]oxazino[3,4-c][1,4]oxazin-3-yl)methyl)-5-methyl-4,5-dihydro-1H-pyrazole-5-carboxamide is prepared methyl 4-(5-chlorofuran-2-yl)-1,3-bis(2,4-difluorophenyl)-5-methyl-4,5-dihydro-1H-pyrazole-5-carboxylate (I.1.32.) in step 1 and ((9aS)-hexahydro-1H-[1,4]oxazino[3,4-c][1,4]oxazin-3-yl)methanamine (R.3.25.1.) in step 2. MS (EI) for $C_{29}H_{27}ClF_4N_4O_4$: 607 [M+H].

Example 6.49. 4-(5-Chlorofuran-2-yl)-1,3-bis(2,4-difluorophenyl)-N-(((9aR)-hexahydro-1H-[1,4]oxazino[3,4-c][1,4]oxazin-3-yl)methyl)-5-methyl-4,5-dihydro-1H-pyrazole-5-carboxamide is prepared using methyl 4-(5-chlorofuran-2-yl)-1,3-bis(2,4-difluorophenyl)-5-methyl-4,5-dihydro-1H-pyrazole-5-carboxylate (I.1.32.) in step 1 and ((9aR)-hexahydro-1H-[1,4]oxazino[3,4-c][1,4]oxazin-3-yl)methanamine (R.3.25.2.) in step 2. MS (EI) for $C_{29}H_{27}ClF_4N_4O_4$: 607 [M+H].

Example 6.50. 4-(5-Chlorofuran-2-yl)-1-(2,4-difluorophenyl)-3-(4-fluorophenyl)-5-methyl-N-((4-methylmorpholin-2-yl)methyl)-4,5-dihydro-1H-pyrazole-5-carboxamide is prepared using methyl 4-(5-chlorofuran-2-yl)-1-(2,4-difluorophenyl)-3-(4-fluorophenyl)-5-methyl-4,5-dihydro-1H-pyrazole-5-carboxylate (I.1.36.) in step 1 and (4-methylmorpholin-2-yl) methanamine in step 2. MS (EI) for $C_{27}H_{26}ClF_3N_4O_3$: 547 [M+H].

Example 7

Logarithmically growing A549, LOX and MelJuSo cells (ATCC) were plated in antibiotic-free RPMI medium (Corning) supplemented with 2% fetal bovine serum (Gemini Bio-products) at a density of 5,000 cells per well in clear-bottom 96-well plates. The next day cells were treated (triplicates) with increasing doses of a compound of the present disclosure (dissolved in DMSO) and DMSO vehicle controls (final DMSO concentration of 0.5%) for 72 hours and subsequently assessed for cell viability by measuring ATP content with CellTiter-Glo Luminescent Cell Viability Assay (Promega). Signal intensity was measured on a Glomax™ 96 Microplate Luminometer (Promega) and percent cell survival was calculated based on the reading of vehicle control cells set as 100%. The half-maximal inhibitory concentration $IC_{50}$ values for the compounds were extrapolated from the cell survival curves and are shown in Table 1 below.

In Table 1, "A" indicates an $IC_{50}$ in the indicated assay of less than 0.25 μM; "B" is 0.25 μM to 0.5 μM; "C" is 0.5 μM to 1 μM; "D" is 1 μM to 2 μM; and "E" is greater than 2 [M. Blank entries indicate that the $IC_{50}$ was not determined.

TABLE 1

| Compound | $IC_{50}$ (μM) | | |
|---|---|---|---|
| | A549 | LOX | MelJuSo |
| 1 | C | C | B |
| 2 | D | D | C |
| 3 | C | C | C |
| 4 | C | C | C |
| 5 | D | D | C |
| 6 | C | C | C |
| 7 | E | D | C |
| 8 | E | E | D |
| 9 | D | C | C |
| 10 | E | D | C |
| 11 | E | E | D |
| 12 | E | D | D |
| 13 | E | E | E |
| 14 | E | D | D |
| 15 | D | B | B |
| 16 | E | E | C |
| 17 | D | D | B |
| 18 | E | E | E |
| 19 | E | E | E |
| 20 | C | C | B |
| 21 | E | E | E |
| 22 | E | E | E |
| 23 | C | C | B |
| 24 | E | E | E |
| 25 | E | E | D |
| 26 | E | E | E |
| 28 | E | D | D |
| 29 | E | E | E |
| 30 | E | E | E |
| 31 | D | D | C |
| 32 | C | C | B |
| 33 | E | D | C |
| 34 | E | C | C |
| 35 | E | D | D |
| 36 | E | E | D |
| 37 | E | E | E |
| 38 | E | E | C |
| 39 | E | E | E |
| 40 | E | E | E |
| 41 | E | E | D |
| 42 | E | E | E |
| 43 | E | E | E |
| 44 | E | E | E |
| 45 | E | E | E |
| 46 | E | E | E |
| 47 | E | E | E |

TABLE 1-continued

| Compound | $IC_{50}$ (μM) | | |
|---|---|---|---|
| | A549 | LOX | MelJuSo |
| 48 | E | E | E |
| 49 | E | E | E |
| 50 | E | E | E |
| 51 | E | E | E |
| 52 | E | E | E |
| 53 | E | E | E |
| 54 | E | E | E |
| 55 | B | A | A |
| 56 | E | D | C |
| 57 | D | C | C |
| 58 | E | D | D |
| 59 | B | A | A |
| 60 | B | A | A |
| 61 | E | D | C |
| 62 | E | C | B |
| 63 | B | A | A |
| 64 | B | A | A |
| 65 | E | E | E |
| 66 | E | E | E |
| 67 | E | E | E |
| 68 | E | D | C |
| 69 | E | E | E |
| 70 | E | D | C |
| 71 | E | E | E |
| 72 | E | E | E |
| 73 | E | D | D |
| 74 | E | E | E |
| 75 | C | E | E |
| 76 | E | E | E |
| 77 | B | E | E |
| 78 | E | E | E |
| 79 | E | E | E |
| 80 | E | E | E |
| 81 | C | C | A |
| 82 | E | E | E |
| 83 | D | D | C |
| 84 | D | D | C |
| 85 | B | A | A |
| 86 | A | A | A |
| 87 | E | E | E |
| 88 | E | E | E |
| 89 | D | C | C |
| 90 | C | C | A |
| 91 | B | B | A |
| 92 | A | A | A |
| 93 | E | | E |
| 94 | E | | E |
| 95 | E | | E |
| 96 | E | | E |
| 97 | E | D | C |
| 98 | E | E | C |
| 99 | E | E | D |
| 100 | E | D | B |
| 101 | E | E | C |
| 102 | D | C | B |
| 103 | C | C | A |
| 104 | E | D | C |
| 105 | E | E | E |
| 106 | E | E | E |
| 107 | E | E | D |
| 108 | E | E | E |
| 109 | E | E | E |
| 110 | E | E | E |
| 111 | E | E | E |
| 112 | E | E | E |
| 113 | E | E | E |
| 114 | E | E | E |
| 115 | C | C | B |
| 116 | B | A | A |
| 117 | C | C | B |
| 118 | A | A | A |
| 119 | C | B | A |
| 120 | A | A | A |
| 121 | A | A | A |
| 122 | E | E | E |
| 123 | E | E | D |

TABLE 1-continued

| Compound | IC$_{50}$ (μM) | | |
|---|---|---|---|
| | A549 | LOX | MelJuSo |
| 124 | E | E | E |
| 125 | E | E | E |
| 126 | E | E | E |
| 127 | C | C | A |
| 128 | C | C | B |
| 129 | C | C | B |
| 130 | E | E | C |
| 131 | C | C | B |
| 132 | E | E | E |
| 133 | A | A | A |
| 134 | A | A | A |
| 135 | A | A | A |
| 136 | E | E | D |
| 137 | E | E | C |
| 138 | E | E | E |

Although the forgoing embodiments have been described in some detail by way of illustration and example for clarity and understanding, it will be readily apparent to one ordinary skill in the art in light of the teachings of this disclosure that certain variations, changes, modifications and substitution of equivalents may be made thereto without necessarily departing from the spirit and scope of this invention. As a result, the embodiments described herein are subject to various modifications, changes and the like, with the scope of this invention being determined solely by reference to the claims appended hereto. Those of skill in the art will readily recognize a variety of non-critical parameters that could be changed, altered or modified to yield essentially similar results.

While each of the elements of the present invention is described herein as containing multiple embodiments, it should be understood that, unless indicated otherwise, each of the embodiments of a given element of the present invention is capable of being used with each of the embodiments of the other elements of the present invention and each such use is intended to form a distinct embodiment of the present invention.

As can be appreciated from the disclosure above, the present invention has a wide variety of applications. The invention is further illustrated by the examples above, which are only illustrative and are not intended to limit the definition and scope of the invention in any way.

What is claimed is:

1. A method for treating a subject with a cancerous condition, the method comprising:
   administering to the subject a therapeutically effective amount of a compound of formula (I):

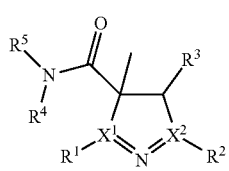

(I)

wherein
X$^1$ is N and X$^2$ is C, and the ring N forms a double bond with X$^2$;
R$^1$ is aryl or substituted aryl;
R$^2$ is aryl or substituted aryl;
R$^3$ is alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl or substituted heteroaryl;
R$^4$ is hydrogen, alkyl or substituted alkyl; and
R$^5$ is alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl or substituted heteroaryl;
or a salt, a hydrate, a solvate, or a stereoisomer thereof, wherein the cancerous condition is characterized by expressing a GLI protein, and wherein the administering results in treatment of the subject.

2. A method for treating a subject with a cancerous condition, the method comprising:
   administering to the subject a therapeutically effective amount of a compound of formula (I):

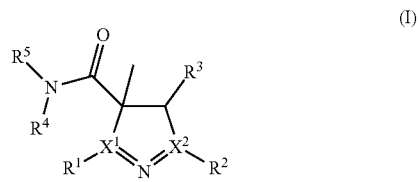

(I)

wherein
X$^1$ is N and X$^2$ is C, and the ring N forms a double bond with X$^2$;
R$^1$ is gal or substituted aryl;
R$^2$ is gal or substituted aryl;
R$^3$ is alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl or substituted heteroaryl;
R$^4$ is hydrogen, alkyl or substituted alkyl; and
R$^5$ is alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl or substituted heteroaryl;
or a salt, a hydrate, a solvate, or a stereoisomer thereof, wherein the cancerous condition is a RAS-mutant cancer, and wherein the administering results in treatment of the subject.

3. A method for treating a fibrosis in a subject, the method comprising:
   administering to the subject a therapeutically effective amount of a compound of formula (I):

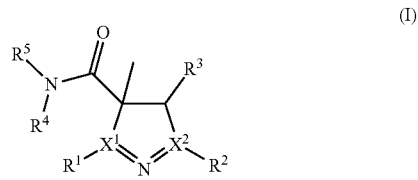

(I)

wherein
X$^1$ is N and X$^2$ is C, and the ring N forms a double bond with X$^2$;

R¹ is aryl or substituted aryl;

R² is aryl or substituted aryl;

R³ is alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl or substituted heteroaryl;

R⁴ is hydrogen, alkyl or substituted alkyl; and

R⁵ is alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl or substituted heteroaryl;

or a salt, a hydrate, a solvate, or a stereoisomer thereof, wherein the administering results in treatment of a fibrosis in the subject.

4. A method for treating brain cancer in a subject, comprising:

administering to the subject a therapeutically effective amount of a compound of formula (I):

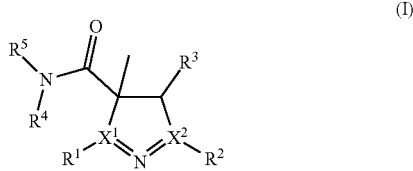

(I)

wherein

X¹ is N and X² is C, and the ring N forms a double bond with X²;

R¹ is aryl or substituted aryl;

R² is aryl or substituted aryl;

R³ is alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl or substituted heteroaryl;

R⁴ is hydrogen, alkyl or substituted alkyl; and

R⁵ is alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl or substituted heteroaryl;

or a salt, a hydrate, a solvate, or a stereoisomer thereof, wherein the administering results in treatment of brain cancer in the subject.

5. The method of claim 2, or a salt, a hydrate, a solvate, or a stereoisomer thereof, wherein R¹ is substituted aryl.

6. The method of claim 2, or a salt, a hydrate, a solvate, or a stereoisomer thereof, wherein R² is substituted aryl.

7. The method of claim 2, or a salt, a hydrate, a solvate, or a stereoisomer thereof, wherein R³ is C₁-C₆ alkyl, heteroaryl or substituted heteroaryl.

8. The method of claim 2, or a salt, a hydrate, a solvate, or a stereoisomer thereof, wherein R⁴ is hydrogen.

9. The method of claim 2, or a salt, a hydrate, a solvate, or a stereoisomer thereof, wherein R⁴ is alkyl or substituted alkyl.

10. The method of claim 2, or a salt, a hydrate, a solvate, or a stereoisomer thereof, wherein R⁵ is substituted alkyl.

11. The method of claim 10, wherein R⁵ is 5-hydroxy-4,4-dimethylpentyl; 5-hydroxy-5-methylhexyl; 3-methoxypropyl; 3-oxo-3-methoxypropyl; 2-methoxyethyl; 3-(dimethylamino)propyl; 4-methoxybutyl; 2-ethoxyethyl; 5-hydroxypentyl; 6-hydroxyhexyl; 4-hydroxybutyl; methyl acetate; (4-methylmorpholin-2-yl)methyl; (4-ethylmorpholin-2-yl)methyl; (4-cyclopropylmorpholin-2-yl)methyl; or (4-isopropylmorpholin-2-yl)methyl, or a salt, a hydrate, a solvate, or a stereoisomer thereof.

12. The method of claim 2, or a salt, a hydrate, a solvate, or a stereoisomer thereof, wherein R⁵ is heterocyclyl or substituted heterocyclyl.

13. The method of claim 2, wherein R⁵ is 4-(methoxymethyl)-1-methylpiperidin-4-yl; 3-(methoxymethyl)-1-methylazetidin-3-yl; 3-(methoxymethyl)oxetan-3-yl; 3-((dimethylamino)methyl)oxetan-3-yl; oxetan-3-yl; 4-methoxy-1-methylpyrrolidin-3-yl; 6-methoxyhexahydrofuro[3,2-b]furan-3-yl; or 6-(dimethylamino)hexahydrofuro[3,2-b]furan-3-yl; or a salt, a hydrate, a solvate, or a stereoisomer thereof.

14. The method of claim 2, wherein the compound is of formula (Ia):

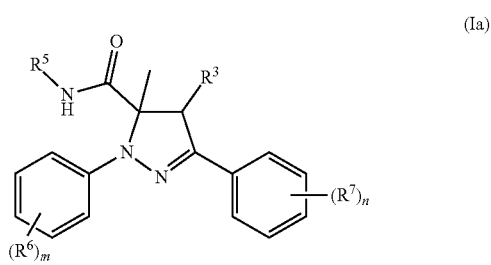

(Ia)

wherein

R³ is alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl or substituted heteroaryl;

R⁵ is alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl or substituted heteroaryl; and R⁶ and R⁷ are each independently hydrogen, halogen, alkyl, substituted alkyl, alkoxy, substituted alkoxy or sulfonyl, wherein m and n are each independently an integer from 1 to 5;

or a salt, a hydrate, a solvate, or a stereoisomer thereof.

15. The method of claim 14, or a salt, a hydrate, a solvate, or a stereoisomer thereof, wherein R³ is C₁-C₆ alkyl, heteroaryl or substituted heteroaryl.

16. The method of claim 14, or a salt, a hydrate, a solvate, or a stereoisomer thereof, wherein at least one R⁶ is halogen.

17. The method of claim 14, or a salt, a hydrate, a solvate, or a stereoisomer thereof, wherein at least one R⁷ is halogen.

18. The method of claim 2, wherein the compound is of formula (Ib):

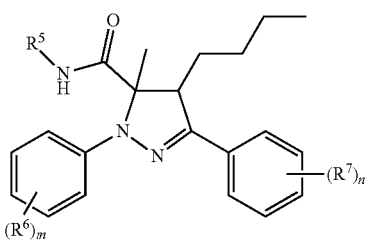

(Ib)

wherein
R⁵ is alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl or substituted heteroaryl; and
R⁶ and R⁷ are each independently hydrogen, halogen, alkyl, substituted alkyl, alkoxy, substituted alkoxy or sulfonyl, wherein m and n are each independently an integer from 1 to 5;
or a salt, a hydrate, a solvate, or a stereoisomer thereof.

19. The method of claim 18, or a salt, a hydrate, a solvate, or a stereoisomer thereof, wherein at least one R⁶ is halogen.

20. The method of claim 18, or a salt, a hydrate, a solvate, or a stereoisomer thereof, wherein at least one R⁷ is halogen.

21. The method of claim 2, wherein the compound is of formula (Ic):

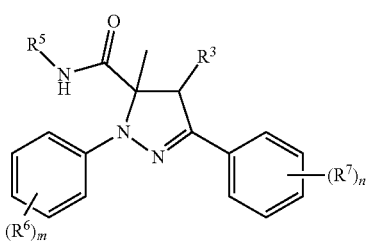

(Ic)

wherein
R³ is furanyl or substituted furanyl;
R⁵ is alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl or substituted heteroaryl; and
R⁶ and R⁷ are each independently hydrogen, halogen, alkyl, substituted alkyl, alkoxy, substituted alkoxy or sulfonyl, wherein m and n are each independently an integer from 1 to 5;
or a salt, a hydrate, a solvate, or a stereoisomer thereof.

22. The method of claim 21, or a salt, a hydrate, a solvate, or a stereoisomer thereof, wherein at least one R⁶ is halogen.

23. The method of claim 21, or a salt, a hydrate, a solvate, or a stereoisomer thereof, wherein at least one R⁷ is halogen.

24. The method of claim 2, wherein the compound selected from the group consisting of:
4-butyl-3-(4-fluorophenyl)-N-(5-hydroxy-4,4-dimethylpentyl)-5-methyl-1-phenyl-4,5-dihydro-1H-pyrazole-5-carboxamide (Compound 1);
4-butyl-3-(4-fluorophenyl)-N-(5-hydroxy-5-methylhexyl)-5-methyl-1-phenyl-4,5-dihydro-1H-pyrazole-5-carboxamide (Compound 2);
4-butyl-1-(2,4-difluorophenyl)-3-(4-fluorophenyl)-N-(5-hydroxy-4,4-dimethylpentyl)-5-methyl-4,5-dihydro-1H-pyrazole-5-carboxamide (Compound 3);
4-butyl-1-(2,4-difluorophenyl)-3-(4-fluorophenyl)-N-(5-hydroxy-5-methylhexyl)-5-methyl-4,5-dihydro-1H-pyrazole-5-carboxamide (Compound 4);
4-butyl-1-(2,4-difluorophenyl)-3-(4-fluorophenyl)-N-(3-methoxypropyl)-5-methyl-4,5-dihydro-1H-pyrazole-5-carboxamide (Compound 5);
4-butyl-1-(2,4-difluorophenyl)-3-(4-fluorophenyl)-N-(2-methoxyethyl)-5-methyl-4,5-dihydro-1H-pyrazole-5-carboxamide (Compound 6);
4-butyl-1-(3-fluorophenyl)-3-(4-fluorophenyl)-N-(5-hydroxy-5-methylhexyl)-5-methyl-4,5-dihydro-1H-pyrazole-5-carboxamide (Compound 7);
4-butyl-1-(3-fluorophenyl)-3-(4-fluorophenyl)-N-(3-methoxypropyl)-5-methyl-4,5-dihydro-1H-pyrazole-5-carboxamide (Compound 8);
4-butyl-1-(2,5-difluorophenyl)-3-(4-fluorophenyl)-N-(5-hydroxy-5-methylhexyl)-5-methyl-4,5-dihydro-1H-pyrazole-5-carboxamide (Compound 9);
4-butyl-3-(3,4-difluorophenyl)-N-(5-hydroxy-5-methylhexyl)-5-methyl-1-phenyl-4,5-dihydro-1H-pyrazole-5-carboxamide (Compound 10);
4-butyl-1-(3-chloro-4-fluorophenyl)-3-(4-fluorophenyl)-N-(5-hydroxy-5-methylhexyl)-5-methyl-4,5-dihydro-1H-pyrazole-5-carboxamide (Compound 11);
4-butyl-1-(4-chlorophenyl)-3-(4-fluorophenyl)-N-(5-hydroxy-4,4-dimethylpentyl)-5-methyl-4,5-dihydro-1H-pyrazole-5-carboxamide (Compound 12);
4-butyl-1-(4-chlorophenyl)-3-(4-fluorophenyl)-N-(3-methoxypropyl)-5-methyl-4,5-dihydro-1H-pyrazole-5-carboxamide (Compound 13);
4-butyl-1,3-bis(4-fluorophenyl)-N-(3-methoxypropyl)-5-methyl-4,5-dihydro-1H-pyrazole-5-carboxamide (Compound 14);
4-butyl-3-(4-fluorophenyl)-N-(5-hydroxy-4,4-dimethylpentyl)-5-methyl-1-p-tolyl-4,5-dihydro-1H-pyrazole-5-carboxamide (Compound 15);
4-butyl-3-(4-fluorophenyl)-N-(3-methoxypropyl)-5-methyl-1-p-tolyl-4,5-dihydro-1H-pyrazole-5-carboxamide (Compound 16);
4-butyl-1-(3-chlorophenyl)-3-(4-fluorophenyl)-N-(5-hydroxy-4,4-dimethylpentyl)-5-methyl-4,5-dihydro-1H-pyrazole-5-carboxamide (Compound 17);
4-butyl-1-(4-fluoro-3-methoxyphenyl)-3-(4-fluorophenyl)-N-(5-hydroxy-4,4-dimethylpentyl)-5-methyl-4,5-dihydro-1H-pyrazole-5-carboxamide (Compound 18);
4-butyl-1-(4-fluoro-3-methoxyphenyl)-3-(4-fluorophenyl)-N-(3-methoxypropyl)-5-methyl-4,5-dihydro-1H-pyrazole-5-carboxamide (Compound 19);
3-(4-fluorophenyl)-N-(5-hydroxy-4,4-dimethylpentyl)-5-methyl-1-phenyl-4-(thiophen-2-yl)-4,5-dihydro-1H-pyrazole-5-carboxamide (Compound 20);
3-(4-fluorophenyl)-N-(5-hydroxy-4,4-dimethylpentyl)-5-methyl-1-phenyl-4-(pyridin-4-yl)-4,5-dihydro-1H-pyrazole-5-carboxamide (Compound 21);
4-butyl-1-(2-chloro-4-fluorophenyl)-3-(4-fluorophenyl)-N-(5-hydroxy-4,4-dimethylpentyl)-5-methyl-4,5-dihydro-1H-pyrazole-5-carboxamide (Compound 22);
4-butyl-1-(4-chloro-2-fluorophenyl)-3-(4-fluorophenyl)-N-(5-hydroxy-4,4-dimethylpentyl)-5-methyl-4,5-dihydro-1H-pyrazole-5-carboxamide (Compound 23);
4-butyl-1-(2,4-difluorophenyl)-N-(3-(dimethylamino)propyl)-3-(4-fluorophenyl)-5-methyl-4,5-dihydro-1H-pyrazole-5-carboxamide (Compound 24);

4-butyl-1-(2,4-difluorophenyl)-3-(4-fluorophenyl)-N-(4-methoxybutyl)-5-methyl-4,5-dihydro-1H-pyrazole-5-carboxamide (Compound 25);

4-butyl-1-(2,4-difluorophenyl)-3-(4-fluorophenyl)-N-(3-methoxypropyl)-N,5-dimethyl-4,5-dihydro-1H-pyrazole-5-carboxamide (Compound 26);

4-butyl-3-(4-fluorophenyl)-N-(5-hydroxy-4,4-dimethylpentyl)-5-methyl-1-(4-(trifluoromethyl)phenyl)-4,5-dihydro-1H-pyrazole-5-carboxamide (Compound 28);

4-butyl-1-(4-chloro-2-methylphenyl)-3-(4-fluorophenyl)-N-(5-hydroxy-4,4-dimethylpentyl)-5-methyl-4,5-dihydro-1H-pyrazole-5-carboxamide (Compound 29);

4-butyl-1-(4-chloro-2-methylphenyl)-3-(4-fluorophenyl)-N-(3-methoxypropyl)-5-methyl-4,5-dihydro-1H-pyrazole-5-carboxamide (Compound 30);

methyl 3-(4-butyl-1-(2,4-difluorophenyl)-3-(4-fluorophenyl)-5-methyl-4,5-dihydro-1H-pyrazole-5-carboxamido)propanoate (Compound 31);

4-butyl-1-(2,4-difluorophenyl)-N-(2-ethoxyethyl)-3-(4-fluorophenyl)-5-methyl-4,5-dihydro-1H-pyrazole-5-carboxamide (Compound 32);

4-butyl-3-(4-fluorophenyl)-N-(5-hydroxypentyl)-5-methyl-1-phenyl-4,5-dihydro-1H-pyrazole-5-carboxamide (Compound 33);

4-butyl-3-(4-fluorophenyl)-N-(6-hydroxyhexyl)-5-methyl-1-phenyl-4,5-dihydro-1H-pyrazole-5-carboxamide (Compound 34);

4-butyl-3-(4-fluorophenyl)-N-(4-hydroxybutyl)-5-methyl-1-phenyl-4,5-dihydro-1H-pyrazole-5-carboxamide (Compound 35);

4-butyl-3-(4-fluorophenyl)-N-(4-hydroxybenzyl)-5-methyl-1-phenyl-4,5-dihydro-1H-pyrazole-5-carboxamide (Compound 36);

4-butyl-3-(4-fluorophenyl)-N-(1-hydroxy-2-methylpropan-2-yl)-5-methyl-1-phenyl-4,5-dihydro-1H-pyrazole-5-carboxamide (Compound 37);

4-butyl-3-(4-fluorophenyl)-N-(4-hydroxyphenethyl)-5-methyl-1-phenyl-4,5-dihydro-1H-pyrazole-5-carboxamide (Compound 38);

4-butyl-N-(3-chlorobenzyl)-3-(4-fluorophenyl)-5-methyl-1-phenyl-4,5-dihydro-1H-pyrazole-5-carboxamide (Compound 39);

4-butyl-N-(3,4-dichlorobenzyl)-3-(4-fluorophenyl)-5-methyl-1-phenyl-4,5-dihydro-1H-pyrazole-5-carboxamide (Compound 40);

4-butyl-N-(3,5-dichlorobenzyl)-3-(4-fluorophenyl)-5-methyl-1-phenyl-4,5-dihydro-1H-pyrazole-5-carboxamide (Compound 41);

4-butyl-3-(4-fluorophenyl)-5-methyl-1-phenyl-N-((S)-1-phenylethyl)-4,5-dihydro-1H-pyrazole-5-carboxamide (Compound 42);

4-butyl-3-(4-fluorophenyl)-5-methyl-1-phenyl-N-((R)-1-phenylethyl)-4,5-dihydro-1H-pyrazole-5-carboxamide (Compound 43);

4-butyl-3-(4-fluorophenyl)-N-(2-methoxybenzyl)-5-methyl-1-phenyl-4,5-dihydro-1H-pyrazole-5-carboxamide (Compound 44);

4-butyl-N-(2,3-dimethoxybenzyl)-3-(4-fluorophenyl)-5-methyl-1-phenyl-4,5-dihydro-1H-pyrazole-5-carboxamide (Compound 45);

4-butyl-N-(2,4-dimethoxybenzyl)-3-(4-fluorophenyl)-5-methyl-1-phenyl-4,5-dihydro-1H-pyrazole-5-carboxamide (Compound 46);

4-butyl-N-(3,4-dimethoxybenzyl)-3-(4-fluorophenyl)-N,5-dimethyl-1-phenyl-4,5-dihydro-1H-pyrazole-5-carboxamide (Compound 47);

4-butyl-N-(4-(dimethylamino)benzyl)-3-(4-fluorophenyl)-5-methyl-1-phenyl-4,5-dihydro-1H-pyrazole-5-carboxamide (Compound 48);

4-butyl-N-(3-(dimethylamino)propyl)-3-(4-fluorophenyl)-5-methyl-1-phenyl-4,5-dihydro-1H-pyrazole-5-carboxamide (Compound 49);

4-butyl-N-(3-(dimethylamino)-2,2-dimethylpropyl)-3-(4-fluorophenyl)-5-methyl-1-phenyl-4,5-dihydro-1H-pyrazole-5-carboxamide (Compound 50);

4-butyl-N-(cyclohexylmethyl)-3-(4-fluorophenyl)-5-methyl-1-phenyl-4,5-dihydro-1H-pyrazole-5-carboxamide (Compound 51);

4-butyl-N-(3,5-dimethoxybenzyl)-3-(4-fluorophenyl)-N,5-dimethyl-1-phenyl-4,5-dihydro-1H-pyrazole-5-carboxamide (Compound 52);

4-butyl-3-(4-chloro-2-fluorophenyl)-N-(5-hydroxy-4,4-dimethylpentyl)-5-methyl-1-phenyl-4,5-dihydro-1H-pyrazole-5-carboxamide (Compound 53);

4-butyl-3-(4-chloro-2-fluorophenyl)-N-(2-methoxyethyl)-5-methyl-1-phenyl-4,5-dihydro-1H-pyrazole-5-carboxamide (Compound 54);

4-butyl-3-(4-fluorophenyl)-N-(2-methoxyethyl)-5-methyl-1-m-tolyl-4,5-dihydro-1H-pyrazole-5-carboxamide (Compound 55);

4-butyl-3-(2,4-difluorophenyl)-N-(5-hydroxy-4,4-dimethylpentyl)-5-methyl-1-phenyl-4,5-dihydro-1H-pyrazole-5-carboxamide (Compound 56);

4-butyl-3-(2,4-difluorophenyl)-N-(2-methoxyethyl)-5-methyl-1-phenyl-4,5-dihydro-1H-pyrazole-5-carboxamide (Compound 57);

4-butyl-3-(4-chlorophenyl)-N-(2-methoxyethyl)-5-methyl-1-phenyl-4,5-dihydro-1H-pyrazole-5-carboxamide (Compound 58);

4-butyl-3-(4-fluorophenyl)-N-(2-methoxyethyl)-5-methyl-1-p-tolyl-4,5-dihydro-1H-pyrazole-5-carboxamide (Compound 59);

1-(2,4-difluorophenyl)-3-(4-fluorophenyl)-N-(2-methoxyethyl)-5-methyl-4-(thiophen-2-yl)-4,5-dihydro-1H-pyrazole-5-carboxamide (Compound 60);

4-butyl-3-(4-fluorophenyl)-N-(5-hydroxy-4,4-dimethylpentyl)-5-methyl-1-m-tolyl-4,5-dihydro-1H-pyrazole-5-carboxamide (Compound 61);

3-(4-fluorophenyl)-N-(2-methoxyethyl)-5-methyl-4-(thiophen-2-yl)-1-p-tolyl-4,5-dihydro-1H-pyrazole-5-carboxamide (Compound 63);

4-butyl-1-(4-chloro-2-fluorophenyl)-3-(4-fluorophenyl)-N-(2-methoxyethyl)-5-methyl-4,5-dihydro-1H-pyrazole-5-carboxamide (Compound 64);

4-butyl-3-(4-fluorophenyl)-5-methyl-N-(3-morpholinopropyl)-1-phenyl-4,5-dihydro-1H-pyrazole-5-carboxamide (Compound 65);

4-butyl-3-(4-fluorophenyl)-N-(4-hydroxy-3-methoxybenzyl)-5-methyl-1-phenyl-4,5-dihydro-1H-pyrazole-5-carboxamide (Compound 66);

4-butyl-3-(4-fluorophenyl)-5-methyl-1-phenyl-N-(thiophen-2-ylmethyl)-4,5-dihydro-1H-pyrazole-5-carboxamide (Compound 67);

4-butyl-3-(4-fluorophenyl)-5-methyl-1-phenyl-N-((tetrahydro-2H-pyran-2-yl)methyl)-4,5-dihydro-1H-pyrazole-5-carboxamide (Compound 68);

4-butyl-3-(4-fluorophenyl)-5-methyl-N-(1-(4-(methylsulfonyl)phenyl)ethyl)-1-phenyl-4,5-dihydro-1H-pyrazole-5-carboxamide (Compound 69);

4-butyl-N-(2-fluoroethyl)-3-(4-fluorophenyl)-5-methyl-1-phenyl-4,5-dihydro-1H-pyrazole-5-carboxamide (Compound 70);

4-butyl-3-(4-fluorophenyl)-5-methyl-1-phenyl-N-(3-(piperidin-1-yl)propyl)-4,5-dihydro-1H-pyrazole-5-carboxamide (Compound 71);

4-butyl-3-(4-fluorophenyl)-5-methyl-N-neopentyl-1-phenyl-4,5-dihydro-1H-pyrazole-5-carboxamide (Compound 72);

4-butyl-N-(cyclopropylmethyl)-3-(4-fluorophenyl)-5-methyl-1-phenyl-4,5-dihydro-1H-pyrazole-5-carboxamide (Compound 73);

4-butyl-N-(2-(dimethylamino)-2-methylpropyl)-3-(4-fluorophenyl)-5-methyl-1-phenyl-4,5-dihydro-1H-pyrazole-5-carboxamide (Compound 74);

4-butyl-N-(3-(dimethylamino)butyl)-3-(4-fluorophenyl)-5-methyl-1-phenyl-4,5-dihydro-1H-pyrazole-5-carboxamide (Compound 75);

4-butyl-N-(2-(dimethylamino)propyl)-3-(4-fluorophenyl)-5-methyl-1-phenyl-4,5-dihydro-1H-pyrazole-5-carboxamide (Compound 76);

4-butyl-N-(3-(dimethylamino)-2-methylpropyl)-3-(4-fluorophenyl)-5-methyl-1-phenyl-4,5-dihydro-1H-pyrazole-5-carboxamide (Compound 77);

N-benzyl-4-butyl-3-(4-fluorophenyl)-N-(2-hydroxyethyl)-5-methyl-1-phenyl-4,5-dihydro-1H-pyrazole-5-carboxamide (Compound 78);

4-butyl-3-(4-fluorophenyl)-5-methyl-N-(2-(methylsulfonyl)ethyl)-1-phenyl-4,5-dihydro-1H-pyrazole-5-carboxamide (Compound 79);

4-butyl-3-(4-fluorophenyl)-5-methyl-N-(4-(morpholinomethyl)benzyl)-1-phenyl-4,5-dihydro-1H-pyrazole-5-carboxamide (Compound 80);

methyl 2-(4-butyl-1-(2,4-difluorophenyl)-3-(4-fluorophenyl)-5-methyl-4,5-dihydro-1H-pyrazole-5-carboxamido)acetate (Compound 81);

2-(4-butyl-1-(2,4-difluorophenyl)-3-(4-fluorophenyl)-5-methyl-4,5-dihydro-1H-pyrazole-5-carboxamido)acetic acid (Compound 82);

4-butyl-N-(2-cyanoethyl)-1-(2,4-difluorophenyl)-3-(4-fluorophenyl)-5-methyl-4,5-dihydro-1H-pyrazole-5-carboxamide (Compound 83);

4-butyl-1-(2,4-difluorophenyl)-3-(4-fluorophenyl)-N-(2-hydroxyethyl)-5-methyl-4,5-dihydro-1H-pyrazole-5-carboxamide (Compound 84);

1-(2,4-difluorophenyl)-3-(4-fluorophenyl)-N-(5-hydroxy-4,4-dimethylpentyl)-5-methyl-4-(thiophen-3-yl)-4,5-dihydro-1H-pyrazole-5-carboxamide (Compound 85);

1-(2,4-difluorophenyl)-3-(4-fluorophenyl)-N-(2-methoxyethyl)-5-methyl-4-(thiophen-3-yl)-4,5-dihydro-1H-pyrazole-5-carboxamide (Compound 86);

4-butyl-1,3-bis(2,4-difluorophenyl)-N-(5-hydroxy-4,4-dimethylpentyl)-5-methyl-4,5-dihydro-1H-pyrazole-5-carboxamide (Compound 89);

4-butyl-1,3-bis(2,4-difluorophenyl)-N-(2-methoxyethyl)-5-methyl-4,5-dihydro-1H-pyrazole-5-carboxamide (Compound 90);

1-(2,4-difluorophenyl)-3-(4-fluorophenyl)-4-(furan-2-yl)-N-(5-hydroxy-4,4-dimethylpentyl)-5-methyl-4,5-dihydro-1H-pyrazole-5-carboxamide (Compound 91);

1-(2,4-difluorophenyl)-3-(4-fluorophenyl)-4-(furan-2-yl)-N-(2-methoxyethyl)-5-methyl-4,5-dihydro-1H-pyrazole-5-carboxamide (Compound 92);

1-(2,4-difluorophenyl)-3-(4-fluorophenyl)-N-(5-hydroxy-4,4-dimethylpentyl)-5-methyl-4-(1-methyl-1H-pyrrol-2-yl)-4,5-dihydro-1H-pyrazole-5-carboxamide (Compound 93);

1-(2,4-difluorophenyl)-3-(4-fluorophenyl)-N-(2-methoxyethyl)-5-methyl-4-(1-methyl-1H-pyrrol-2-yl)-4,5-dihydro-1H-pyrazole-5-carboxamide (Compound 94);

1-(2,4-difluorophenyl)-3-(4-fluorophenyl)-N-(5-hydroxy-4,4-dimethylpentyl)-5-methyl-4-(1-methyl-1H-pyrazol-4-yl)-4,5-dihydro-1H-pyrazole-5-carboxamide (Compound 95);

1-(2,4-difluorophenyl)-3-(4-fluorophenyl)-N-(2-methoxyethyl)-5-methyl-4-(1-methyl-1H-pyrazol-4-yl)-4,5-dihydro-1H-pyrazole-5-carboxamide (Compound 96);

4-butyl-1-(2,4-difluorophenyl)-N-(5-hydroxy-4,4-dimethylpentyl)-5-methyl-3-(2,4,6-trifluorophenyl)-4,5-dihydro-1H-pyrazole-5-carboxamide (Compound 97);

methyl 2-(4-butyl-1-(2,4-difluorophenyl)-5-methyl-3-(2,4,6-trifluorophenyl)-4,5-dihydro-1H-pyrazole-5-carboxamido)acetate (Compound 98);

1-(2,4-difluorophenyl)-3-(4-fluorophenyl)-N-(5-hydroxy-4,4-dimethylpentyl)-5-methyl-4-(5-methylthiophen-2-yl)-4,5-dihydro-1H-pyrazole-5-carboxamide (Compound 99);

1-(2,4-difluorophenyl)-3-(4-fluorophenyl)-N-(2-methoxyethyl)-5-methyl-4-(5-methylthiophen-2-yl)-4,5-dihydro-1H-pyrazole-5-carboxamide (Compound 100);

4-(5-chlorothiophen-2-yl)-1-(2,4-difluorophenyl)-3-(4-fluorophenyl)-N-(5-hydroxy-4,4-dimethylpentyl)-5-methyl-4,5-dihydro-1H-pyrazole-5-carboxamide (Compound 101);

4-(5-chlorothiophen-2-yl)-1-(2,4-difluorophenyl)-3-(4-fluorophenyl)-N-(2-methoxyethyl)-5-methyl-4,5-dihydro-1H-pyrazole-5-carboxamide (Compound 102);

methyl 2-(1-(2,4-difluorophenyl)-3-(4-fluorophenyl)-5-methyl-4-(thiophen-2-yl)-4,5-dihydro-1H-pyrazole-5-carboxamido)acetate (Compound 103);

1-(2,4-difluorophenyl)-3-(4-fluorophenyl)-N-(2-(2-hydroxy-2-methylpropylamino)-2-oxoethyl)-5-methyl-4-(thiophen-2-yl)-4,5-dihydro-1H-pyrazole-5-carboxamide (Compound 104);

1-(2,4-difluorophenyl)-3-(4-fluorophenyl)-5-methyl-N-(1,1-dioxo-1-thiomorpholine-2-oxoethyl)-4-(thiophen-2-yl)-4,5-dihydro-1H-pyrazole-5-carboxamide (Compound 105);

1-(2,4-difluorophenyl)-3-(4-fluorophenyl)-5-methyl-N-(2-morpholino-2-oxoethyl)-4-(thiophen-2-yl)-4,5-dihydro-1H-pyrazole-5-carboxamide (Compound 106);

1-(2,4-difluorophenyl)-N-(2-(2-(dimethylamino)ethylamino)-2-oxoethyl)-3-(4-fluorophenyl)-5-methyl-4-(thiophen-2-yl)-4,5-dihydro-1H-pyrazole-5-carboxamide (Compound 107);

1-(2,4-difluorophenyl)-3-(4-fluorophenyl)-5-methyl-N-(2-(oxetan-3-ylamino)-2-oxoethyl)-4-(thiophen-2-yl)-4,5-dihydro-1H-pyrazole-5-carboxamide (Compound 108);

1-(2,4-difluorophenyl)-3-(4-fluorophenyl)-5-methyl-N-(2-(2-(methylsulfonyl)ethylamino)-2-oxoethyl)-4-(thiophen-2-yl)-4,5-dihydro-1H-pyrazole-5-carboxamide (Compound 109);

1-(2,4-difluorophenyl)-3-(4-fluorophenyl)-N-(2-(3-hydroxy-3-methylcyclobutylamino)-2-oxoethyl)-5-methyl-4-(thiophen-2-yl)-4,5-dihydro-1H-pyrazole-5-carboxamide (Compound 110);

1-(2,4-difluorophenyl)-3-(4-fluorophenyl)-N-(2-(methoxy(methyl)amino)-2-oxoethyl)-5-methyl-4-(thiophen-2-yl)-4,5-dihydro-1H-pyrazole-5-carboxamide (Compound 111);

1-(2,4-difluorophenyl)-3-(4-fluorophenyl)-N-(2-(2-hydroxyethylamino)-2-oxoethyl)-5-methyl-4-(thiophen-2-yl)-4,5-dihydro-1H-pyrazole-5-carboxamide (Compound 112);

4-butyl-1-(2,4-difluorophenyl)-N-(5-hydroxy-4,4-dimethylpentyl)-5-methyl-3-(4-(methylsulfonyl)phenyl)-4,5-dihydro-1H-pyrazole-5-carboxamide (Compound 113);

4-butyl-1-(2,4-difluorophenyl)-N-(2-methoxyethyl)-5-methyl-3-(4-(methylsulfonyl)phenyl)-4,5-dihydro-1H-pyrazole-5-carboxamide (Compound 114);

1,3-bis(2,4-difluorophenyl)-4-(furan-2-yl)-N-(5-hydroxy-4,4-dimethylpentyl)-5-methyl-4,5-dihydro-1H-pyrazole-5-carboxamide (Compound 115);

1,3-bis(2,4-difluorophenyl)-4-(furan-2-yl)-N-(2-methoxyethyl)-5-methyl-4,5-dihydro-1H-pyrazole-5-carboxamide (Compound 116);

1,3-bis(2,4-difluorophenyl)-N-(5-hydroxy-4,4-dimethylpentyl)-5-methyl-4-(thiophen-3-yl)-4,5-dihydro-1H-pyrazole-5-carboxamide (Compound 117);

1,3-bis(2,4-difluorophenyl)-N-(2-methoxyethyl)-5-methyl-4-(thiophen-3-yl)-4,5-dihydro-1H-pyrazole-5-carboxamide (Compound 118);

methyl 2-(1,3-bis(2,4-difluorophenyl)-5-methyl-4-(thiophen-3-yl)-4,5-dihydro-1H-pyrazole-5-carboxamido)acetate (Compound 119);

4-(5-chlorofuran-2-yl)-1,3-bis(2,4-difluorophenyl)-N-(2-methoxyethyl)-5-methyl-4,5-dihydro-1H-pyrazole-5-carboxamide (Compound 120);

methyl 2-(4-(5-chlorofuran-2-yl)-1,3-bis(2,4-difluorophenyl)-5-methyl-4,5-dihydro-1H-pyrazole-5-carboxamido)acetate (Compound 121);

1-(2,4-difluorophenyl)-3-(4-fluorophenyl)-5-methyl-N-(3-morpholinopropyl)-4-(thiophen-2-yl)-4,5-dihydro-1H-pyrazole-5-carboxamide (Compound 122);

1-(2,4-difluorophenyl)-3-(4-fluorophenyl)-5-methyl-N-(2-(methylamino)-2-oxoethyl)-4-(thiophen-2-yl)-4,5-dihydro-1H-pyrazole-5-carboxamide (Compound 123);

1-(2,4-difluorophenyl)-N-(2,4-dihydroxybutyl)-3-(4-fluorophenyl)-5-methyl-4-(thiophen-2-yl)-4,5-dihydro-1H-pyrazole-5-carboxamide (Compound 124);

1-(2,4-difluorophenyl)-3-(4-fluorophenyl)-5-methyl-N-(2-(5-((3aS,6aR)-2-oxohexahydro-1H-thieno[3,4-d]imidazol-4-yl)pentanamido)ethyl)-4-(thiophen-2-yl)-4,5-dihydro-1H-pyrazole-5-carboxamide (Compound 125);

1-(2,4-difluorophenyl)-3-(4-fluorophenyl)-5-methyl-N-(2-morpholinoethyl)-4-(thiophen-2-yl)-4,5-dihydro-1H-pyrazole-5-carboxamide (Compound 126);

1-(2,4-difluorophenyl)-3-(4-fluorophenyl)-5-methyl-N-((4-methylmorpholin-2-yl)methyl)-4-(thiophen-2-yl)-4,5-dihydro-1H-pyrazole-5-carboxamide (Compound 127);

2-hydroxyethyl 2-(1-(2,4-difluorophenyl)-3-(4-fluorophenyl)-5-methyl-4-(thiophen-2-yl)-4,5-dihydro-1H-pyrazole-5-carboxamido)acetate (Compound 128);

1,3-bis(2,4-difluorophenyl)-4-(furan-3-yl)-N-(5-hydroxy-4,4-dimethylpentyl)-5-methyl-4,5-dihydro-1H-pyrazole-5-carboxamide (Compound 129);

1,3-bis(2,4-difluorophenyl)-4-(furan-3-yl)-N-(2-methoxyethyl)-5-methyl-4,5-dihydro-1H-pyrazole-5-carboxamide (Compound 130);

methyl 2-(1,3-bis(2,4-difluorophenyl)-4-(furan-3-yl)-5-methyl-4,5-dihydro-1H-pyrazole-5-carboxamido)acetate (Compound 131);

(2S)-methyl 2-(1,3-bis(2,4-difluorophenyl)-4-(furan-3-yl)-5-methyl-4,5-dihydro-1H-pyrazole-5-carboxamido)propanoate (Compound 132);

4-(5-chlorofuran-2-yl)-1,3-bis(2,4-difluorophenyl)-N-(5-hydroxy-4,4-dimethylpentyl)-5-methyl-4,5-dihydro-1H-pyrazole-5-carboxamide (Compound 133);

4-(5-chlorofuran-2-yl)-1,3-bis(2,4-difluorophenyl)-5-methyl-N-((4-methylmorpholin-2-yl)methyl)-4,5-dihydro-1H-pyrazole-5-carboxamide (Compound 135);

5-(5-chlorofuran-2-yl)-1,3-bis(2,4-difluorophenyl)-N-(5-hydroxy-4,4-dimethylpentyl)-4-methyl-4,5-dihydro-1H-pyrazole-4-carboxamide (Compound 136);

methyl 2-(5-(5-chlorofuran-2-yl)-1,3-bis(2,4-difluorophenyl)-4-methyl-4,5-dihydro-1H-pyrazole-4-carboxamido)acetate (Compound 137);

tert-butyl 2-((4-(5-chlorofuran-2-yl)-1,3-bis(2,4-difluorophenyl)-5-methyl-4,5-dihydro-1H-pyrazole-5-carboxamido)methyl)morpholine-4-carboxylate (Compound 138);

4-(5-chlorofuran-2-yl)-1,3-bis(2,4-difluorophenyl)-5-methyl-N-(((R)-4-methylmorpholin-2-yl)methyl)-4,5-dihydro-1H-pyrazole-5-carboxamide (Compound 139);

(4S,5R)-4-(5-chlorofuran-2-yl)-1,3-bis(2,4-difluorophenyl)-5-methyl-N-(((R)-4-methylmorpholin-2-yl)methyl)-4,5-dihydro-1H-pyrazole-5-carboxamide (Compound 140);

(4R,5S)-4-(5-chlorofuran-2-yl)-1,3-bis(2,4-difluorophenyl)-5-methyl-N-(((R)-4-methylmorpholin-2-yl)methyl)-4,5-dihydro-1H-pyrazole-5-carboxamide (Compound 141);

4-(5-chlorofuran-2-yl)-1,3-bis(2,4-difluorophenyl)-5-methyl-N-(((S)-4-methylmorpholin-2-yl)methyl)-4,5-dihydro-1H-pyrazole-5-carboxamide (Compound 142);

(4S,5R)-4-(5-chlorofuran-2-yl)-1,3-bis(2,4-difluorophenyl)-5-methyl-N-(((S)-4-methylmorpholin-2-yl)methyl)-4,5-dihydro-1H-pyrazole-5-carboxamide (Compound 143);

(4R,5S)-4-(5-chlorofuran-2-yl)-1,3-bis(2,4-difluorophenyl)-5-methyl-N-(((S)-4-methylmorpholin-2-yl)methyl)-4,5-dihydro-1H-pyrazole-5-carboxamide (Compound 144);

4-(5-chlorofuran-2-yl)-1,3-bis(2,4-difluorophenyl)-N-((4-ethylmorpholin-2-yl)methyl)-5-methyl-4,5-dihydro-1H-pyrazole-5-carboxamide (Compound 145);

4-(5-chlorofuran-2-yl)-N-((4-cyclopropylmorpholin-2-yl)methyl)-1,3-bis(2,4-difluorophenyl)-5-methyl-4,5-dihydro-1H-pyrazole-5-carboxamide (Compound 146);

4-(5-chlorofuran-2-yl)-1,3-bis(2,4-difluorophenyl)-N-((4-isopropylmorpholin-2-yl)methyl)-5-methyl-4,5-dihydro-1H-pyrazole-5-carboxamide (Compound 147);

1,3-bis(2,4-difluorophenyl)-5-methyl-4-(5-methylfuran-2-yl)-N-((4-methylmorpholin-2-yl)methyl)-4,5-dihydro-1H-pyrazole-5-carboxamide (Compound 148);

1,3-bis(2,4-difluorophenyl)-5-methyl-N-((4-methylmorpholin-2-yl)methyl)-4-(5-(trifluoromethyl)furan-2-yl)-4,5-dihydro-1H-pyrazole-5-carboxamide (Compound 149);

1,3-bis(2,4-difluorophenyl)-5-methyl-4-(5-(methylcarbamoyl)furan-2-yl)-N-((4-methylmorpholin-2-yl)methyl)-4,5-dihydro-1H-pyrazole-5-carboxamide (Compound 150);

4-(5-chlorofuran-2-yl)-1,3-bis(2,4-difluorophenyl)-N-((4-methoxy-1-methylpiperidin-3-yl)methyl)-5-methyl-4,5-dihydro-1H-pyrazole-5-carboxamide (Compound 151);

4-(5-chlorofuran-2-yl)-1,3-bis(2,4-difluorophenyl)-N-(4-(methoxymethyl)-1-methylpiperidin-4-yl)-5-methyl-4,5-dihydro-1H-pyrazole-5-carboxamide (Compound 152);

4-(5-chlorofuran-2-yl)-1,3-bis(2,4-difluorophenyl)-N-((3-methoxy-1-methylazetidin-3-yl)methyl)-5-methyl-4,5-dihydro-1H-pyrazole-5-carboxamide (Compound 153);

4-(5-chlorofuran-2-yl)-1,3-bis(2,4-difluorophenyl)-N-(3-(methoxymethyl)-1-methylazetidin-3-yl)-5-methyl-4,5-dihydro-1H-pyrazole-5-carboxamide (Compound 154);

4-(5-chlorofuran-2-yl)-1,3-bis(2,4-difluorophenyl)-N-((3-methoxyoxetan-3-yl)methyl)-5-methyl-4,5-dihydro-1H-pyrazole-5-carboxamide (Compound 155);

4-(5-chlorofuran-2-yl)-1,3-bis(2,4-difluorophenyl)-N-(3-(methoxymethyl)oxetan-3-yl)-5-methyl-4,5-dihydro-1H-pyrazole-5-carboxamide (Compound 156);

4-(5-chlorofuran-2-yl)-1,3-bis(2,4-difluorophenyl)-N-((3-(dimethylamino)oxetan-3-yl)methyl)-5-methyl-4,5-dihydro-1H-pyrazole-5-carboxamide (Compound 157);

4-(5-chlorofuran-2-yl)-1,3-bis(2,4-difluorophenyl)-N-(3-((dimethylamino)methyl)oxetan-3-yl)-5-methyl-4,5-dihydro-1H-pyrazole-5-carboxamide (Compound 158);

4-(5-chlorofuran-2-yl)-1,3-bis(2,4-difluorophenyl)-N-((4,6-dimethylmorpholin-2-yl)methyl)-5-methyl-4,5-dihydro-1H-pyrazole-5-carboxamide (Compound 159);

4-(5-chlorofuran-2-yl)-1,3-bis(2,4-difluorophenyl)-5-methyl-N-((4,6,6-trimethylmorpholin-2-yl)methyl)-4,5-dihydro-1H-pyrazole-5-carboxamide (Compound 160);

4-(5-chlorofuran-2-yl)-1,3-bis(2,4-difluorophenyl)-5-methyl-N-((7-methyl-4-oxa-7-azaspiro[2.5]octan-5-yl)methyl)-4,5-dihydro-1H-pyrazole-5-carboxamide (Compound 161);

4-(5-chlorofuran-2-yl)-1,3-bis(2,4-difluorophenyl)-5-methyl-N-((8-methyl-2,5-dioxa-8-azaspiro[3.5]nonan-6-yl)methyl)-4,5-dihydro-1H-pyrazole-5-carboxamide (Compound 162);

4-(5-chlorofuran-2-yl)-1,3-bis(2,4-difluorophenyl)-N-((2,8-dimethyl-5-oxa-2,8-diazaspiro[3.5]nonan-6-yl)methyl)-5-methyl-4,5-dihydro-1H-pyrazole-5-carboxamide (Compound 163);

4-(5-chlorofuran-2-yl)-1,3-bis(2,4-difluorophenyl)-N-((4,5-dimethylmorpholin-2-yl)methyl)-5-methyl-4,5-dihydro-1H-pyrazole-5-carboxamide (Compound 164);

4-(5-chlorofuran-2-yl)-1,3-bis(2,4-difluorophenyl)-5-methyl-N-((4,5,5-trimethylmorpholin-2-yl)methyl)-4,5-dihydro-1H-pyrazole-5-carboxamide (Compound 165);

4-(5-chlorofuran-2-yl)-1,3-bis(2,4-difluorophenyl)-5-methyl-N-((4-methyl-7-oxa-4-azaspiro[2.5]octan-6-yl)methyl)-4,5-dihydro-1H-pyrazole-5-carboxamide (Compound 166);

4-(5-chlorofuran-2-yl)-1,3-bis(2,4-difluorophenyl)-5-methyl-N-((5-methyl-2,8-dioxa-5-azaspiro[3.5]nonan-7-yl)methyl)-4,5-dihydro-1H-pyrazole-5-carboxamide (Compound 167);

4-(5-chlorofuran-2-yl)-1,3-bis(2,4-difluorophenyl)-N-((2,5-dimethyl-8-oxa-2,5-diazaspiro[3.5]nonan-7-yl)methyl)-5-methyl-4,5-dihydro-1H-pyrazole-5-carboxamide (Compound 168);

4-(5-chlorofuran-2-yl)-1,3-bis(2,4-difluorophenyl)-5-methyl-N-((4,5,6-trimethylmorpholin-2-yl)methyl)-4,5-dihydro-1H-pyrazole-5-carboxamide (Compound 169);

4-(5-chlorofuran-2-yl)-1,3-bis(2,4-difluorophenyl)-5-methyl-N-(oxetan-3-yl)-4,5-dihydro-1H-pyrazole-5-carboxamide (Compound 170);

4-(5-chlorofuran-2-yl)-1,3-bis(2,4-difluorophenyl)-N-(2-(2-(dimethylamino)ethoxy)ethyl)-5-methyl-4,5-dihydro-1H-pyrazole-5-carboxamide (Compound 171);

4-(5-chlorofuran-2-yl)-1,3-bis(2,4-difluorophenyl)-N-(3-(dimethylamino)-2-methoxypropyl)-5-methyl-4,5-dihydro-1H-pyrazole-5-carboxamide (Compound 172);

4-(5-chlorofuran-2-yl)-1,3-bis(2,4-difluorophenyl)-N-(4-methoxy-1-methylpyrrolidin-3-yl)-5-methyl-4,5-dihydro-1H-pyrazole-5-carboxamide (Compound 173);

4-(5-chlorofuran-2-yl)-1,3-bis(2,4-difluorophenyl)-N-((3S,6R)-6-methoxyhexahydrofuro[3,2-b]furan-3-yl)-5-methyl-4,5-dihydro-1H-pyrazole-5-carboxamide (Compound 174);

4-(5-chlorofuran-2-yl)-1,3-bis(2,4-difluorophenyl)-N-((3S,6S)-6-(dimethylamino)hexahydrofuro[3,2-b]furan-3-yl)-5-methyl-4,5-dihydro-1H-pyrazole-5-carboxamide (Compound 175);

4-(5-chlorofuran-2-yl)-1,3-bis(2,4-difluorophenyl)-N-(((8aS)-hexahydro-1H-pyrrolo[2,1-c][1,4]oxazin-3-yl)methyl)-5-methyl-4,5-dihydro-1H-pyrazole-5-carboxamide (Compound 176);

4-(5-chlorofuran-2-yl)-1,3-bis(2,4-difluorophenyl)-N-(((8aR)-hexahydro-1H-pyrrolo[2,1-c][1,4]oxazin-3-yl)methyl)-5-methyl-4,5-dihydro-1H-pyrazole-5-carboxamide (Compound 177);

4-(5-chlorofuran-2-yl)-1,3-bis(2,4-difluorophenyl)-N-(((9aS)-hexahydro-1H-[1,4]oxazino[3,4-c][1,4]oxazin-3-yl)methyl)-5-methyl-4,5-dihydro-1H-pyrazole-5-carboxamide (Compound 178);

4-(5-chlorofuran-2-yl)-1,3-bis(2,4-difluorophenyl)-N-(((9aR)-hexahydro-1H-[1,4]oxazino[3,4-c][1,4]oxazin-3-yl)methyl)-5-methyl-4,5-dihydro-1H-pyrazole-5-carboxamide (Compound 179);

4-(5-chlorofuran-2-yl)-1-(2,4-difluorophenyl)-3-(4-fluorophenyl)-5-methyl-N-((4-methylmorpholin-2-yl)methyl)-4,5-dihydro-1H-pyrazole-5-carboxamide (Compound 180);

4-butyl-1-(4-chloro-2-fluorophenyl)-3-(4-fluorophenyl)-5-methyl-N-((4-methylmorpholin-2-yl)methyl)-4,5-dihydro-1H-pyrazole-5-carboxamide (Compound 181);

4-butyl-1-(4-chloro-2-fluorophenyl)-3-(4-fluorophenyl)-N-((3-methoxy-1-methylazetidin-3-yl)methyl)-5-methyl-4,5-dihydro-1H-pyrazole-5-carboxamide (Compound 182);

1-(4-chloro-2-fluorophenyl)-4-(5-chlorofuran-2-yl)-3-(4-fluorophenyl)-5-methyl-N-((4-methylmorpholin-2-yl)methyl)-4,5-dihydro-1H-pyrazole-5-carboxamide (Compound 183);

4-(5-chlorofuran-2-yl)-3-(4-chlorophenyl)-1-(2,4-difluorophenyl)-5-methyl-N-((4-methylmorpholin-2-yl)methyl)-4,5-dihydro-1H-pyrazole-5-carboxamide (Compound 184);

4-butyl-1-(2,4-difluorophenyl)-3-(4-fluorophenyl)-5-methyl-N-((4-methylmorpholin-2-yl)methyl)-4,5-dihydro-1H-pyrazole-5-carboxamide (Compound 185);

4-butyl-1-(2,4-difluorophenyl)-3-(4-fluorophenyl)-N-((3-methoxy-1-methylazetidin-3-yl)methyl)-5-methyl-4,5-dihydro-1H-pyrazole-5-carboxamide (Compound 186);

4-butyl-1-(2,4-difluorophenyl)-3-(4-fluorophenyl)-N-((3-methoxyoxetan-3-yl)methyl)-5-methyl-4,5-dihydro-1H-pyrazole-5-carboxamide (Compound 187);

4-(5-chlorofuran-2-yl)-3-(4-fluorophenyl)-5-methyl-N-((4-methylmorpholin-2-yl)methyl)-1-(p-tolyl)-4,5-dihydro-1H-pyrazole-5-carboxamide (Compound 188);

4-butyl-3-(4-fluorophenyl)-5-methyl-N-((4-methylmorpholin-2-yl)methyl)-1-(p-tolyl)-4,5-dihydro-1H-pyrazole-5-carboxamide (Compound 189);

4-butyl-3-(4-fluorophenyl)-N-((3-methoxy-1-methylazetidin-3-yl)methyl)-5-methyl-1-(p-tolyl)-4,5-dihydro-1H-pyrazole-5-carboxamide (Compound 190); and 4-butyl-3-(4-fluorophenyl)-N-((3-methoxyoxetan-3-yl)methyl)-5-methyl-1-(p-tolyl)-4,5-dihydro-1H-pyrazole-5-carboxamide (Compound 191), or a salt, a hydrate, a solvate, or a stereoisomer thereof.

25. The method of claim 2, wherein the compound of formula (I) is administered in a pharmaceutical composition, comprising
    (i) the compound of formula (I), or a salt, a hydrate, a solvate, or a stereoisomer thereof, and
    (ii) a pharmaceutically acceptable carrier.

26. The method of claim 2, wherein the compound of formula (I) is selected from the group consisting of:

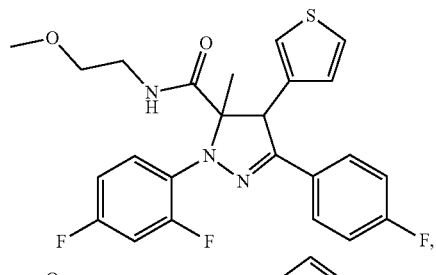

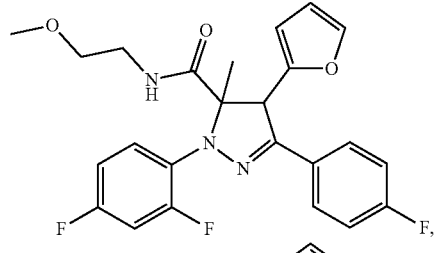

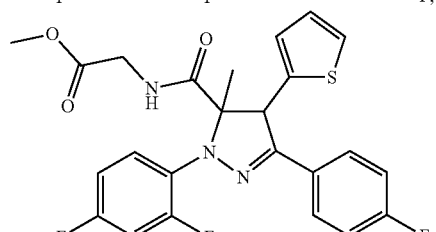

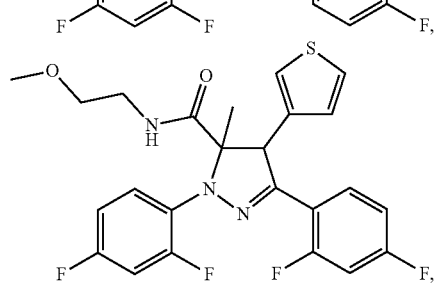

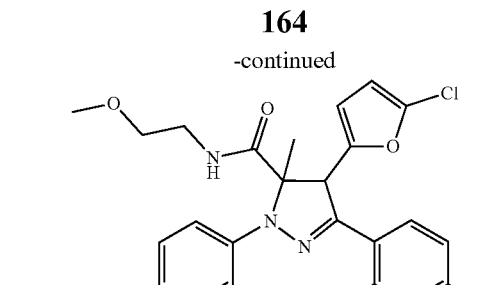

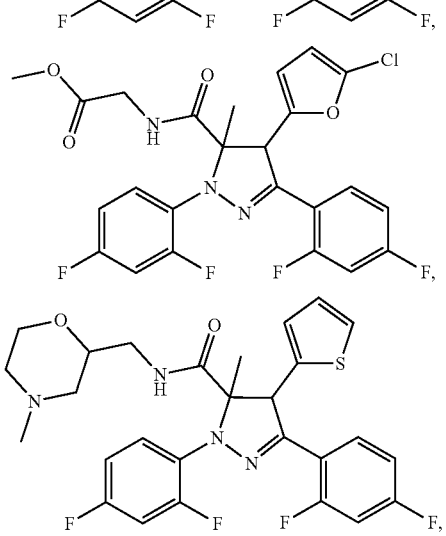

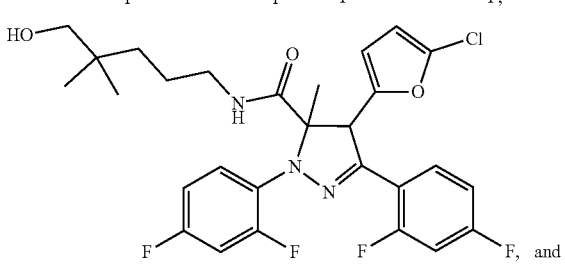, and

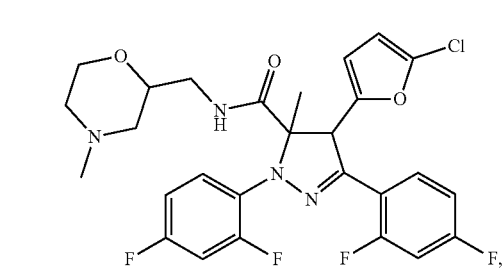

or a salt, a hydrate, or a solvate, or a stereoisomer thereof.

27. The method of claim 2, wherein the compound of formula (I) is selected from the group consisting of:

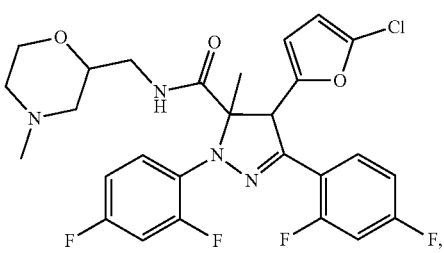

-continued
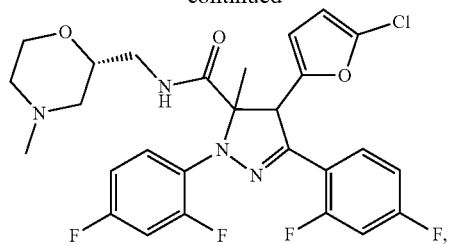
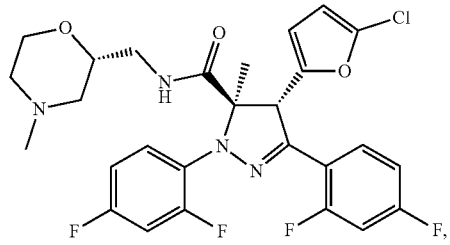
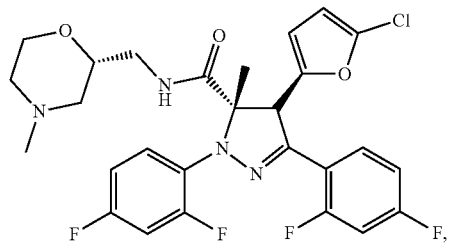
-continued
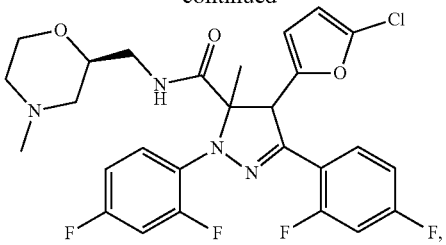
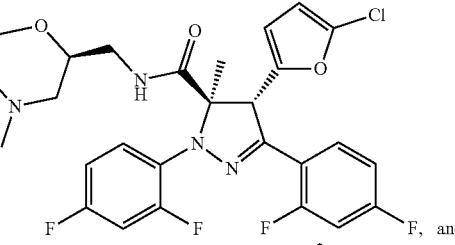
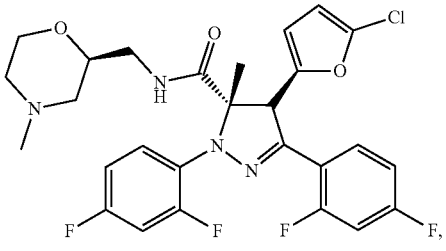, and
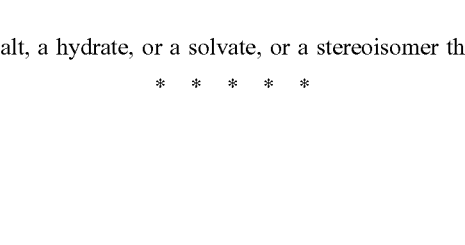
or a salt, a hydrate, or a solvate, or a stereoisomer thereof.
* * * * *